(12) United States Patent
Berry et al.

(10) Patent No.: US 10,117,933 B2
(45) Date of Patent: Nov. 6, 2018

(54) ANTIBODIES AGAINST *CLOSTRIDIUM DIFFICILE*

(71) Applicant: Emergent BioSolutions Canada Inc., Winnipeg (CA)

(72) Inventors: Jody Berry, Carlsbad, CA (US); Cory Nykiforuk, Winnipeg (CA); Darrell Johnstone, Winnipeg (CA); Joyee Antony George, Winnipeg (CA)

(73) Assignee: EMERGENT BIOSOLUTIONS CANADA INC., Winnipeg, MB (CA)

( * ) Notice: Subject to any disclaimer, the term of this patent is extended or adjusted under 35 U.S.C. 154(b) by 32 days.

(21) Appl. No.: 14/648,234

(22) PCT Filed: Nov. 29, 2013

(86) PCT No.: PCT/US2013/072467
§ 371 (c)(1),
(2) Date: May 28, 2015

(87) PCT Pub. No.: WO2014/085749
PCT Pub. Date: Jun. 5, 2014

(65) Prior Publication Data
US 2015/0290319 A1 Oct. 15, 2015

Related U.S. Application Data

(60) Provisional application No. 61/730,790, filed on Nov. 28, 2012.

(51) Int. Cl.
| *C07K 16/12* | (2006.01) |
| *A61K 39/40* | (2006.01) |
| *A61K 45/06* | (2006.01) |
| *A61K 39/00* | (2006.01) |

(52) U.S. Cl.
CPC .............. *A61K 39/40* (2013.01); *A61K 45/06* (2013.01); *C07K 16/1282* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,085,862 | A | | 2/1992 | Klein et al. |
| 5,221,618 | A | | 6/1993 | Klein et al. |
| 5,244,657 | A | | 9/1993 | Klein et al. |
| 5,332,583 | A | | 7/1994 | Klein et al. |
| 5,358,868 | A | | 10/1994 | Klein et al. |
| 5,435,945 | A | | 7/1995 | De Paoli et al. |
| 7,625,559 | B2 | * | 12/2009 | Ambrosino ............ A61K 39/08 424/130.1 |
| 8,236,311 | B2 | | 8/2012 | Ambrosino et al. |
| 8,257,709 | B2 | * | 9/2012 | Ambrosino ............ A61K 39/08 424/141.1 |
| 8,609,111 | B2 | * | 12/2013 | Ambrosino ............ A61K 39/08 424/130.1 |
| 8,697,374 | B2 | * | 4/2014 | Rajagopal ........... C07K 16/1282 435/7.32 |
| 8,986,697 | B2 | * | 3/2015 | Ma ..................... C07K 16/1282 424/136.1 |
| 9,217,029 | B2 | * | 12/2015 | Ambrosino ............ A61K 39/08 |
| 9,505,847 | B2 | * | 11/2016 | Cassan ............... C07K 16/1282 |
| 9,873,732 | B2 | * | 1/2018 | Maiti ..................... C07K 16/02 |
| 2002/0164326 | A1 | | 11/2002 | Young et al. |
| 2004/0137601 | A1 | * | 7/2004 | Von Eichel-Streiber .................... C07K 14/33 435/252.3 |
| 2005/0042664 | A1 | | 2/2005 | Wu et al. |
| 2005/0287150 | A1 | * | 12/2005 | Ambrosino ............ A61K 39/08 424/167.1 |
| 2007/0021595 | A1 | | 1/2007 | Hong |
| 2007/0071763 | A1 | * | 3/2007 | Burnie ............... C07K 16/1282 424/167.1 |
| 2008/0107673 | A1 | * | 5/2008 | Ballard ............ G01N 33/56911 424/190.1 |
| 2008/0286269 | A1 | | 11/2008 | Violette et al. |
| 2010/0104553 | A1 | | 4/2010 | Frey et al. |
| 2010/0233182 | A1 | * | 9/2010 | Ambrosino ............ A61K 39/08 424/150.1 |
| 2013/0202618 | A1 | * | 8/2013 | Ma ..................... C07K 16/1282 424/167.1 |
| 2013/0230537 | A1 | * | 9/2013 | Hussack ............ C07K 16/1282 424/167.1 |
| 2013/0266583 | A1 | * | 10/2013 | Shone ................... C07K 14/33 424/167.1 |

(Continued)

FOREIGN PATENT DOCUMENTS

| WO | 2007065037 | A2 | | 6/2007 |
| WO | WO 2011/063346 | A1 | * | 5/2011 |

(Continued)

OTHER PUBLICATIONS

Lowy et al, New England Journal Medicine, Jan. 21, 2010, 362/3:197-205.*

(Continued)

*Primary Examiner* — Nita M. Minnifield
(74) *Attorney, Agent, or Firm* — Thompson Coburn LLP; William A. Holtz

(57) ABSTRACT

Compositions and methods for the treatment or prevention of *Clostridium difficile* infection in a subject are provided. The compositions comprise antibodies to *Clostridium difficile* toxin B. The methods provide for administering the antibodies to a subject in an amount effective to reduce or eliminate or prevent relapse from *Clostridium difficile* bacterial infection.

23 Claims, 46 Drawing Sheets

Specification includes a Sequence Listing.

(56) References Cited

U.S. PATENT DOCUMENTS

| | | | |
|---|---|---|---|
| 2014/0004118 A1* | 1/2014 | Cassan | C07K 16/1282 424/139.1 |
| 2014/0127215 A1* | 5/2014 | Berry | C07K 16/1282 424/139.1 |
| 2014/0348844 A1* | 11/2014 | Humphreys | C07K 16/1282 424/139.1 |
| 2015/0175681 A1* | 6/2015 | Ma | C07K 16/1282 424/150.1 |
| 2015/0259402 A1* | 9/2015 | Takada | C07K 16/1282 424/167.1 |
| 2015/0290319 A1* | 10/2015 | Berry | C07K 16/1282 424/139.1 |
| 2015/0368320 A1* | 12/2015 | Maiti | A61K 39/08 424/158.1 |
| 2016/0068591 A1* | 3/2016 | Anderson | C07K 16/1282 424/136.1 |
| 2016/0137724 A1* | 5/2016 | Seeberger | C07K 16/1282 424/137.1 |
| 2016/0152694 A1* | 6/2016 | Ambrosino | A61K 39/08 530/387.3 |
| 2017/0051047 A1* | 2/2017 | Berry | C07K 16/1282 |
| 2018/0022784 A1* | 1/2018 | Gaudreau | C07K 14/33 |
| 2018/0037614 A1* | 2/2018 | Pollock | C07K 14/33 |

FOREIGN PATENT DOCUMENTS

| | | |
|---|---|---|
| WO | 2011130650 A2 | 10/2011 |
| WO | WO 2011/130650 A2 * | 10/2011 |
| WO | WO 2012/046061 A2 * | 4/2012 |
| WO | WO 2012/055030 A1 * | 5/2012 |
| WO | WO 2012/092469 A2 * | 7/2012 |
| WO | WO 2013/028810 A2 * | 2/2013 |
| WO | WO 2013/038156 A1 * | 3/2013 |
| WO | WO 2013/087857 A2 * | 6/2013 |
| WO | WO 2014/085749 A2 * | 6/2014 |

OTHER PUBLICATIONS

Meyers, Mount Sinai Journal Medicine, May 1995, 62/3:183-187.*
Babcock et al, Infection and Immunity, Nov. 2006, 74/11:6339-6347.*
Gerding, Discovery Medicine, Jan. 2012, 13/68:75-83.*
Hussack et al, Clinical and Experimental Gastroenterology, 2016, 9:209-224.*
Leav et al, Vaccine 28 (2010) 965-969.*
Aslam et al, Lancet Infect. Dis., 2005, 5:549-557.*
Kink et al, Infection and Immunity, May 1998, 66/5:2018-2025.*
Mizrahi et al, Anaerobe 30 (2014) 210-219.*
Ghose, Emerging Microbes and Infections (2013) 2 e62; doi; 10.1038/emi.2013.62; published online Sep. 18, 2013.*
Hussack et al, Toxin, 2010, 2:998-1018' published May 7, 2010.*
Humphreys et al, Clinical and vaccine Immunology, Jul. 2014, 21/7:913-923.*
Parks et al, New England Journal Medicine, Apr. 15, 2010, 362/15:1444-1446.*
Greenspan et al. 1999 (Defining epitopes: It's not as easy as it seems; Nature Biotechnology, 17:936-937).*
Guo et al. 2004 ("Protein tolerance to random amino acid change", Proceedings of the National Academy of Sciences USA, vol. 101, No. 5, pp. 9205-9210, 2004).*
Kelly et al., Current Concepts: Clostridium difficile Colitis, New England J. Med. 330:257-262, Jan. 1994.
Babcock et al., Human Monoclonal Antibodies Directed against Toxins A and B Prevent Clostridium difficile-Induced Mortality in Hamsters, Infection and Immunity, 74:6339-6347, Nov. 2006.
Relyveld et al., "Preparation of Vaccines by the Action of Glutaraldehyde on Toxins, Bacteria, Viruses, Allergens and Cells," Methods in Enzymology, 93:24 (1983).
Genth et al., Inf. and Immun., New Method to Generate Enzymatically Deficient Clostridium difficile Toxin B as an Antigen for Immunization 68(3): 1094-1101, Mar. 2000.
Marozsan et al., Protection Against Clostridium difficile Infection with Broadly Neutralizing Antitoxin Monoclonal Antibodies, J. Infect. Dis. 206(5):706-713, Jun. 2012.
Tan et al., Superhumanized Antibodies: Reduction of Immunogenic Potential by Complementarity-Determining Region Grafting with Human Germline Sequences: Application to an Anti-CD28; Journal of Immunology, 169:1119-1125, Jul. 2002.
Stundnicka et al, Human-Engineered Monoclonal Antibodies Retain Full Specific Binding Activity by Preserving non-CDR Complementarity-Modulating Residues, Protein Eng., 7(6):805-814, Jun. 1994.
Brown et al., : Tolerance to Single, But Not Multiple, Amino Acid Replacements in Antibody V-H CDR2: A Means of Minimizing B Cell Wastage from Somatic Hypermutation?, Journal of Immunology, Amercian Association of Immunologists, Jan. 1, 1996, pp. 3285-3291, vol. 156, No. 9.

* cited by examiner

Western immunoblot using murine CAN46G4 and CAN46G19

1. Toxin B Fragment 1
2. Toxin B Fragment 4
3. Toxin B
4. BSA (negative control)

Blot A: Probed with CAN46G4 at 2 μg/ml, protein loaded at 2 μg

Blot B: Probed with CAN46G19 at 2 μg/ml, protein loaded at 2 μg

FIG. 4

Western immunoblot using murine CAN46G13 and murine CAN46G13a

1. Toxin B Fragment 1
2. Toxin B Fragment 4
3. Toxin B
4. BSA (negative control)

Blot A: Probed with CAN46G13 at 2 μg/ml, protein loaded at 2 μg

Blot B: Probed with CAN46G13a at 2 μg/ml, protein loaded at 2 μg

FIG. 5

Western immunoblot using murine CAN46G24

1 Toxin B Fragment 1
2 Toxin B Fragment 4
3 Toxin B
4 BSA (negative control)

Blot A: Probed with CAN46G24 at 5 µg/ml, protein loaded at 5 µg

FIG. 6

Example Primer Set Used for V-Gene Amplification from RNA (Modified from Rohatgi, 2008)

| Primer ID | Sequence | Primer ID | Sequence |
|---|---|---|---|
| RT-VH1-1 | agRtYcagctgcaRcagtct | RT-VK1 | tgatgacccaRactccact |
| RT-VH1-2 | aggtccaactgcagcagcc | RT-VK2 | gcttgtgctctggatccc |
| RT-VH2 | tctgcctggtgacWttccca | RT-VK3 | ctgctgctctgggttcc |
| RT-VH3 | gtgcagcttcaggagtcag | RT-VK4 | cagcttcctgctaatcagtg |
| RT-VH4 | gaggtgaagcttctcgagtc | RT-VK5 | ctcagatccttggacttHtg |
| RT-VH5 | gaagtgaagctggtggagtc | RT-VK6 | tggagtcacagacYcagg |
| RT-VH6 | atgKacttgggactgaRctgt | RT-VK7 | tggagtttcagacccagg |
| RT-VH7 | cagtgtgaggtgaagctggt | RT-VK8 | ctgctMtggggtatctggt |
| RT-VH8 | ccaggttactctgaaagagtc | RT-VK9 | cWtcttgttgctctggtttc |
| RT-VH9 | tgtggaccttgctattcctga | RT-VK10 | gatgtcctctgctcagttc |
| RT-VH10 | tgttggggctgaagtgggttt | RT-VK11 | cctgctgagttccttggg |
| RT-VH11 | atggagtgggaactgagctta | RT-VK12 | ctgctgctgtggcttaca |
| RT-VH12 | agcttcaggagtcaggacc | RT-VK13 | ccttctcaacttctgctct |
| RT-VH13 | caggtgcagcttgtagagac | RT-VK14 | agggcccYtgctcagttt |
| RT-VH14 | atgcagctgggtcatcttctt | RT-VK15 | atgagggtccttgctgag |
| RT-VH15 | gactggatttggatcacKctc | RT-VK16 | gaggttccaggttcaggt |
| RT-VH16 | tggagtttggacttagttggg | RT-VK17 | ccatgaccatgYtctcact |
| RTCGamma | cagggatccaKagttc | RT-VK18 | atggaaactccagcttcattt |
| | | RT-VH19 | atgagaccgtctattcagtt |
| | | RTCK | tcaagaagcacacgac |

FIG. 10

V-Gene Sequencing Results

>CAN46G4 HEAVY
Amino Acid:
EVQLLQSGPELVKPGASVKISCKASDYSFTGYYMHWVKQSHVKSLEWIGRIFPYNGAASYNQNFKDKATLTVDKSSSTAYMELHSLTSEDSAVYYCTRWLRVYFDYWGQGTTLTVSS

| Result summary: | Productive IGH Rearranged Sequence (no Stop Codon and in-frame Junction) | | |
|---|---|---|---|
| V-GENE and Allele | Musmus IGHV1-31*01 F, or Musmus IGHV1-34*02 F | Score = 1219 | Identity = 91,67% (264/288 nt) |
| J-GENE and Allele | Musmus IGHJ2*01 F | Score = 231 | Identity = 97,92% (47/48 nt) |
| D-GENE and Allele by IMGT/Junction Analysis | Musmus IGHD2-2*01 F | D-REGION is in Reading Frame 2 | |
| FR-IMGT Lengths, CDR-IMGT Lengths and AA JUNCTION | [25.17.38.11] | [8.8.10] | CTRWLRVYFDYW |

>CAN46G4 KAPPA
Amino Acid:
EKVLTQSPAIMSASPGEEVTMTCSASSSVSYMHWYQQKSSTSPKLWIYETSKLAFGVPGRFSGSGSGNSYSLTISSMEAEDVATYYCFQGSGYPFTFGSGTKLEVK

| Result summary: | Productive IGK Rearranged Sequence (no Stop Codon and in-frame Junction) | | |
|---|---|---|---|
| V-GENE and Allele | Musmus IGKV4-63*01 F | Score = 1321 | Identity = 97,83% (270/276 nt) |
| J-GENE and Allele | Musmus IGKJ4*01 F | Score = 156 | Identity = 96,97% (32/33 nt) |
| FR-IMGT Lengths, CDR-IMGT Lengths and AA JUNCTION | [26.17.36.10] | [5.3.9] | CFQGSGYPFTF |

>CAN46G13a HEAVY
Amino Acid:
DVQLQESGPGLVKPSQSLSLTCTVTGYSITSDSAWNWIRQFPGNNLEWMGYISYSGSTSYNPSLKSRISITRDTSKNQFFLQLNSVTTEDTATYYCARRSRVSFYFDYWGQGTTLTVSS

| Result summary: | Productive IGH Rearranged Sequence (no Stop Codon and in-frame Junction) | | |
|---|---|---|---|
| V-GENE and Allele | Musmus IGHV3-2*02 F | Score = 1393 | Identity = 98,95% (282/285 nt) |
| J-GENE and Allele | Musmus IGHJ2*01 F | Score = 231 | Identity = 97,92% (47/48 nt) |
| D-GENE and Allele by IMGT/Junction Analysis | Musmus IGHD1-3*01 F | D-REGION is in Reading Frame 3 | |
| FR-IMGT Lengths, CDR-IMGT Lengths and AA JUNCTION | [24.17.38.11] | [9.7.12] | CARRSRVSFYFDYW |

FIG. 11

>CAN46G13a KAPPA
Amino Acid:
ENVLTQSPAIMAASLGQKVTMTCSASSSVSSSYLHWYQQKSGASPKPLIHRTSTLASGVPARFSGSGSGTSYSLTISSVEAEDDATYYCQQWSGYPYTFGGGTKLEIK

| Result Summary: | Productive IGK Rearranged Sequence (no Stop Codon and in-frame Junction) | | |
|---|---|---|---|
| V-GENE and Allele | Musmus IGKV4-58*01 F | Score = 1387 | Identity = 99,29% (280/282 nt) |
| J-GENE and Allele | Musmus IGKJ2*01 F | Score = 165 | Identity = 100,00% (33/33 nt) |
| FR-IMGT Lengths, CDR-IMGT Lengths and AA JUNCTION | [26.17.36.10] | [7.3.9] | CQQWSGYPYTF |

>CAN46G19 HEAVY
Amino Acid:
EVQLLQSGPELVKPGTSVKISCKASGYSFTGYYIHWVKQTHVKSLEWVGRIFPYNGAASYNQNFKGKATLTVDKSSTTAYMELHSLTSEDSAVYFCARWLRVYFDYWGQGTTLTVSS

| Result Summary: | Productive IGH Rearranged Sequence (no Stop Codon and in-frame Junction) | | |
|---|---|---|---|
| V-GENE and Allele | Musmus IGHV1-31*01 F, or Musmus IGHV1-34*02 F | Score = 1210 | Identity = 91,32% (263/288 nt) |
| J-GENE and Allele | Musmus IGHJ2*01 F | Score = 231 | Identity = 97,92% (47/48 nt) |
| D-GENE and Allele by IMGT/Junction Analysis | Musmus IGHD2-2*01 F | D-REGION is in Reading Frame 2 | |
| FR-IMGT Lengths, CDR-IMGT Lengths and AA JUNCTION | [25.17.38.11] | [8.8.10] | CARWLRVYFDYW |

>CAN46G19 KAPPA
Amino Acid:
ENVLTQSPTIMSASPGEEVTMTCSASSSVTYMHWYQQKSITSPKLWIYETSKLASGVPGRFSGSGSGNSYSLTISSMEAEDVATYYCFQGSGYPFTFGSGTKLEIK

| Result Summary: | Productive IGK Rearranged Sequence (no Stop Codon and in-frame Junction) | | |
|---|---|---|---|
| V-GENE and Allele | Musmus IGKV4-63*01 F | Score = 1330 | Identity = 98,19% (271/276 nt) |
| J-GENE and Allele | Musmus IGKJ4*01 F | Score = 165 | Identity = 100,00% (33/33 nt) |
| FR-IMGT Lengths, CDR-IMGT Lengths and AA JUNCTION | [26.17.36.10] | [5.3.9] | CFQGSGYPFTF |

FIG. 11 (Cont.)

>CAN46G24 HEAVY
Amino Acid:
EVQLLQSGPELVKPGTSVKISCKASGYSFTGYYIHWVKQTHVKSLEWVGRIFPYNGAASYNQNFKGKATLTVDKSSSTAYMELHSLTSEDSAVYF
CARWLRVYFDYWGQGTTLTVSS

| Result Summary: | Productive IGH Rearranged Sequence (no Stop Codon and in-frame Junction) | | |
|---|---|---|---|
| V-GENE and Allele | Musmus IGHV1-34*02 F | Score = 1228 | Identity = 92,01% (265/288 nt) |
| J-GENE and Allele | Musmus IGHJ2*01 F | Score = 231 | Identity = 97,92% (47/48 nt) |
| D-GENE and Allele by IMGT/Junction Analysis | Musmus IGHD2-2*01 F | D-REGION is in Reading Frame 2 | |
| FR-IMGT Lengths, CDR-IMGT Lengths and AA JUNCTION | [25.17.38.11] | [8.8.10] | CARWLRVYFDYW |

>CAN46G24 KAPPA
Amino Acid:
EIVLTQSPAIMSTSPGEKVTMSCSASSSVTYMHWYQQKSITSPKLWIYETSKLASGVPGRFSGSGSGNSYSLTISSMEAEDVATYYCFQGSGYPFTF
GSGTKLEIK

| Result Summary: | Productive IGH Rearranged Sequence (no Stop Codon and in-frame Junction) | | |
|---|---|---|---|
| V-GENE and Allele | Musmus IGKV4-63*01 F | Score = 1312 | Identity = 97,46% (269/276 nt) |
| J-GENE and Allele | Musmus IGKJ4*01 F | Score = 165 | Identity = 100,00% (33/33 nt) |
| FR-IMGT Lengths, CDR-IMGT Lengths and AA JUNCTION | [26.17.36.10] | [5.3.9] | CFQGSGYPFTF |

>CAN46G13 HEAVY
Amino Acid:
EVQLLQSGPELVKPGTSVKISCKASGYSFTGYYIHWVKQTHVKSLEWVGRIFPYNGAASYNQNFKGKATLTVDKSSSTAYMELHSLTSEDSAVYF
CARWLRVYFDYWGQGTTLTVSS

| Result Summary: | Productive IGH Rearranged Sequence (no Stop Codon and in-frame Junction) | | |
|---|---|---|---|
| V-GENE and Allele | Musmus IGHV1-34*02 F | Score = 1228 | Identity = 92,01% (265/288 nt) |
| J-GENE and Allele | Musmus IGHJ2*01 F | Score = 231 | Identity =97,92% (47/48 nt) |
| D-GENE and Allele by IMGT/Junction Analysis | Musmus IGHD2-2*01 F | D-REGION is in Reading Frame 2 | |
| FR-IMGT Lengths, CDR-IMGT Lengths and AA JUNCTION | [25.17.38.11] | [8.8.10] | CARWLRVYFDYW |

FIG. 11 (Cont.)

\>CAN46G13 KAPPA
Amino Acid:
EIVLTQSPAIMSTSPGEKVTMSCSASSSVTYMHWYQQKSITSPKLWIYETSKLASGVPGRFSGSGSGNSYSLTISSMEAEDVATYYCFQGSGYPFTFGSGTKLEIK

| Result Summary: | Productive IGK Rearranged Sequence (no Stop Codon and in-frame Junction) | | |
|---|---|---|---|
| V-GENE and Allele | Musmus IGKV4-63*01 F | Score = 1312 | Identity =97,46% (269/276 nt) |
| J-GENE and Allele | Musmus IGKJ4*01 F | Score = 165 | Identity =100,00% (33/33 nt) |
| FR-IMGT Lengths, CDR-IMGT Lengths and AA JUNCTION | [26.17.36.10] | [5.3.9] | CFQGSGYPFTF |

CAN33G1 HEAVY
Amino Acid:
EVQLQQSGPDLVKPGASVKISCKASGYSFTGYYMHWVKQSHGKSLEWIGRVNPYNGDTNYNQNFKDKAILTVDKSASTAYMEFRSLTSEDSAVYYCTRSNWENYFDYWGQGSTLTVSS

| Result Summary: | Productive IGH Rearranged Sequence (no Stop Codon and in-frame Junction) | | |
|---|---|---|---|
| V-GENE and Allele | Musmus IGHV1-31*01 F | Score = 1210 | Identity = 91,32% (263/288 nt) |
| J-GENE and Allele | Musmus IGHJ2*01 F | Score = 231 | Identity = 97,92% (47/48 nt) |
| D-GENE and Allele by IMGT/Junction Analysis | Musmus IGHD4-1*01 F | D-REGION is in Reading Frame 3 | |
| FR-IMGT Lengths, CDR-IMGT Lengths and AA JUNCTION | [25.17.38.11] | [8.8.11] | CTRSNWENYFDYW |

CAN33G1 KAPPA
Amino Acid:
DIQLTQSSSSFSVSLGDRVTITCKASEDIYNRLAWYQQRPGNAPRLLISGATSLETGIPSRFSGSGSGKEYTLSIASLQTEDFVTYYCQQYWNIPTFGGGTRLEIK

| Result Summary: | Productive IGK Rearranged Sequence (no Stop Codon and in-frame Junction) | | |
|---|---|---|---|
| V-GENE and Allele | Musmus IGKV13-84*01 F | Score = 1291 | Identity = 96,06% (268/279 nt) |
| J-GENE and Allele | Musmus IGKJ1*01 F | Score = 166 | Identity = 97,14% (34/35 nt) |
| FR-IMGT Lengths, CDR-IMGT Lengths and AA JUNCTION | [26.17.36.10] | [6.3.8] | CQQYWNIPTF |

FIG. 11 (Cont.)

Humanized CDR Grafted cdrCAN46G Design cdrCAN46G4
KAPPA
EIVLTQSPATLSLSPGERATLSCSASSSVSYMHWYQQKPGQAPRLLIYETSKLAFGIPARF
SGSGSGTDFTLTISSLEPEDFAVYYCFQGSGYPFTFGQGTRLEIK HEAVY
QVQLVQSGAEVKKPGSSVKVSCKASGYTFTGYYMHWVRQAPGQGLEWIGRIFPYNGA
ASYNQNFKDKATITADESTNTAYMELSSLRSEDTAVYYCARWLRVYFDYWGQGTLVT
VSS cdrCAN46G13a
KAPPA
DIQMTQSPSSLSASVGDRVTITCSASSSVSSSYLHWYQQKPGKAPKLLIYRTSTLASGVPS
RFSGSGSGTDFTFTISSLQPEDIATYYCQQWSGYPYTFGQGTKVEIK HEAVY
QVQLQESGPGLVKPSQTLSLTCTVSGGSISSDSAWNWIRQPPGKGLEWIGYISYSGSTSY
NPSLKSRVTMSVDTSKNQFSLKVNSVTAADTAVYYCARRSRVSFYFDYWGQGTLVTVS
S cdrCAN46G19
KAPPA
DIQMTQSPSSLSASVGDRVTITCSASSSVTYMHWYQQKPGKAPKLLIYETSKLASGVPSR
FSGSGSGTDYTFTISSLQPEDIATYYCFQGSGYPFTFGQGTKVEIK HEAVY
AQVQLVQSGAEVKKPGESVKVSCKASGYTFTGYYIHWVRQAPGQGLEWMGRIFPYNG
AASYNQNFKGRVTITADKSTSTAYMELSSLRSEDTAVYYCARWLRVYFDYWGQGTTV
TVSS cdrCAN46G24
KAPPA
DIQMTQSPSSLSASVGDRVTITCSASSSVTYMHWYQQKPGKAPKLLIYETSKLASGVPSR
FSGSGSGTDYTFTISSLQPEDIATYYCFQGSGYPFTFGQGTKVEIK HEAVY
QVQLVQSGAEVKKPGESVKVSCKASGYTFTGYYIHWVRQAPGQGLEWMGRIFPYNGA
ASYNQNFKGRVTITADKSTSTAYMELSSLRSEDTAVYYCARWLRVYFDYWGQGTTVT
VSS

FIG. 12

Humanized huCAN46G Design huCAN46G4
KAPPA
EKVLTQSPATLSLSPGERATMTCSASSSVSYMHWYQQKPGTSPKLWIYETSKLAFGVPA
RFSGSGSGNSYSLTISSLEPEDFAVYYCFQGSGYPFTFGQGTRLEIK

HEAVY
EVQLLQSGAEVKKPGSSVKISCKASDYSFTGYYMHWVKQAPGQGLEWIGRIFPYNGAA
SYNQNFKDKATLTVDKSSSTAYMELHSLRSEDTAVYYCTRWLRVYFDYWGQGTLVTV
SS huCAN46G13a
KAPPA
ENVLTQSPSSLSASVGDRVTMTCSASSSVSSSYLHWYQQKPGKSPKPLIHRTSTLASGVP
SRFSGSGSGTSYSLTISSLQPEDIATYYCQQWSGYPYTFGGGTKVEIK

HEAVY
QVQLQESGPGLVKPSQTLSLTCTVTGYSITSDSAWNWIRQFPGNNLEWMGYISYSGSTS
YNPSLKSRISITRDTSKNQFSLKVNSVTAADTAVYYCARRSRVSFYFDYWGQGTLVTVS
S huCAN46G19
KAPPA
ENVLTQSPSSLSASVGDRVTITCSASSSVTYMHWYQQKPGKAPKLWIYETSKLASGVPG
RFSGSGSGNSYTFTISSLQPEDIATYYCFQGSGYPFTFGQGTKVEIK

HEAVY
EVQLVQSGAEVKKPGESVKVSCKASGYSFTGYYIHWVKQAPGQGLEWVGRIFPYNGA
ASYNQNFKGKATLTVDKSSTTAYMELSSLRSEDTAVYFCARWLRVYFDYWGQGTTVT
VSS huCAN46G24
KAPPA
EIVLTQSPSSLSTSVGDRVTISCSASSSVTYMHWYQQKPGKAPKLWIYETSKLASGVPGR
FSGSGSGNSYTFTISSLQPEDIATYYCFQGSGYPFTFGQGTKVEIK

HEAVY
EVQLVQSGAEVKKPGESVKVSCKASGYSFTGYYIHWVKQAPGQGLEWVGRIFPYNGA
ASYNQNFKGKATLTVDKSSSTAYMELSSLRSEDTAVYFCARWLRVYFDYWGQGTTVT
VSS

FIG. 13

Humanized Resurfaced rehuCAN46G Design rehuCAN46G4
KAPPA
EKVLTQSPATLSASPGERVTMSCSASSSVSYMHWYQQKPGQSPKLWIYETSKLAFGVPA
RFSGSGSGTDYSLTISSMEPEDFATYYCFQGSGYPFTFGQGTRLEIK HEAVY
EVQLLQSGAEVVKPGSSVKISCKASGYSFTGYYMHWVKQAPGQGLEWIGRIFPYNGAA
SYNQNFKDKATLTADKSTNTAYMELSSLRSEDSAVYYCTRWLRVYFDYWGQGTLVTV
SS rehuCAN46G13a
KAPPA
ENVLTQSPSSMSASVGDRVTMTCSASSSVSSSYLHWYQQKPGKAPKPLIHRTSTLASGV
PSRFSGSGSGTSYSLTISSVQPEDIATYYCQQWSGYPYTFGGGTKVEIKR HEAVY
QVQLQESGPGLVKPSQTLSLTCTVTGYSITSDSAWNWIRQPPGNGLEWMGYISYSGSTS
YNPSLKSRISITRDTSKNQFSLKLNSVTAADTATYYCARRSRVSFYFDYWGQGTLVTVSS rehuCAN46G19
KAPPA
ENVLTQSPSSMSASVGDRVTMTCSASSSVTYMHWYQQKPGKSPKLWIYETSKLASGVP
SRFSGSGSGNDYSLTISSMQPEDVATYYCFQGSGYPFTFGQGTKLEIK HEAVY
EVQLVQSGAEVVKPGESVKISCKASGYSFTGYYIHWVKQTPGQSLEWVGRIFPYNGAAS
YNQNFKGKATLTVDKSTTTAYMELSSLRSEDSAVYFCARWLRVYFDYWGQGTTLTVSS rehuCAN46G24
KAPPA
EIVLTQSPSSMSTSVGDRVTMSCSASSSVTYMHWYQQKPGKSPKLWIYETSKLASGVPS
RFSGSGSGNDYSLTISSMQPEDVATYYCFQGSGYPFTFGQGTKLEIK HEAVY
EVQLVQSGAEVVKPGESVKISCKASGYSFTGYYIHWVKQTPGQSLEWVGRIFPYNGAAS
YNQNFKGKATLTVDKSTSTAYMELSSLRSEDSAVYFCARWLRVYFDYWGQGTTLTVSS

FIG. 14

Toxin B Neutralization Assay using humanized CAN46G4 mAbs purified from HEK293F cells expressing the Per.C6-based construct

FIG.15A

Total Human IgG ELISA using humanized CAN46 mAbs Purified from HEK293F cells expressing the Per.C6-based construct

| Group | Test Antibodies | mAb Serum Concentration 12 hours pre-toxin injection (µg/mL) | mAb Serum Concentration at End of Study (Day 4) (ug/mL) | Linear Rate of Decline in detectable Circulating mAbs from 12-96 hours (delta 84 Hours) during the study (ug/ml/hour) |
|---|---|---|---|---|
| A | huCAN46G19 (250ug) | 61.83 | 31.98 | 0.36 |
| B | huCAN46G24 (250ug) | 40.83 | 31.22 | 0.11 |
| C | huCAN46G19 (75ug) | 22.31 | 16.11 | 0.07 |
| D | huCAN46G24 (75ug) | 17.98 | 12.69 | 0.06 |
| F | rehuCAN46G19 (250ug) | 14.57 | 12.64 | 0.02 |
| G | rehuCAN46G24 (250ug) | 44.15 | 27.12 | 0.20 |

FIG. 18

Toxin B Affinity Analysis using humanized CAN46 mAbs purified from HEK293F cells expressing the Per.C6-based construct

| mAb | sensor | KD (nM) | Kdis (1/s) | Kon (1/Ms) | Model |
|---|---|---|---|---|---|
| murine CAN46G4 | SA | 1.41E-9 | 1.01E-4 | 7.18E4 | 2:1 |
| huCAN46G4 | SA | 1.57E-9 | 9.28E-4 | 5.90E5 | 2:1 |
|  | AHC | 3.56E-10 | 7.54E-4 | 2.12E6 | 2:1 |
| rehuCAN46G4 | SA | 3.99E-10 | 2.35E-4 | 5.90E5 | 1:1 |
|  |  |  |  |  |  |
| murine CAN46G13 | SA | 1.17E-9 | 1.49E-4 | 1.28E5 | 2:1 |
|  |  |  |  |  |  |
| murine CAN46G13a | SA | 5.26E-9 | 3.57E-3 | 6.78E5 | 2:1 |
|  | SA | 8.57E-9 | 6.93E-3 | 8.08E5 | 2:1 |
|  | SA | 8.11E-8 | 5.98E-3 | 7.37E4 | 2:1 |
| rehuCAN46G13a | SA | 6.8E-9 | 2.40E-3 | 3.53E5 | 2:1 |
| huCAN46G13a | SA | 4.23E-10 | 2.34E-4 | 5.52E5 | 1:1 |
|  |  |  |  |  |  |
| murine CAN46G19 | SA | 1.27E-9 | 1.45E-4 | 1.14E5 | 2:1 |
| huCAN46G19 | AHC | 1.78E-10 | 2.07E-4 | 1.16E6 | 2:1 |
| rehuCAN46G19 | SA | 1.54E-10 | 2.1E-4 | 1.36E6 | 1:1 |

FIG. 24

Toxin B Neutralization Assay using humanized CAN46 mAbs purified from CHOK1SV cells expressing the CHO-based construct

Toxin B/Lonza mAbs Neutralization Assay

Legend:
- ◇ CHO MDX1388
- □ CHO huCAN46G19
- △ CHO rehuCAN46G19
- ✕ CHO huCAN46G13a
- ✲ CHO rehuCAN46G13a
- ○ CHO rehuCAN46G24
- + CHO huCAN46G24
- ▽ 293F hPA-41

X-axis: Antibody Concentration (ug/ml) — 2.000, 1.000, 0.500, 0.250, 0.125, 0.063, 0.031, 0.016
Y-axis: Percent Neutralization (0.0 – 140.0)

FIG. 25

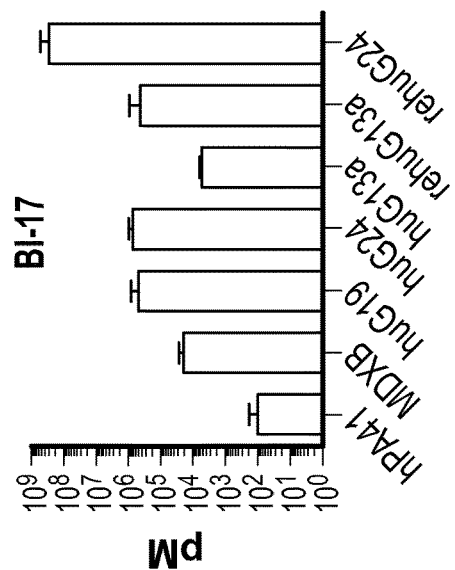
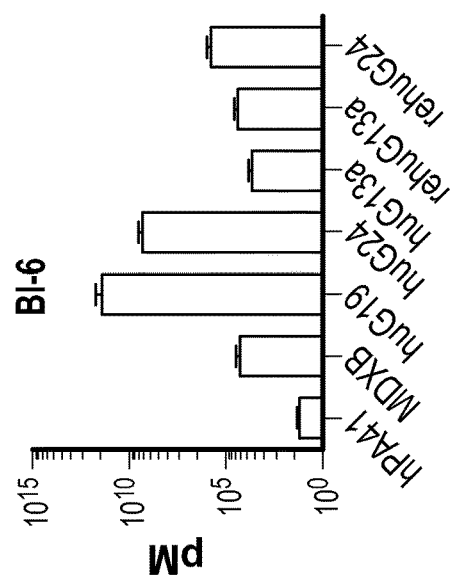
FIG. 26 (Cont.)

Cross-Reactivity Study using humanized CAN46 mAbs purified from HEK293F cells expressing the Per.C6-based construct

| *C. difficile* concentrates | Cross-Reactivity Responses of Cangene Toxin B mAbs to *C. difficile* Toxin B | | | | | | |
|---|---|---|---|---|---|---|---|
| | huCAN46G24 | rehuCAN46G24 | huCAN46G13a | rehuCAN46G13a | hPA41 | MDX-1388 | pAbs |
| BI-1 | L | L | H | L | H | M | M |
| BI-6 | L | L | H | L | H | M | M |
| BI-17 | M | L | H | M | H | M | H |
| B1 | L | L | M | L | L | L | M |
| R23 | L | L | L | L | L | L | M |
| K14 | L | L | M | L | L | L | M |
| J9 | L | L | L | L | L | L | H |
| CF-2 | L | L | L | L | L | L | M |
| Y2 | L | L | M | L | L | L | M |
| ATCC 43255 | H | H | H | H | H | H | H |

Detection of TcdB levels in Non-NAP1 and NAP1 strains using humanized TcdB mAbs purified from HEK293F cells expressing the Per.C6-based construct

FIG. 31

Western immunoblot with humanized TcdB mAbs purified from CHOK1SV cells expressing the CHO-based construct

1. Toxin A
2. Toxin B Fragment 1
3. Toxin B
4. Toxin B Fragment 4

Blot Probed with huCAN46G13a at 5ug/mL, protein loaded at 3ug

Blot Probed with rehuCAN46G13a at 5ug/mL, protein loaded at 3ug

FIG. 34

1. Toxin A
2. Toxin B Fragment 1
3. Toxin B
4. Toxin B Fragment 4

Blot Probed with MDX1388 expressed in CHO cells at 0.5ug/mL, protein loaded at 0.5ug Blot Probed with hPA-41 expressed in CHO cells at 0.5ug/mL, protein loaded at 0.5ug

FIG. 34 (Cont.)

Western immunoblots with humanized TcdB mAbs Purified from HEK293F cells expressing the Per.C6-based construct

1. Toxin A
2. Toxin B Fragment 1
3. Toxin B
4. Toxin B Fragment 4

Blot Probed with PerC6 MDX1388 at 5ug/mL, protein loaded at 0.5 ug

Blot Probed with PerC6 hPA-41 at 5ug/mL, protein loaded at 0.5 ug

FIG. 35

1. Toxin A
2. Toxin B Fragment 1
3. Toxin B
4. Toxin B Fragment 4

Blot Probed with perC6 huCAN46G19 at 5 ug/mL, protein loaded at 3 ug

Fig. 35 (Cont.)

Affinity Analysis of humanized CAN46 mAbs purified from CHOK1SV cells expressing the CHO-based construct

| mAb | KD1 (nM) | KD2 (nM) | kdis1 (nM) | kdis2 (1/s) | $R^2$ | $X^2$ |
|---|---|---|---|---|---|---|
| huCAN46G24 | 1.2E-11 | 3.28E-10 | 2.2E-5 | 8.1E-5 | 0.996 | 1.47 |
| rehuCAN46G24 | 7.1E-10 | 4.7E-11 | 2.1E-3 | 1.2E-5 | 0.960 | 0.14 |
| huCAN46G13a | 1.2E-9 | <1E-12 | 3.4E-3 | <1E-7 | 0.988 | 2.08 |
| rehuCAN46G13a | 3.5E-10 | 1.2E-9 | 2.0E-4 | 4E-3 | 0.997 | 1.55 |

ELISA data for humanized CAN46 mAbs purified from CHOS1KV cells expressing the CHO-based construct

SEQUENCE LISTING

```
<160> NUMBER OF SEQ ID NOS: 835

<210> SEQ ID NO 1
<211> LENGTH: 546
<212> TYPE: PRT
<213> ORGANISM: Clostridium difficile
<220> FEATURE:
<223> OTHER INFORMATION: Fragment 1 of Toxin B; TcdB, Frag 1, aa 1-546

<400> SEQUENCE: 1

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
```

```
                210                 215                 220
Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
                260                 265                 270

Arg Ile Ser Ala Leu Lys Glu Ile Gly Gly Met Tyr Leu Asp Val Asp
                275                 280                 285

Met Leu Pro Gly Ile Gln Pro Asp Leu Phe Glu Ser Ile Glu Lys Pro
                290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
                370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
                435                 440                 445

Glu Leu Gly Lys Tyr Leu Arg Val Gly Phe Phe Pro Asp Val Lys Thr
                450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Arg Asn Tyr Phe Glu Gly Ser Leu Gly
                530                 535                 540

Glu Asp
545

<210> SEQ ID NO 2
<211> LENGTH: 590
<212> TYPE: PRT
<213> ORGANISM: Clostridium difficile
<220> FEATURE:
<223> OTHER INFORMATION: Fragment 4 of Toxin B; TcdB, Frag 4, aa 1777-
      2366

<400> SEQUENCE: 2

Ala Asn Lys Leu Ser Phe Asn Phe Ser Asp Lys Gln Asp Val Pro Val
1               5                   10                  15
```

```
Ser Glu Ile Ile Leu Ser Phe Thr Pro Ser Tyr Tyr Glu Asp Gly Leu
             20                  25                  30
Ile Gly Tyr Asp Leu Gly Leu Val Ser Leu Tyr Asn Glu Lys Phe Tyr
         35                  40                  45
Ile Asn Asn Phe Gly Met Met Val Ser Gly Leu Ile Tyr Ile Asn Asp
     50                  55                  60
Ser Leu Tyr Tyr Phe Lys Pro Pro Val Asn Asn Leu Ile Thr Gly Phe
 65                  70                  75                  80
Val Thr Val Gly Asp Asp Lys Tyr Tyr Phe Asn Pro Ile Asn Gly Gly
                 85                  90                  95
Ala Ala Ser Ile Gly Glu Thr Ile Ile Asp Asp Lys Asn Tyr Tyr Phe
             100                 105                 110
Asn Gln Ser Gly Val Leu Gln Thr Gly Val Phe Ser Thr Glu Asp Gly
         115                 120                 125
Phe Lys Tyr Phe Ala Pro Ala Asn Thr Leu Asp Glu Asn Leu Glu Gly
     130                 135                 140
Glu Ala Ile Asp Phe Thr Gly Lys Leu Ile Ile Asp Glu Asn Ile Tyr
145                 150                 155                 160
Tyr Phe Asp Asp Asn Tyr Arg Gly Ala Val Glu Trp Lys Glu Leu Asp
                 165                 170                 175
Gly Glu Met His Tyr Phe Ser Pro Glu Thr Gly Lys Ala Phe Lys Gly
             180                 185                 190
Leu Asn Gln Ile Gly Asp Tyr Lys Tyr Tyr Phe Asn Ser Asp Gly Val
         195                 200                 205
Met Gln Lys Gly Phe Val Ser Ile Asn Asp Asn Lys His Tyr Phe Asp
     210                 215                 220
Asp Ser Gly Val Met Lys Val Gly Tyr Thr Glu Ile Asp Gly Lys His
225                 230                 235                 240
Phe Tyr Phe Ala Glu Asn Gly Glu Met Gln Ile Gly Val Phe Asn Thr
                 245                 250                 255
Glu Asp Gly Phe Lys Tyr Phe Ala His His Asn Glu Asp Leu Gly Asn
             260                 265                 270
Glu Glu Gly Glu Glu Ile Ser Tyr Ser Gly Ile Leu Asn Phe Asn Asn
         275                 280                 285
Lys Ile Tyr Tyr Phe Asp Asp Ser Phe Thr Ala Val Val Gly Trp Lys
     290                 295                 300
Asp Leu Glu Asp Gly Ser Lys Tyr Tyr Phe Asp Glu Asp Thr Ala Glu
305                 310                 315                 320
Ala Tyr Ile Gly Leu Ser Leu Ile Asn Asp Gly Gln Tyr Tyr Phe Asn
                 325                 330                 335
Asp Asp Gly Ile Met Gln Val Gly Phe Val Thr Ile Asn Asp Lys Val
             340                 345                 350
Phe Tyr Phe Ser Asp Ser Gly Ile Ile Glu Ser Gly Val Gln Asn Ile
         355                 360                 365
Asp Asp Asn Tyr Phe Tyr Ile Asp Asp Asn Gly Ile Val Gln Ile Gly
     370                 375                 380
Val Phe Asp Thr Ser Asp Gly Tyr Lys Tyr Phe Ala Pro Ala Asn Thr
385                 390                 395                 400
Val Asn Asp Asn Ile Tyr Gly Gln Ala Val Glu Tyr Ser Gly Leu Val
                 405                 410                 415
Arg Val Gly Glu Asp Val Tyr Tyr Phe Gly Glu Thr Tyr Thr Ile Glu
             420                 425                 430
Thr Gly Trp Ile Tyr Asp Met Glu Asn Glu Ser Asp Lys Tyr Tyr Phe
```

```
                      435                 440                 445
Asn Pro Glu Thr Lys Lys Ala Cys Lys Gly Ile Asn Leu Ile Asp Asp
    450                 455                 460
Ile Lys Tyr Tyr Phe Asp Glu Lys Gly Ile Met Arg Thr Gly Leu Ile
465                 470                 475                 480
Ser Phe Glu Asn Asn Asn Tyr Tyr Phe Asn Glu Asn Gly Glu Met Gln
                485                 490                 495
Phe Gly Tyr Ile Asn Ile Glu Asp Lys Met Phe Tyr Phe Gly Glu Asp
            500                 505                 510
Gly Val Met Gln Ile Gly Val Phe Asn Thr Pro Asp Gly Phe Lys Tyr
        515                 520                 525
Phe Ala His Gln Asn Thr Leu Asp Glu Asn Phe Glu Gly Glu Ser Ile
    530                 535                 540
Asn Tyr Thr Gly Trp Leu Asp Leu Asp Glu Lys Arg Tyr Tyr Phe Thr
545                 550                 555                 560
Asp Glu Tyr Ile Ala Ala Thr Gly Ser Val Ile Ile Asp Gly Glu Glu
                565                 570                 575
Tyr Tyr Phe Asp Pro Asp Thr Ala Gln Leu Val Ile Ser Glu
            580                 585                 590

<210> SEQ ID NO 3
<211> LENGTH: 106
<212> TYPE: PRT
<213> ORGANISM: Mus musculus
<220> FEATURE:
<223> OTHER INFORMATION: CAN46G4; K, variable region

<400> SEQUENCE: 3

Glu Lys Val Leu Thr Gln Ser Pro Ala Ile Met Ser Ala Ser Pro Gly
1               5                   10                  15
Glu Glu Val Thr Met Thr Cys Ser Ala Ser Ser Ser Val Ser Tyr Met
            20                  25                  30
His Trp Tyr Gln Gln Lys Ser Ser Thr Ser Pro Lys Leu Trp Ile Tyr
        35                  40                  45
Glu Thr Ser Lys Leu Ala Phe Gly Val Pro Gly Arg Phe Ser Gly Ser
    50                  55                  60
Gly Ser Gly Asn Ser Tyr Ser Leu Thr Ile Ser Ser Met Glu Ala Glu
65                  70                  75                  80
Asp Val Ala Thr Tyr Tyr Cys Phe Gln Gly Ser Gly Tyr Pro Phe Thr
                85                  90                  95
Phe Gly Ser Gly Thr Lys Leu Glu Val Lys
            100                 105

<210> SEQ ID NO 4
<211> LENGTH: 5
<212> TYPE: PRT
<213> ORGANISM: Mus musculus
<220> FEATURE:
<223> OTHER INFORMATION: CAN46G4; K, CDR1

<400> SEQUENCE: 4

Ser Ser Val Ser Tyr
1               5

<210> SEQ ID NO 5
<211> LENGTH: 3
<212> TYPE: PRT
<213> ORGANISM: Mus musculus
<220> FEATURE:
```

<223> OTHER INFORMATION: CAN46G4; K, CDR2

<400> SEQUENCE: 5

Glu Thr Ser
1

<210> SEQ ID NO 6
<211> LENGTH: 9
<212> TYPE: PRT
<213> ORGANISM: Mus musculus
<220> FEATURE:
<223> OTHER INFORMATION: CAN46G4; K, CDR3

<400> SEQUENCE: 6

Phe Gln Gly Ser Gly Tyr Pro Phe Thr
1               5

<210> SEQ ID NO 7
<211> LENGTH: 26
<212> TYPE: PRT
<213> ORGANISM: Mus musculus
<220> FEATURE:
<223> OTHER INFORMATION: CAN46G4; K, FR1

<400> SEQUENCE: 7

Glu Lys Val Leu Thr Gln Ser Pro Ala Ile Met Ser Ala Ser Pro Gly
1               5                   10                  15

Glu Glu Val Thr Met Thr Cys Ser Ala Ser
            20                  25

<210> SEQ ID NO 8
<211> LENGTH: 17
<212> TYPE: PRT
<213> ORGANISM: Mus musculus
<220> FEATURE:
<223> OTHER INFORMATION: CAN46G4; K, FR2

<400> SEQUENCE: 8

Met His Trp Tyr Gln Gln Lys Ser Ser Thr Ser Pro Lys Leu Trp Ile
1               5                   10                  15

Tyr

<210> SEQ ID NO 9
<211> LENGTH: 36
<212> TYPE: PRT
<213> ORGANISM: Mus musculus
<220> FEATURE:
<223> OTHER INFORMATION: CAN46G4; K, FR3

<400> SEQUENCE: 9

Lys Leu Ala Phe Gly Val Pro Gly Arg Phe Ser Gly Ser Gly Ser Gly
1               5                   10                  15

Asn Ser Tyr Ser Leu Thr Ile Ser Ser Met Glu Ala Glu Asp Val Ala
            20                  25                  30

Thr Tyr Tyr Cys
        35

<210> SEQ ID NO 10
<211> LENGTH: 10
<212> TYPE: PRT
<213> ORGANISM: Mus musculus
<220> FEATURE:
<223> OTHER INFORMATION: CAN46G4; K, FR4

<400> SEQUENCE: 10

```
Phe Gly Ser Gly Thr Lys Leu Glu Val Lys
1               5                   10

<210> SEQ ID NO 11
<211> LENGTH: 117
<212> TYPE: PRT
<213> ORGANISM: Mus musculus
<220> FEATURE:
<223> OTHER INFORMATION: CAN46G4; H, variable region

<400> SEQUENCE: 11

Glu Val Gln Leu Leu Gln Ser Gly Pro Glu Leu Val Lys Pro Gly Ala
1               5                   10                  15

Ser Val Lys Ile Ser Cys Lys Ala Ser Asp Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Phe Pro Tyr Asn Gly Ala Ala Ser Tyr Asn Gln Asn Phe
    50                  55                  60

Lys Asp Lys Ala Thr Leu Thr Val Asp Lys Ser Ser Thr Ala Tyr
65                  70                  75                  80

Met Glu Leu His Ser Leu Thr Ser Glu Asp Ser Ala Val Tyr Tyr Cys
                85                  90                  95

Thr Arg Trp Leu Arg Val Tyr Phe Asp Tyr Trp Gly Gln Gly Thr Thr
            100                 105                 110

Leu Thr Val Ser Ser
        115

<210> SEQ ID NO 12
<211> LENGTH: 8
<212> TYPE: PRT
<213> ORGANISM: Mus musculus
<220> FEATURE:
<223> OTHER INFORMATION: CAN46G4; H, CDR1

<400> SEQUENCE: 12

Asp Tyr Ser Phe Thr Gly Tyr Tyr
1               5

<210> SEQ ID NO 13
<211> LENGTH: 8
<212> TYPE: PRT
<213> ORGANISM: Mus musculus
<220> FEATURE:
<223> OTHER INFORMATION: CAN46G4; H, CDR2

<400> SEQUENCE: 13

Ile Phe Pro Tyr Asn Gly Ala Ala
1               5

<210> SEQ ID NO 14
<211> LENGTH: 10
<212> TYPE: PRT
<213> ORGANISM: Mus musculus
<220> FEATURE:
<223> OTHER INFORMATION: CAN46G4; H, CDR3

<400> SEQUENCE: 14

Thr Arg Trp Leu Arg Val Tyr Phe Asp Tyr
1               5                   10

<210> SEQ ID NO 15
```

```
<211> LENGTH: 25
<212> TYPE: PRT
<213> ORGANISM: Mus musculus
<220> FEATURE:
<223> OTHER INFORMATION: CAN46G4; H, FR1

<400> SEQUENCE: 15

Glu Val Gln Leu Leu Gln Ser Gly Pro Glu Leu Val Lys Pro Gly Ala
1               5                   10                  15

Ser Val Lys Ile Ser Cys Lys Ala Ser
            20                  25

<210> SEQ ID NO 16
<211> LENGTH: 17
<212> TYPE: PRT
<213> ORGANISM: Mus musculus
<220> FEATURE:
<223> OTHER INFORMATION: CAN46G4; H, FR2

<400> SEQUENCE: 16

Met His Trp Val Lys Gln Ser His Val Lys Ser Leu Glu Trp Ile Gly
1               5                   10                  15

Arg

<210> SEQ ID NO 17
<211> LENGTH: 38
<212> TYPE: PRT
<213> ORGANISM: Mus musculus
<220> FEATURE:
<223> OTHER INFORMATION: CAN46G4; H, FR3

<400> SEQUENCE: 17

Ser Tyr Asn Gln Asn Phe Lys Asp Lys Ala Thr Leu Thr Val Asp Lys
1               5                   10                  15

Ser Ser Ser Thr Ala Tyr Met Glu Leu His Ser Leu Thr Ser Glu Asp
            20                  25                  30

Ser Ala Val Tyr Tyr Cys
        35

<210> SEQ ID NO 18
<211> LENGTH: 11
<212> TYPE: PRT
<213> ORGANISM: Mus musculus
<220> FEATURE:
<223> OTHER INFORMATION: CAN46G4; H, FR4

<400> SEQUENCE: 18

Trp Gly Gln Gly Thr Thr Leu Thr Val Ser Ser
1               5                   10

<210> SEQ ID NO 19
<211> LENGTH: 106
<212> TYPE: PRT
<213> ORGANISM: Mus musculus
<220> FEATURE:
<223> OTHER INFORMATION: CAN46G13; K, variable region

<400> SEQUENCE: 19

Glu Ile Val Leu Thr Gln Ser Pro Ala Ile Met Ser Thr Ser Pro Gly
1               5                   10                  15

Glu Lys Val Thr Met Ser Cys Ser Ala Ser Ser Ser Val Thr Tyr Met
            20                  25                  30

His Trp Tyr Gln Gln Lys Ser Ile Thr Ser Pro Lys Leu Trp Ile Tyr
        35                  40                  45
```

```
Glu Thr Ser Lys Leu Ala Ser Gly Val Pro Gly Arg Phe Ser Gly Ser
         50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Phe Thr
                 85                  90                  95

Phe Gly Ser Gly Thr Lys Leu Glu Ile Lys
            100                 105

<210> SEQ ID NO 20
<211> LENGTH: 5
<212> TYPE: PRT
<213> ORGANISM: Mus musculus
<220> FEATURE:
<223> OTHER INFORMATION: CAN46G13; K, CDR1

<400> SEQUENCE: 20

Ser Ser Val Thr Tyr
1               5

<210> SEQ ID NO 21
<211> LENGTH: 3
<212> TYPE: PRT
<213> ORGANISM: Mus musculus
<220> FEATURE:
<223> OTHER INFORMATION: CAN46G13; K, CDR2

<400> SEQUENCE: 21

Glu Thr Ser
1

<210> SEQ ID NO 22
<211> LENGTH: 9
<212> TYPE: PRT
<213> ORGANISM: Mus musculus
<220> FEATURE:
<223> OTHER INFORMATION: CAN46G13; K, CDR3

<400> SEQUENCE: 22

Phe Gln Gly Ser Gly Tyr Pro Phe Thr
1               5

<210> SEQ ID NO 23
<211> LENGTH: 26
<212> TYPE: PRT
<213> ORGANISM: Mus musculus
<220> FEATURE:
<223> OTHER INFORMATION: CAN46G13; K, FR1

<400> SEQUENCE: 23

Glu Ile Val Leu Thr Gln Ser Pro Ala Ile Met Ser Thr Ser Pro Gly
1               5                   10                  15

Glu Lys Val Thr Met Ser Cys Ser Ala Ser
            20                  25

<210> SEQ ID NO 24
<211> LENGTH: 17
<212> TYPE: PRT
<213> ORGANISM: Mus musculus
<220> FEATURE:
<223> OTHER INFORMATION: CAN46G13; K, FR2

<400> SEQUENCE: 24

Met His Trp Tyr Gln Gln Lys Ser Ile Thr Ser Pro Lys Leu Trp Ile
```

Tyr

<210> SEQ ID NO 25
<211> LENGTH: 36
<212> TYPE: PRT
<213> ORGANISM: Mus musculus
<220> FEATURE:
<223> OTHER INFORMATION: CAN46G13; K, FR3

<400> SEQUENCE: 25

Lys Leu Ala Ser Gly Val Pro Gly Arg Phe Ser Gly Ser Gly Ser Gly
1               5                   10                  15

Asn Ser Tyr Ser Leu Thr Ile Ser Ser Met Glu Ala Glu Asp Val Ala
            20                  25                  30

Thr Tyr Tyr Cys
            35

<210> SEQ ID NO 26
<211> LENGTH: 10
<212> TYPE: PRT
<213> ORGANISM: Mus musculus
<220> FEATURE:
<223> OTHER INFORMATION: CAN46G13; K, FR4

<400> SEQUENCE: 26

Phe Gly Ser Gly Thr Lys Leu Glu Ile Lys
1               5                   10

<210> SEQ ID NO 27
<211> LENGTH: 117
<212> TYPE: PRT
<213> ORGANISM: Mus musculus
<220> FEATURE:
<223> OTHER INFORMATION: CAN46G13; H, variable region

<400> SEQUENCE: 27

Glu Val Gln Leu Leu Gln Ser Gly Pro Glu Leu Val Lys Pro Gly Thr
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Thr His Val Lys Ser Leu Glu Trp Val
        35                  40                  45

Gly Arg Ile Phe Pro Tyr Asn Gly Ala Ala Ser Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Phe Cys
                85                  90                  95

Ala Arg Trp Leu Arg Val Tyr Phe Asp Tyr Trp Gly Gln Gly Thr Thr
            100                 105                 110

Leu Thr Val Ser Ser
        115

<210> SEQ ID NO 28
<211> LENGTH: 8
<212> TYPE: PRT
<213> ORGANISM: Mus musculus
<220> FEATURE:
<223> OTHER INFORMATION: CAN46G13; H, CDR1

<400> SEQUENCE: 28

```
Gly Tyr Ser Phe Thr Gly Tyr Tyr
1               5

<210> SEQ ID NO 29
<211> LENGTH: 8
<212> TYPE: PRT
<213> ORGANISM: Mus musculus
<220> FEATURE:
<223> OTHER INFORMATION: CAN46G13; H, CDR2

<400> SEQUENCE: 29

Ile Phe Pro Tyr Asn Gly Ala Ala
1               5

<210> SEQ ID NO 30
<211> LENGTH: 10
<212> TYPE: PRT
<213> ORGANISM: Mus musculus
<220> FEATURE:
<223> OTHER INFORMATION: CAN46G13; H, CDR3

<400> SEQUENCE: 30

Ala Arg Trp Leu Arg Val Tyr Phe Asp Tyr
1               5                   10

<210> SEQ ID NO 31
<211> LENGTH: 25
<212> TYPE: PRT
<213> ORGANISM: Mus musculus
<220> FEATURE:
<223> OTHER INFORMATION: CAN46G13; H, FR1

<400> SEQUENCE: 31

Glu Val Gln Leu Leu Gln Ser Gly Pro Glu Leu Val Lys Pro Gly Thr
1               5                   10                  15

Ser Val Lys Ile Ser Cys Lys Ala Ser
            20                  25

<210> SEQ ID NO 32
<211> LENGTH: 17
<212> TYPE: PRT
<213> ORGANISM: Mus musculus
<220> FEATURE:
<223> OTHER INFORMATION: CAN46G13; H, FR2

<400> SEQUENCE: 32

Ile His Trp Val Lys Gln Thr His Val Lys Ser Leu Glu Trp Val Gly
1               5                   10                  15

Arg

<210> SEQ ID NO 33
<211> LENGTH: 38
<212> TYPE: PRT
<213> ORGANISM: Mus musculus
<220> FEATURE:
<223> OTHER INFORMATION: CAN46G13; H, FR3

<400> SEQUENCE: 33

Ser Tyr Asn Gln Asn Phe Lys Gly Lys Ala Thr Leu Thr Val Asp Lys
1               5                   10                  15

Ser Ser Ser Thr Ala Tyr Met Glu Leu His Ser Leu Thr Ser Glu Asp
            20                  25                  30

Ser Ala Val Tyr Phe Cys
            35
```

<210> SEQ ID NO 34
<211> LENGTH: 11
<212> TYPE: PRT
<213> ORGANISM: Mus musculus
<220> FEATURE:
<223> OTHER INFORMATION: CAN46G13; H, FR4

<400> SEQUENCE: 34

Trp Gly Gln Gly Thr Thr Leu Thr Val Ser Ser
1               5                   10

<210> SEQ ID NO 35
<211> LENGTH: 108
<212> TYPE: PRT
<213> ORGANISM: Mus musculus
<220> FEATURE:
<223> OTHER INFORMATION: CAN46G13a; K, variable region

<400> SEQUENCE: 35

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser Ser
            20                  25                  30

Tyr Leu His Trp Tyr Gln Gln Lys Ser Gly Ala Ser Pro Lys Pro Leu
        35                  40                  45

Ile His Arg Thr Ser Thr Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Tyr Thr Phe Gly Gly Gly Thr Lys Leu Glu Ile Lys
            100                 105

<210> SEQ ID NO 36
<211> LENGTH: 7
<212> TYPE: PRT
<213> ORGANISM: Mus musculus
<220> FEATURE:
<223> OTHER INFORMATION: CAN46G13a; K, CDR1

<400> SEQUENCE: 36

Ser Ser Val Ser Ser Ser Tyr
1               5

<210> SEQ ID NO 37
<211> LENGTH: 3
<212> TYPE: PRT
<213> ORGANISM: Mus musculus
<220> FEATURE:
<223> OTHER INFORMATION: CAN46G13a; K, CDR2

<400> SEQUENCE: 37

Arg Thr Ser
1

<210> SEQ ID NO 38
<211> LENGTH: 9
<212> TYPE: PRT
<213> ORGANISM: Mus musculus
<220> FEATURE:
<223> OTHER INFORMATION: CAN46G13a; K, CDR3

```
<400> SEQUENCE: 38

Gln Gln Trp Ser Gly Tyr Pro Tyr Thr
1               5

<210> SEQ ID NO 39
<211> LENGTH: 26
<212> TYPE: PRT
<213> ORGANISM: Mus musculus
<220> FEATURE:
<223> OTHER INFORMATION: CAN46G13a; K, FR1

<400> SEQUENCE: 39

Glu Asn Val Leu Thr Gln Ser Pro Ala Ile Met Ala Ala Ser Leu Gly
1               5                   10                  15

Gln Lys Val Thr Met Thr Cys Ser Ala Ser
            20                  25

<210> SEQ ID NO 40
<211> LENGTH: 17
<212> TYPE: PRT
<213> ORGANISM: Mus musculus
<220> FEATURE:
<223> OTHER INFORMATION: CAN46G13a; K, FR2

<400> SEQUENCE: 40

Leu His Trp Tyr Gln Gln Lys Ser Gly Ala Ser Pro Lys Pro Leu Ile
1               5                   10                  15

His

<210> SEQ ID NO 41
<211> LENGTH: 36
<212> TYPE: PRT
<213> ORGANISM: Mus musculus
<220> FEATURE:
<223> OTHER INFORMATION: CAN46G13a; K, FR3

<400> SEQUENCE: 41

Thr Leu Ala Ser Gly Val Pro Ala Arg Phe Ser Gly Ser Gly Ser Gly
1               5                   10                  15

Thr Ser Tyr Ser Leu Thr Ile Ser Ser Val Glu Ala Glu Asp Asp Ala
            20                  25                  30

Thr Tyr Tyr Cys
        35

<210> SEQ ID NO 42
<211> LENGTH: 10
<212> TYPE: PRT
<213> ORGANISM: Mus musculus
<220> FEATURE:
<223> OTHER INFORMATION: CAN46G13a; K, FR4

<400> SEQUENCE: 42

Phe Gly Gly Gly Thr Lys Leu Glu Ile Lys
1               5                   10

<210> SEQ ID NO 43
<211> LENGTH: 119
<212> TYPE: PRT
<213> ORGANISM: Mus musculus
<220> FEATURE:
<223> OTHER INFORMATION: CAN46G13a; H, variable region

<400> SEQUENCE: 43

Asp Val Gln Leu Gln Glu Ser Gly Pro Gly Leu Val Lys Pro Ser Gln
```

```
            1               5                  10                 15
        Ser Leu Ser Leu Thr Cys Thr Val Thr Gly Tyr Ser Ile Thr Ser Asp
                    20                  25                 30

Ser Ala Trp Asn Trp Ile Arg Gln Phe Pro Gly Asn Asn Leu Glu Trp
                    35                  40                 45

Met Gly Tyr Ile Ser Tyr Ser Gly Ser Thr Ser Tyr Asn Pro Ser Leu
                    50                  55                 60

Lys Ser Arg Ile Ser Ile Thr Arg Asp Thr Ser Lys Asn Gln Phe Phe
         65                  70                 75                 80

Leu Gln Leu Asn Ser Val Thr Thr Glu Asp Thr Ala Thr Tyr Tyr Cys
                         85                 90                 95

Ala Arg Arg Ser Arg Val Ser Phe Tyr Phe Asp Tyr Trp Gly Gln Gly
                        100                105                110

Thr Thr Leu Thr Val Ser Ser
                        115
```

```
<210> SEQ ID NO 44
<211> LENGTH: 9
<212> TYPE: PRT
<213> ORGANISM: Mus musculus
<220> FEATURE:
<223> OTHER INFORMATION: CAN46G13a; H, CDR1

<400> SEQUENCE: 44

Gly Tyr Ser Ile Thr Ser Asp Ser Ala
1               5

<210> SEQ ID NO 45
<211> LENGTH: 7
<212> TYPE: PRT
<213> ORGANISM: Mus musculus
<220> FEATURE:
<223> OTHER INFORMATION: CAN46G13a; H, CDR2

<400> SEQUENCE: 45

Ile Ser Tyr Ser Gly Ser Thr
1               5

<210> SEQ ID NO 46
<211> LENGTH: 12
<212> TYPE: PRT
<213> ORGANISM: Mus musculus
<220> FEATURE:
<223> OTHER INFORMATION: CAN46G13a; H, CDR3

<400> SEQUENCE: 46

Ala Arg Arg Ser Arg Val Ser Phe Tyr Phe Asp Tyr
1               5                  10

<210> SEQ ID NO 47
<211> LENGTH: 25
<212> TYPE: PRT
<213> ORGANISM: Mus musculus
<220> FEATURE:
<223> OTHER INFORMATION: CAN46G13a; H, FR1

<400> SEQUENCE: 47

Asp Val Gln Leu Gln Glu Ser Gly Pro Gly Leu Val Lys Pro Ser Gln
1               5                  10                 15

Ser Leu Ser Leu Thr Cys Thr Val Thr
                20                  25
```

```
<210> SEQ ID NO 48
<211> LENGTH: 17
<212> TYPE: PRT
<213> ORGANISM: Mus musculus
<220> FEATURE:
<223> OTHER INFORMATION: CAN46G13a; H, FR2

<400> SEQUENCE: 48

Trp Asn Trp Ile Arg Gln Phe Pro Gly Asn Asn Leu Glu Trp Met Gly
1               5                   10                  15

Tyr

<210> SEQ ID NO 49
<211> LENGTH: 38
<212> TYPE: PRT
<213> ORGANISM: Mus musculus
<220> FEATURE:
<223> OTHER INFORMATION: CAN46G13a; H, FR3

<400> SEQUENCE: 49

Ser Tyr Asn Pro Ser Leu Lys Ser Arg Ile Ser Ile Thr Arg Asp Thr
1               5                   10                  15

Ser Lys Asn Gln Phe Phe Leu Gln Leu Asn Ser Val Thr Thr Glu Asp
            20                  25                  30

Thr Ala Thr Tyr Tyr Cys
        35

<210> SEQ ID NO 50
<211> LENGTH: 11
<212> TYPE: PRT
<213> ORGANISM: Mus musculus
<220> FEATURE:
<223> OTHER INFORMATION: CAN46G13a; H, FR4

<400> SEQUENCE: 50

Trp Gly Gln Gly Thr Thr Leu Thr Val Ser Ser
1               5                   10

<210> SEQ ID NO 51
<211> LENGTH: 106
<212> TYPE: PRT
<213> ORGANISM: Mus musculus
<220> FEATURE:
<223> OTHER INFORMATION: CAN46G19; K, variable region

<400> SEQUENCE: 51

Glu Asn Val Leu Thr Gln Ser Pro Thr Ile Met Ser Ala Ser Pro Gly
1               5                   10                  15

Glu Glu Val Thr Met Thr Cys Ser Ala Ser Ser Ser Val Thr Tyr Met
            20                  25                  30

His Trp Tyr Gln Gln Lys Ser Ile Thr Ser Pro Lys Leu Trp Ile Tyr
        35                  40                  45

Glu Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys
            100                 105

<210> SEQ ID NO 52
```

```
<211> LENGTH: 5
<212> TYPE: PRT
<213> ORGANISM: Mus musculus
<220> FEATURE:
<223> OTHER INFORMATION: CAN46G19; K, CDR1

<400> SEQUENCE: 52

Ser Ser Val Thr Tyr
1               5

<210> SEQ ID NO 53
<211> LENGTH: 3
<212> TYPE: PRT
<213> ORGANISM: Mus musculus
<220> FEATURE:
<223> OTHER INFORMATION: CAN46G19; K, CDR2

<400> SEQUENCE: 53

Glu Thr Ser
1

<210> SEQ ID NO 54
<211> LENGTH: 9
<212> TYPE: PRT
<213> ORGANISM: Mus musculus
<220> FEATURE:
<223> OTHER INFORMATION: CAN46G19; K, CDR3

<400> SEQUENCE: 54

Phe Gln Gly Ser Gly Tyr Pro Phe Thr
1               5

<210> SEQ ID NO 55
<211> LENGTH: 26
<212> TYPE: PRT
<213> ORGANISM: Mus musculus
<220> FEATURE:
<223> OTHER INFORMATION: CAN46G19; K, FR1

<400> SEQUENCE: 55

Glu Asn Val Leu Thr Gln Ser Pro Thr Ile Met Ser Ala Ser Pro Gly
1               5                   10                  15

Glu Glu Val Thr Met Thr Cys Ser Ala Ser
            20                  25

<210> SEQ ID NO 56
<211> LENGTH: 17
<212> TYPE: PRT
<213> ORGANISM: Mus musculus
<220> FEATURE:
<223> OTHER INFORMATION: CAN46G19; K, FR2

<400> SEQUENCE: 56

Met His Trp Tyr Gln Gln Lys Ser Ile Thr Ser Pro Lys Leu Trp Ile
1               5                   10                  15

Tyr

<210> SEQ ID NO 57
<211> LENGTH: 36
<212> TYPE: PRT
<213> ORGANISM: Mus musculus
<220> FEATURE:
<223> OTHER INFORMATION: CAN46G19; K, FR3

<400> SEQUENCE: 57

Lys Leu Ala Ser Gly Val Pro Gly Arg Phe Ser Gly Ser Gly Ser Gly
```

-continued

```
                1               5                  10                 15
Asn Ser Tyr Ser Leu Thr Ile Ser Ser Met Glu Ala Glu Asp Val Ala
                20                 25                 30
Thr Tyr Tyr Cys
        35
```

<210> SEQ ID NO 58
<211> LENGTH: 10
<212> TYPE: PRT
<213> ORGANISM: Mus musculus
<220> FEATURE:
<223> OTHER INFORMATION: CAN46G19; K, FR4

<400> SEQUENCE: 58

```
Phe Gly Ser Gly Thr Lys Leu Glu Ile Lys
1               5                  10
```

<210> SEQ ID NO 59
<211> LENGTH: 117
<212> TYPE: PRT
<213> ORGANISM: Mus musculus
<220> FEATURE:
<223> OTHER INFORMATION: CAN46G19; H, variable region

<400> SEQUENCE: 59

```
Glu Val Gln Leu Leu Gln Ser Gly Pro Glu Leu Val Lys Pro Gly Thr
1               5                  10                 15
Ser Val Lys Ile Ser Cys Lys Ala Ser Gly Tyr Ser Phe Thr Gly Tyr
                20                 25                 30
Tyr Ile His Trp Val Lys Gln Thr His Val Lys Ser Leu Glu Trp Val
        35                 40                 45
Gly Arg Ile Phe Pro Tyr Asn Gly Ala Ala Ser Tyr Asn Gln Asn Phe
    50                 55                 60
Lys Gly Lys Ala Thr Leu Thr Val Asp Lys Ser Ser Thr Thr Ala Tyr
65                 70                 75                 80
Met Glu Leu His Ser Leu Thr Ser Glu Asp Ser Ala Val Tyr Phe Cys
                85                 90                 95
Ala Arg Trp Leu Arg Val Tyr Phe Asp Tyr Trp Gly Gln Gly Thr Thr
            100                105                110
Leu Thr Val Ser Ser
        115
```

<210> SEQ ID NO 60
<211> LENGTH: 8
<212> TYPE: PRT
<213> ORGANISM: Mus musculus
<220> FEATURE:
<223> OTHER INFORMATION: CAN46G19; H, CDR1

<400> SEQUENCE: 60

```
Gly Tyr Ser Phe Thr Gly Tyr Tyr
1               5
```

<210> SEQ ID NO 61
<211> LENGTH: 8
<212> TYPE: PRT
<213> ORGANISM: Mus musculus
<220> FEATURE:
<223> OTHER INFORMATION: CAN46G19; H, CDR2

<400> SEQUENCE: 61

Ile Phe Pro Tyr Asn Gly Ala Ala

-continued

<210> SEQ ID NO 62
<211> LENGTH: 10
<212> TYPE: PRT
<213> ORGANISM: Mus musculus
<220> FEATURE:
<223> OTHER INFORMATION: CAN46G19; H, CDR3

<400> SEQUENCE: 62

Ala Arg Trp Leu Arg Val Tyr Phe Asp Tyr
1               5                   10

<210> SEQ ID NO 63
<211> LENGTH: 25
<212> TYPE: PRT
<213> ORGANISM: Mus musculus
<220> FEATURE:
<223> OTHER INFORMATION: CAN46G19; H, FR1

<400> SEQUENCE: 63

Glu Val Gln Leu Leu Gln Ser Gly Pro Glu Leu Val Lys Pro Gly Thr
1               5                   10                  15

Ser Val Lys Ile Ser Cys Lys Ala Ser
            20                  25

<210> SEQ ID NO 64
<211> LENGTH: 17
<212> TYPE: PRT
<213> ORGANISM: Mus musculus
<220> FEATURE:
<223> OTHER INFORMATION: CAN46G19; H, FR2

<400> SEQUENCE: 64

Ile His Trp Val Lys Gln Thr His Val Lys Ser Leu Glu Trp Val Gly
1               5                   10                  15

Arg

<210> SEQ ID NO 65
<211> LENGTH: 38
<212> TYPE: PRT
<213> ORGANISM: Mus musculus
<220> FEATURE:
<223> OTHER INFORMATION: CAN46G19; H, FR3

<400> SEQUENCE: 65

Ser Tyr Asn Gln Asn Phe Lys Gly Lys Ala Thr Leu Thr Val Asp Lys
1               5                   10                  15

Ser Ser Thr Thr Ala Tyr Met Glu Leu His Ser Leu Thr Ser Glu Asp
            20                  25                  30

Ser Ala Val Tyr Phe Cys
        35

<210> SEQ ID NO 66
<211> LENGTH: 11
<212> TYPE: PRT
<213> ORGANISM: Mus musculus
<220> FEATURE:
<223> OTHER INFORMATION: CAN46G19; H, FR4

<400> SEQUENCE: 66

Trp Gly Gln Gly Thr Thr Leu Thr Val Ser Ser
1               5                   10

```
<210> SEQ ID NO 67
<211> LENGTH: 106
<212> TYPE: PRT
<213> ORGANISM: Mus musculus
<220> FEATURE:
<223> OTHER INFORMATION: CAN46G24; K, variable region

<400> SEQUENCE: 67

Glu Ile Val Leu Thr Gln Ser Pro Ala Ile Met Ser Thr Ser Pro Gly
1               5                   10                  15

Glu Lys Val Thr Met Ser Cys Ser Ala Ser Ser Ser Val Thr Tyr Met
            20                  25                  30

His Trp Tyr Gln Gln Lys Ser Ile Thr Ser Pro Lys Leu Trp Ile Tyr
        35                  40                  45

Glu Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys
            100                 105

<210> SEQ ID NO 68
<211> LENGTH: 5
<212> TYPE: PRT
<213> ORGANISM: Mus musculus
<220> FEATURE:
<223> OTHER INFORMATION: CAN46G24; K, CDR1

<400> SEQUENCE: 68

Ser Ser Val Thr Tyr
1               5

<210> SEQ ID NO 69
<211> LENGTH: 3
<212> TYPE: PRT
<213> ORGANISM: Mus musculus
<220> FEATURE:
<223> OTHER INFORMATION: CAN46G24; K, CDR2

<400> SEQUENCE: 69

Glu Thr Ser
1

<210> SEQ ID NO 70
<211> LENGTH: 9
<212> TYPE: PRT
<213> ORGANISM: Mus musculus
<220> FEATURE:
<223> OTHER INFORMATION: CAN46G24; K, CDR3

<400> SEQUENCE: 70

Phe Gln Gly Ser Gly Tyr Pro Phe Thr
1               5

<210> SEQ ID NO 71
<211> LENGTH: 26
<212> TYPE: PRT
<213> ORGANISM: Mus musculus
<220> FEATURE:
<223> OTHER INFORMATION: CAN46G24; K, FR1

<400> SEQUENCE: 71
```

```
Glu Ile Val Leu Thr Gln Ser Pro Ala Ile Met Ser Thr Ser Pro Gly
1               5                  10                  15

Glu Lys Val Thr Met Ser Cys Ser Ala Ser
            20                  25

<210> SEQ ID NO 72
<211> LENGTH: 17
<212> TYPE: PRT
<213> ORGANISM: Mus musculus
<220> FEATURE:
<223> OTHER INFORMATION: CAN46G24; K, FR2

<400> SEQUENCE: 72

Met His Trp Tyr Gln Gln Lys Ser Ile Thr Ser Pro Lys Leu Trp Ile
1               5                  10                  15

Tyr

<210> SEQ ID NO 73
<211> LENGTH: 36
<212> TYPE: PRT
<213> ORGANISM: Mus musculus
<220> FEATURE:
<223> OTHER INFORMATION: CAN46G24; K, FR3

<400> SEQUENCE: 73

Lys Leu Ala Ser Gly Val Pro Gly Arg Phe Ser Gly Ser Gly Ser Gly
1               5                  10                  15

Asn Ser Tyr Ser Leu Thr Ile Ser Ser Met Glu Ala Glu Asp Val Ala
            20                  25                  30

Thr Tyr Tyr Cys
            35

<210> SEQ ID NO 74
<211> LENGTH: 10
<212> TYPE: PRT
<213> ORGANISM: Mus musculus
<220> FEATURE:
<223> OTHER INFORMATION: CAN46G24; K, FR4

<400> SEQUENCE: 74

Phe Gly Ser Gly Thr Lys Leu Glu Ile Lys
1               5                  10

<210> SEQ ID NO 75
<211> LENGTH: 117
<212> TYPE: PRT
<213> ORGANISM: Mus musculus
<220> FEATURE:
<223> OTHER INFORMATION: CAN46G24; H, variable region

<400> SEQUENCE: 75

Glu Val Gln Leu Leu Gln Ser Gly Pro Glu Leu Val Lys Pro Gly Thr
1               5                  10                  15

Ser Val Lys Ile Ser Cys Lys Ala Ser Gly Tyr Ser Phe Thr Gly Tyr
            20                  25                  30

Tyr Ile His Trp Val Lys Gln Thr His Val Lys Ser Leu Glu Trp Val
        35                  40                  45

Gly Arg Ile Phe Pro Tyr Asn Gly Ala Ala Ser Tyr Asn Gln Asn Phe
    50                  55                  60

Lys Gly Lys Ala Thr Leu Thr Val Asp Lys Ser Ser Thr Ala Tyr
65                  70                  75                  80

Met Glu Leu His Ser Leu Thr Ser Glu Asp Ser Ala Val Tyr Phe Cys
```

```
                    85                  90                  95
Ala Arg Trp Leu Arg Val Tyr Phe Asp Tyr Trp Gly Gln Gly Thr Thr
            100                 105                 110

Leu Thr Val Ser Ser
        115

<210> SEQ ID NO 76
<211> LENGTH: 8
<212> TYPE: PRT
<213> ORGANISM: Mus musculus
<220> FEATURE:
<223> OTHER INFORMATION: CAN46G24; H, CDR1

<400> SEQUENCE: 76

Gly Tyr Ser Phe Thr Gly Tyr Tyr
1               5

<210> SEQ ID NO 77
<211> LENGTH: 8
<212> TYPE: PRT
<213> ORGANISM: Mus musculus
<220> FEATURE:
<223> OTHER INFORMATION: CAN46G24; H, CDR2

<400> SEQUENCE: 77

Ile Phe Pro Tyr Asn Gly Ala Ala
1               5

<210> SEQ ID NO 78
<211> LENGTH: 10
<212> TYPE: PRT
<213> ORGANISM: Mus musculus
<220> FEATURE:
<223> OTHER INFORMATION: CAN46G24; H, CDR3

<400> SEQUENCE: 78

Ala Arg Trp Leu Arg Val Tyr Phe Asp Tyr
1               5                   10

<210> SEQ ID NO 79
<211> LENGTH: 25
<212> TYPE: PRT
<213> ORGANISM: Mus musculus
<220> FEATURE:
<223> OTHER INFORMATION: CAN46G24; H, FR1

<400> SEQUENCE: 79

Glu Val Gln Leu Leu Gln Ser Gly Pro Glu Leu Val Lys Pro Gly Thr
1               5                   10                  15

Ser Val Lys Ile Ser Cys Lys Ala Ser
            20                  25

<210> SEQ ID NO 80
<211> LENGTH: 17
<212> TYPE: PRT
<213> ORGANISM: Mus musculus
<220> FEATURE:
<223> OTHER INFORMATION: CAN46G24; H, FR2

<400> SEQUENCE: 80

Ile His Trp Val Lys Gln Thr His Val Lys Ser Leu Glu Trp Val Gly
1               5                   10                  15

Arg
```

```
<210> SEQ ID NO 81
<211> LENGTH: 38
<212> TYPE: PRT
<213> ORGANISM: Mus musculus
<220> FEATURE:
<223> OTHER INFORMATION: CAN46G24; H, FR3

<400> SEQUENCE: 81

Ser Tyr Asn Gln Asn Phe Lys Gly Lys Ala Thr Leu Thr Val Asp Lys
1               5                   10                  15

Ser Ser Ser Thr Ala Tyr Met Glu Leu His Ser Leu Thr Ser Glu Asp
            20                  25                  30

Ser Ala Val Tyr Phe Cys
        35

<210> SEQ ID NO 82
<211> LENGTH: 11
<212> TYPE: PRT
<213> ORGANISM: Mus musculus
<220> FEATURE:
<223> OTHER INFORMATION: CAN46G24; H, FR4

<400> SEQUENCE: 82

Trp Gly Gln Gly Thr Thr Leu Thr Val Ser Ser
1               5                   10

<210> SEQ ID NO 83
<211> LENGTH: 2366
<212> TYPE: PRT
<213> ORGANISM: Clostridium difficile
<220> FEATURE:
<223> OTHER INFORMATION: Toxin B (tcdB)
<300> PUBLICATION INFORMATION:
<308> DATABASE ACCESSION NUMBER: NC_009089, GenBank
<309> DATABASE ENTRY DATE: 2007-03-07

<400> SEQUENCE: 83

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190
```

```
Gln Arg Glu Glu Asn Pro Glu Leu Ile Ile Asp Asp Ile Val Lys Thr
        195                 200                 205
Tyr Leu Ser Asn Glu Tyr Ser Lys Glu Ile Asp Glu Leu Asn Thr Tyr
        210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Ile Gly Gly Met Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
        515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
        595                 600                 605
```

```
Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
```

```
                1025                1030                1035
Val Ser Leu Gly Ala Ala Ile Lys Glu Leu Ser Glu Thr Ser Asp
        1040                1045                1050
Pro Leu Leu Arg Gln Glu Ile Glu Ala Lys Ile Gly Ile Met Ala
        1055                1060                1065
Val Asn Leu Thr Thr Ala Thr Thr Ala Ile Ile Thr Ser Ser Leu
        1070                1075                1080
Gly Ile Ala Ser Gly Phe Ser Ile Leu Leu Val Pro Leu Ala Gly
        1085                1090                1095
Ile Ser Ala Gly Ile Pro Ser Leu Val Asn Asn Glu Leu Val Leu
        1100                1105                1110
Arg Asp Lys Ala Thr Lys Val Val Asp Tyr Phe Lys His Val Ser
        1115                1120                1125
Leu Val Glu Thr Glu Gly Val Phe Thr Leu Leu Asp Asp Lys Ile
        1130                1135                1140
Met Met Pro Gln Asp Asp Leu Val Ile Ser Glu Ile Asp Phe Asn
        1145                1150                1155
Asn Asn Ser Ile Val Leu Gly Lys Cys Glu Ile Trp Arg Met Glu
        1160                1165                1170
Gly Gly Ser Gly His Thr Val Thr Asp Asp Ile Asp His Phe Phe
        1175                1180                1185
Ser Ala Pro Ser Ile Thr Tyr Arg Glu Pro His Leu Ser Ile Tyr
        1190                1195                1200
Asp Val Leu Glu Val Gln Lys Glu Glu Leu Asp Leu Ser Lys Asp
        1205                1210                1215
Leu Met Val Leu Pro Asn Ala Pro Asn Arg Val Phe Ala Trp Glu
        1220                1225                1230
Thr Gly Trp Thr Pro Gly Leu Arg Ser Leu Glu Asn Asp Gly Thr
        1235                1240                1245
Lys Leu Leu Asp Arg Ile Arg Asp Asn Tyr Glu Gly Glu Phe Tyr
        1250                1255                1260
Trp Arg Tyr Phe Ala Phe Ile Ala Asp Ala Leu Ile Thr Thr Leu
        1265                1270                1275
Lys Pro Arg Tyr Glu Asp Thr Asn Ile Arg Ile Asn Leu Asp Ser
        1280                1285                1290
Asn Thr Arg Ser Phe Ile Val Pro Ile Ile Thr Thr Glu Tyr Ile
        1295                1300                1305
Arg Glu Lys Leu Ser Tyr Ser Phe Tyr Gly Ser Gly Gly Thr Tyr
        1310                1315                1320
Ala Leu Ser Leu Ser Gln Tyr Asn Met Gly Ile Asn Ile Glu Leu
        1325                1330                1335
Ser Glu Ser Asp Val Trp Ile Ile Asp Val Asp Asn Val Val Arg
        1340                1345                1350
Asp Val Thr Ile Glu Ser Asp Lys Ile Lys Lys Gly Asp Leu Ile
        1355                1360                1365
Glu Gly Ile Leu Ser Thr Leu Ser Ile Glu Glu Asn Lys Ile Ile
        1370                1375                1380
Leu Asn Ser His Glu Ile Asn Phe Ser Gly Glu Val Asn Gly Ser
        1385                1390                1395
Asn Gly Phe Val Ser Leu Thr Phe Ser Ile Leu Glu Gly Ile Asn
        1400                1405                1410
Ala Ile Ile Glu Val Asp Leu Leu Ser Lys Ser Tyr Lys Leu Leu
        1415                1420                1425
```

```
Ile Ser Gly Glu Leu Lys Ile Leu Met Leu Asn Ser Asn His Ile
1430                1435                1440

Gln Gln Lys Ile Asp Tyr Ile Gly Phe Asn Ser Glu Leu Gln Lys
1445                1450                1455

Asn Ile Pro Tyr Ser Phe Val Asp Ser Glu Gly Lys Glu Asn Gly
1460                1465                1470

Phe Ile Asn Gly Ser Thr Lys Glu Gly Leu Phe Val Ser Glu Leu
1475                1480                1485

Pro Asp Val Val Leu Ile Ser Lys Val Tyr Met Asp Asp Ser Lys
1490                1495                1500

Pro Ser Phe Gly Tyr Tyr Ser Asn Asn Leu Lys Asp Val Lys Val
1505                1510                1515

Ile Thr Lys Asp Asn Val Asn Ile Leu Thr Gly Tyr Tyr Leu Lys
1520                1525                1530

Asp Asp Ile Lys Ile Ser Leu Ser Leu Thr Leu Gln Asp Glu Lys
1535                1540                1545

Thr Ile Lys Leu Asn Ser Val His Leu Asp Glu Ser Gly Val Ala
1550                1555                1560

Glu Ile Leu Lys Phe Met Asn Arg Lys Gly Asn Thr Asn Thr Ser
1565                1570                1575

Asp Ser Leu Met Ser Phe Leu Glu Ser Met Asn Ile Lys Ser Ile
1580                1585                1590

Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
1805                1810                1815
```

-continued

```
Tyr Asn Glu Lys Phe Tyr Ile Asn Asn Phe Gly Met Met Val Ser
    1820            1825            1830

Gly Leu Ile Tyr Ile Asn Asp Ser Leu Tyr Tyr Phe Lys Pro Pro
    1835            1840            1845

Val Asn Asn Leu Ile Thr Gly Phe Val Thr Val Gly Asp Asp Lys
    1850            1855            1860

Tyr Tyr Phe Asn Pro Ile Asn Gly Gly Ala Ala Ser Ile Gly Glu
    1865            1870            1875

Thr Ile Ile Asp Asp Lys Asn Tyr Tyr Phe Asn Gln Ser Gly Val
    1880            1885            1890

Leu Gln Thr Gly Val Phe Ser Thr Glu Asp Gly Phe Lys Tyr Phe
    1895            1900            1905

Ala Pro Ala Asn Thr Leu Asp Glu Asn Leu Glu Gly Glu Ala Ile
    1910            1915            1920

Asp Phe Thr Gly Lys Leu Ile Ile Asp Glu Asn Ile Tyr Tyr Phe
    1925            1930            1935

Asp Asp Asn Tyr Arg Gly Ala Val Glu Trp Lys Glu Leu Asp Gly
    1940            1945            1950

Glu Met His Tyr Phe Ser Pro Glu Thr Gly Lys Ala Phe Lys Gly
    1955            1960            1965

Leu Asn Gln Ile Gly Asp Tyr Lys Tyr Tyr Phe Asn Ser Asp Gly
    1970            1975            1980

Val Met Gln Lys Gly Phe Val Ser Ile Asn Asp Asn Lys His Tyr
    1985            1990            1995

Phe Asp Asp Ser Gly Val Met Lys Val Gly Tyr Thr Glu Ile Asp
    2000            2005            2010

Gly Lys His Phe Tyr Phe Ala Glu Asn Gly Glu Met Gln Ile Gly
    2015            2020            2025

Val Phe Asn Thr Glu Asp Gly Phe Lys Tyr Phe Ala His His Asn
    2030            2035            2040

Glu Asp Leu Gly Asn Glu Gly Gly Glu Glu Ile Ser Tyr Ser Gly
    2045            2050            2055

Ile Leu Asn Phe Asn Asn Lys Ile Tyr Tyr Phe Asp Asp Ser Phe
    2060            2065            2070

Thr Ala Val Val Gly Trp Lys Asp Leu Glu Asp Gly Ser Lys Tyr
    2075            2080            2085

Tyr Phe Asp Glu Asp Thr Ala Glu Ala Tyr Ile Gly Leu Ser Leu
    2090            2095            2100

Ile Asn Asp Gly Gln Tyr Tyr Phe Asn Asp Asp Gly Ile Met Gln
    2105            2110            2115

Val Gly Phe Val Thr Ile Asn Asp Lys Val Phe Tyr Phe Ser Asp
    2120            2125            2130

Ser Gly Ile Ile Glu Ser Gly Val Gln Asn Ile Asp Asp Asn Tyr
    2135            2140            2145

Phe Tyr Ile Asp Asp Asn Gly Ile Val Gln Ile Gly Val Phe Asp
    2150            2155            2160

Thr Ser Asp Gly Tyr Lys Tyr Phe Ala Pro Ala Asn Thr Val Asn
    2165            2170            2175

Asp Asn Ile Tyr Gly Gln Ala Val Glu Tyr Ser Gly Leu Val Arg
    2180            2185            2190

Val Gly Glu Asp Val Tyr Tyr Phe Gly Glu Thr Tyr Thr Ile Glu
    2195            2200            2205

Thr Gly Trp Ile Tyr Asp Met Glu Asn Glu Ser Asp Lys Tyr Tyr
```

```
                 2210                2215                2220
Phe Asn Pro Glu Thr Lys Lys Ala Cys Lys Gly Ile Asn Leu Ile
        2225                2230                2235
Asp Asp Ile Lys Tyr Tyr Phe Asp Glu Lys Gly Ile Met Arg Thr
    2240                2245                2250
Gly Leu Ile Ser Phe Glu Asn Asn Tyr Tyr Phe Asn Glu Asn
        2255                2260                2265
Gly Glu Met Gln Phe Gly Tyr Ile Asn Ile Glu Asp Lys Met Phe
    2270                2275                2280
Tyr Phe Gly Glu Asp Gly Val Met Gln Ile Gly Val Phe Asn Thr
    2285                2290                2295
Pro Asp Gly Phe Lys Tyr Phe Ala His Gln Asn Thr Leu Asp Glu
    2300                2305                2310
Asn Phe Glu Gly Glu Ser Ile Asn Tyr Thr Gly Trp Leu Asp Leu
    2315                2320                2325
Asp Glu Lys Arg Tyr Tyr Phe Thr Asp Glu Tyr Ile Ala Ala Thr
    2330                2335                2340
Gly Ser Val Ile Ile Asp Gly Glu Glu Tyr Tyr Phe Asp Pro Asp
    2345                2350                2355
Thr Ala Gln Leu Val Ile Ser Glu
    2360                2365
```

<210> SEQ ID NO 84
<211> LENGTH: 1520
<212> TYPE: DNA
<213> ORGANISM: Clostridium difficile
<220> FEATURE:
<223> OTHER INFORMATION: Toxin B tcdB
<300> PUBLICATION INFORMATION:
<308> DATABASE ACCESSION NUMBER: NC_009089, GenBank
<309> DATABASE ENTRY DATE: 2007-03-07

<400> SEQUENCE: 84

```
atgagtttag ttaatagaaa acagttagaa aaaatggcaa atgtaagatt tcgtactcaa     60
gaagatgaat atgttgcaat attggatgct ttagaagaat atcataatat gtcagagaat    120
actgtagtcg aaaatatatt aaaattaaaa gatataaata gtttaacaga tatttatata    180
gatacatata aaaaatctgg tagaaataaa gccttaaaaa aatttaagga atatctagtt    240
acagaagtat tagagctaaa gaataataat ttaactccag ttgagaaaaa tttacatttt    300
gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
ttaaatgacc ctagatttga ctataataaa ttccttcagaa aacgtatgga ataaatttat    540
gataaacaga aaaatttcat aaactactat aaagctcaaa gagaagaaaa tcctgaactt    600
ataattgatg atattgtaaa acatatcctt tcaaatgagt attcaaagga tagatgaa    660
cttaatacct atattgaaga tccttaaaat aaaattacac agaatagtgg aaatgatgtt    720
agaaactttg aagaatttaa aaatggagag tcattcaact tatatgaaca agagttggta    780
gaaaggtgga ttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca agaatatat accagaatat acctcagaac atttggacat gttagacgaa   1020
```

```
gaagttcaaa gtagttttga atctgttcta gcttctaagt cagataaatc agaaatattc    1080
tcatcacttg gtgatatgga ggcatcacca ctagaagtta aaattgcatt taatagtaag    1140
ggtattataa atcaagggct aatttctgtg aaagactcat attgtagcaa tttaatagta    1200
aaacaaatcg agaatagata taaaatattg aataatagtt taaatccagc tattagcgag    1260
gataatgatt ttaatactac aacgaatacc tttattgata gtataatggc tgaagctaat    1320
gcagataatg gtagatttat gatggaacta ggaaagtatt taagagttgg tttcttccca    1380
gatgttaaaa ctactattaa cttaagtggc cctgaagcat atgcggcagc ttatcaagat    1440
ttattaatgt ttaagaagg cagtatgaat atccatttga tagaagctga tttaagaaac    1500
tttgaaatct ctaaaactaa                                                1520
```

<210> SEQ ID NO 85
<211> LENGTH: 106
<212> TYPE: PRT
<213> ORGANISM: Mus musculus
<220> FEATURE:
<223> OTHER INFORMATION: CAN33G1; K, variable region

<400> SEQUENCE: 85

Asp Ile Gln Leu Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Arg Pro Gly Asn Ala Pro Arg Leu Leu Ile
        35                  40                  45

Ser Gly Ala Thr Ser Leu Glu Thr Gly Ile Pro Ser Arg Phe Ser Gly
    50                  55                  60

Ser Gly Ser Gly Lys Glu Tyr Thr Leu Ser Ile Ala Ser Leu Gln Thr
65                  70                  75                  80

Glu Asp Phe Val Thr Tyr Tyr Cys Gln Gln Tyr Trp Asn Ile Pro Thr
                85                  90                  95

Phe Gly Gly Gly Thr Arg Leu Glu Ile Lys
            100                 105

<210> SEQ ID NO 86
<211> LENGTH: 6
<212> TYPE: PRT
<213> ORGANISM: Mus musculus
<220> FEATURE:
<223> OTHER INFORMATION: CAN33G1; K, CDR1

<400> SEQUENCE: 86

Glu Asp Ile Tyr Asn Arg
1               5

<210> SEQ ID NO 87
<211> LENGTH: 3
<212> TYPE: PRT
<213> ORGANISM: Mus musculus
<220> FEATURE:
<223> OTHER INFORMATION: CAN33G1; K, CDR2

<400> SEQUENCE: 87

Gly Ala Thr
1

<210> SEQ ID NO 88
<211> LENGTH: 8
<212> TYPE: PRT

-continued

<213> ORGANISM: Mus musculus
<220> FEATURE:
<223> OTHER INFORMATION: CAN33G1; K, CDR3

<400> SEQUENCE: 88

Gln Gln Tyr Trp Asn Ile Pro Thr
1               5

<210> SEQ ID NO 89
<211> LENGTH: 26
<212> TYPE: PRT
<213> ORGANISM: Mus musculus
<220> FEATURE:
<223> OTHER INFORMATION: CAN33G1; K, FR1

<400> SEQUENCE: 89

Asp Ile Gln Leu Thr Gln Ser Ser Ser Phe Ser Val Ser Leu Gly
1               5                   10                  15

Asp Arg Val Thr Ile Thr Cys Lys Ala Ser
            20                  25

<210> SEQ ID NO 90
<211> LENGTH: 17
<212> TYPE: PRT
<213> ORGANISM: Mus musculus
<220> FEATURE:
<223> OTHER INFORMATION: CAN33G1; K, FR2

<400> SEQUENCE: 90

Leu Ala Trp Tyr Gln Gln Arg Pro Gly Asn Ala Pro Arg Leu Leu Ile
1               5                   10                  15

Ser

<210> SEQ ID NO 91
<211> LENGTH: 36
<212> TYPE: PRT
<213> ORGANISM: Mus musculus
<220> FEATURE:
<223> OTHER INFORMATION: CAN33G1; K, FR3

<400> SEQUENCE: 91

Ser Leu Glu Thr Gly Ile Pro Ser Arg Phe Ser Gly Ser Gly Ser Gly
1               5                   10                  15

Lys Glu Tyr Thr Leu Ser Ile Ala Ser Leu Gln Thr Glu Asp Phe Val
            20                  25                  30

Thr Tyr Tyr Cys
        35

<210> SEQ ID NO 92
<211> LENGTH: 10
<212> TYPE: PRT
<213> ORGANISM: Mus musculus
<220> FEATURE:
<223> OTHER INFORMATION: CAN33G1; K, FR4

<400> SEQUENCE: 92

Phe Gly Gly Gly Thr Arg Leu Glu Ile Lys
1               5                   10

<210> SEQ ID NO 93
<211> LENGTH: 118
<212> TYPE: PRT
<213> ORGANISM: Mus musculus
<220> FEATURE:
<223> OTHER INFORMATION: CAN33G1; H, variable region

<400> SEQUENCE: 93

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Val Asn Pro Tyr Asn Gly Asp Thr Asn Tyr Asn Gln Asn Phe
    50                  55                  60

Lys Asp Lys Ala Ile Leu Thr Val Asp Lys Ser Ala Ser Thr Ala Tyr
65                  70                  75                  80

Met Glu Phe Arg Ser Leu Thr Ser Glu Asp Ser Ala Val Tyr Tyr Cys
                85                  90                  95

Thr Arg Ser Asn Trp Glu Asn Tyr Phe Asp Tyr Trp Gly Gln Gly Ser
            100                 105                 110

Thr Leu Thr Val Ser Ser
        115

<210> SEQ ID NO 94
<211> LENGTH: 8
<212> TYPE: PRT
<213> ORGANISM: Mus musculus
<220> FEATURE:
<223> OTHER INFORMATION: CAN33G1; H, CDR1

<400> SEQUENCE: 94

Gly Tyr Ser Phe Thr Gly Tyr Tyr
1               5

<210> SEQ ID NO 95
<211> LENGTH: 8
<212> TYPE: PRT
<213> ORGANISM: Mus musculus
<220> FEATURE:
<223> OTHER INFORMATION: CAN33G1; H, CDR2

<400> SEQUENCE: 95

Val Asn Pro Tyr Asn Gly Asp Thr
1               5

<210> SEQ ID NO 96
<211> LENGTH: 11
<212> TYPE: PRT
<213> ORGANISM: Mus musculus
<220> FEATURE:
<223> OTHER INFORMATION: CAN33G1; H, CDR3

<400> SEQUENCE: 96

Thr Arg Ser Asn Trp Glu Asn Tyr Phe Asp Tyr
1               5                   10

<210> SEQ ID NO 97
<211> LENGTH: 25
<212> TYPE: PRT
<213> ORGANISM: Mus musculus
<220> FEATURE:
<223> OTHER INFORMATION: CAN33G1; H, FR1

<400> SEQUENCE: 97

Glu Val Gln Leu Gln Gln Ser Gly Pro Asp Leu Val Lys Pro Gly Ala
1               5                   10                  15

Ser Val Lys Ile Ser Cys Lys Ala Ser
            20                  25

<210> SEQ ID NO 98
<211> LENGTH: 17
<212> TYPE: PRT
<213> ORGANISM: Mus musculus
<220> FEATURE:
<223> OTHER INFORMATION: CAN33G1; H, FR2

<400> SEQUENCE: 98

Met His Trp Val Lys Gln Ser His Gly Lys Ser Leu Glu Trp Ile Gly
1               5                   10                  15

Arg

<210> SEQ ID NO 99
<211> LENGTH: 38
<212> TYPE: PRT
<213> ORGANISM: Mus musculus
<220> FEATURE:
<223> OTHER INFORMATION: CAN33G1; H, FR3

<400> SEQUENCE: 99

Asn Tyr Asn Gln Asn Phe Lys Asp Lys Ala Ile Leu Thr Val Asp Lys
1               5                   10                  15

Ser Ala Ser Thr Ala Tyr Met Glu Phe Arg Ser Leu Thr Ser Glu Asp
            20                  25                  30

Ser Ala Val Tyr Tyr Cys
        35

<210> SEQ ID NO 100
<211> LENGTH: 11
<212> TYPE: PRT
<213> ORGANISM: Mus musculus
<220> FEATURE:
<223> OTHER INFORMATION: CAN33G1; H, FR4

<400> SEQUENCE: 100

Trp Gly Gln Gly Ser Thr Leu Thr Val Ser Ser
1               5                   10

<210> SEQ ID NO 101
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G13a; K, variable region

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Trp Ser Gly Tyr Pro

```
                    85                  90                  95

Tyr Thr Phe Gly Gln Gly Thr Lys Val Glu Ile Lys
            100                 105

<210> SEQ ID NO 102
<211> LENGTH: 7
<212> TYPE: PRT
<213> ORGANISM: Mus Musculus
<220> FEATURE:
<223> OTHER INFORMATION: cdrCAN46G13a; K, CDR1

<400> SEQUENCE: 102

Ser Ser Val Ser Ser Ser Tyr
1               5

<210> SEQ ID NO 103
<211> LENGTH: 3
<212> TYPE: PRT
<213> ORGANISM: Mus Musculus
<220> FEATURE:
<223> OTHER INFORMATION: cdrCAN46G13a; K, CDR2

<400> SEQUENCE: 103

Arg Thr Ser
1

<210> SEQ ID NO 104
<211> LENGTH: 9
<212> TYPE: PRT
<213> ORGANISM: Mus Musculus
<220> FEATURE:
<223> OTHER INFORMATION: cdrCAN46G13a; K, CDR3

<400> SEQUENCE: 104

Gln Gln Trp Ser Gly Tyr Pro Tyr Thr
1               5

<210> SEQ ID NO 105
<211> LENGTH: 26
<212> TYPE: PRT
<213> ORGANISM: Homo sapiens
<220> FEATURE:
<223> OTHER INFORMATION: cdrCAN46G13a; K, FR1

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 106
<211> LENGTH: 17
<212> TYPE: PRT
<213> ORGANISM: Homo sapiens
<220> FEATURE:
<223> OTHER INFORMATION: cdrCAN46G13a; K, FR2

<400> SEQUENCE: 106

Leu His Trp Tyr Gln Gln Lys Pro Gly Lys Ala Pro Lys Leu Leu Ile
1               5                   10                  15

Tyr

<210> SEQ ID NO 107
<211> LENGTH: 36
<212> TYPE: PRT
```

-continued

```
<213> ORGANISM: Homo sapiens
<220> FEATURE:
<223> OTHER INFORMATION: cdrCAN46G13a; K, FR3

<400> SEQUENCE: 107

Thr Leu Ala Ser Gly Val Pro Ser Arg Phe Ser Gly Ser Gly
1               5                   10                  15

Thr Asp Phe Thr Phe Thr Ile Ser Ser Leu Gln Pro Glu Asp Ile Ala
                20                  25                  30

Thr Tyr Tyr Cys
        35

<210> SEQ ID NO 108
<211> LENGTH: 10
<212> TYPE: PRT
<213> ORGANISM: Mus musculus
<220> FEATURE:
<223> OTHER INFORMATION: cdrCAN46G13a; K, FR4

<400> SEQUENCE: 108

Phe Gly Gln Gly Thr Lys Val Glu Ile Lys
1               5                   10

<210> SEQ ID NO 109
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G13a; H, variable region

<400> SEQUENCE: 109

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
                20                  25                  30

Ser Ala Trp Asn Trp Ile Arg Gln Pro Pro Gly Lys Gly Leu Glu Trp
            35                  40                  45

Ile Gly Tyr Ile Ser Tyr Ser Gly Ser Thr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Val Asn Ser Val Thr Ala Ala Asp Thr Ala Val Tyr Tyr Cys
                85                  90                  95

Ala Arg Arg Ser Arg Val Ser Phe Tyr Phe Asp Tyr Trp Gly Gln Gly
                100                 105                 110

Thr Leu Val Thr Val Ser Ser
    115

<210> SEQ ID NO 110
<211> LENGTH: 9
<212> TYPE: PRT
<213> ORGANISM: Mus Musculus
<220> FEATURE:
<223> OTHER INFORMATION: cdrCAN46G13a; H, CDR1

<400> SEQUENCE: 110

Gly Gly Ser Ile Ser Ser Asp Ser Ala
1               5
```

```
<210> SEQ ID NO 111
<211> LENGTH: 7
<212> TYPE: PRT
<213> ORGANISM: Mus Musculus
<220> FEATURE:
<223> OTHER INFORMATION: cdrCAN46G13a; H, CDR2

<400> SEQUENCE: 111

Ile Ser Tyr Ser Gly Ser Thr
1               5

<210> SEQ ID NO 112
<211> LENGTH: 12
<212> TYPE: PRT
<213> ORGANISM: Mus Musculus
<220> FEATURE:
<223> OTHER INFORMATION: cdrCAN46G13a; H, CDR3

<400> SEQUENCE: 112

Ala Arg Arg Ser Arg Val Ser Phe Tyr Phe Asp Tyr
1               5                   10

<210> SEQ ID NO 113
<211> LENGTH: 25
<212> TYPE: PRT
<213> ORGANISM: Homo sapiens
<220> FEATURE:
<223> OTHER INFORMATION: cdrCAN46G13a; H, FR1

<400> SEQUENCE: 113

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 114
<211> LENGTH: 17
<212> TYPE: PRT
<213> ORGANISM: Homo sapiens
<220> FEATURE:
<223> OTHER INFORMATION: cdrCAN46G13a; H, FR2

<400> SEQUENCE: 114

Trp Asn Trp Ile Arg Gln Pro Pro Gly Lys Gly Leu Glu Trp Ile Gly
1               5                   10                  15

Tyr

<210> SEQ ID NO 115
<211> LENGTH: 38
<212> TYPE: PRT
<213> ORGANISM: Homo sapiens
<220> FEATURE:
<223> OTHER INFORMATION: cdrCAN46G13a; H, FR3

<400> SEQUENCE: 115

Ser Tyr Asn Pro Ser Leu Lys Ser Arg Val Thr Met Ser Val Asp Thr
1               5                   10                  15

Ser Lys Asn Gln Phe Ser Leu Lys Val Asn Ser Val Thr Ala Ala Asp
            20                  25                  30

Thr Ala Val Tyr Tyr Cys
                35

<210> SEQ ID NO 116
<211> LENGTH: 11
<212> TYPE: PRT
```

<213> ORGANISM: Mus musculus
<220> FEATURE:
<223> OTHER INFORMATION: cdrCAN46G13a; H, FR4

<400> SEQUENCE: 116

Trp Gly Gln Gly Thr Leu Val Thr Val Ser Ser
1               5                   10

<210> SEQ ID NO 117
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G13a; K, variable region

<400> SEQUENCE: 117

Glu Asn Val Leu Thr Gln Ser Pro Ser Ser Leu Ser Ala Ser Val Gly
1               5                   10                  15

Asp Arg Val Thr Met Thr Cys Ser Ala Ser Ser Ser Val Ser Ser Ser
            20                  25                  30

Tyr Leu His Trp Tyr Gln Gln Lys Pro Gly Lys Ser Pro Lys Pro Leu
        35                  40                  45

Ile His Arg Thr Ser Thr Leu Ala Ser Gly Val Pro Ser Arg Phe Ser
    50                  55                  60

Gly Ser Gly Ser Gly Thr Ser Tyr Ser Leu Thr Ile Ser Ser Leu Gln
65                  70                  75                  80

Pro Glu Asp Ile Ala Thr Tyr Tyr Cys Gln Gln Trp Ser Gly Tyr Pro
                85                  90                  95

Tyr Thr Phe Gly Gly Gly Thr Lys Val Glu Ile Lys
            100                 105

<210> SEQ ID NO 118
<211> LENGTH: 7
<212> TYPE: PRT
<213> ORGANISM: Mus musculus
<220> FEATURE:
<223> OTHER INFORMATION: huCAN46G13a; K, CDR1

<400> SEQUENCE: 118

Ser Ser Val Ser Ser Ser Tyr
1               5

<210> SEQ ID NO 119
<211> LENGTH: 3
<212> TYPE: PRT
<213> ORGANISM: Mus musculus
<220> FEATURE:
<223> OTHER INFORMATION: huCAN46G13a; K, CDR2

<400> SEQUENCE: 119

Arg Thr Ser
1

<210> SEQ ID NO 120
<211> LENGTH: 9
<212> TYPE: PRT
<213> ORGANISM: Mus musculus
<220> FEATURE:
<223> OTHER INFORMATION: huCAN46G13a; K, CDR3

<400> SEQUENCE: 120

```
Gln Gln Trp Ser Gly Tyr Pro Tyr Thr
1               5

<210> SEQ ID NO 121
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G13a; K, FR1

<400> SEQUENCE: 121

Glu Asn Val Leu Thr Gln Ser Pro Ser Ser Leu Ser Ala Ser Val Gly
1               5                   10                  15

Asp Arg Val Thr Met Thr Cys Ser Ala Ser
            20                  25

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G13a; K, FR2

<400> SEQUENCE: 122

Leu His Trp Tyr Gln Gln Lys Pro Gly Lys Ser Pro Lys Pro Leu Ile
1               5                   10                  15

His

<210> SEQ ID NO 123
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G13a; K, FR3

<400> SEQUENCE: 123

Thr Leu Ala Ser Gly Val Pro Ser Arg Phe Ser Gly Ser Gly Ser Gly
1               5                   10                  15

Thr Ser Tyr Ser Leu Thr Ile Ser Ser Leu Gln Pro Glu Asp Ile Ala
            20                  25                  30

Thr Tyr Tyr Cys
        35

<210> SEQ ID NO 124
<211> LENGTH: 10
<212> TYPE: PRT
<213> ORGANISM: Mus musculus
<220> FEATURE:
<223> OTHER INFORMATION: huCAN46G13a; K, FR4

<400> SEQUENCE: 124

Phe Gly Gly Gly Thr Lys Val Glu Ile Lys
1               5                   10

<210> SEQ ID NO 125
<211> LENGTH: 119
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G13a; H, variable region

<400> SEQUENCE: 125

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Ser Ala Trp Asn Trp Ile Arg Gln Phe Pro Gly Asn Asn Leu Glu Trp
        35                  40                  45

Met Gly Tyr Ile Ser Tyr Ser Gly Ser Thr Tyr Asn Pro Ser Leu
50                  55                  60

Lys Ser Arg Ile Ser Ile Thr Arg Asp Thr Ser Lys Asn Gln Phe Ser
65                  70                  75                  80

Leu Lys Val Asn Ser Val Thr Ala Ala Asp Thr Ala Val Tyr Tyr Cys
                85                  90                  95

Ala Arg Arg Ser Arg Val Ser Phe Tyr Phe Asp Tyr Trp Gly Gln Gly
            100                 105                 110

Thr Leu Val Thr Val Ser Ser
    115

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G13a; H, CDR1

<400> SEQUENCE: 126

Gly Tyr Ser Ile Thr Ser Asp Ser Ala
1               5

<210> SEQ ID NO 127
<211> LENGTH: 7
<212> TYPE: PRT
<213> ORGANISM: Mus musculus
<220> FEATURE:
<223> OTHER INFORMATION: huCAN46G13a; H, CDR2

<400> SEQUENCE: 127

Ile Ser Tyr Ser Gly Ser Thr
1               5

<210> SEQ ID NO 128
<211> LENGTH: 12
<212> TYPE: PRT
<213> ORGANISM: Mus musculus
<220> FEATURE:
<223> OTHER INFORMATION: huCAN46G13a; H, CDR3

<400> SEQUENCE: 128

Ala Arg Arg Ser Arg Val Ser Phe Tyr Phe Asp Tyr
1               5                   10

<210> SEQ ID NO 129
<211> LENGTH: 25
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G13a; H, FR1

<400> SEQUENCE: 129

Gln Val Gln Leu Gln Glu Ser Gly Pro Gly Leu Val Lys Pro Ser Gln
1               5                   10                  15

Thr Leu Ser Leu Thr Cys Thr Val Thr
            20                  25

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G13a; H, FR2

<400> SEQUENCE: 130

Trp Asn Trp Ile Arg Gln Phe Pro Gly Asn Asn Leu Glu Trp Met Gly
1               5                   10                  15

Tyr

<210> SEQ ID NO 131
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G13a; H, FR3

<400> SEQUENCE: 131

Ser Tyr Asn Pro Ser Leu Lys Ser Arg Ile Ser Ile Thr Arg Asp Thr
1               5                   10                  15

Ser Lys Asn Gln Phe Ser Leu Lys Val Asn Ser Val Thr Ala Ala Asp
            20                  25                  30

Thr Ala Val Tyr Tyr Cys
        35

<210> SEQ ID NO 132
<211> LENGTH: 11
<212> TYPE: PRT
<213> ORGANISM: Mus musculus
<220> FEATURE:
<223> OTHER INFORMATION: huCAN46G13a; H, FR4

<400> SEQUENCE: 132

Trp Gly Gln Gly Thr Leu Val Thr Val Ser Ser
1               5                   10

<210> SEQ ID NO 133
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G13a; K, variable region

<400> SEQUENCE: 133

Glu Asn Val Leu Thr Gln Ser Pro Ser Ser Met Ser Ala Ser Val Gly
1               5                   10                  15

Asp Arg Val Thr Met Thr Cys Ser Ala Ser Ser Val Ser Ser
            20                  25                  30

Tyr Leu His Trp Tyr Gln Lys Pro Gly Lys Ala Pro Lys Pro Leu
        35                  40                  45

Ile His Arg Thr Ser Thr Leu Ala Ser Gly Val Pro Ser Arg Phe Ser
    50                  55                  60

Gly Ser Gly Ser Gly Thr Ser Tyr Ser Leu Thr Ile Ser Ser Val Gln
65                  70                  75                  80

Pro Glu Asp Ile Ala Thr Tyr Tyr Cys Gln Gln Trp Ser Gly Tyr Pro
                85                  90                  95

Tyr Thr Phe Gly Gly Gly Thr Lys Val Glu Ile Lys
            100                 105

<210> SEQ ID NO 134
<211> LENGTH: 7
<212> TYPE: PRT
<213> ORGANISM: Mus musculus
<220> FEATURE:
<223> OTHER INFORMATION: rehuCAN46G13a; K, CDR1

<400> SEQUENCE: 134

Ser Ser Val Ser Ser Ser Tyr
1               5

<210> SEQ ID NO 135
<211> LENGTH: 3
<212> TYPE: PRT
<213> ORGANISM: Mus musculus
<220> FEATURE:
<223> OTHER INFORMATION: rehuCAN46G13a; K, CDR2

<400> SEQUENCE: 135

Arg Thr Ser
1

<210> SEQ ID NO 136
<211> LENGTH: 9
<212> TYPE: PRT
<213> ORGANISM: Mus musculus
<220> FEATURE:
<223> OTHER INFORMATION: rehuCAN46G13a; K, CDR3

<400> SEQUENCE: 136

Gln Gln Trp Ser Gly Tyr Pro Tyr Thr
1               5

<210> SEQ ID NO 137
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G13a; K, FR1

<400> SEQUENCE: 137

Glu Asn Val Leu Thr Gln Ser Pro Ser Ser Met Ser Ala Ser Val Gly
1               5                   10                  15

Asp Arg Val Thr Met Thr Cys Ser Ala Ser

```
                20                  25

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G13a; K, FR2

<400> SEQUENCE: 138

Leu His Trp Tyr Gln Gln Lys Pro Gly Lys Ala Pro Lys Pro Leu Ile
1               5                   10                  15

His

<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G13a; K, FR3

<400> SEQUENCE: 139

Thr Leu Ala Ser Gly Val Pro Ser Arg Phe Ser Gly Ser Gly Ser Gly
1               5                   10                  15

Thr Ser Tyr Ser Leu Thr Ile Ser Ser Val Gln Pro Glu Asp Ile Ala
            20                  25                  30

Thr Tyr Tyr Cys
        35

<210> SEQ ID NO 140
<211> LENGTH: 10
<212> TYPE: PRT
<213> ORGANISM: Mus musculus
<220> FEATURE:
<223> OTHER INFORMATION: rehuCAN46G13a; K, FR4

<400> SEQUENCE: 140

Phe Gly Gly Gly Thr Lys Val Glu Ile Lys
1               5                   10

<210> SEQ ID NO 141
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G13a; H, variable region

<400> SEQUENCE: 141

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Ser Ala Trp Asn Trp Ile Arg Gln Pro Pro Gly Asn Gly Leu Glu Trp
        35                  40                  45

Met Gly Tyr Ile Ser Tyr Ser Gly Ser Thr Ser Tyr Asn Pro Ser Leu
    50                  55                  60
```

-continued

```
Lys Ser Arg Ile Ser Ile Thr Arg Asp Thr Ser Lys Asn Gln Phe Ser
65                  70                  75                  80

Leu Lys Leu Asn Ser Val Thr Ala Ala Asp Thr Ala Thr Tyr Tyr Cys
                85                  90                  95

Ala Arg Arg Ser Arg Val Ser Phe Tyr Phe Asp Tyr Trp Gly Gln Gly
            100                 105                 110

Thr Leu Val Thr Val Ser Ser
        115

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G13a; H, CDR1

<400> SEQUENCE: 142

Gly Tyr Ser Ile Thr Ser Asp Ser Ala
1               5

<210> SEQ ID NO 143
<211> LENGTH: 7
<212> TYPE: PRT
<213> ORGANISM: Mus musculus
<220> FEATURE:
<223> OTHER INFORMATION: rehuCAN46G13a; H, CDR2

<400> SEQUENCE: 143

Ile Ser Tyr Ser Gly Ser Thr
1               5

<210> SEQ ID NO 144
<211> LENGTH: 12
<212> TYPE: PRT
<213> ORGANISM: Mus musculus
<220> FEATURE:
<223> OTHER INFORMATION: rehuCAN46G13a; H, CDR3

<400> SEQUENCE: 144

Ala Arg Arg Ser Arg Val Ser Phe Tyr Phe Asp Tyr
1               5                   10

<210> SEQ ID NO 145
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G13a; H, FR1

<400> SEQUENCE: 145

Gln Val Gln Leu Gln Glu Ser Gly Pro Gly Leu Val Lys Pro Ser Gln
1               5                   10                  15

Thr Leu Ser Leu Thr Cys Thr Val Thr
            20                  25

<210> SEQ ID NO 146
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: rehuCAN46G13a; H, FR2

<400> SEQUENCE: 146

Trp Asn Trp Ile Arg Gln Pro Pro Gly Asn Gly Leu Glu Trp Met Gly
1               5                   10                  15
Tyr

<210> SEQ ID NO 147
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G13a; H, FR3

<400> SEQUENCE: 147

Ser Tyr Asn Pro Ser Leu Lys Ser Arg Ile Ser Ile Thr Arg Asp Thr
1               5                   10                  15

Ser Lys Asn Gln Phe Ser Leu Lys Leu Asn Ser Val Thr Ala Ala Asp
            20                  25                  30

Thr Ala Thr Tyr Tyr Cys
        35

<210> SEQ ID NO 148
<211> LENGTH: 11
<212> TYPE: PRT
<213> ORGANISM: Mus musculus
<220> FEATURE:
<223> OTHER INFORMATION: rehuCAN46G13a; H, FR4

<400> SEQUENCE: 148

Trp Gly Gln Gly Thr Leu Val Thr Val Ser Ser
1               5                   10

<210> SEQ ID NO 149
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G19; K, variable region

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

His Trp Tyr Gln Gln Lys Pro Gly Lys Ala Pro Lys Leu Leu Ile Tyr
        35                  40                  45

Glu Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Phe Gln Gly Ser Gly Tyr Pro Phe Thr
                85                  90                  95
```

Phe Gly Gln Gly Thr Lys Val Glu Ile Lys
            100                 105

<210> SEQ ID NO 150
<211> LENGTH: 5
<212> TYPE: PRT
<213> ORGANISM: Mus musculus
<220> FEATURE:
<223> OTHER INFORMATION: cdrCAN46G19; K, CDR1

<400> SEQUENCE: 150

Ser Ser Val Thr Tyr
1               5

<210> SEQ ID NO 151
<211> LENGTH: 3
<212> TYPE: PRT
<213> ORGANISM: Mus musculus
<220> FEATURE:
<223> OTHER INFORMATION: cdrCAN46G19; K, CDR2

<400> SEQUENCE: 151

Glu Thr Ser
1

<210> SEQ ID NO 152
<211> LENGTH: 9
<212> TYPE: PRT
<213> ORGANISM: Mus musculus
<220> FEATURE:
<223> OTHER INFORMATION: cdrCAN46G19; K, CDR3

<400> SEQUENCE: 152

Phe Gln Gly Ser Gly Tyr Pro Phe Thr
1               5

<210> SEQ ID NO 153
<211> LENGTH: 26
<212> TYPE: PRT
<213> ORGANISM: Homo sapiens
<220> FEATURE:
<223> OTHER INFORMATION: cdrCAN46G19; K, FR1

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 154
<211> LENGTH: 17
<212> TYPE: PRT
<213> ORGANISM: Homo sapiens
<220> FEATURE:
<223> OTHER INFORMATION: cdrCAN46G19; K, FR2

<400> SEQUENCE: 154

Met His Trp Tyr Gln Gln Lys Pro Gly Lys Ala Pro Lys Leu Leu Ile
1               5                   10                  15

Tyr

<210> SEQ ID NO 155
<211> LENGTH: 36
<212> TYPE: PRT
<213> ORGANISM: Homo sapiens
<220> FEATURE:

<223> OTHER INFORMATION: cdrCAN46G19; K, FR3

<400> SEQUENCE: 155

Lys Leu Ala Ser Gly Val Pro Ser Arg Phe Ser Gly Ser Gly Ser Gly
1               5                   10                  15

Thr Asp Tyr Thr Phe Thr Ile Ser Ser Leu Gln Pro Glu Asp Ile Ala
            20                  25                  30

Thr Tyr Tyr Cys
        35

<210> SEQ ID NO 156
<211> LENGTH: 10
<212> TYPE: PRT
<213> ORGANISM: Homo sapiens
<220> FEATURE:
<223> OTHER INFORMATION: cdrCAN46G19; K, FR4

<400> SEQUENCE: 156

Phe Gly Gln Gly Thr Lys Val Glu Ile Lys
1               5                   10

<210> SEQ ID NO 157
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G19; H, variable region

<400> SEQUENCE: 157

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Arg Ile Phe Pro Tyr Asn Gly Ala Ala Ser Tyr Asn Gln Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Leu Arg Val Tyr Phe Asp Tyr Trp Gly Gln Gly Thr Thr
            100                 105                 110

Val Thr Val Ser Ser
        115

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G19; H, CDR1

<400> SEQUENCE: 158

Gly Tyr Thr Phe Thr Gly Tyr Tyr
1               5

<210> SEQ ID NO 159
<211> LENGTH: 8
<212> TYPE: PRT
<213> ORGANISM: Mus musculus
<220> FEATURE:
<223> OTHER INFORMATION: cdrCAN46G19; H, CDR2

<400> SEQUENCE: 159

Ile Phe Pro Tyr Asn Gly Ala Ala
1               5

<210> SEQ ID NO 160
<211> LENGTH: 10
<212> TYPE: PRT
<213> ORGANISM: Mus musculus
<220> FEATURE:
<223> OTHER INFORMATION: cdrCAN46G19; H, CDR3

<400> SEQUENCE: 160

Ala Arg Trp Leu Arg Val Tyr Phe Asp Tyr
1               5                   10

<210> SEQ ID NO 161
<211> LENGTH: 25
<212> TYPE: PRT
<213> ORGANISM: Homo sapiens
<220> FEATURE:
<223> OTHER INFORMATION: cdrCAN46G19; H, FR1

<400> SEQUENCE: 161

Gln Val Gln Leu Val Gln Ser Gly Ala Glu Val Lys Lys Pro Gly Glu
1               5                   10                  15

Ser Val Lys Val Ser Cys Lys Ala Ser
            20                  25

<210> SEQ ID NO 162
<211> LENGTH: 17
<212> TYPE: PRT
<213> ORGANISM: Homo sapiens
<220> FEATURE:
<223> OTHER INFORMATION: cdrCAN46G19; H, FR2

<400> SEQUENCE: 162

Ile His Trp Val Arg Gln Ala Pro Gly Gln Gly Leu Glu Trp Met Gly
1               5                   10                  15

Arg

<210> SEQ ID NO 163
<211> LENGTH: 38
<212> TYPE: PRT
<213> ORGANISM: Homo sapiens
<220> FEATURE:
<223> OTHER INFORMATION: cdrCAN46G19; H, FR3

<400> SEQUENCE: 163

Ser Tyr Asn Gln Asn Phe Lys Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
                35

<210> SEQ ID NO 164
<211> LENGTH: 11

<212> TYPE: PRT
<213> ORGANISM: Homo sapiens
<220> FEATURE:
<223> OTHER INFORMATION: cdrCAN46G19; H, FR4

<400> SEQUENCE: 164

Trp Gly Gln Gly Thr Thr Val Thr Val Ser Ser
1               5                   10

<210> SEQ ID NO 165
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G19; K, variable region

<400> SEQUENCE: 165

Glu Asn Val Leu Thr Gln Ser Pro Ser Leu Ser Ala Ser Val Gly
1               5                   10                  15

Asp Arg Val Thr Ile Thr Cys Ser Ala Ser Ser Ser Val Thr Tyr Met
                20                  25                  30

His Trp Tyr Gln Gln Lys Pro Gly Lys Ala Pro Lys Leu Trp Ile Tyr
            35                  40                  45

Glu Thr Ser Lys Leu Ala Ser Gly Val Pro Gly Arg Phe Ser Gly Ser
    50                  55                  60

Gly Ser Gly Asn Ser Tyr Thr Phe Thr Ile Ser Ser Leu Gln Pro Glu
65                  70                  75                  80

Asp Ile Ala Thr Tyr Tyr Cys Phe Gln Gly Ser Gly Tyr Pro Phe Thr
                85                  90                  95

Phe Gly Gln Gly Thr Lys Val Glu Ile Lys
            100                 105

<210> SEQ ID NO 166
<211> LENGTH: 5
<212> TYPE: PRT
<213> ORGANISM: Mus musculus
<220> FEATURE:
<223> OTHER INFORMATION: huCAN46G19; K, CDR1

<400> SEQUENCE: 166

Ser Ser Val Thr Tyr
1               5

<210> SEQ ID NO 167
<211> LENGTH: 3
<212> TYPE: PRT
<213> ORGANISM: Mus musculus
<220> FEATURE:
<223> OTHER INFORMATION: huCAN46G19; K, CDR2

<400> SEQUENCE: 167

Glu Thr Ser
1

<210> SEQ ID NO 168
<211> LENGTH: 9
<212> TYPE: PRT
<213> ORGANISM: Mus musculus
<220> FEATURE:
<223> OTHER INFORMATION: huCAN46G19; K, CDR3

<400> SEQUENCE: 168

Phe Gln Gly Ser Gly Tyr Pro Phe Thr
1               5

<210> SEQ ID NO 169
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G19; K, FR1

<400> SEQUENCE: 169

Glu Asn Val Leu Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G19; K, FR2

<400> SEQUENCE: 170

Met His Trp Tyr Gln Gln Lys Pro Gly Lys Ala Pro Lys Leu Trp Ile
1               5                   10                  15

Tyr

<210> SEQ ID NO 171
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G19; K, FR3

<400> SEQUENCE: 171

Lys Leu Ala Ser Gly Val Pro Gly Arg Phe Ser Gly Ser Gly Ser Gly
1               5                   10                  15

Asn Ser Tyr Thr Phe Thr Ile Ser Ser Leu Gln Pro Glu Asp Ile Ala
            20                  25                  30

Thr Tyr Tyr Cys
        35

<210> SEQ ID NO 172
<211> LENGTH: 10
<212> TYPE: PRT
<213> ORGANISM: Homo sapiens
<220> FEATURE:
<223> OTHER INFORMATION: huCAN46G19; K, FR4

<400> SEQUENCE: 172

Phe Gly Gln Gly Thr Lys Val Glu Ile Lys
1               5                   10

<210> SEQ ID NO 173
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G19; H, variable region

<400> SEQUENCE: 173

Glu Val Gln Leu Val Gln Ser Gly Ala Glu Val Lys Lys Pro Gly Glu
1               5                   10                  15

Ser Val Lys Val Ser Cys Lys Ala Ser Gly Tyr Ser Phe Thr Gly Tyr
                20                  25                  30

Tyr Ile His Trp Val Lys Gln Ala Pro Gly Gln Gly Leu Glu Trp Val
            35                  40                  45

Gly Arg Ile Phe Pro Tyr Asn Gly Ala Ala Ser Tyr Asn Gln Asn Phe
50                  55                  60

Lys Gly Lys Ala Thr Leu Thr Val Asp Lys Ser Ser Thr Thr Ala Tyr
65                  70                  75                  80

Met Glu Leu Ser Ser Leu Arg Ser Glu Asp Thr Ala Val Tyr Phe Cys
                85                  90                  95

Ala Arg Trp Leu Arg Val Tyr Phe Asp Tyr Trp Gly Gln Gly Thr Thr
            100                 105                 110

Val Thr Val Ser Ser
            115

<210> SEQ ID NO 174
<211> LENGTH: 8
<212> TYPE: PRT
<213> ORGANISM: Mus musculus
<220> FEATURE:
<223> OTHER INFORMATION: huCAN46G19; H, CDR1

<400> SEQUENCE: 174

Gly Tyr Ser Phe Thr Gly Tyr Tyr
1               5

<210> SEQ ID NO 175
<211> LENGTH: 8
<212> TYPE: PRT
<213> ORGANISM: Mus musculus
<220> FEATURE:
<223> OTHER INFORMATION: huCAN46G19; H, CDR2

<400> SEQUENCE: 175

Ile Phe Pro Tyr Asn Gly Ala Ala
1               5

<210> SEQ ID NO 176
<211> LENGTH: 10
<212> TYPE: PRT
<213> ORGANISM: Mus musculus
<220> FEATURE:
<223> OTHER INFORMATION: huCAN46G19; H, CDR3

<400> SEQUENCE: 176

Ala Arg Trp Leu Arg Val Tyr Phe Asp Tyr
1               5                   10

<210> SEQ ID NO 177
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: huCAN46G19; H, FR1

<400> SEQUENCE: 177

Glu Val Gln Leu Val Gln Ser Gly Ala Glu Val Lys Lys Pro Gly Glu
1               5                   10                  15

Ser Val Lys Val Ser Cys Lys Ala Ser
            20                  25

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G19; H, FR2

<400> SEQUENCE: 178

Ile His Trp Val Lys Gln Ala Pro Gly Gln Gly Leu Glu Trp Val Gly
1               5                   10                  15

Arg

<210> SEQ ID NO 179
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G19; H, FR3

<400> SEQUENCE: 179

Ser Tyr Asn Gln Asn Phe Lys Gly Lys Ala Thr Leu Thr Val Asp Lys
1               5                   10                  15

Ser Ser Thr Thr Ala Tyr Met Glu Leu Ser Ser Leu Arg Ser Glu Asp
            20                  25                  30

Thr Ala Val Tyr Phe Cys
        35

<210> SEQ ID NO 180
<211> LENGTH: 11
<212> TYPE: PRT
<213> ORGANISM: Homo sapiens
<220> FEATURE:
<223> OTHER INFORMATION: huCAN46G19; H, FR4

<400> SEQUENCE: 180

Trp Gly Gln Gly Thr Thr Val Thr Val Ser Ser
1               5                   10

<210> SEQ ID NO 181
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G19; K, variable region

<400> SEQUENCE: 181

```
Glu Asn Val Leu Thr Gln Ser Pro Ser Ser Met Ser Ala Ser Val Gly
1               5                   10                  15

Asp Arg Val Thr Met Thr Cys Ser Ala Ser Ser Val Thr Tyr Met
            20                  25                  30

His Trp Tyr Gln Gln Lys Pro Gly Lys Ser Pro Lys Leu Trp Ile Tyr
        35                  40                  45

Glu Thr Ser Lys Leu Ala Ser Gly Val Pro Ser Arg Phe Ser Gly Ser
    50                  55                  60

Gly Ser Gly Asn Asp Tyr Ser Leu Thr Ile Ser Ser Met Gln Pro Glu
65                  70                  75                  80

Asp Val Ala Thr Tyr Tyr Cys Phe Gln Gly Ser Gly Tyr Pro Phe Thr
                85                  90                  95

Phe Gly Gln Gly Thr Lys Leu Glu Ile Lys
            100                 105
```

<210> SEQ ID NO 182
<211> LENGTH: 5
<212> TYPE: PRT
<213> ORGANISM: Mus musculus
<220> FEATURE:
<223> OTHER INFORMATION: rehuCAN46G19; K, CDR1

<400> SEQUENCE: 182

```
Ser Ser Val Thr Tyr
1               5
```

<210> SEQ ID NO 183
<211> LENGTH: 3
<212> TYPE: PRT
<213> ORGANISM: Mus musculus
<220> FEATURE:
<223> OTHER INFORMATION: rehuCAN46G19; K, CDR2

<400> SEQUENCE: 183

```
Glu Thr Ser
1
```

<210> SEQ ID NO 184
<211> LENGTH: 9
<212> TYPE: PRT
<213> ORGANISM: Mus musculus
<220> FEATURE:
<223> OTHER INFORMATION: rehuCAN46G19; K, CDR3

<400> SEQUENCE: 184

```
Phe Gln Gly Ser Gly Tyr Pro Phe Thr
1               5
```

<210> SEQ ID NO 185
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G19; K, FR1

<400> SEQUENCE: 185

```
Glu Asn Val Leu Thr Gln Ser Pro Ser Ser Met Ser Ala Ser Val Gly
1               5                   10                  15

Asp Arg Val Thr Met Thr Cys Ser Ala Ser
            20                  25
```

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G19; K, FR2

<400> SEQUENCE: 186

Met His Trp Tyr Gln Gln Lys Pro Gly Lys Ser Pro Lys Leu Trp Ile
1               5                   10                  15

Tyr

<210> SEQ ID NO 187
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G19; K, FR3

<400> SEQUENCE: 187

Lys Leu Ala Ser Gly Val Pro Ser Arg Phe Ser Gly Ser Gly Ser Gly
1               5                   10                  15

Asn Asp Tyr Ser Leu Thr Ile Ser Ser Met Gln Pro Glu Asp Val Ala
            20                  25                  30

Thr Tyr Tyr Cys
            35

<210> SEQ ID NO 188
<211> LENGTH: 10
<212> TYPE: PRT
<213> ORGANISM: Homo sapiens
<220> FEATURE:
<223> OTHER INFORMATION: rehuCAN46G19; K, FR4

<400> SEQUENCE: 188

Phe Gly Gln Gly Thr Lys Leu Glu Ile Lys
1               5                   10

<210> SEQ ID NO 189
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G19; H, variable region

<400> SEQUENCE: 189

Glu Val Gln Leu Val Gln Ser Gly Ala Glu Val Val Lys Pro Gly Glu
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Thr Pro Gly Gln Ser Leu Glu Trp Val
            35                  40                  45

Gly Arg Ile Phe Pro Tyr Asn Gly Ala Ala Ser Tyr Asn Gln Asn Phe
        50                  55                  60

Lys Gly Lys Ala Thr Leu Thr Val Asp Lys Ser Thr Thr Thr Ala Tyr

```
                65                  70                  75                  80
Met Glu Leu Ser Ser Leu Arg Ser Glu Asp Ser Ala Val Tyr Phe Cys
                    85                  90                  95

Ala Arg Trp Leu Arg Val Tyr Phe Asp Tyr Trp Gly Gln Gly Thr Thr
            100                 105                 110

Leu Thr Val Ser Ser
        115

<210> SEQ ID NO 190
<211> LENGTH: 8
<212> TYPE: PRT
<213> ORGANISM: Mus musculus
<220> FEATURE:
<223> OTHER INFORMATION: rehuCAN46G19; H, CDR1

<400> SEQUENCE: 190

Gly Tyr Ser Phe Thr Gly Tyr Tyr
1               5

<210> SEQ ID NO 191
<211> LENGTH: 8
<212> TYPE: PRT
<213> ORGANISM: Mus musculus
<220> FEATURE:
<223> OTHER INFORMATION: rehuCAN46G19; H, CDR2

<400> SEQUENCE: 191

Ile Phe Pro Tyr Asn Gly Ala Ala
1               5

<210> SEQ ID NO 192
<211> LENGTH: 10
<212> TYPE: PRT
<213> ORGANISM: Mus musculus
<220> FEATURE:
<223> OTHER INFORMATION: rehuCAN46G19; H, CDR3

<400> SEQUENCE: 192

Ala Arg Trp Leu Arg Val Tyr Phe Asp Tyr
1               5                   10

<210> SEQ ID NO 193
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G19; H, FR1

<400> SEQUENCE: 193

Glu Val Gln Leu Val Gln Ser Gly Ala Glu Val Val Lys Pro Gly Glu
1               5                   10                  15

Ser Val Lys Ile Ser Cys Lys Ala Ser
            20                  25

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G19; H, FR2
```

-continued

<400> SEQUENCE: 194

Ile His Trp Val Lys Gln Thr Pro Gly Gln Ser Leu Glu Trp Val Gly
1               5                   10                  15

Arg

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G19; H, FR3

<400> SEQUENCE: 195

Ser Tyr Asn Gln Asn Phe Lys Gly Lys Ala Thr Leu Thr Val Asp Lys
1               5                   10                  15

Ser Thr Thr Thr Ala Tyr Met Glu Leu Ser Ser Leu Arg Ser Glu Asp
            20                  25                  30

Ser Ala Val Tyr Phe Cys
        35

<210> SEQ ID NO 196
<211> LENGTH: 11
<212> TYPE: PRT
<213> ORGANISM: Mus musculus
<220> FEATURE:
<223> OTHER INFORMATION: rehuCAN46G19; H, FR4

<400> SEQUENCE: 196

Trp Gly Gln Gly Thr Thr Leu Thr Val Ser Ser
1               5                   10

<210> SEQ ID NO 197
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G24; K, variable region

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

His Trp Tyr Gln Gln Lys Pro Gly Lys Ala Pro Lys Leu Leu Ile Tyr
        35                  40                  45

Glu Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Phe Gln Gly Ser Gly Tyr Pro Phe Thr
                85                  90                  95

Phe Gly Gln Gly Thr Lys Val Glu Ile Lys
            100                 105

<210> SEQ ID NO 198

```
<211> LENGTH: 5
<212> TYPE: PRT
<213> ORGANISM: Mus musculus
<220> FEATURE:
<223> OTHER INFORMATION: cdrCAN46G24; K, CDR1

<400> SEQUENCE: 198

Ser Ser Val Thr Tyr
1               5

<210> SEQ ID NO 199
<211> LENGTH: 3
<212> TYPE: PRT
<213> ORGANISM: Mus musculus
<220> FEATURE:
<223> OTHER INFORMATION: cdrCAN46G24; K, CDR2

<400> SEQUENCE: 199

Glu Thr Ser
1

<210> SEQ ID NO 200
<211> LENGTH: 9
<212> TYPE: PRT
<213> ORGANISM: Mus musculus
<220> FEATURE:
<223> OTHER INFORMATION: cdrCAN46G24; K, CDR3

<400> SEQUENCE: 200

Phe Gln Gly Ser Gly Tyr Pro Phe Thr
1               5

<210> SEQ ID NO 201
<211> LENGTH: 26
<212> TYPE: PRT
<213> ORGANISM: Homo sapiens
<220> FEATURE:
<223> OTHER INFORMATION: cdrCAN46G24; K, FR1

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 202
<211> LENGTH: 17
<212> TYPE: PRT
<213> ORGANISM: Homo sapiens
<220> FEATURE:
<223> OTHER INFORMATION: cdrCAN46G24; K, FR2

<400> SEQUENCE: 202

Met His Trp Tyr Gln Gln Lys Pro Gly Lys Ala Pro Lys Leu Leu Ile
1               5                   10                  15

Tyr

<210> SEQ ID NO 203
<211> LENGTH: 36
<212> TYPE: PRT
<213> ORGANISM: Homo sapiens
<220> FEATURE:
<223> OTHER INFORMATION: cdrCAN46G24; K, FR3

<400> SEQUENCE: 203

Lys Leu Ala Ser Gly Val Pro Ser Arg Phe Ser Gly Ser Gly Ser Gly
```

```
1               5                   10                  15
Thr Asp Tyr Thr Phe Thr Ile Ser Ser Leu Gln Pro Glu Asp Ile Ala
                20                  25                  30

Thr Tyr Tyr Cys
        35
```

<210> SEQ ID NO 204
<211> LENGTH: 10
<212> TYPE: PRT
<213> ORGANISM: Homo sapiens
<220> FEATURE:
<223> OTHER INFORMATION: cdrCAN46G24; K, FR4

<400> SEQUENCE: 204

```
Phe Gly Gln Gly Thr Lys Val Glu Ile Lys
1               5                   10
```

<210> SEQ ID NO 205
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G24; H, variable region

<400> SEQUENCE: 205

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Arg Ile Phe Pro Tyr Asn Gly Ala Ala Ser Tyr Asn Gln Asn Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Leu Arg Val Tyr Phe Asp Tyr Trp Gly Gln Gly Thr Thr
                100                 105                 110

Val Thr Val Ser Ser
        115
```

<210> SEQ ID NO 206
<211> LENGTH: 8
<212> TYPE: PRT
<213> ORGANISM: Mus musculus
<220> FEATURE:
<223> OTHER INFORMATION: cdrCAN46G24; H, CDR1

<400> SEQUENCE: 206

```
Gly Tyr Thr Phe Thr Gly Tyr Tyr
1               5
```

<210> SEQ ID NO 207
<211> LENGTH: 8
<212> TYPE: PRT
<213> ORGANISM: Mus musculus
<220> FEATURE:
<223> OTHER INFORMATION: cdrCAN46G24; H, CDR2

```
<400> SEQUENCE: 207

Ile Phe Pro Tyr Asn Gly Ala Ala
1               5

<210> SEQ ID NO 208
<211> LENGTH: 10
<212> TYPE: PRT
<213> ORGANISM: Mus musculus
<220> FEATURE:
<223> OTHER INFORMATION: cdrCAN46G24; H, CDR3

<400> SEQUENCE: 208

Ala Arg Trp Leu Arg Val Tyr Phe Asp Tyr
1               5                   10

<210> SEQ ID NO 209
<211> LENGTH: 25
<212> TYPE: PRT
<213> ORGANISM: Homo sapiens
<220> FEATURE:
<223> OTHER INFORMATION: cdrCAN46G24; H, FR1

<400> SEQUENCE: 209

Gln Val Gln Leu Val Gln Ser Gly Ala Glu Val Lys Lys Pro Gly Glu
1               5                   10                  15

Ser Val Lys Val Ser Cys Lys Ala Ser
            20                  25

<210> SEQ ID NO 210
<211> LENGTH: 17
<212> TYPE: PRT
<213> ORGANISM: Homo sapiens
<220> FEATURE:
<223> OTHER INFORMATION: cdrCAN46G24; H, FR2

<400> SEQUENCE: 210

Ile His Trp Val Arg Gln Ala Pro Gly Gln Gly Leu Glu Trp Met Gly
1               5                   10                  15

Arg

<210> SEQ ID NO 211
<211> LENGTH: 38
<212> TYPE: PRT
<213> ORGANISM: Homo sapiens
<220> FEATURE:
<223> OTHER INFORMATION: cdrCAN46G24; H, FR3

<400> SEQUENCE: 211

Ser Tyr Asn Gln Asn Phe Lys Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 212
<211> LENGTH: 11
<212> TYPE: PRT
<213> ORGANISM: Homo sapiens
<220> FEATURE:
<223> OTHER INFORMATION: cdrCAN46G24; H, FR4

<400> SEQUENCE: 212

Trp Gly Gln Gly Thr Thr Val Thr Val Ser Ser
```

<210> SEQ ID NO 213
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G24; K, variable region

<400> SEQUENCE: 213

Glu Ile Val Leu Thr Gln Ser Pro Ser Ser Leu Ser Thr Ser Val Gly
1               5                   10                  15
Asp Arg Val Thr Ile Ser Cys Ser Ala Ser Ser Ser Val Thr Tyr Met
            20                  25                  30
His Trp Tyr Gln Gln Lys Pro Gly Lys Ala Pro Lys Leu Trp Ile Tyr
        35                  40                  45
Glu Thr Ser Lys Leu Ala Ser Gly Val Pro Gly Arg Phe Ser Gly Ser
    50                  55                  60
Gly Ser Gly Asn Ser Tyr Thr Phe Thr Ile Ser Ser Leu Gln Pro Glu
65                  70                  75                  80
Asp Ile Ala Thr Tyr Tyr Cys Phe Gln Gly Ser Gly Tyr Pro Phe Thr
                85                  90                  95
Phe Gly Gln Gly Thr Lys Val Glu Ile Lys
            100                 105

<210> SEQ ID NO 214
<211> LENGTH: 5
<212> TYPE: PRT
<213> ORGANISM: Mus musculus
<220> FEATURE:
<223> OTHER INFORMATION: huCAN46G24; K, CDR1

<400> SEQUENCE: 214

Ser Ser Val Thr Tyr
1               5

<210> SEQ ID NO 215
<211> LENGTH: 3
<212> TYPE: PRT
<213> ORGANISM: Mus musculus
<220> FEATURE:
<223> OTHER INFORMATION: huCAN46G24; K, CDR2

<400> SEQUENCE: 215

Glu Thr Ser
1

<210> SEQ ID NO 216
<211> LENGTH: 9
<212> TYPE: PRT
<213> ORGANISM: Mus musculus
<220> FEATURE:
<223> OTHER INFORMATION: huCAN46G24; K, CDR3

<400> SEQUENCE: 216

Phe Gln Gly Ser Gly Tyr Pro Phe Thr
1               5

<210> SEQ ID NO 217
<211> LENGTH: 26
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G24; K, FR1

<400> SEQUENCE: 217

Glu Ile Val Leu Thr Gln Ser Pro Ser Ser Leu Ser Thr Ser Val Gly
1               5                   10                  15

Asp Arg Val Thr Ile Ser Cys Ser Ala Ser
            20                  25

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G24; K, FR2

<400> SEQUENCE: 218

Met His Trp Tyr Gln Gln Lys Pro Gly Lys Ala Pro Lys Leu Trp Ile
1               5                   10                  15

Tyr

<210> SEQ ID NO 219
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G24; K, FR3

<400> SEQUENCE: 219

Lys Leu Ala Ser Gly Val Pro Gly Arg Phe Ser Gly Ser Gly Ser Gly
1               5                   10                  15

Asn Ser Tyr Thr Phe Thr Ile Ser Ser Leu Gln Pro Glu Asp Ile Ala
            20                  25                  30

Thr Tyr Tyr Cys
        35

<210> SEQ ID NO 220
<211> LENGTH: 10
<212> TYPE: PRT
<213> ORGANISM: Homo sapiens
<220> FEATURE:
<223> OTHER INFORMATION: huCAN46G24; K, FR4

<400> SEQUENCE: 220

Phe Gly Gln Gly Thr Lys Val Glu Ile Lys
1               5                   10

<210> SEQ ID NO 221
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G24; H, variable region
```

<400> SEQUENCE: 221

Glu Val Gln Leu Val Gln Ser Gly Ala Glu Val Lys Lys Pro Gly Glu
1               5                   10                  15

Ser Val Lys Val Ser Cys Lys Ala Ser Gly Tyr Ser Phe Thr Gly Tyr
            20                  25                  30

Tyr Ile His Trp Val Lys Gln Ala Pro Gly Gln Gly Leu Glu Trp Val
        35                  40                  45

Gly Arg Ile Phe Pro Tyr Asn Gly Ala Ala Ser Tyr Asn Gln Asn Phe
50                  55                  60

Lys Gly Lys Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Arg Trp Leu Arg Val Tyr Phe Asp Tyr Trp Gly Gln Gly Thr Thr
            100                 105                 110

Val Thr Val Ser Ser
        115

<210> SEQ ID NO 222
<211> LENGTH: 8
<212> TYPE: PRT
<213> ORGANISM: Mus musculus
<220> FEATURE:
<223> OTHER INFORMATION: huCAN46G24; H, CDR1

<400> SEQUENCE: 222

Gly Tyr Ser Phe Thr Gly Tyr Tyr
1               5

<210> SEQ ID NO 223
<211> LENGTH: 8
<212> TYPE: PRT
<213> ORGANISM: Mus musculus
<220> FEATURE:
<223> OTHER INFORMATION: huCAN46G24; H, CDR2

<400> SEQUENCE: 223

Ile Phe Pro Tyr Asn Gly Ala Ala
1               5

<210> SEQ ID NO 224
<211> LENGTH: 10
<212> TYPE: PRT
<213> ORGANISM: Mus musculus
<220> FEATURE:
<223> OTHER INFORMATION: huCAN46G24; H, CDR3

<400> SEQUENCE: 224

Ala Arg Trp Leu Arg Val Tyr Phe Asp Tyr
1               5                   10

<210> SEQ ID NO 225
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G24; H, FR1

<400> SEQUENCE: 225

Glu Val Gln Leu Val Gln Ser Gly Ala Glu Val Lys Lys Pro Gly Glu

```
                1               5                   10                  15
Ser Val Lys Val Ser Cys Lys Ala Ser
            20              25
```

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G24; H, FR2

<400> SEQUENCE: 226

```
Ile His Trp Val Lys Gln Ala Pro Gly Gln Gly Leu Glu Trp Val Gly
1               5                   10                  15
Arg
```

<210> SEQ ID NO 227
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G24; H, FR3

<400> SEQUENCE: 227

```
Ser Tyr Asn Gln Asn Phe Lys Gly Lys Ala Thr Leu Thr Val Asp Lys
1               5                   10                  15

Ser Ser Ser Thr Ala Tyr Met Glu Leu Ser Ser Leu Arg Ser Glu Asp
            20                  25                  30

Thr Ala Val Tyr Phe Cys
            35
```

<210> SEQ ID NO 228
<211> LENGTH: 11
<212> TYPE: PRT
<213> ORGANISM: Homo sapiens
<220> FEATURE:
<223> OTHER INFORMATION: huCAN46G24; H, FR4

<400> SEQUENCE: 228

```
Trp Gly Gln Gly Thr Thr Val Thr Val Ser Ser
1               5                   10
```

<210> SEQ ID NO 229
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G24; K, variable region

<400> SEQUENCE: 229

```
Glu Ile Val Leu Thr Gln Ser Pro Ser Ser Met Ser Thr Ser Val Gly
1               5                   10                  15

Asp Arg Val Thr Met Ser Cys Ser Ala Ser Ser Ser Val Thr Tyr Met
            20                  25                  30

His Trp Tyr Gln Gln Lys Pro Gly Lys Ser Pro Lys Leu Trp Ile Tyr
            35                  40                  45
```

Glu Thr Ser Lys Leu Ala Ser Gly Val Pro Ser Arg Phe Ser Gly Ser
        50                  55                  60

Gly Ser Gly Asn Asp Tyr Ser Leu Thr Ile Ser Ser Met Gln Pro Glu
65                  70                  75                  80

Asp Val Ala Thr Tyr Tyr Cys Phe Gln Gly Ser Gly Tyr Pro Phe Thr
                85                  90                  95

Phe Gly Gln Gly Thr Lys Leu Glu Ile Lys
            100                 105

<210> SEQ ID NO 230
<211> LENGTH: 5
<212> TYPE: PRT
<213> ORGANISM: Mus musculus
<220> FEATURE:
<223> OTHER INFORMATION: rehuCAN46G24; K, CDR1

<400> SEQUENCE: 230

Ser Ser Val Thr Tyr
1               5

<210> SEQ ID NO 231
<211> LENGTH: 3
<212> TYPE: PRT
<213> ORGANISM: Mus musculus
<220> FEATURE:
<223> OTHER INFORMATION: rehuCAN46G24; K, CDR2

<400> SEQUENCE: 231

Glu Thr Ser
1

<210> SEQ ID NO 232
<211> LENGTH: 9
<212> TYPE: PRT
<213> ORGANISM: Mus musculus
<220> FEATURE:
<223> OTHER INFORMATION: rehuCAN46G24; K, CDR3

<400> SEQUENCE: 232

Phe Gln Gly Ser Gly Tyr Pro Phe Thr
1               5

<210> SEQ ID NO 233
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G24; K, FR1

<400> SEQUENCE: 233

Glu Ile Val Leu Thr Gln Ser Pro Ser Ser Met Ser Thr Ser Val Gly
1               5                   10                  15

Asp Arg Val Thr Met Ser Cys Ser Ala Ser
            20                  25

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: rehuCAN46G24; K, FR2

<400> SEQUENCE: 234

Met His Trp Tyr Gln Gln Lys Pro Gly Lys Ser Pro Lys Leu Trp Ile
1               5                   10                  15
Tyr

<210> SEQ ID NO 235
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G24; K, FR3

<400> SEQUENCE: 235

Lys Leu Ala Ser Gly Val Pro Ser Arg Phe Ser Gly Ser Gly Ser Gly
1               5                   10                  15

Asn Asp Tyr Ser Leu Thr Ile Ser Ser Met Gln Pro Glu Asp Val Ala
            20                  25                  30

Thr Tyr Tyr Cys
        35

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G24; K, FR4

<400> SEQUENCE: 236

Phe Gly Gln Gly Thr Lys Leu Glu Ile Lys
1               5                   10

<210> SEQ ID NO 237
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G24; H, variable region

<400> SEQUENCE: 237

Glu Val Gln Leu Val Gln Ser Gly Ala Glu Val Val Lys Pro Gly Glu
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Thr Pro Gly Gln Ser Leu Glu Trp Val
        35                  40                  45

Gly Arg Ile Phe Pro Tyr Asn Gly Ala Ala Ser Tyr Asn Gln Asn Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Ser Ala Val Tyr Phe Cys
                85                  90                  95
```

Ala Arg Trp Leu Arg Val Tyr Phe Asp Tyr Trp Gly Gln Gly Thr Thr
            100                 105                 110

Leu Thr Val Ser Ser
        115

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G24; H, CDR1

<400> SEQUENCE: 238

Gly Tyr Ser Phe Thr Gly Tyr Tyr
1               5

<210> SEQ ID NO 239
<211> LENGTH: 8
<212> TYPE: PRT
<213> ORGANISM: Mus musculus
<220> FEATURE:
<223> OTHER INFORMATION: rehuCAN46G24; H, CDR2

<400> SEQUENCE: 239

Ile Phe Pro Tyr Asn Gly Ala Ala
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G24; H, CDR3

<400> SEQUENCE: 240

Ala Arg Trp Leu Arg Val Tyr Phe Asp Tyr
1               5                   10

<210> SEQ ID NO 241
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G24; H, FR1

<400> SEQUENCE: 241

Glu Val Gln Leu Val Gln Ser Gly Ala Glu Val Val Lys Pro Gly Glu
1               5                   10                  15

Ser Val Lys Ile Ser Cys Lys Ala Ser
            20                  25

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: rehuCAN46G24; H, FR2

<400> SEQUENCE: 242

Ile His Trp Val Lys Gln Thr Pro Gly Gln Ser Leu Glu Trp Val Gly
1               5                   10                  15

Arg

<210> SEQ ID NO 243
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G24; H, FR3

<400> SEQUENCE: 243

Ser Tyr Asn Gln Asn Phe Lys Gly Lys Ala Thr Leu Thr Val Asp Lys
1               5                   10                  15

Ser Thr Ser Thr Ala Tyr Met Glu Leu Ser Ser Leu Arg Ser Glu Asp
            20                  25                  30

Ser Ala Val Tyr Phe Cys
        35

<210> SEQ ID NO 244
<211> LENGTH: 11
<212> TYPE: PRT
<213> ORGANISM: Mus musculus
<220> FEATURE:
<223> OTHER INFORMATION: rehuCAN46G24; H, FR4

<400> SEQUENCE: 244

Trp Gly Gln Gly Thr Thr Leu Thr Val Ser Ser
1               5                   10

<210> SEQ ID NO 245
<211> LENGTH: 318
<212> TYPE: DNA
<213> ORGANISM: Mus musculus
<220> FEATURE:
<223> OTHER INFORMATION: CAN46G4; K, variable region

<400> SEQUENCE: 245
gaaaaggttc tcacccagtc tccagcaatc atgtctgcat ctccagggga agaggtcacc      60
atgacctgca gtgccagctc aagtgtaagt tacatgcatt ggtaccagca gaagtcaagc     120
acctccccca aactctggat ttatgaaaca tccaaactgg cttttggagt cccaggtcgc     180
ttcagtggca gtggatctgg aaactcttac tctctcacga tcagcagcat ggaggctgaa     240
gatgttgcca cttattactg ttttcagggg agtgggtacc cattcacgtt cggctcgggg     300
acaaagttgg aagtaaaa                                                   318

<210> SEQ ID NO 246
<211> LENGTH: 15
<212> TYPE: DNA
<213> ORGANISM: Mus musculus
<220> FEATURE:
<223> OTHER INFORMATION: CAN46G4; K, CDR1

<400> SEQUENCE: 246
tcaagtgtaa gttac                                                       15

```
<210> SEQ ID NO 247
<211> LENGTH: 9
<212> TYPE: DNA
<213> ORGANISM: Mus musculus
<220> FEATURE:
<223> OTHER INFORMATION: CAN46G4; K, CDR2

<400> SEQUENCE: 247 gaaacatcc                                                                  9

<210> SEQ ID NO 248
<211> LENGTH: 27
<212> TYPE: DNA
<213> ORGANISM: Mus musculus
<220> FEATURE:
<223> OTHER INFORMATION: CAN46G4; K, CDR3

<400> SEQUENCE: 248
tttcagggga gtgggtaccc attcacg                                             27

<210> SEQ ID NO 249
<211> LENGTH: 78
<212> TYPE: DNA
<213> ORGANISM: Mus musculus
<220> FEATURE:
<223> OTHER INFORMATION: CAN46G4; K, FR1

<400> SEQUENCE: 249
gaaaaggttc tcacccagtc tccagcaatc atgtctgcat ctccagggga agaggtcacc         60
atgacctgca gtgccagc                                                       78

<210> SEQ ID NO 250
<211> LENGTH: 51
<212> TYPE: DNA
<213> ORGANISM: Mus musculus
<220> FEATURE:
<223> OTHER INFORMATION: CAN46G4; K, FR2

<400> SEQUENCE: 250
atgcattggt accagcagaa gtcaagcacc tcccccaaac tctggattta t                  51

<210> SEQ ID NO 251
<211> LENGTH: 108
<212> TYPE: DNA
<213> ORGANISM: Mus musculus
<220> FEATURE:
<223> OTHER INFORMATION: CAN46G4; K, FR3

<400> SEQUENCE: 251
aaactggctt ttggagtccc aggtcgcttc agtggcagtg gatctggaaa ctcttactct         60
ctcacgatca gcagcatgga ggctgaagat gttgccactt attactgt                     108

<210> SEQ ID NO 252
<211> LENGTH: 30
<212> TYPE: DNA
<213> ORGANISM: Mus musculus
<220> FEATURE:
<223> OTHER INFORMATION: CAN46G4; K, FR4

<400> SEQUENCE: 252
ttcggctcgg ggacaaagtt ggaagtaaaa                                          30

<210> SEQ ID NO 253
<211> LENGTH: 351
<212> TYPE: DNA
```

<213> ORGANISM: Mus musculus
<220> FEATURE:
<223> OTHER INFORMATION: CAN46G4; H, variable region

<400> SEQUENCE: 253

| | | | | | |
|---|---|---|---|---|---|
| gaggtccagc | tgctacagtc | tggccctgag | ctggtgaagc | ctggggcttc | agtgaagata | 60 |
| tcctgcaagg | cttctgatta | ctcattcact | ggctactaca | tgcactgggt | gaagcaaagc | 120 |
| catgtaaaga | gccttgagtg | gattggacgt | attttccctt | acaatggtgc | tgctagctac | 180 |
| aaccagaatt | tcaaggacaa | ggccaccttg | actgtagata | agtcttccag | cacagcctac | 240 |
| atggagctcc | acagcctgac | atctgaggac | tctgcagtct | attattgtac | aagatggtta | 300 |
| agggtctact | ttgactactg | gggccaaggc | accactctca | cagtctcctc | a | 351 |

<210> SEQ ID NO 254
<211> LENGTH: 24
<212> TYPE: DNA
<213> ORGANISM: Mus musculus
<220> FEATURE:
<223> OTHER INFORMATION: CAN46G4; H, CDR1

<400> SEQUENCE: 254
gattactcat tcactggcta ctac            24

<210> SEQ ID NO 255
<211> LENGTH: 24
<212> TYPE: DNA
<213> ORGANISM: Mus musculus
<220> FEATURE:
<223> OTHER INFORMATION: CAN46G4; H, CDR2

<400> SEQUENCE: 255
attttccctt acaatggtgc tgct            24

<210> SEQ ID NO 256
<211> LENGTH: 30
<212> TYPE: DNA
<213> ORGANISM: Mus musculus
<220> FEATURE:
<223> OTHER INFORMATION: CAN46G4; H, CDR3

<400> SEQUENCE: 256
acaagatggt taagggtcta ctttgactac            30

<210> SEQ ID NO 257
<211> LENGTH: 75
<212> TYPE: DNA
<213> ORGANISM: Mus musculus
<220> FEATURE:
<223> OTHER INFORMATION: CAN46G4; H, FR1

<400> SEQUENCE: 257

| | | | | | |
|---|---|---|---|---|---|
| gaggtccagc | tgctacagtc | tggccctgag | ctggtgaagc | ctggggcttc | agtgaagata | 60 |
| tcctgcaagg | cttct | | | | | 75 |

<210> SEQ ID NO 258
<211> LENGTH: 51
<212> TYPE: DNA
<213> ORGANISM: Mus musculus
<220> FEATURE:
<223> OTHER INFORMATION: CAN46G4; H, FR2

<400> SEQUENCE: 258
atgcactggg tgaagcaaag ccatgtaaag agccttgagt ggattggacg t            51

<210> SEQ ID NO 259
<211> LENGTH: 114
<212> TYPE: DNA
<213> ORGANISM: Mus musculus
<220> FEATURE:
<223> OTHER INFORMATION: CAN46G4; H, FR3

<400> SEQUENCE: 259

```
agctacaacc agaatttcaa ggacaaggcc accttgactg tagataagtc ttccagcaca    60
gcctacatgg agctccacag cctgacatct gaggactctg cagtctatta ttgt         114
```

<210> SEQ ID NO 260
<211> LENGTH: 33
<212> TYPE: DNA
<213> ORGANISM: Mus musculus
<220> FEATURE:
<223> OTHER INFORMATION: CAN46G4; H, FR4

<400> SEQUENCE: 260

```
tggggccaag gcaccactct cacagtctcc tca                                  33
```

<210> SEQ ID NO 261
<211> LENGTH: 319
<212> TYPE: DNA
<213> ORGANISM: Mus musculus
<220> FEATURE:
<223> OTHER INFORMATION: CAN46G13; K, variable region

<400> SEQUENCE: 261

```
gaaattgttc tcacccagtc tccagcaatc atgtctacat ctccagggga aaaggtcacc    60
atgtcctgca gtgccagctc aagtgtaact tacatgcact ggtaccagca gaagtcaatc   120
acctccccca aactctggat ttatgaaaca tccaaactgg cttctggagt ccccggtcgc   180
ttcagtggca gtgggtctgg aaactcttac tctctcacga tcagcagcat ggaggctgaa   240
gatgttgcca cttattactg ttttcagggg agtgggtacc cattcacgtt cggctcgggg   300
acaaagttgg aaataaaac                                                319
```

<210> SEQ ID NO 262
<211> LENGTH: 15
<212> TYPE: DNA
<213> ORGANISM: Mus musculus
<220> FEATURE:
<223> OTHER INFORMATION: CAN46G13; K, CDR1

<400> SEQUENCE: 262

```
tcaagtgtaa cttac                                                      15
```

<210> SEQ ID NO 263
<211> LENGTH: 9
<212> TYPE: DNA
<213> ORGANISM: Mus musculus
<220> FEATURE:
<223> OTHER INFORMATION: CAN46G13; K, CDR2

<400> SEQUENCE: 263

```
gaaacatcc                                                              9
```

<210> SEQ ID NO 264
<211> LENGTH: 27
<212> TYPE: DNA
<213> ORGANISM: Mus musculus
<220> FEATURE:

<223> OTHER INFORMATION: CAN46G13; K, CDR3

<400> SEQUENCE: 264
tttcagggga gtgggtaccc attcacg                                    27

<210> SEQ ID NO 265
<211> LENGTH: 78
<212> TYPE: DNA
<213> ORGANISM: Mus musculus
<220> FEATURE:
<223> OTHER INFORMATION: CAN46G13; K, FR1

<400> SEQUENCE: 265
gaaattgttc tcacccagtc tccagcaatc atgtctacat ctccagggga aaaggtcacc    60
atgtcctgca gtgccagc                                               78

<210> SEQ ID NO 266
<211> LENGTH: 51
<212> TYPE: DNA
<213> ORGANISM: Mus musculus
<220> FEATURE:
<223> OTHER INFORMATION: CAN46G13; K, FR2

<400> SEQUENCE: 266
atgcactggt accagcagaa gtcaatcacc tcccccaaac tctggattta t             51

<210> SEQ ID NO 267
<211> LENGTH: 108
<212> TYPE: DNA
<213> ORGANISM: Mus musculus
<220> FEATURE:
<223> OTHER INFORMATION: CAN46G13; K, FR3

<400> SEQUENCE: 267
aaactggctt ctggagtccc cggtcgcttc agtggcagtg ggtctgggaa ctcttactct    60
ctcacgatca gcagcatgga ggctgaagat gttgccactt attactgt              108

<210> SEQ ID NO 268
<211> LENGTH: 31
<212> TYPE: DNA
<213> ORGANISM: Mus musculus
<220> FEATURE:
<223> OTHER INFORMATION: CAN46G13; K, FR4

<400> SEQUENCE: 268
ttcggctcgg ggacaaagtt ggaaataaaa c                                31

<210> SEQ ID NO 269
<211> LENGTH: 352
<212> TYPE: DNA
<213> ORGANISM: Mus musculus
<220> FEATURE:
<223> OTHER INFORMATION: CAN46G13; H, variable region

<400> SEQUENCE: 269
gaggtccagc tgctacagtc tggccctgag ctggtgaagc ctgggacttc agtgaagata    60
tcctgcaagg cttctggtta ctcattcact ggctactaca tacactgggt gaagcagacc   120
catgtaaaga gccttgagtg ggttggacgt attttttcctt acaatggtgc tgctagctac   180
aatcagaatt tcaagggcaa ggccaccttg actgtagata gtcctccag cacagcctac    240 atggagctcc acagcctgac atctgaggac tctgcagtct atttctgtgc aagatggtta    300
agggtctact ttgactactg gggccaaggc accactctca cagtctcctc ag           352

<210> SEQ ID NO 270
<211> LENGTH: 24
<212> TYPE: DNA
<213> ORGANISM: Mus musculus
<220> FEATURE:
<223> OTHER INFORMATION: CAN46G13; H, CDR1

<400> SEQUENCE: 270
ggttactcat tcactggcta ctac                                            24

<210> SEQ ID NO 271
<211> LENGTH: 24
<212> TYPE: DNA
<213> ORGANISM: Mus musculus
<220> FEATURE:
<223> OTHER INFORMATION: CAN46G13; H, CDR2

<400> SEQUENCE: 271
atttttcctt acaatggtgc tgct                                            24

<210> SEQ ID NO 272
<211> LENGTH: 30
<212> TYPE: DNA
<213> ORGANISM: Mus musculus
<220> FEATURE:
<223> OTHER INFORMATION: CAN46G13; H, CDR3

<400> SEQUENCE: 272
gcaagatggt taagggtcta ctttgactac                                      30

<210> SEQ ID NO 273
<211> LENGTH: 75
<212> TYPE: DNA
<213> ORGANISM: Mus musculus
<220> FEATURE:
<223> OTHER INFORMATION: CAN46G13; H, FR1

<400> SEQUENCE: 273
gaggtccagc tgctacagtc tggccctgag ctggtgaagc ctgggacttc agtgaagata     60
tcctgcaagg cttct                                                      75

<210> SEQ ID NO 274
<211> LENGTH: 51
<212> TYPE: DNA
<213> ORGANISM: Mus musculus
<220> FEATURE:
<223> OTHER INFORMATION: CAN46G13; H, FR2

<400> SEQUENCE: 274
atacactggg tgaagcagac ccatgtaaag agccttgagt gggttggacg t              51

<210> SEQ ID NO 275
<211> LENGTH: 114
<212> TYPE: DNA
<213> ORGANISM: Mus musculus
<220> FEATURE:
<223> OTHER INFORMATION: CAN46G13; H, FR3

<400> SEQUENCE: 275
agctacaatc agaatttcaa gggcaaggcc accttgactg tagataagtc ctccagcaca     60
gcctacatgg agctccacag cctgacatct gaggactctg cagtctattt ctgt          114

<210> SEQ ID NO 276

```
<211> LENGTH: 34
<212> TYPE: DNA
<213> ORGANISM: Mus musculus
<220> FEATURE:
<223> OTHER INFORMATION: CAN46G13; H, FR4

<400> SEQUENCE: 276
tggggccaag gcaccactct cacagtctcc tcag                              34

<210> SEQ ID NO 277
<211> LENGTH: 324
<212> TYPE: DNA
<213> ORGANISM: Mus musculus
<220> FEATURE:
<223> OTHER INFORMATION: CAN46G13a; K, variable region

<400> SEQUENCE: 277
gaaaatgtgc tcacccagtc tccagcaata atggctgcct ctctggggca gaaggtcacc  60
atgacctgca gtgccagctc aagtgtaagt tccagttact tgcactggta ccagcagaag 120
tcaggcgctt cccccaaacc cttgattcat aggacatcca ccctggcttc tggcgtccca 180
gctcgcttca gtggcagtgg gtctgggacc tcttactctc tcacaatcag cagcgtggag 240
gctgaagatg atgcaactta ttactgccag cagtggagtg gttacccgta cacgttcgga 300
ggggggacca agctggaaat aaaa                                        324

<210> SEQ ID NO 278
<211> LENGTH: 21
<212> TYPE: DNA
<213> ORGANISM: Mus musculus
<220> FEATURE:
<223> OTHER INFORMATION: CAN46G13a; K, CDR1

<400> SEQUENCE: 278
tcaagtgtaa gttccagtta c                                           21

<210> SEQ ID NO 279
<211> LENGTH: 9
<212> TYPE: DNA
<213> ORGANISM: Mus musculus
<220> FEATURE:
<223> OTHER INFORMATION: CAN46G13a; K, CDR2

<400> SEQUENCE: 279 aggacatcc                                                          9

<210> SEQ ID NO 280
<211> LENGTH: 27
<212> TYPE: DNA
<213> ORGANISM: Mus musculus
<220> FEATURE:
<223> OTHER INFORMATION: CAN46G13a; K, CDR3

<400> SEQUENCE: 280
cagcagtgga gtggttaccc gtacacg                                     27

<210> SEQ ID NO 281
<211> LENGTH: 78
<212> TYPE: DNA
<213> ORGANISM: Mus musculus
<220> FEATURE:
<223> OTHER INFORMATION: CAN46G13a; K, FR1

<400> SEQUENCE: 281
gaaaatgtgc tcacccagtc tccagcaata atggctgcct ctctggggca gaaggtcacc  60
```

```
atgacctgca gtgccagc                                                     78
```

<210> SEQ ID NO 282
<211> LENGTH: 51
<212> TYPE: DNA
<213> ORGANISM: Mus musculus
<220> FEATURE:
<223> OTHER INFORMATION: CAN46G13a; K, FR2

<400> SEQUENCE: 282

```
ttgcactggt accagcagaa gtcaggcgct tcccccaaac ccttgattca t                51
```

<210> SEQ ID NO 283
<211> LENGTH: 108
<212> TYPE: DNA
<213> ORGANISM: Mus musculus
<220> FEATURE:
<223> OTHER INFORMATION: CAN46G13a; K, FR3

<400> SEQUENCE: 283

```
accctggctt ctggcgtccc agctcgcttc agtggcagtg ggtctgggac ctcttactct       60
ctcacaatca gcagcgtgga ggctgaagat gatgcaactt attactgc                   108
```

<210> SEQ ID NO 284
<211> LENGTH: 30
<212> TYPE: DNA
<213> ORGANISM: Mus musculus
<220> FEATURE:
<223> OTHER INFORMATION: CAN46G13a; K, FR4

<400> SEQUENCE: 284

```
ttcggagggg ggaccaagct ggaaataaaa                                        30
```

<210> SEQ ID NO 285
<211> LENGTH: 358
<212> TYPE: DNA
<213> ORGANISM: Mus musculus
<220> FEATURE:
<223> OTHER INFORMATION: CAN46G13a; H, variable region

<400> SEQUENCE: 285

```
gatgtgcagc ttcaggagtc aggacctggc ctggtgaaac cttctcagtc tctgtccctc       60
acctgcactg tcactggcta ctcaatcacc agtgattctg cctggaactg gatccggcag      120
tttccaggaa acaacctgga gtggatgggc tacataagct acagtggtag cactagctac      180
aacccatctc tcaaaagtcg aatctctatc actcgagaca catccaagaa ccagttcttc      240
ctgcagttga attctgtgac tactgaggac acagccacat attactgtgc aagaaggagt      300
agggtctcat ctactttga ctactggggc caaggcacca ctctcacagt ctcctcag        358
```

<210> SEQ ID NO 286
<211> LENGTH: 27
<212> TYPE: DNA
<213> ORGANISM: Mus musculus
<220> FEATURE:
<223> OTHER INFORMATION: CAN46G13a; H, CDR1

<400> SEQUENCE: 286

```
ggctactcaa tcaccagtga ttctgcc                                           27
```

<210> SEQ ID NO 287
<211> LENGTH: 21
<212> TYPE: DNA

```
<213> ORGANISM: Mus musculus
<220> FEATURE:
<223> OTHER INFORMATION: CAN46G13a; H, CDR2

<400> SEQUENCE: 287
ataagctaca gtggtagcac t                                              21

<210> SEQ ID NO 288
<211> LENGTH: 36
<212> TYPE: DNA
<213> ORGANISM: Mus musculus
<220> FEATURE:
<223> OTHER INFORMATION: CAN46G13a; H, CDR3

<400> SEQUENCE: 288
gcaagaagga gtagggtctc attctacttt gactac                              36

<210> SEQ ID NO 289
<211> LENGTH: 75
<212> TYPE: DNA
<213> ORGANISM: Mus musculus
<220> FEATURE:
<223> OTHER INFORMATION: CAN46G13a; H, FR1

<400> SEQUENCE: 289
gatgtgcagc ttcaggagtc aggacctggc ctggtgaaac cttctcagtc tctgtccctc    60
acctgcactg tcact                                                     75

<210> SEQ ID NO 290
<211> LENGTH: 51
<212> TYPE: DNA
<213> ORGANISM: Mus musculus
<220> FEATURE:
<223> OTHER INFORMATION: CAN46G13a; H, FR2

<400> SEQUENCE: 290
tggaactgga tccggcagtt tccaggaaac aacctggagt ggatgggcta c             51

<210> SEQ ID NO 291
<211> LENGTH: 114
<212> TYPE: DNA
<213> ORGANISM: Mus musculus
<220> FEATURE:
<223> OTHER INFORMATION: CAN46G13a; H, FR3

<400> SEQUENCE: 291
agctacaacc catctctcaa aagtcgaatc tctatcactc gagacacatc caagaaccag    60
ttcttcctgc agttgaattc tgtgactact gaggacacag ccacatatta ctgt         114

<210> SEQ ID NO 292
<211> LENGTH: 34
<212> TYPE: DNA
<213> ORGANISM: Mus musculus
<220> FEATURE:
<223> OTHER INFORMATION: CAN46G13a; H, FR4

<400> SEQUENCE: 292
tggggccaag gcaccactct cacagtctcc tcag                                34

<210> SEQ ID NO 293
<211> LENGTH: 319
<212> TYPE: DNA
<213> ORGANISM: Mus musculus
<220> FEATURE:
<223> OTHER INFORMATION: CAN46G19; K, variable region
```

<400> SEQUENCE: 293

| | |
|---|---|
| gaaaatgttc tcacccagtc tccaacaatc atgtctgcat ctccagggga agaggtcacc | 60 |
| atgacctgca gtgccagctc aagtgtaact tacatgcact ggtaccagca gaagtcaatc | 120 |
| acctccccca aactctggat ttatgaaaca tccaaactgg cttctggagt cccaggtcgc | 180 |
| ttcagtggca gtgggtctgg aaactcttac tctctcacga tcagcagcat ggaggctgaa | 240 |
| gatgttgcca cttattactg tttcagggg agtgggtacc cattcacgtt cggctcgggg | 300 |
| acaaagttgg aaataaaac | 319 |

<210> SEQ ID NO 294
<211> LENGTH: 15
<212> TYPE: DNA
<213> ORGANISM: Mus musculus
<220> FEATURE:
<223> OTHER INFORMATION: CAN46G19; K, CDR1

<400> SEQUENCE: 294

| | |
|---|---|
| tcaagtgtaa cttac | 15 |

<210> SEQ ID NO 295
<211> LENGTH: 9
<212> TYPE: DNA
<213> ORGANISM: Mus musculus
<220> FEATURE:
<223> OTHER INFORMATION: CAN46G19; K, CDR2

<400> SEQUENCE: 295

| | |
|---|---|
| gaaacatcc | 9 |

<210> SEQ ID NO 296
<211> LENGTH: 27
<212> TYPE: DNA
<213> ORGANISM: Mus musculus
<220> FEATURE:
<223> OTHER INFORMATION: CAN46G19; K, CDR3

<400> SEQUENCE: 296

| | |
|---|---|
| tttcagggga gtgggtaccc attcacg | 27 |

<210> SEQ ID NO 297
<211> LENGTH: 78
<212> TYPE: DNA
<213> ORGANISM: Mus musculus
<220> FEATURE:
<223> OTHER INFORMATION: CAN46G19; K, FR1

<400> SEQUENCE: 297

| | |
|---|---|
| gaaaatgttc tcacccagtc tccaacaatc atgtctgcat ctccagggga agaggtcacc | 60 |
| atgacctgca gtgccagc | 78 |

<210> SEQ ID NO 298
<211> LENGTH: 51
<212> TYPE: DNA
<213> ORGANISM: Mus musculus
<220> FEATURE:
<223> OTHER INFORMATION: CAN46G19; K, FR2

<400> SEQUENCE: 298

| | |
|---|---|
| atgcactggt accagcagaa gtcaatcacc tcccccaaac tctggattta t | 51 |

<210> SEQ ID NO 299

```
<211> LENGTH: 108
<212> TYPE: DNA
<213> ORGANISM: Mus musculus
<220> FEATURE:
<223> OTHER INFORMATION: CAN46G19; K, FR3

<400> SEQUENCE: 299
aaactggctt ctggagtccc aggtcgcttc agtggcagtg ggtctggaaa ctcttactct      60
ctcacgatca gcagcatgga ggctgaagat gttgccactt attactgt                  108

<210> SEQ ID NO 300
<211> LENGTH: 31
<212> TYPE: DNA
<213> ORGANISM: Mus musculus
<220> FEATURE:
<223> OTHER INFORMATION: CAN46G19; K, FR4

<400> SEQUENCE: 300
ttcggctcgg ggacaaagtt ggaaataaaa c                                     31

<210> SEQ ID NO 301
<211> LENGTH: 352
<212> TYPE: DNA
<213> ORGANISM: Mus musculus
<220> FEATURE:
<223> OTHER INFORMATION: CAN46G19; H, variable region

<400> SEQUENCE: 301
gaggtccagc tgctacagtc tggccctgag ctggtgaagc ctgggacttc agtgaagata      60
tcctgcaagg cttctggtta ctcattcact ggctactaca ttcactgggt gaagcagacc     120
catgtaaaga gccttgagtg ggttggacgt attttttcctt acaatggtgc tgctagctac    180
aaccagaatt caagggcaa ggccaccttg actgtagata gtcctccac cacagcctac       240 atggagctcc acagcctgac atctgaggac tctgcagtct atttctgtgc aagatggtta    300
agggtctact ttgactactg gggccaaggc accactctca cagtctcctc ag            352

<210> SEQ ID NO 302
<211> LENGTH: 24
<212> TYPE: DNA
<213> ORGANISM: Mus musculus
<220> FEATURE:
<223> OTHER INFORMATION: CAN46G19; H, CDR1

<400> SEQUENCE: 302
ggttactcat tcactggcta ctac                                             24

<210> SEQ ID NO 303
<211> LENGTH: 24
<212> TYPE: DNA
<213> ORGANISM: Mus musculus
<220> FEATURE:
<223> OTHER INFORMATION: CAN46G19; H, CDR2

<400> SEQUENCE: 303 attttttcctt acaatggtgc tgct                                            24

<210> SEQ ID NO 304
<211> LENGTH: 30
<212> TYPE: DNA
<213> ORGANISM: Mus musculus
<220> FEATURE:
<223> OTHER INFORMATION: CAN46G19; H, CDR3

<400> SEQUENCE: 304
```

```
gcaagatggt taagggtcta ctttgactac                                              30

<210> SEQ ID NO 305
<211> LENGTH: 75
<212> TYPE: DNA
<213> ORGANISM: Mus musculus
<220> FEATURE:
<223> OTHER INFORMATION: CAN46G19; H, FR1

<400> SEQUENCE: 305
gaggtccagc tgctacagtc tggccctgag ctggtgaagc ctgggacttc agtgaagata           60
tcctgcaagg cttct                                                            75

<210> SEQ ID NO 306
<211> LENGTH: 51
<212> TYPE: DNA
<213> ORGANISM: Mus musculus
<220> FEATURE:
<223> OTHER INFORMATION: CAN46G19; H, FR2

<400> SEQUENCE: 306
attcactggg tgaagcagac ccatgtaaag agccttgagt gggttggacg t                    51

<210> SEQ ID NO 307
<211> LENGTH: 114
<212> TYPE: DNA
<213> ORGANISM: Mus musculus
<220> FEATURE:
<223> OTHER INFORMATION: CAN46G19; H, FR3

<400> SEQUENCE: 307
agctacaacc agaatttcaa gggcaaggcc accttgactg tagataagtc ctccaccaca           60
gcctacatgg agctccacag cctgacatct gaggactctg cagtctattt ctgt               114

<210> SEQ ID NO 308
<211> LENGTH: 34
<212> TYPE: DNA
<213> ORGANISM: Mus musculus
<220> FEATURE:
<223> OTHER INFORMATION: CAN46G19; H, FR4

<400> SEQUENCE: 308
tggggccaag gcaccactct cacagtctcc tcag                                       34

<210> SEQ ID NO 309
<211> LENGTH: 319
<212> TYPE: DNA
<213> ORGANISM: Mus musculus
<220> FEATURE:
<223> OTHER INFORMATION: CAN46G24; K, variable region

<400> SEQUENCE: 309
gaaattgttc tcacccagtc tccagcaatc atgtctacat ctccagggga aaaggtcacc           60
atgtcctgca gtgccagctc aagtgtaact tacatgcact ggtaccagca gaagtcaatc          120
acctccccca aactctggat ttatgaaaca tccaaactgg cttctggagt ccccggtcgc          180
ttcagtggca gtgggtctgg aaactcttac tctctcacga tcagcagcat ggaggctgaa          240
gatgttgcca cttattactg ttttcagggg agtgggtacc cattcacgtt cggctcgggg          300
acaaagttgg aaataaaac                                                       319

<210> SEQ ID NO 310
```

```
<211> LENGTH: 15
<212> TYPE: DNA
<213> ORGANISM: Mus musculus
<220> FEATURE:
<223> OTHER INFORMATION: CAN46G24; K, CDR1

<400> SEQUENCE: 310
tcaagtgtaa cttac                                                    15

<210> SEQ ID NO 311
<211> LENGTH: 9
<212> TYPE: DNA
<213> ORGANISM: Mus musculus
<220> FEATURE:
<223> OTHER INFORMATION: CAN46G24; K, CDR2

<400> SEQUENCE: 311 gaaacatcc                                                            9

<210> SEQ ID NO 312
<211> LENGTH: 27
<212> TYPE: DNA
<213> ORGANISM: Mus musculus
<220> FEATURE:
<223> OTHER INFORMATION: CAN46G24; K, CDR3

<400> SEQUENCE: 312
tttcagggga gtgggtaccc attcacg                                       27

<210> SEQ ID NO 313
<211> LENGTH: 78
<212> TYPE: DNA
<213> ORGANISM: Mus musculus
<220> FEATURE:
<223> OTHER INFORMATION: CAN46G24; K, FR1

<400> SEQUENCE: 313
gaaattgttc tcacccagtc tccagcaatc atgtctacat ctccagggga aaaggtcacc   60
atgtcctgca gtgccagc                                                 78

<210> SEQ ID NO 314
<211> LENGTH: 51
<212> TYPE: DNA
<213> ORGANISM: Mus musculus
<220> FEATURE:
<223> OTHER INFORMATION: CAN46G24; K, FR2

<400> SEQUENCE: 314
atgcactggt accagcagaa gtcaatcacc tcccccaaac tctggattta t            51

<210> SEQ ID NO 315
<211> LENGTH: 108
<212> TYPE: DNA
<213> ORGANISM: Mus musculus
<220> FEATURE:
<223> OTHER INFORMATION: CAN46G24; K, FR3

<400> SEQUENCE: 315
aaactggctt ctggagtccc cggtcgcttc agtggcagtg ggtctggaaa ctcttactct   60
ctcacgatca gcagcatgga ggctgaagat gttgccactt attactgt               108

<210> SEQ ID NO 316
<211> LENGTH: 31
<212> TYPE: DNA
<213> ORGANISM: Mus musculus
```

```
<220> FEATURE:
<223> OTHER INFORMATION: CAN46G24; K, FR4

<400> SEQUENCE: 316
ttcggctcgg ggacaaagtt ggaaataaaa c                              31

<210> SEQ ID NO 317
<211> LENGTH: 352
<212> TYPE: DNA
<213> ORGANISM: Mus musculus
<220> FEATURE:
<223> OTHER INFORMATION: CAN46G24; H, variable region

<400> SEQUENCE: 317
gaggtccagc tgctacagtc tggccctgag ctggtgaagc ctgggacttc agtgaagata     60
tcctgcaagg cttctggtta ctcattcact ggctactaca tacactgggt gaagcagacc    120
catgtaaaga gccttgagtg ggttggacgt attttccctt acaatggtgc tgctagctac    180
aatcagaatt tcaagggcaa ggccaccttg actgtagata gtcctccag cacagcctac     240 atggagctcc acagcctgac atctgaggac tctgcagtct atttctgtgc aagatggtta    300
agggtctact ttgactactg gggccaaggc accactctca cagtctcctc ag            352

<210> SEQ ID NO 318
<211> LENGTH: 24
<212> TYPE: DNA
<213> ORGANISM: Mus musculus
<220> FEATURE:
<223> OTHER INFORMATION: CAN46G24; H, CDR1

<400> SEQUENCE: 318
ggttactcat tcactggcta ctac                                      24

<210> SEQ ID NO 319
<211> LENGTH: 24
<212> TYPE: DNA
<213> ORGANISM: Mus musculus
<220> FEATURE:
<223> OTHER INFORMATION: CAN46G24; H, CDR2

<400> SEQUENCE: 319
attttccctt acaatggtgc tgct                                      24

<210> SEQ ID NO 320
<211> LENGTH: 30
<212> TYPE: DNA
<213> ORGANISM: Mus musculus
<220> FEATURE:
<223> OTHER INFORMATION: CAN46G24; H, CDR3

<400> SEQUENCE: 320
gcaagatggt taagggtcta ctttgactac                                30

<210> SEQ ID NO 321
<211> LENGTH: 75
<212> TYPE: DNA
<213> ORGANISM: Mus musculus
<220> FEATURE:
<223> OTHER INFORMATION: CAN46G24; H, FR1

<400> SEQUENCE: 321
gaggtccagc tgctacagtc tggccctgag ctggtgaagc ctgggacttc agtgaagata     60
tcctgcaagg cttct                                                75
```

<210> SEQ ID NO 322
<211> LENGTH: 51
<212> TYPE: DNA
<213> ORGANISM: Mus musculus
<220> FEATURE:
<223> OTHER INFORMATION: CAN46G24; H, FR2

<400> SEQUENCE: 322
atacactggg tgaagcagac ccatgtaaag agccttgagt gggttggacg t          51

<210> SEQ ID NO 323
<211> LENGTH: 114
<212> TYPE: DNA
<213> ORGANISM: Mus musculus
<220> FEATURE:
<223> OTHER INFORMATION: CAN46G24; H, FR3

<400> SEQUENCE: 323
agctacaatc agaatttcaa gggcaaggcc accttgactg tagataagtc ctccagcaca    60
gcctacatgg agctccacag cctgacatct gaggactctg cagtctattt ctgt        114

<210> SEQ ID NO 324
<211> LENGTH: 34
<212> TYPE: DNA
<213> ORGANISM: Mus musculus
<220> FEATURE:
<223> OTHER INFORMATION: CAN46G24; H, FR4

<400> SEQUENCE: 324
tggggccaag gcaccactct cacagtctcc tcag                              34

<210> SEQ ID NO 325
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G4 Codon optimized; K, variable region

<400> SEQUENCE: 325
gaaaaggttc tcacccagtc tccagcaatc atgtctgcat ctccagggga agaggtcacc    60
atgacctgca gtgccagctc aagtgtaagt tacatgcatt ggtaccagca gaagtcaagc   120
acctccccca aactctggat ttatgaaaca tccaaactgg cttttggagt cccaggtcgc   180
ttcagtggca gtggatctgg aaactcttac tctctcacga tcagcagcat ggaggctgaa   240
gatgttgcca cttattactg ttttcagggg agtgggtacc cattcacgtt cggctcgggg   300
acaaagttgg aagtaaaac                                               319

<210> SEQ ID NO 326
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G4 Codon optimized; K, CDR1

<400> SEQUENCE: 326
tcaagtgtaa gttac                                                   15

<210> SEQ ID NO 327
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G4 Codon optimized; K, CDR2

<400> SEQUENCE: 327 gaaacatcc                                                                 9

<210> SEQ ID NO 328
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G4 Codon optimized; K, CDR3

<400> SEQUENCE: 328
tttcagggga gtgggtaccc attcacg                                            27

<210> SEQ ID NO 329
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G4 Codon optimized; K, FR1

<400> SEQUENCE: 329
gaaaaggttc tcacccagtc tccagcaatc atgtctgcat ctccagggga agaggtcacc         60
atgacctgca gtgccagc                                                      78

<210> SEQ ID NO 330
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G4 Codon optimized; K, FR2

<400> SEQUENCE: 330
atgcattggt accagcagaa gtcaagcacc tcccccaaac tctggattta t                 51

<210> SEQ ID NO 331
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G4 Codon optimized; K, FR3

<400> SEQUENCE: 331
aaactggctt ttggagtccc aggtcgcttc agtggcagtg gatctggaaa ctcttactct         60
ctcacgatca gcagcatgga ggctgaagat gttgccactt attactgt                    108

<210> SEQ ID NO 332
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CAN46G4 Codon optimized; K, FR4

<400> SEQUENCE: 332
ttcggctcgg ggacaaagtt ggaagtaaaa c                                31

<210> SEQ ID NO 333
<211> LENGTH: 325
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CAN46G13a Codon optimized; K, variable region

<400> SEQUENCE: 333
gaaaatgtgc tcacccagtc tccagcaata atggctgcct ctctggggca gaaggtcacc    60
atgacctgca gtgccagctc aagtgtaagt tccagttact tgcactggta ccagcagaag   120
tcaggcgctt cccccaaacc cttgattcat aggacatcca ccctggcttc tggcgtccca   180
gctcgcttca gtggcagtgg gtctgggacc tcttactctc tcacaatcag cagcgtggag   240
gctgaagatg atgcaactta ttactgccag cagtggagtg gttacccgta cacgttcgga   300
ggggggacca agctggaaat aaaac                                        325

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CAN46G13a Codon optimized; K, CDR1

<400> SEQUENCE: 334
tcaagtgtaa gttccagtta c                                           21

<210> SEQ ID NO 335
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CAN46G13a Codon optimized; K, CDR2

<400> SEQUENCE: 335 aggacatcc                                                          9

<210> SEQ ID NO 336
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CAN46G13a Codon optimized; K, CDR3

<400> SEQUENCE: 336
cagcagtgga gtggttaccc gtacacg                               27

<210> SEQ ID NO 337
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; K, FR1

<400> SEQUENCE: 337
gaaaatgtgc tcacccagtc tccagcaata atggctgcct ctctggggca gaaggtcacc    60
atgacctgca gtgccagc                                                 78

<210> SEQ ID NO 338
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; K, FR2

<400> SEQUENCE: 338
ttgcactggt accagcagaa gtcaggcgct tcccccaaac ccttgattca t             51

<210> SEQ ID NO 339
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G13a Codon optimized; K, FR3

<400> SEQUENCE: 339
accctggctt ctggcgtccc agctcgcttc agtggcagtg ggtctgggac ctcttactct    60
ctcacaatca gcagcgtgga ggctgaagat gatgcaactt attactgc                108

<210> SEQ ID NO 340
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; K, FR4

<400> SEQUENCE: 340
ttcggagggg ggaccaagct ggaaataaaa c                                   31

<210> SEQ ID NO 341
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G13a Codon optimized; H, variable region

<400> SEQUENCE: 341

```
gatgtgcagc ttcaggagtc aggacctggc ctggtgaaac cttctcagtc tctgtccctc    60
acctgcactg tcactggcta ctcaatcacc agtgattctg cctggaactg gattcggcag   120
tttccaggaa acaacctgga gtggatgggc tacataagct acagtggtag cactagctac   180
aacccatctc tcaaaagtcg aatctctatc actcgagaca catccaagaa ccagttcttc   240
ctgcagttga actctgtgac tactgaggac acagccacat attactgtgc aagaaggagt   300
agggtctcat tctactttga ctactggggc caaggcacca ctctcacagt ctcctcag    358
```

<210> SEQ ID NO 342
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, CDR1

<400> SEQUENCE: 342

```
ggctactcaa tcaccagtga ttctgcc                                        27
```

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, CDR2

<400> SEQUENCE: 343

```
ataagctaca gtggtagcac t                                              21
```

<210> SEQ ID NO 344
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, CDR3

<400> SEQUENCE: 344

```
gcaagaagga gtagggtctc attctacttt gactac                              36
```

<210> SEQ ID NO 345
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, FR1

<400> SEQUENCE: 345

```
gatgtgcagc ttcaggagtc aggacctggc ctggtgaaac cttctcagtc tctgtccctc    60
acctgcactg tcact                                                     75
```

<210> SEQ ID NO 346

<210> SEQ ID NO 346
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, FR2

<400> SEQUENCE: 346
tggaactgga ttcggcagtt tccaggaaac aacctggagt ggatgggcta c        51

<210> SEQ ID NO 347
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G13a Codon optimized; H, FR3

<400> SEQUENCE: 347
agctacaacc catctctcaa aagtcgaatc tctatcactc gagacacatc caagaaccag    60
ttcttcctgc agttgaactc tgtgactact gaggacacag ccacatatta ctgt          114

<210> SEQ ID NO 348
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G13a Codon optimized; H, FR4

<400> SEQUENCE: 348
tggggccaag gcaccactct cacagtctcc tcag        34

<210> SEQ ID NO 349
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G19 Codon optimized; K, variable region

<400> SEQUENCE: 349
gaaaatgttc tcacccagtc tccaacaatc atgtctgcat ctccagggga agaggtcacc    60
atgacctgca gtgccagctc aagtgtaact tacatgcact ggtaccagca gaagtcaatc    120
acctccccca aactctggat ttatgaaaca tccaaactgg cttctggagt cccaggtcgc    180
ttcagtggca gtgggtctgg aaactcttac tctctcacga tcagcagcat ggaggctgaa    240
gatgttgcca cttattactg ttttcagggg agtgggtacc cattcacgtt cggctcgggg    300
acaaagttgg aaataaaac                                                319

<210> SEQ ID NO 350
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: CAN46G19 Codon optimized; K, CDR1

<400> SEQUENCE: 350
tcaagtgtaa cttac                                                    15

<210> SEQ ID NO 351
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; K, CDR2

<400> SEQUENCE: 351 gaaacatcc                                                            9

<210> SEQ ID NO 352
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; K, CDR3

<400> SEQUENCE: 352
tttcagggga gtgggtaccc attcacg                                       27

<210> SEQ ID NO 353
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; K, FR1

<400> SEQUENCE: 353
gaaaatgttc tcacccagtc tccaacaatc atgtctgcat ctccagggga agaggtcacc   60
atgacctgca gtgccagc                                                 78

<210> SEQ ID NO 354
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; K, FR2

<400> SEQUENCE: 354
atgcactggt accagcagaa gtcaatcacc tcccccaaac tctggattta t             51

<210> SEQ ID NO 355
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G19 Codon optimized; K, FR3

<400> SEQUENCE: 355
aaactggctt ctggagtccc aggtcgcttc agtggcagtg ggtctggaaa ctcttactct    60
ctcacgatca gcagcatgga ggctgaagat gttgccactt attactgt                108

<210> SEQ ID NO 356
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; K, FR4

<400> SEQUENCE: 356
ttcggctcgg ggacaaagtt ggaaataaaa c                                    31

<210> SEQ ID NO 357
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G19 Codon optimized; H, variable region

<400> SEQUENCE: 357
gaggtccagc tgctacagtc tggccctgag ctggtgaagc ctgggacttc agtgaagata    60
tcctgcaagg cttctggtta ctcattcact ggctactaca ttcactgggt gaagcagacc   120
catgtaaaga gccttgagtg ggttggacgt attttttcct tacaatggtgc tgcaagctac   180 aaccagaatt caagggcaa ggccaccttg actgtagata gtcctccac cacagcctac    240 atggagctcc acagcctgac atctgaggac tctgcagtct atttctgtgc aagatggtta   300
agggtctact ttgactactg gggccaaggc accactctca cagtctcctc ag           352

<210> SEQ ID NO 358
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, CDR1

<400> SEQUENCE: 358
ggttactcat tcactggcta ctac                                            24

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, CDR2

<400> SEQUENCE: 359 attttttcctt acaatggtgc tgca                                           24

<210> SEQ ID NO 360
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, CDR3

<400> SEQUENCE: 360
gcaagatggt taagggtcta ctttgactac                                      30

<210> SEQ ID NO 361
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, FR1

<400> SEQUENCE: 361
gaggtccagc tgctacagtc tggccctgag ctggtgaagc ctgggacttc agtgaagata     60
tcctgcaagg cttct                                                      75

<210> SEQ ID NO 362
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, FR2

<400> SEQUENCE: 362
attcactggg tgaagcagac ccatgtaaag agccttgagt gggttggacg t              51

<210> SEQ ID NO 363
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G19 Codon optimized; H, FR3

<400> SEQUENCE: 363
agctacaacc agaatttcaa gggcaaggcc accttgactg tagataagtc ctccaccaca     60
gcctacatgg agctccacag cctgacatct gaggactctg cagtctattt ctgt          114

<210> SEQ ID NO 364
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G19 Codon optimized; H, FR4

<400> SEQUENCE: 364
tggggccaag gcaccactct cacagtctcc tcag                                 34

<210> SEQ ID NO 365
<211> LENGTH: 319
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G24 Codon optimized; K, variable region

<400> SEQUENCE: 365
gaaattgttc tcacccagtc tccagcaatc atgtctacat ctccagggga aaaggtcacc     60
atgtcctgca gtgccagctc aagtgtaact tacatgcact ggtaccagca gaagtcaatc    120
acctccccca aactctggat ttatgaaaca tccaaactgg cttctggagt ccccggtcgc    180
ttcagtggca gtgggtctgg aaactcttac tctctcacga tcagcagcat ggaggctgaa    240
gatgttgcca cttattactg ttttcagggg agtgggtacc cattcacgtt cggctcgggg    300
acaaagttgg aaataaaac                                                 319

<210> SEQ ID NO 366
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, CDR1

<400> SEQUENCE: 366
tcaagtgtaa cttac                                                      15

<210> SEQ ID NO 367
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, CDR2

<400> SEQUENCE: 367 gaaacatcc                                                              9

<210> SEQ ID NO 368
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, CDR3

<400> SEQUENCE: 368
tttcagggga gtgggtaccc attcacg                                         27

<210> SEQ ID NO 369
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, FR1

<400> SEQUENCE: 369
```
gaaattgttc tcacccagtc tccagcaatc atgtctacat ctccagggga aaaggtcacc    60
atgtcctgca gtgccagc                                                  78

<210> SEQ ID NO 370
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, FR2

<400> SEQUENCE: 370
atgcactggt accagcagaa gtcaatcacc tcccccaaac tctggattta t             51

<210> SEQ ID NO 371
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G24 Codon optimized; K, FR3

<400> SEQUENCE: 371
aaactggctt ctggagtccc cggtcgcttc agtggcagtg ggtctggaaa ctcttactct   60
ctcacgatca gcagcatgga ggctgaagat gttgccactt attactgt               108

<210> SEQ ID NO 372
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; K, FR4

<400> SEQUENCE: 372
ttcggctcgg ggacaaagtt ggaaataaaa c                                   31

<210> SEQ ID NO 373
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G24 Codon optimized; H, variable region

<400> SEQUENCE: 373
gaggtccagc tgctacagtc tggccctgag ctggtgaagc ctgggacttc agtgaagata   60
tcctgcaagg cttctggtta ctcattcact ggctactaca tacactgggt gaagcagacc  120
catgtaaaga gccttgagtg ggttggacgt attttttcctt acaatggtgc tgctagctac  180
aatcagaatt tcaagggcaa ggccaccttg actgtagata gtcctccag cacagcctac   240 atggagctcc acagcctgac atctgaggac tctgcagtct atttctgtgc aagatggtta  300
agggtctact ttgactactg gggccaaggc accactctca cagtctcctc ag          352

<210> SEQ ID NO 374

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, CDR1

<400> SEQUENCE: 374
ggttactcat tcactggcta ctac                                          24

<210> SEQ ID NO 375
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, CDR2

<400> SEQUENCE: 375
atttttcctt acaatggtgc tgct                                          24

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, CDR3

<400> SEQUENCE: 376
gcaagatggt taagggtcta ctttgactac                                    30

<210> SEQ ID NO 377
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, FR1

<400> SEQUENCE: 377
gaggtccagc tgctacagtc tggccctgag ctggtgaagc ctgggacttc agtgaagata   60
tcctgcaagg cttct                                                    75

<210> SEQ ID NO 378
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, FR2

<400> SEQUENCE: 378
atacactggg tgaagcagac ccatgtaaag agccttgagt gggttggacg t             51

<210> SEQ ID NO 379
<211> LENGTH: 114
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CAN46G24 Codon optimized; H, FR3

<400> SEQUENCE: 379

```
agctacaatc agaatttcaa gggcaaggcc accttgactg tagataagtc ctccagcaca    60
gcctacatgg agctccacag cctgacatct gaggactctg cagtctattt ctgt         114
```

<210> SEQ ID NO 380
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CAN46G24 Codon optimized; H, FR4

<400> SEQUENCE: 380

```
tggggccaag gcaccactct cacagtctcc tcag                                34
```

<210> SEQ ID NO 381
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a; K, variable region

<400> SEQUENCE: 381

```
gacatccaga tgacccagtc cccctcctcc ctgtccgcct ccgtgggcga ccgcgtgacc    60
atcacctgct ccgcctcctc ctccgtgtcc tcctcctacc tgcactggta ccagcagaag   120
cccggcaagg cccccaagct gctgatctac cgcacctcca ccctggcctc cggcgtgccc   180
tcccgcttct ccggctccgg ctccggcacc gacttcacct tcaccatctc ctccctgcag   240
cccgaggaca tcgccaccta ctactgccag cagtggtccg gctaccccta caccttcggc   300
cagggcacca aggtggagat caagc                                         325
```

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, CDR1

<400> SEQUENCE: 382

```
tcctccgtgt cctcctccta c                                              21
```

<210> SEQ ID NO 383
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, CDR2

```
<400> SEQUENCE: 383 cgcacctcc                                                                9

<210> SEQ ID NO 384
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, CDR3

<400> SEQUENCE: 384
cagcagtggt ccggctaccc ctacacc                                           27

<210> SEQ ID NO 385
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, FR1

<400> SEQUENCE: 385
gacatccaga tgacccagtc cccctcctcc ctgtccgcct ccgtgggcga ccgcgtgacc       60
atcacctgct ccgcctcc                                                    78

<210> SEQ ID NO 386
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, FR2

<400> SEQUENCE: 386
ctgcactggt accagcagaa gcccggcaag gcccccaagc tgctgatcta c                51

<210> SEQ ID NO 387
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a; K, FR3

<400> SEQUENCE: 387
accctggcct ccggcgtgcc ctcccgcttc tccggctccg gctccggcac cgacttcacc       60
ttcaccatct cctccctgca gcccgaggac atcgccacct actactgc                  108

<210> SEQ ID NO 388
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; K, FR4
```

```
<400> SEQUENCE: 388
ttcggccagg gcaccaaggt ggagatcaag c                              31

<210> SEQ ID NO 389
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a; H, variable region

<400> SEQUENCE: 389
caggtgcagc tgcaggagtc cggccccggc ctggtgaagc cctcccagac cctgtccctg    60
acctgcaccg tgtccggcgg ctccatctcc tccgactccg cctggaactg gatccgccag   120
ccccccggca agggcctgga gtggatcggc tacatctcct actccggctc cacctcctac   180
aaccccctcc cgaagtcccg cgtgaccatg tccgtggaca cctccaagaa ccagttctcc   240
ctgaaggtga actccgtgac cgccgccgac accgccgtgt actactgcgc ccgccgctcc   300
cgcgtgtcct ctacttcga ctactggggc cagggcaccc tggtgaccgt gtcctccg     358

<210> SEQ ID NO 390
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; H, CDR1

<400> SEQUENCE: 390
ggcggctcca tctcctccga ctccgcc                                   27

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; H, CDR2

<400> SEQUENCE: 391
atctcctact ccggctccac c                                         21

<210> SEQ ID NO 392
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; H, CDR3

<400> SEQUENCE: 392
gcccgccgct cccgcgtgtc cttctacttc gactac                         36

<210> SEQ ID NO 393
<211> LENGTH: 75
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: cdrCAN46G13a; H, FR1

<400> SEQUENCE: 393
caggtgcagc tgcaggagtc cggccccggc ctggtgaagc cctcccagac cctgtccctg    60
acctgcaccg tgtcc                                                    75

<210> SEQ ID NO 394
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; H, FR2

<400> SEQUENCE: 394
tggaactgga tccgccagcc ccccggcaag ggcctggagt ggatcggcta c             51

<210> SEQ ID NO 395
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a; H, FR3

<400> SEQUENCE: 395
tcctacaacc cctccctgaa gtcccgcgtg accatgtccg tggacacctc caagaaccag    60
ttctccctga aggtgaactc cgtgaccgcc gccgacaccg ccgtgtacta ctgc         114

<210> SEQ ID NO 396
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a; H, FR4

<400> SEQUENCE: 396
tggggccagg gcaccctggt gaccgtgtcc tccg                                34

<210> SEQ ID NO 397
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a; K, variable region

<400> SEQUENCE: 397
gagaacgtgc tgacccagtc cccctcctcc ctgtccgcct ccgtgggcga ccgcgtgacc    60
atgacctgct ccgcctcctc ctccgtgtcc tcctcctacc tgcactggta ccagcagaag   120
cccggcaagt cccccaagcc cctgatccac cgcacctcca ccctggcctc cggcgtgccc   180
tcccgcttct ccggctccgg ctccggcacc tcctactccc tgaccatctc ctccctgcag   240
```
cccgaggaca tcgccaccta ctactgccag cagtggtccg gctacccta caccttcggc    300 ggcggcacca aggtggagat caagc    325

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, CDR1

<400> SEQUENCE: 398
tcctccgtgt cctcctccta c    21

<210> SEQ ID NO 399
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, CDR2

<400> SEQUENCE: 399 cgcacctcc    9

<210> SEQ ID NO 400
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, CDR3

<400> SEQUENCE: 400
cagcagtggt ccggctaccc ctacacc    27

<210> SEQ ID NO 401
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, FR1

<400> SEQUENCE: 401
gagaacgtgc tgacccagtc cccctcctcc ctgtccgcct ccgtgggcga ccgcgtgacc    60
atgacctgct ccgcctcc    78

<210> SEQ ID NO 402
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, FR2

<400> SEQUENCE: 402
ctgcactggt accagcagaa gcccggcaag tcccccaagc ccctgatcca c    51

<210> SEQ ID NO 403
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a; K, FR3

<400> SEQUENCE: 403
accctggcct ccggcgtgcc ctcccgcttc tccggctccg gctccggcac ctcctactcc    60
ctgaccatct cctccctgca gcccgaggac atcgccacct actactgc    108

<210> SEQ ID NO 404
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; K, FR4

<400> SEQUENCE: 404
ttcggcggcg gcaccaaggt ggagatcaag c    31

<210> SEQ ID NO 405
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a; H, variable region

<400> SEQUENCE: 405
caggtgcagc tgcaggagtc cggccccggc ctggtgaagc cctcccagac cctgtccctg    60
acctgcaccg tgaccggcta ctccatcacc tccgactccg cctggaactg gatccgccag    120
ttccccggca caacctgga gtggatgggc tacatctcct actccggctc cacctcctac    180
aaccnctccc tgaagtcccg catctccatc acccgcgaca cctccaagaa ccagttctcc    240
ctgaaggtga actccgtgac cgccgccgac accgccgtgt actactgcgc ccgccgctcc    300
cgcgtgtcct tctacttcga ctactggggc cagggcaccc tggtgaccgt gtcctccg    358

<210> SEQ ID NO 406
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; H, CDR1

<400> SEQUENCE: 406
ggctactcca tcacctccga ctccgcc    27

<210> SEQ ID NO 407
<211> LENGTH: 21
<212> TYPE: DNA

<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G13a; H, CDR2

<400> SEQUENCE: 407
atctcctact ccggctccac c                                           21

<210> SEQ ID NO 408
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G13a; H, CDR3

<400> SEQUENCE: 408
gcccgccgct cccgcgtgtc cttctacttc gactac                           36

<210> SEQ ID NO 409
<211> LENGTH: 75
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G13a; H, FR1

<400> SEQUENCE: 409
caggtgcagc tgcaggagtc cggccccggc ctggtgaagc cctcccagac cctgtccctg   60
acctgcaccg tgacc                                                   75

<210> SEQ ID NO 410
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G13a; H, FR2

<400> SEQUENCE: 410
tggaactgga tccgccagtt ccccggcaac aacctggagt ggatgggcta c           51

<210> SEQ ID NO 411
<211> LENGTH: 114
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: huCAN46G13a; H, FR3

<400> SEQUENCE: 411
tcctacaacc cctccctgaa gtcccgcatc tccatcaccc gcgacacctc caagaaccag   60
ttctccctga aggtgaactc cgtgaccgcc gccgacaccg ccgtgtacta ctgc        114

<210> SEQ ID NO 412
<211> LENGTH: 34
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a; H, FR4

<400> SEQUENCE: 412
tggggccagg gcaccctggt gaccgtgtcc tccg                                 34

<210> SEQ ID NO 413
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a; K, variable region

<400> SEQUENCE: 413
gagaacgtgc tgacccagtc ccctcctcc atgtccgcct ccgtgggcga ccgcgtgacc     60
atgacctgct ccgcctcctc ctccgtgtcc tcctcctacc tgcactggta ccagcagaag   120
cccggcaagg cccccaagcc cctgatccac cgcacctcca ccctggcctc cggcgtgccc   180
tcccgcttct ccggctccgg ctccggcacc tcctactccc tgaccatctc ctccgtgcag   240
cccgaggaca cgccaccta ctactgccag cagtggtccg gctacccta caccttcggc     300 ggcggcacca aggtggagat caagc                                          325

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; K, CDR1

<400> SEQUENCE: 414
tcctccgtgt cctcctccta c                                              21

<210> SEQ ID NO 415
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; K, CDR2

<400> SEQUENCE: 415 cgcacctcc                                                             9

<210> SEQ ID NO 416
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; K, CDR3

<400> SEQUENCE: 416

```
cagcagtggt ccggctaccc ctacacc                                        27
```

<210> SEQ ID NO 417
<211> LENGTH: 78
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G13a; K, FR1

<400> SEQUENCE: 417

```
gagaacgtgc tgacccagtc cccctcctcc atgtccgcct ccgtgggcga ccgcgtgacc    60
atgacctgct ccgcctcc                                                  78
```

<210> SEQ ID NO 418
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G13a; K, FR2

<400> SEQUENCE: 418

```
ctgcactggt accagcagaa gcccggcaag gcccccaagc ccctgatcca c             51
```

<210> SEQ ID NO 419
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G13a; K, FR3

<400> SEQUENCE: 419

```
accctggcct ccggcgtgcc ctcccgcttc tccggctccg gctccggcac ctcctactcc    60
ctgaccatct cctccgtgca gcccgaggac atcgccacct actactgc                108
```

<210> SEQ ID NO 420
<211> LENGTH: 31
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G13a; K, FR4

<400> SEQUENCE: 420

```
ttcggcggcg gcaccaaggt ggagatcaag c                                   31
```

<210> SEQ ID NO 421
<211> LENGTH: 358
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G13a; H, variable region

<400> SEQUENCE: 421

```
caggtgcagc tgcaggagtc cggccccggc ctggtgaagc cctcccagac cctgtccctg    60
acctgcaccg tgaccggcta ctccatcacc tccgactccg cctggaactg gatccgccag   120
ccccccggca acggcctgga gtggatgggc tacatctcct actccggctc cacctcctac   180
aaccctcccc tgaagtcccg catctccatc acccgcgaca cctccaagaa ccagttctcc   240
ctgaagctga actccgtgac cgccgccgac accgccacct actactgcgc ccgccgctcc   300
cgcgtgtcct tctacttcga ctactggggc cagggcaccc tggtgaccgt gtcctccg    358
```

<210> SEQ ID NO 422
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; H, CDR1

<400> SEQUENCE: 422

```
ggctactcca tcacctccga ctccgcc                                         27
```

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; H, CDR2

<400> SEQUENCE: 423

```
atctcctact ccggctccac c                                               21
```

<210> SEQ ID NO 424
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; H, CDR3

<400> SEQUENCE: 424

```
gcccgccgct cccgcgtgtc cttctacttc gactac                               36
```

<210> SEQ ID NO 425
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; H, FR1

<400> SEQUENCE: 425

```
caggtgcagc tgcaggagtc cggccccggc ctggtgaagc cctcccagac cctgtccctg    60
acctgcaccg tgacc                                                      75
```

<210> SEQ ID NO 426
<211> LENGTH: 51
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: rehuCAN46G13a; H, FR2

<400> SEQUENCE: 426
tggaactgga tccgccagcc ccccggcaac ggcctggagt ggatgggcta c            51

<210> SEQ ID NO 427
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a; H, FR3

<400> SEQUENCE: 427
tcctacaacc cctccctgaa gtcccgcatc tccatcaccc gcgacacctc caagaaccag    60
ttctccctga agctgaactc cgtgaccgcc gccgacaccg ccacctacta ctgc         114

<210> SEQ ID NO 428
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a; H, FR4

<400> SEQUENCE: 428
tggggccagg gcaccctggt gaccgtgtcc tccg                               34

<210> SEQ ID NO 429
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19; K, variable region

<400> SEQUENCE: 429
gacatccaga tgacccagtc cccctcctcc ctgtccgcct ccgtgggcga ccgcgtgacc    60
atcacctgct ccgcctcctc ctccgtgacc tacatgcact ggtaccagca gaagcccggc   120
aaggccccca gctgctgat ctacgagacc tccaagctgg cctccggcgt gccctcccgc    180
ttctccggct ccggctccgg caccgactac accttcacca tctcctccct gcagcccgag   240
gacatcgcca cctactactg cttccagggc tccggctacc ccttcacctt cggccagggc   300
accaaggtgg agatcaagc                                               319

<210> SEQ ID NO 430
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, CDR1

<400> SEQUENCE: 430
```
tcctccgtga cctac                                                          15

<210> SEQ ID NO 431
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, CDR2

<400> SEQUENCE: 431 gagacctcc                                                                  9

<210> SEQ ID NO 432
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, CDR3

<400> SEQUENCE: 432
ttccagggct ccggctaccc cttcacc                                              27

<210> SEQ ID NO 433
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, FR1

<400> SEQUENCE: 433
gacatccaga tgacccagtc cccctcctcc ctgtccgcct ccgtgggcga ccgcgtgacc          60
atcacctgct ccgcctcc                                                       78

<210> SEQ ID NO 434
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, FR2

<400> SEQUENCE: 434
atgcactggt accagcagaa gcccggcaag gcccccaagc tgctgatcta c                  51

<210> SEQ ID NO 435
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19; K, FR3

<400> SEQUENCE: 435
aagctggcct ccggcgtgcc ctcccgcttc tccggctccg gctccggcac cgactacacc          60

```
ttcaccatct cctccctgca gcccgaggac atcgccacct actactgc        108
```

<210> SEQ ID NO 436
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; K, FR4

<400> SEQUENCE: 436

```
ttcggccagg gcaccaaggt ggagatcaag c                           31
```

<210> SEQ ID NO 437
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19; H, variable region

<400> SEQUENCE: 437

```
caggtgcagc tggtgcagtc cggcgccgag gtgaagaagc ccggcgagtc cgtgaaggtg    60
tcctgcaagg cctccggcta caccttcacc ggctactaca tccactgggt gcgccaggcc   120
cccggccagg gcctggagtg gatgggccgc atcttcccct acaacggcgc cgcctcctac   180
aaccagaact tcaagggccg cgtgaccatc accgccgaca gtccacctc caccgcctac    240 atggagctgt cctccctgcg ctccgaggac accgccgtgt actactgcgc ccgctggctg   300
cgcgtgtact cgactactg gggccagggc accaccgtga ccgtgtcctc cg            352
```

<210> SEQ ID NO 438
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; H, CDR1

<400> SEQUENCE: 438

```
ggctacacct tcaccggcta ctac                                   24
```

<210> SEQ ID NO 439
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; H, CDR2

<400> SEQUENCE: 439

```
atcttcccct acaacggcgc cgcc                                   24
```

<210> SEQ ID NO 440
<211> LENGTH: 30
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: cdrCAN46G19; H, CDR3

<400> SEQUENCE: 440
gcccgctggc tgcgcgtgta cttcgactac                                      30

<210> SEQ ID NO 441
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; H, FR1

<400> SEQUENCE: 441
caggtgcagc tggtgcagtc cggcgccgag gtgaagaagc ccggcgagtc cgtgaaggtg     60
tcctgcaagg cctcc                                                      75

<210> SEQ ID NO 442
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; H, FR2

<400> SEQUENCE: 442
atccactggg tgcgccaggc ccccggccag ggcctggagt ggatgggccg c              51

<210> SEQ ID NO 443
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19; H, FR3

<400> SEQUENCE: 443
tcctacaacc agaacttcaa gggccgcgtg accatcaccg ccgacaagtc cacctccacc     60
gcctacatgg agctgtcctc cctgcgctcc gaggacaccg ccgtgtacta ctgc          114

<210> SEQ ID NO 444
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19; H, FR4

<400> SEQUENCE: 444
tggggccagg gcaccaccgt gaccgtgtcc tccg                                 34

<210> SEQ ID NO 445
<211> LENGTH: 318
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<223> OTHER INFORMATION: huCAN46G19; K, variable region

<400> SEQUENCE: 445
gagaacgtgc tgacccagtc ccctcctcc ctgtccgcct ccgtgggcga ccgcgtgacc      60
atcacctgct ccgcctcctc ctccgtgacc tacatgcact ggtaccagca gaagcccggc     120
aaggccccca agctgtggat ctacgagacc tccaagctgg cctccggcgt gcccggccgc    180
ttctccggct ccggctccgg caactcctac accttcacca tctcctccct gcagcccgag    240
gacatcgcca cctactactg cttccagggc tccggctacc ccttcacctt cggccagggc    300
accaaggtgg agatcaag                                                   318

<210> SEQ ID NO 446
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; K, CDR1

<400> SEQUENCE: 446
tcctccgtga cctac                                                      15

<210> SEQ ID NO 447
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; K, CDR2

<400> SEQUENCE: 447 gagacctcc                                                              9

<210> SEQ ID NO 448
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; K, CDR3

<400> SEQUENCE: 448
ttccagggct ccggctaccc cttcacc                                         27

<210> SEQ ID NO 449
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; K, FR1

<400> SEQUENCE: 449
gagaacgtgc tgacccagtc ccctcctcc ctgtccgcct ccgtgggcga ccgcgtgacc      60
```
atcacctgct ccgcctcc					78

<210> SEQ ID NO 450
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G19; K, FR2

<400> SEQUENCE: 450
atgcactggt accagcagaa gcccggcaag gcccccaagc tgtggatcta c				51

<210> SEQ ID NO 451
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: huCAN46G19; K, FR3

<400> SEQUENCE: 451
aagctggcct ccggcgtgcc cggccgcttc tccggctccg gctccggcaa ctcctacacc			60 ttcaccatct cctccctgca gcccgaggac atcgccacct actactgc					108

<210> SEQ ID NO 452
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G19; K, FR4

<400> SEQUENCE: 452
ttcggccagg gcaccaaggt ggagatcaag							30

<210> SEQ ID NO 453
<211> LENGTH: 352
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: huCAN46G19; H, variable region

<400> SEQUENCE: 453
gaggtgcagc tggtgcagtc cggcgccgag gtgaagaagc ccggcgagtc cgtgaaggtg			60 tcctgcaagg cctccggcta ctccttcacc ggctactaca tccactgggt gaagcaggcc			120 cccggccagg gcctggagtg ggtgggccgc atcttcccct acaacggcgc cgcctcctac			180 aaccagaact tcaagggcaa ggccaccctg accgtggaca gtcctccac caccgcctac			240 atggagctgt cctccctgcg ctccgaggac accgccgtgt acttctgcgc ccgctggctg			300 cgcgtgtact cgactactg ggccagggc accaccgtga ccgtgtcctc cg				352

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, CDR1

<400> SEQUENCE: 454
ggctactcct tcaccggcta ctac                                              24

<210> SEQ ID NO 455
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, CDR2

<400> SEQUENCE: 455
atcttcccct acaacggcgc cgcc                                              24

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, CDR3

<400> SEQUENCE: 456
gcccgctggc tgcgcgtgta cttcgactac                                        30

<210> SEQ ID NO 457
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, FR1

<400> SEQUENCE: 457
gaggtgcagc tggtgcagtc cggcgccgag gtgaagaagc ccggcgagtc cgtgaaggtg       60
tcctgcaagg cctcc                                                        75

<210> SEQ ID NO 458
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, FR2

<400> SEQUENCE: 458
atccactggg tgaagcaggc ccccggccag ggcctggagt gggtgggccg c                51

<210> SEQ ID NO 459
<211> LENGTH: 114
<212> TYPE: DNA
<213> ORGANISM: Artificial Sequence
<220> FEATURE:
<223> OTHER INFORMATION: Description of Artificial Sequence: Synthetic

```
            polynucleotide
<220> FEATURE:
<223> OTHER INFORMATION: huCAN46G19; H, FR3

<400> SEQUENCE: 459
tcctacaacc agaacttcaa gggcaaggcc accctgaccg tggacaagtc ctccaccacc    60
gcctacatgg agctgtcctc cctgcgctcc gaggacaccg ccgtgtactt ctgc          114

<210> SEQ ID NO 460
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19; H, FR4

<400> SEQUENCE: 460
tggggccagg gcaccaccgt gaccgtgtcc tccg                                 34

<210> SEQ ID NO 461
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19; K, variable region

<400> SEQUENCE: 461
gagaacgtgc tgacccagtc ccctcctcc atgtccgcct ccgtgggcga ccgcgtgacc     60
atgacctgct ccgcctcctc ctccgtgacc tacatgcact ggtaccagca gaagcccggc   120
aagtccccca agctgtggat ctacgagacc tccaagctgg cctccggcgt gccctcccgc   180
ttctccggct ccggctccgg caacgactac tccctgacca tctcctccat gcagcccgag   240
gacgtggcca cctactactg cttccagggc tccggctacc ccttcacctt cggccagggc   300
accaagctgg agatcaagc                                                 319

<210> SEQ ID NO 462
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; K, CDR1

<400> SEQUENCE: 462
tcctccgtga cctac                                                     15

<210> SEQ ID NO 463
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; K, CDR2

<400> SEQUENCE: 463 gagacctcc                                                             9
```

<210> SEQ ID NO 464
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G19; K, CDR3

<400> SEQUENCE: 464
ttccagggct ccggctaccc cttcacc                                         27

<210> SEQ ID NO 465
<211> LENGTH: 78
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G19; K, FR1

<400> SEQUENCE: 465
gagaacgtgc tgacccagtc ccctcctcc atgtccgcct ccgtgggcga ccgcgtgacc        60
atgacctgct ccgcctcc                                                    78

<210> SEQ ID NO 466
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G19; K, FR2

<400> SEQUENCE: 466
atgcactggt accagcagaa gcccggcaag tcccccaagc tgtggatcta c               51

<210> SEQ ID NO 467
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G19; K, FR3

<400> SEQUENCE: 467
aagctggcct ccggcgtgcc ctcccgcttc tccggctccg gctccggcaa cgactactcc       60
ctgaccatct cctccatgca gcccgaggac gtggccacct actactgc                  108

<210> SEQ ID NO 468
<211> LENGTH: 31
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G19; K, FR4

<400> SEQUENCE: 468
ttcggccagg gcaccaagct ggagatcaag c                                    31

<210> SEQ ID NO 469
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19; H, variable region

<400> SEQUENCE: 469
gaggtgcagc tggtgcagtc cggcgccgag gtggtgaagc ccggcgagtc cgtgaagatc      60
tcctgcaagg cctccggcta ctccttcacc ggctactaca tccactgggt gaagcagacc     120
cccggccagt ccctggagtg ggtgggccgc atcttcccct acaacggcgc cgcctcctac     180
aaccagaact tcaagggcaa ggccaccctg accgtggaca gtccaccac caccgcctac     240 atggagctgt cctccctgcg ctccgaggac tccgccgtgt acttctgcgc ccgctggctg     300
cgcgtgtact cgactactg gggccagggc accaccctga ccgtgtcctc cg             352

<210> SEQ ID NO 470
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; H, CDR1

<400> SEQUENCE: 470
ggctactcct tcaccggcta ctac                                              24

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; H, CDR2

<400> SEQUENCE: 471
atcttcccct acaacggcgc cgcc                                              24

<210> SEQ ID NO 472
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; H, CDR3

<400> SEQUENCE: 472
gcccgctggc tgcgcgtgta cttcgactac                                        30

<210> SEQ ID NO 473
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: rehuCAN46G19; H, FR1

<400> SEQUENCE: 473
gaggtgcagc tggtgcagtc cggcgccgag gtggtgaagc ccggcgagtc cgtgaagatc    60
tcctgcaagg cctcc                                                    75

<210> SEQ ID NO 474
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; H, FR2

<400> SEQUENCE: 474
atccactggg tgaagcagac ccccggccag tccctggagt gggtgggccg c             51

<210> SEQ ID NO 475
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19; H, FR3

<400> SEQUENCE: 475
tcctacaacc agaacttcaa gggcaaggcc accctgaccg tggacaagtc caccaccacc    60
gcctacatgg agctgtcctc cctgcgctcc gaggactccg ccgtgtactt ctgc         114

<210> SEQ ID NO 476
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19; H, FR4

<400> SEQUENCE: 476
tggggccagg gcaccaccct gaccgtgtcc tccg                                34

<210> SEQ ID NO 477
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24; K, variable region

<400> SEQUENCE: 477
gacatccaga tgacccagtc cccctcctcc ctgtccgcct ccgtgggcga ccgcgtgacc    60
atcacctgct ccgcctcctc ctccgtgacc tacatgcact ggtaccagca gaagcccggc   120
aaggccccca gctgctgat ctacgagacc tccaagctgg cctccggcgt gccctcccgc   180
ttctccggct ccggctccgg caccgactac accttcacca tctcctccct gcagcccgag   240
gacatcgcca cctactactg cttccagggc tccggctacc ccttcacctt cggccagggc   300
```

```
accaaggtgg agatcaagc                                              319
```

<210> SEQ ID NO 478
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, CDR1

<400> SEQUENCE: 478

```
tcctccgtga cctac                                                   15
```

<210> SEQ ID NO 479
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, CDR2

<400> SEQUENCE: 479

```
gagacctcc                                                           9
```

<210> SEQ ID NO 480
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, CDR3

<400> SEQUENCE: 480

```
ttccagggct ccggctaccc cttcacc                                      27
```

<210> SEQ ID NO 481
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, FR1

<400> SEQUENCE: 481

```
gacatccaga tgacccagtc cccctcctcc ctgtccgcct ccgtgggcga ccgcgtgacc   60
atcacctgct ccgcctcc                                                78
```

<210> SEQ ID NO 482
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, FR2

<400> SEQUENCE: 482

```
atgcactggt accagcagaa gcccggcaag gcccccaagc tgctgatcta c            51
```

<210> SEQ ID NO 483
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24; K, FR3

<400> SEQUENCE: 483
aagctggcct ccggcgtgcc ctcccgcttc tccggctccg gctccggcac cgactacacc    60
ttcaccatct cctccctgca gcccgaggac atcgccacct actactgc                108

<210> SEQ ID NO 484
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; K, FR4

<400> SEQUENCE: 484
ttcggccagg gcaccaaggt ggagatcaag c                                    31

<210> SEQ ID NO 485
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24; H, variable region

<400> SEQUENCE: 485
caggtgcagc tggtgcagtc cggcgccgag gtgaagaagc ccggcgagtc cgtgaaggtg    60
tcctgcaagg cctccggcta caccttcacc ggctactaca tccactgggt gcgccaggcc   120
cccggccagg gcctggagtg gatgggccgc atcttcccct acaacggcgc cgcctcctac   180
aaccagaact tcaagggccg cgtgaccatc accgccgaca gtccacctc caccgcctac   240 atggagctgt cctccctgcg ctccgaggac accgccgtgt actactgcgc ccgctggctg   300
cgcgtgtact cgactactg gggccagggc accaccgtga ccgtgtcctc cg            352

<210> SEQ ID NO 486
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; H, CDR1

<400> SEQUENCE: 486
ggctacacct tcaccggcta ctac                                            24

<210> SEQ ID NO 487
<211> LENGTH: 24
<212> TYPE: DNA
<213> ORGANISM: Artificial Sequence
<220> FEATURE:
<223> OTHER INFORMATION: Description of Artificial Sequence: Synthetic

```
    oligonucleotide
<220> FEATURE:
<223> OTHER INFORMATION: cdrCAN46G24; H, CDR2

<400> SEQUENCE: 487
atcttcccct acaacggcgc cgcc                                              24

<210> SEQ ID NO 488
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; H, CDR3

<400> SEQUENCE: 488
gcccgctggc tgcgcgtgta cttcgactac                                        30

<210> SEQ ID NO 489
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; H, FR1

<400> SEQUENCE: 489
caggtgcagc tggtgcagtc cggcgccgag gtgaagaagc ccggcgagtc cgtgaaggtg       60
tcctgcaagg cctcc                                                        75

<210> SEQ ID NO 490
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24; H, FR2

<400> SEQUENCE: 490
atccactggg tgcgccaggc ccccggccag ggcctggagt ggatgggccg c                51

<210> SEQ ID NO 491
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24; H, FR3

<400> SEQUENCE: 491
tcctacaacc agaacttcaa gggccgcgtg accatcaccg ccgacaagtc cacctccacc       60
gcctacatgg agctgtcctc cctgcgctcc gaggacaccg ccgtgtacta ctgc            114

<210> SEQ ID NO 492
<211> LENGTH: 34
<212> TYPE: DNA
<213> ORGANISM: Artificial Sequence
<220> FEATURE:
<223> OTHER INFORMATION: Description of Artificial Sequence: Synthetic
```

```
              oligonucleotide
<220> FEATURE:
<223> OTHER INFORMATION: cdrCAN46G24; H, FR4

<400> SEQUENCE: 492
tggggccagg gcaccaccgt gaccgtgtcc tccg                                34

<210> SEQ ID NO 493
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24; K, variable region

<400> SEQUENCE: 493
gagatcgtgc tgacccagtc cccctcctcc ctgtccacct ccgtgggcga ccgcgtgacc     60
atctcctgct ccgcctcctc ctccgtgacc tacatgcact ggtaccagca gaagcccggc   120
aaggccccca agctgtggat ctacgagacc tccaagctgg cctccggcgt gcccggccgc   180
ttctccggct ccggctccgg caactcctac accttcacca tctcctccct gcagcccgag   240
gacatcgcca cctactactg cttccagggc tccggctacc ccttcacctt cggccagggc   300
accaaggtgg agatcaagc                                                319

<210> SEQ ID NO 494
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, CDR1

<400> SEQUENCE: 494
tcctccgtga cctac                                                    15

<210> SEQ ID NO 495
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, CDR2

<400> SEQUENCE: 495 gagacctcc                                                            9

<210> SEQ ID NO 496
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, CDR3

<400> SEQUENCE: 496
ttccagggct ccggctaccc cttcacc                                       27
```

```
<210> SEQ ID NO 497
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, FR1

<400> SEQUENCE: 497
gagatcgtgc tgacccagtc cccctcctcc ctgtccacct ccgtgggcga ccgcgtgacc    60
atctcctgct ccgcctcc                                                  78

<210> SEQ ID NO 498
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, FR2

<400> SEQUENCE: 498
atgcactggt accagcagaa gcccggcaag gcccccaagc tgtggatcta c             51

<210> SEQ ID NO 499
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24; K, FR3

<400> SEQUENCE: 499
aagctggcct ccggcgtgcc cggccgcttc tccggctccg gctccggcaa ctcctacacc    60
ttcaccatct cctccctgca gcccgaggac atcgccacct actactgc                108

<210> SEQ ID NO 500
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; K, FR4

<400> SEQUENCE: 500
ttcggccagg gcaccaaggt ggagatcaag c                                   31

<210> SEQ ID NO 501
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24; H, variable region

<400> SEQUENCE: 501
gaggtgcagc tggtgcagtc cggcgccgag gtgaagaagc ccggcgagtc cgtgaaggtg    60
tcctgcaagg cctccggcta ctccttcacc ggctactaca tccactgggt gaagcaggcc   120
```

```
cccggccagg gcctggagtg ggtgggccgc atcttcccct acaacggcgc cgcctcctac    180
aaccagaact tcaagggcaa ggccaccctg accgtggaca gtcctcctc caccgcctac     240 atggagctgt cctccctgcg ctccgaggac accgccgtgt acttctgcgc ccgctggctg    300
cgcgtgtact cgactactg gggccagggc accaccgtga ccgtgtcctc cg             352

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; H, CDR1

<400> SEQUENCE: 502
ggctactcct tcaccggcta ctac                                            24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; H, CDR2

<400> SEQUENCE: 503
atcttcccct acaacggcgc cgcc                                            24

<210> SEQ ID NO 504
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; H, CDR3

<400> SEQUENCE: 504
gcccgctggc tgcgcgtgta cttcgactac                                      30

<210> SEQ ID NO 505
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; H, FR1

<400> SEQUENCE: 505
gaggtgcagc tggtgcagtc cggcgccgag gtgaagaagc ccggcgagtc cgtgaaggtg    60
tcctgcaagg cctcc                                                      75

<210> SEQ ID NO 506
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: huCAN46G24; H, FR2

<400> SEQUENCE: 506
atccactggg tgaagcaggc ccccggccag ggcctggagt gggtgggccg c        51

<210> SEQ ID NO 507
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24; H, FR3

<400> SEQUENCE: 507
tcctacaacc agaacttcaa gggcaaggcc accctgaccg tggacaagtc ctcctccacc        60
gcctacatgg agctgtcctc cctgcgctcc gaggacaccg ccgtgtactt ctgc             114

<210> SEQ ID NO 508
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24; H, FR4

<400> SEQUENCE: 508
tggggccagg gcaccaccgt gaccgtgtcc tccg        34

<210> SEQ ID NO 509
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24; K, variable region

<400> SEQUENCE: 509
gagatcgtgc tgacccagtc cccctcctcc atgtccacct ccgtgggcga ccgcgtgacc        60
atgtcctgct ccgcctcctc ctccgtgacc tacatgcact ggtaccagca gaagcccggc       120
aagtccccca agctgtggat ctacgagacc tccaagctgg cctccggcgt gccctcccgc       180
ttctccggct ccggctccgg caacgactac tccctgacca tctcctccat gcagcccgag       240
gacgtggcca cctactactg cttccagggc tccggctacc ccttcacctt cggccagggc       300
accaagctgg agatcaagc                                                   319

<210> SEQ ID NO 510
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; K, CDR1

<400> SEQUENCE: 510
tcctccgtga cctac        15
```

<210> SEQ ID NO 511
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24; K, CDR2

<400> SEQUENCE: 511 gagacctcc                                                                    9

<210> SEQ ID NO 512
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24; K, CDR3

<400> SEQUENCE: 512
ttccagggct ccggctaccc cttcacc                                                27

<210> SEQ ID NO 513
<211> LENGTH: 78
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24; K, FR1

<400> SEQUENCE: 513
gagatcgtgc tgacccagtc cccctcctcc atgtccacct ccgtgggcga ccgcgtgacc          60
atgtcctgct ccgcctcc                                                         78

<210> SEQ ID NO 514
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24; K, FR2

<400> SEQUENCE: 514
atgcactggt accagcagaa gcccggcaag tcccccaagc tgtggatcta c                   51

<210> SEQ ID NO 515
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G24; K, FR3

<400> SEQUENCE: 515
aagctggcct ccggcgtgcc ctcccgcttc tccggctccg gctccggcaa cgactactcc          60
ctgaccatct cctccatgca gcccgaggac gtggccacct actactgc                      108

```
<210> SEQ ID NO 516
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; K, FR4

<400> SEQUENCE: 516
ttcggccagg gcaccaagct ggagatcaag c                                    31

<210> SEQ ID NO 517
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24; H, variable region

<400> SEQUENCE: 517
gaggtgcagc tggtgcagtc cggcgccgag gtggtgaagc ccggcgagtc cgtgaagatc      60
tcctgcaagg cctccggcta ctccttcacc ggctactaca tccactgggt gaagcagacc     120
cccggccagt ccctggagtg gtgggccgc atcttcccct acaacggcgc cgcctcctac      180
aaccagaact tcaagggcaa ggccaccctg accgtggaca gtccacctc caccgcctac      240 atggagctgt cctccctgcg ctccgaggac tccgccgtgt acttctgcgc ccgctggctg     300
cgcgtgtact cgactactg gggccagggc accaccctga ccgtgtcctc cg              352

<210> SEQ ID NO 518
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; H, CDR1

<400> SEQUENCE: 518
ggctactcct tcaccggcta ctac                                            24

<210> SEQ ID NO 519
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; H, CDR2

<400> SEQUENCE: 519
atcttcccct acaacggcgc cgcc                                            24

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: rehuCAN46G24; H, CDR3

<400> SEQUENCE: 520
gcccgctggc tgcgcgtgta cttcgactac                                              30

<210> SEQ ID NO 521
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; H, FR1

<400> SEQUENCE: 521
gaggtgcagc tggtgcagtc cggcgccgag gtggtgaagc cggcgagtc cgtgaagatc              60 tcctgcaagg cctcc                                                              75

<210> SEQ ID NO 522
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; H, FR2

<400> SEQUENCE: 522
atccactggg tgaagcagac ccccggccag tccctggagt gggtgggccg c                      51

<210> SEQ ID NO 523
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24; H, FR3

<400> SEQUENCE: 523
tcctacaacc agaacttcaa gggcaaggcc accctgaccg tggacaagtc cacctccacc             60
gcctacatgg agctgtcctc cctgcgctcc gaggactccg ccgtgtactt ctgc                  114

<210> SEQ ID NO 524
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24; H, FR4

<400> SEQUENCE: 524
tggggccagg gcaccaccct gaccgtgtcc tccg                                         34

<210> SEQ ID NO 525
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: cdrCAN46G13a Codon Optimized; K, variable
      region

<400> SEQUENCE: 525
gacattcaga tgactcagtc tccctcctcc ctgtctgctt ccgtggggga ccgcgtcact    60
attacctgtt ccgcttcctc ctccgtcagc tcctcttacc tgcactggta tcagcagaag   120
ccaggaaaag cccccaagct gctgatctac cggacctcca cactggcttc tggcgtgccc   180
agtagattct ctggcagtgg gtcaggaaca gacttcactt ttaccatcag ttcactgcag   240
cctgaggata ttgccactta ctattgccag cagtggagcg gctacccata tacctttggc   300
caggggacaa aagtggagat caaga                                         325

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, CDR1

<400> SEQUENCE: 526
tcctccgtca gctcctctta c                                              21

<210> SEQ ID NO 527
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, CDR2

<400> SEQUENCE: 527 cggacctcc                                                             9

<210> SEQ ID NO 528
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, CDR3

<400> SEQUENCE: 528
cagcagtgga gcggctaccc atatacc                                        27

<210> SEQ ID NO 529
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, FR1

<400> SEQUENCE: 529
gacattcaga tgactcagtc tccctcctcc ctgtctgctt ccgtggggga ccgcgtcact    60
attacctgtt ccgcttcc                                                  78

<210> SEQ ID NO 530
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, FR2

<400> SEQUENCE: 530
ctgcactggt atcagcagaa gccaggaaaa gcccccaagc tgctgatcta c          51

<210> SEQ ID NO 531
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a Codon Optimized; K, FR3

<400> SEQUENCE: 531
acactggctt ctggcgtgcc cagtagattc tctggcagtg ggtcaggaac agacttcact      60
tttaccatca gttcactgca gcctgaggat attgccactt actattgc                 108

<210> SEQ ID NO 532
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; K, FR4

<400> SEQUENCE: 532
tttggccagg ggacaaaagt ggagatcaag a                                    31

<210> SEQ ID NO 533
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G13a Codon Optimized; H, variable
      region

<400> SEQUENCE: 533
caggtgcagc tgcaggaatc tgggcctgga ctggtcaaac cctctcagac tctgtctctg      60
acttgtactg tgtccggggg gagcatcagc tccgatagcg cctggaactg gatcagacag     120
ccccctggga agggactgga gtggatcggg tacattagtt attcaggaag cacctcctac     180
aatccctccc tgaaatctag ggtcactatg tcagtggaca ccagcaagaa ccagttctcc     240
ctgaaagtca attctgtgac tgccgctgat accgccgtgt actattgcgc tcggagaagt     300
agggtgtcat tctactttga ctattggggc caggggaccc tggtcacagt gtctagtg      358

<210> SEQ ID NO 534
<211> LENGTH: 27
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: cdrCAN46G13a Codon Optimized; H, CDR1

<400> SEQUENCE: 534 gggggagca tcagctccga tagcgcc                                            27

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; H, CDR2

<400> SEQUENCE: 535
attagttatt caggaagcac c                                                 21

<210> SEQ ID NO 536
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; H, CDR3

<400> SEQUENCE: 536
gctcggagaa gtagggtgtc attctacttt gactat                                 36

<210> SEQ ID NO 537
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; H, FR1

<400> SEQUENCE: 537
caggtgcagc tgcaggaatc tgggcctgga ctggtcaaac cctctcagac tctgtctctg       60
acttgtactg tgtcc                                                        75

<210> SEQ ID NO 538
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; H, FR2

<400> SEQUENCE: 538
tggaactgga tcagacagcc ccctgggaag ggactggagt ggatcgggta c                51

<210> SEQ ID NO 539
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: cdrCAN46G13a Codon Optimized; H, FR3

<400> SEQUENCE: 539
tcctacaatc cctccctgaa atctagggtc actatgtcag tggacaccag caagaaccag    60 ttctcccctga aagtcaattc tgtgactgcc gctgataccg ccgtgtacta ttgc         114

<210> SEQ ID NO 540
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G13a Codon Optimized; H, FR4

<400> SEQUENCE: 540
tggggccagg ggaccctggt cacagtgtct agtg                                 34

<210> SEQ ID NO 541
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a Codon Optimized; K, variable region

<400> SEQUENCE: 541
gaaaatgtgc tgactcagtc cccttccagc ctgtccgcaa gcgtcggcga cagggtgact    60
atgacctgca gcgcctctag ttcagtgtcc agctcttacc tgcactggta tcagcagaag   120
cccgggaaat ctcctaagcc actgatccat aggacatcta ctctggctag tggtgtgcct   180
tcacggttct ctggtagtgg ctcaggaaca tcctacagcc tgactatcag ttcactgcag   240
ccagaggaca ttgcaaccta ctattgccag cagtggtctg ataccccta tacctttggc    300 ggagggacaa agtggagat caagc                                          325

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, CDR1

<400> SEQUENCE: 542
agttcagtgt ccagctctta c                                               21

<210> SEQ ID NO 543
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, CDR2

<400> SEQUENCE: 543 aggacatct                                                              9

<210> SEQ ID NO 544
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, CDR3

<400> SEQUENCE: 544
cagcagtggt ctggataccc ctatacc                                           27

<210> SEQ ID NO 545
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, FR1

<400> SEQUENCE: 545
gaaaatgtgc tgactcagtc cccttccagc ctgtccgcaa gcgtcggcga cagggtgact        60
atgacctgca gcgcctct                                                     78

<210> SEQ ID NO 546
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, FR2

<400> SEQUENCE: 546
ctgcactggt atcagcagaa gcccgggaaa tctcctaagc cactgatcca t                 51

<210> SEQ ID NO 547
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a Codon Optimized; K, FR3

<400> SEQUENCE: 547
actctggcta gtggtgtgcc ttcacggttc tctggtagtg gctcaggaac atcctacagc        60
ctgactatca gttcactgca gccagaggac attgcaacct actattgc                    108

<210> SEQ ID NO 548
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; K, FR4

<400> SEQUENCE: 548
tttggcggag ggacaaaagt ggagatcaag c                                      31

<210> SEQ ID NO 549
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a Codon Optimized; H, variable region

<400> SEQUENCE: 549
caggtccagc tgcaggaatc cgggcctggt ctggtgaagc catctcagac cctgagtctg      60
acttgtaccg tgacagggta cagcatcaca tctgacagtg cctggaactg gattagacag     120
ttccctggta caatctgga gtggatgggc tacatttcat attccggaag cacctcttat      180
aatcccagtc tgaagtcaag aatctccatt acccgcgaca tcaaaaaaa ccagttttcc      240 ctgaaggtca atagcgtgac agctgcagat actgctgtct actattgcgc aaggcggagc     300
cgcgtgtctt tctactttga ctattggggc caggaactc tggtcaccgt gtcatccg        358

<210> SEQ ID NO 550
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; H, CDR1

<400> SEQUENCE: 550
gggtacagca tcacatctga cagtgcc                                         27

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; H, CDR2

<400> SEQUENCE: 551
atttcatatt ccggaagcac c                                               21

<210> SEQ ID NO 552
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; H, CDR3

<400> SEQUENCE: 552
gcaaggcgga gccgcgtgtc tttctacttt gactat                               36

<210> SEQ ID NO 553
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: huCAN46G13a Codon Optimized; H, FR1

<400> SEQUENCE: 553

```
caggtccagc tgcaggaatc cgggcctggt ctggtgaagc catctcagac cctgagtctg    60
acttgtaccg tgaca                                                    75
```

<210> SEQ ID NO 554
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; H, FR2

<400> SEQUENCE: 554

```
tggaactgga ttagacagtt ccctggtaac aatctggagt ggatgggcta c             51
```

<210> SEQ ID NO 555
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G13a Codon Optimized; H, FR3

<400> SEQUENCE: 555

```
tcttataatc ccagtctgaa gtcaagaatc tccattaccc gcgacacatc aaaaaaccag   60
ttttccctga aggtcaatag cgtgacagct gcagatactg ctgtctacta ttgc        114
```

<210> SEQ ID NO 556
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G13a Codon Optimized; H, FR4

<400> SEQUENCE: 556

```
tggggccagg gaactctggt caccgtgtca tccg                                34
```

<210> SEQ ID NO 557
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a Codon Optimized; K, variable
      region

<400> SEQUENCE: 557

```
gagaacgtcc tgacacagtc cccttccagc atgtccgcaa gcgtcggcga cagggtgact    60
atgacctgct ccgcctctag ttcagtgtcc agctcttacc tgcactggta tcagcagaag   120
ccaggcaaag ctcccaagcc tctgatccat aggacatcta ctctggcaag tggagtgccc   180
tcacggttct ctggtagtgg ctcaggaaca tcctacagcc tgactatcag ttcagtgcag   240
cctgaggaca ttgctaccta ctattgccag cagtggagcg gctacccata tacctttggc   300
```

```
ggagggacaa aagtggagat caagc                                           325

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, CDR1

<400> SEQUENCE: 558
agttcagtgt ccagctctta c                                                21

<210> SEQ ID NO 559
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, CDR2

<400> SEQUENCE: 559 aggacatct                                                               9

<210> SEQ ID NO 560
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, CDR3

<400> SEQUENCE: 560
cagcagtgga gcggctaccc atatacc                                          27

<210> SEQ ID NO 561
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, FR1

<400> SEQUENCE: 561
gagaacgtcc tgacacagtc cccttccagc atgtccgcaa gcgtcggcga cagggtgact    60
atgacctgct ccgcctct                                                    78

<210> SEQ ID NO 562
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, FR2

<400> SEQUENCE: 562
ctgcactggt atcagcagaa gccaggcaaa gctcccaagc tctgatcca t                51
```

<210> SEQ ID NO 563
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a Codon Optimized; K, FR3

<400> SEQUENCE: 563
actctggcaa gtggagtgcc ctcacggttc tctggtagtg gctcaggaac atcctacagc      60
ctgactatca gttcagtgca gcctgaggac attgctacct actattgc                  108

<210> SEQ ID NO 564
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; K, FR4

<400> SEQUENCE: 564
tttggcggag ggacaaaagt ggagatcaag c                                    31

<210> SEQ ID NO 565
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a Codon Optimized; H, variable
      region

<400> SEQUENCE: 565
caggtccagc tgcaggaaag cgggcccggt ctggtgaagc cttctcagac cctgagtctg      60
acttgtaccg tgacaggata ctctatcaca tctgacagtg cctggaactg gattagacag     120
ccacccggca atggactgga gtggatgggg tacatttcat attccggtag cacatcttat     180
aatccaagtc tgaagtcaag aatctccatt actcgcgaca cctcaaaaaa ccagttctcc     240
ctgaagctga atagcgtgac tgctgcagat actgctacct actattgcgc aaggcggagc     300
cgcgtgtctt ctactttga ctattgggg cagggtacac tggtcactgt gtcatccg         358

<210> SEQ ID NO 566
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; H, CDR1

<400> SEQUENCE: 566
ggatactcta tcacatctga cagtgcc                                         27

<210> SEQ ID NO 567
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: rehuCAN46G13a Codon Optimized; H, CDR2

<400> SEQUENCE: 567
atttcatatt ccggtagcac a                                              21

<210> SEQ ID NO 568
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; H, CDR3

<400> SEQUENCE: 568
gcaaggcgga gccgcgtgtc tttctacttt gactat                              36

<210> SEQ ID NO 569
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; H, FR1

<400> SEQUENCE: 569
caggtccagc tgcaggaaag cgggcccggt ctggtgaagc cttctcagac cctgagtctg    60
acttgtaccg tgaca                                                     75

<210> SEQ ID NO 570
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, FR4

<400> SEQUENCE: 570
tttggacagg gcactaaagt ggagatcaag c                                   31

<210> SEQ ID NO 571
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19 Codon Optimized; H, variable region

<400> SEQUENCE: 571
caggtgcagc tggtccagtc cggggccgag gtcaaaaagc ctggggagtc cgtcaaagtg    60
tcttgtaaag catctgggta catttacc gggtactata tccactgggt gagacaggca     120
cctggacagg gactggagtg gatggggagg attttcccat acaacggagc cgccagctat   180
aaccagaact tcaagggccg cgtgacaatc actgcagaca aagtaccctc aacagcctac   240
atggagctga gctccctgcg aagcgaagac acagccgtct actattgcgc tcggtggctg   300
```
agagtgtact tcgattattg gggccagggg accacagtca ccgtgtctag tg        352

<210> SEQ ID NO 572
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, CDR1

<400> SEQUENCE: 572
gggtatacat ttaccgggta ctat                                       24

<210> SEQ ID NO 573
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, CDR2

<400> SEQUENCE: 573
attttcccat acaacggagc cgcc                                       24

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, CDR3

<400> SEQUENCE: 574
gctcggtggc tgagagtgta cttcgattat                                 30

<210> SEQ ID NO 575
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, FR1

<400> SEQUENCE: 575
caggtgcagc tggtccagtc cggggccgag gtcaaaaagc tggggagtc cgtcaaagtg  60 tcttgtaaag catct                                                 75

<210> SEQ ID NO 576
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, FR2

<400> SEQUENCE: 576
atccactggg tgagacaggc acctggacag ggactggagt ggatggggag g          51

```
<210> SEQ ID NO 577
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19 Codon Optimized; H, FR3

<400> SEQUENCE: 577
agctataacc agaacttcaa gggccgcgtg acaatcactg cagacaaaag tacctcaaca      60
gcctacatgg agctgagctc cctgcgaagc gaagacacag ccgtctacta ttgc          114

<210> SEQ ID NO 578
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; H, FR4

<400> SEQUENCE: 578
tggggccagg ggaccacagt caccgtgtct agtg                                  34

<210> SEQ ID NO 579
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G19 Codon Optimized; K, variable region

<400> SEQUENCE: 579
gagaacgtcc tgacacagtc accttccagc ctgagcgcct ctgtcggtga cagagtgacc      60
atcacatgct ctgcttctag ttcagtgaca tacatgcact ggtatcagca gaagccaggc    120
aaagcaccca gctgtggat ctacgagact tctaagctgg caagtggtgt gccaggacgc     180
ttcagtggat caggatccgg gaactcttat actttaccca tctccagcct gcagccagaa    240
gatattgcta cctactattg cttccagggt tccggctacc ccttcacatt tggacagggg    300
actaaagtgg agatcaaga                                                 319

<210> SEQ ID NO 580
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; K, CDR1

<400> SEQUENCE: 580
agttcagtga catac                                                       15

<210> SEQ ID NO 581
<211> LENGTH: 9
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: huCAN46G19 Codon Optimized; K, CDR2

<400> SEQUENCE: 581 gagacttct                                                                  9

<210> SEQ ID NO 582
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; K, CDR3

<400> SEQUENCE: 582
ttccagggtt ccggctaccc cttcaca                                             27

<210> SEQ ID NO 583
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; K, FR1

<400> SEQUENCE: 583
gagaacgtcc tgacacagtc accttccagc ctgagcgcct ctgtcggtga cagagtgacc         60
atcacatgct ctgcttct                                                       78

<210> SEQ ID NO 584
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; K, FR2

<400> SEQUENCE: 584
atgcactggt atcagcagaa gccaggcaaa gcacccaagc tgtggatcta c                  51

<210> SEQ ID NO 585
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G19 Codon Optimized; K, FR3

<400> SEQUENCE: 585
aagctggcaa gtggtgtgcc aggacgcttc agtggatcag gatccgggaa ctcttatact         60
tttaccatct ccagcctgca gccagaagat attgctacct actattgc                     108

<210> SEQ ID NO 586
<211> LENGTH: 31
<212> TYPE: DNA
<213> ORGANISM: Artificial Sequence
<220> FEATURE:
<223> OTHER INFORMATION: Description of Artificial Sequence: Synthetic
```

```
    oligonucleotide
<220> FEATURE:
<223> OTHER INFORMATION: huCAN46G19 Codon Optimized; K, FR4

<400> SEQUENCE: 586
tttggacagg ggactaaagt ggagatcaag a                                    31

<210> SEQ ID NO 587
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G19 Codon Optimized; H, variable region

<400> SEQUENCE: 587
gaagtccagc tggtgcagag cggagcagag gtgaagaaac ctggggaaag cgtcaaagtg       60
tcttgtaagg ctagcggata ctctttcacc gggtactata tccactgggt caagcaggca      120
cctggtcagg gactggagtg ggtgggtaga attttcccct acaatggcgc tgcaagctat      180
aaccagaatt ttaagggcaa agcaaccctg acagtggaca gagctctac cacagcctac       240 atggagctga gttcactgcg ctctgaagac accgctgtct atttctgcgc aaggtggctg      300
cgggtgtact tgattattg gggacagggg actaccgtca ctgtgtccag cg               352

<210> SEQ ID NO 588
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, CDR1

<400> SEQUENCE: 588
ggatactctt tcaccgggta ctat                                            24

<210> SEQ ID NO 589
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, CDR2

<400> SEQUENCE: 589
attttcccct acaatggcgc tgca                                            24

<210> SEQ ID NO 590
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, CDR3

<400> SEQUENCE: 590
gcaaggtggc tgcgggtgta ctttgattat                                      30
```

```
<210> SEQ ID NO 591
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, FR1

<400> SEQUENCE: 591
gaagtccagc tggtgcagag cggagcagag gtgaagaaac ctggggaaag cgtcaaagtg    60
tcttgtaagg ctagc                                                     75

<210> SEQ ID NO 592
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, FR2

<400> SEQUENCE: 592
atccactggg tcaagcaggc acctggtcag ggactggagt gggtgggtag a              51

<210> SEQ ID NO 593
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G19 Codon Optimized; H, FR3

<400> SEQUENCE: 593
agctataacc agaattttaa ggcaaagca accctgacag tggacaagag ctctaccaca     60
gcctacatgg agctgagttc actgcgctct gaagacaccg ctgtctattt ctgc         114

<210> SEQ ID NO 594
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G19 Codon Optimized; H, FR4

<400> SEQUENCE: 594
tggggacagg ggactaccgt cactgtgtcc agcg                                34

<210> SEQ ID NO 595
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19 Codon Optimized; K, variable
      region

<400> SEQUENCE: 595
gagaacgtcc tgacacagag tccttccagc atgtcagcct ccgtcggaga cagagtgaca    60
```

```
atgacttgct ctgcttctag ttcagtgaca tacatgcact ggtatcagca gaagccaggg    120
aaatccccca agctgtggat ctacgagact tctaagctgg caagtggtgt gccctcacgc    180
ttcagcggct ctggaagtgg gaacgactat agcctgacaa tttccagcat gcagccagaa    240
gatgtggcca cttactattg ctttcagggt tctggctacc ccttcacctt tggacagggg    300
acaaaactgg agatcaaga                                                 319

<210> SEQ ID NO 596
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; K, CDR1

<400> SEQUENCE: 596
agttcagtga catac                                                     15

<210> SEQ ID NO 597
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; K, CDR2

<400> SEQUENCE: 597 gagacttct                                                             9

<210> SEQ ID NO 598
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; K, CDR3

<400> SEQUENCE: 598
tttcagggtt ctggctaccc cttcacc                                        27

<210> SEQ ID NO 599
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; K, FR1

<400> SEQUENCE: 599
gagaacgtcc tgacacagag tccttccagc atgtcagcct ccgtcggaga cagagtgaca    60
atgacttgct ctgcttct                                                  78

<210> SEQ ID NO 600
<211> LENGTH: 51
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: rehuCAN46G19 Codon Optimized; K, FR2

<400> SEQUENCE: 600
atgcactggt atcagcagaa gccagggaaa tcccccaagc tgtggatcta c    51

<210> SEQ ID NO 601
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19 Codon Optimized; K, FR3

<400> SEQUENCE: 601
aagctggcaa gtggtgtgcc ctcacgcttc agcggctctg gaagtgggaa cgactatagc    60
ctgacaattt ccagcatgca gccagaagat gtggccactt actattgc                108

<210> SEQ ID NO 602
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; K, FR4

<400> SEQUENCE: 602
tttggacagg ggacaaaact ggagatcaag a    31

<210> SEQ ID NO 603
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19 Codon Optimized; H, variable
      region

<400> SEQUENCE: 603
gaagtccagc tggtgcagtc cggagcagag gtggtcaaac tggggaatc tgtgaaaatc    60 agttgtaagg cctcaggata ctccttcact gggtactata ttcactgggt caagcagacc    120
cctggtcaga gcctggagtg ggtgggcaga attttcccct acaatggagc tgcatcttat    180
aaccagaatt ttaagggcaa agcaactctg accgtggaca gagcaccac aactgcctac    240 atggagctga gctctctgcg cagcgaagac tctgctgtct atttctgcgc aaggtggctg    300
cgggtgtact ttgattattg gggtcagggc accacactga cagtcagttc ag    352

<210> SEQ ID NO 604
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, CDR1

<400> SEQUENCE: 604
ggatactcct tcactgggta ctat                                                24

<210> SEQ ID NO 605
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, CDR2

<400> SEQUENCE: 605
attttcccct acaatggagc tgca                                                24

<210> SEQ ID NO 606
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, CDR3

<400> SEQUENCE: 606
gcaaggtggc tgcgggtgta ctttgattat                                          30

<210> SEQ ID NO 607
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, FR1

<400> SEQUENCE: 607
gaagtccagc tggtgcagtc cggagcagag gtggtcaaac ctggggaatc tgtgaaaatc          60
agttgtaagg cctca                                                          75

<210> SEQ ID NO 608
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, FR2

<400> SEQUENCE: 608
attcactggg tcaagcagac ccctggtcag agcctggagt gggtgggcag a                   51

<210> SEQ ID NO 609
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G19 Codon Optimized; H, FR3

<400> SEQUENCE: 609
tcttataacc agaattttaa gggcaaagca actctgaccg tggacaagag caccacaact          60

```
gcctacatgg agctgagctc tctgcgcagc gaagactctg ctgtctattt ctgc        114
```

<210> SEQ ID NO 610
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G19 Codon Optimized; H, FR4

<400> SEQUENCE: 610

```
tggggtcagg gcaccacact gacagtcagt tcag                              34
```

<210> SEQ ID NO 611
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24 Codon Optimized; K, variable region

<400> SEQUENCE: 611

```
gatattcaga tgacccagtc cccctcctcc ctgtcagctt ccgtcggcga tagagtcacc    60
attacctgtt ccgctagttc ctccgtcaca tacatgcact ggtatcagca gaagccaggg   120
aaagccccca agctgctgat ctacgagact agtaaactgg cttcaggagt gccaagcagg   180
ttctcaggca gcgggtccgg aactgactat acctttacaa tcagctccct gcagcctgaa   240
gatattgcca cctactattg cttccagggc agcgggtacc cattcacatt tggacagggc   300
actaaagtgg agatcaagc                                                319
```

<210> SEQ ID NO 612
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; K, CDR1

<400> SEQUENCE: 612

```
tcctccgtca catac                                                    15
```

<210> SEQ ID NO 613
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; K, CDR2

<400> SEQUENCE: 613

```
gagactagt                                                            9
```

<210> SEQ ID NO 614
<211> LENGTH: 27
<212> TYPE: DNA
<213> ORGANISM: Artificial Sequence
<220> FEATURE:
<223> OTHER INFORMATION: Description of Artificial Sequence: Synthetic

```
    oligonucleotide
<220> FEATURE:
<223> OTHER INFORMATION: cdrCAN46G24 Codon Optimized; K, CDR3

<400> SEQUENCE: 614
ttccagggca gcgggtaccc attcaca                                          27

<210> SEQ ID NO 615
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; K, FR1

<400> SEQUENCE: 615
gatattcaga tgacccagtc cccctcctcc ctgtcagctt ccgtcggcga tagagtcacc      60
attacctgtt ccgctagt                                                   78

<210> SEQ ID NO 616
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; K, FR2

<400> SEQUENCE: 616
atgcactggt atcagcagaa gccagggaaa gcccccaagc tgctgatcta c              51

<210> SEQ ID NO 617
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24 Codon Optimized; K, FR3

<400> SEQUENCE: 617
aaactggctt caggagtgcc aagcaggttc tcaggcagcg gtccggaac tgactatacc       60 tttacaatca gctccctgca gcctgaagat attgccacct actattgc                 108

<210> SEQ ID NO 618
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; K, FR4

<400> SEQUENCE: 618
tttggacagg gcactaaagt ggagatcaag c                                    31

<210> SEQ ID NO 619
<211> LENGTH: 352
<212> TYPE: DNA
<213> ORGANISM: Artificial Sequence
<220> FEATURE:
<223> OTHER INFORMATION: Description of Artificial Sequence: Synthetic
```

```
            polynucleotide
<220> FEATURE:
<223> OTHER INFORMATION: cdrCAN46G24 Codon Optimized; H, variable region

<400> SEQUENCE: 619
caggtgcagc tggtccagtc cggggccgag gtcaaaaagc tggggagtc cgtcaaagtg      60 tcttgtaaag catctgggta tacatttacc gggtactata tccactgggt gagacaggca    120
cctggacagg gactggagtg gatggggagg attttcccat acaacggagc cgccagctat    180
aaccagaact tcaagggccg cgtgacaatc actgcagaca aaagtacctc aacagcctac    240
atggagctga gctccctgcg aagcgaagac acagccgtct actattgcgc tcggtggctg    300
agagtgtact cgattattg gggccagggg accacagtca ccgtgtctag tg             352

<210> SEQ ID NO 620
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, CDR1

<400> SEQUENCE: 620
gggtatacat ttaccgggta ctat                                            24

<210> SEQ ID NO 621
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, CDR2

<400> SEQUENCE: 621
attttcccat acaacggagc cgcc                                            24

<210> SEQ ID NO 622
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, CDR3

<400> SEQUENCE: 622
gctcggtggc tgagagtgta cttcgattat                                      30

<210> SEQ ID NO 623
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, FR1

<400> SEQUENCE: 623
caggtgcagc tggtccagtc cggggccgag gtcaaaaagc tggggagtc cgtcaaagtg      60 tcttgtaaag catct                                                      75
```

<210> SEQ ID NO 624
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, FR2

<400> SEQUENCE: 624
atccactggg tgagacaggc acctggacag ggactggagt ggatggggag g          51

<210> SEQ ID NO 625
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G24 Codon Optimized; H, FR3

<400> SEQUENCE: 625
agctataacc agaacttcaa gggccgcgtg acaatcactg cagacaaaag tacctcaaca     60
gcctacatgg agctgagctc cctgcgaagc gaagacacag ccgtctacta ttgc          114

<210> SEQ ID NO 626
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G24 Codon Optimized; H, FR4

<400> SEQUENCE: 626
tggggccagg ggaccacagt caccgtgtct agtg                              34

<210> SEQ ID NO 627
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24 Codon Optimized; K, variable region

<400> SEQUENCE: 627
gagatcgtcc tgactcagtc cccttccagc ctgtctacca gtgtcggtga cagagtgaca     60
atctcatgct ccgcttctag ttcagtgaca tacatgcact ggtatcagca gaagccaggc    120
aaagccccca agctgtggat ctacgagact tccaagctgg ctagcggtgt gccaggacgc    180
ttcagcggat ctggaagtgg gaactcttat accttcacca tctccagcct gcagccagaa    240
gatattgcta cctactattg cttccagggt tccggctacc ccttcacctt tggacagggg    300
acaaaagtgg agatcaaga                                                319

<210> SEQ ID NO 628
<211> LENGTH: 15
<212> TYPE: DNA
<213> ORGANISM: Artificial Sequence
<220> FEATURE:

<223> OTHER INFORMATION: Description of Artificial Sequence: Synthetic
       oligonucleotide
<220> FEATURE:
<223> OTHER INFORMATION: huCAN46G24 Codon Optimized; K, CDR1

<400> SEQUENCE: 628
agttcagtga catac                                                    15

<210> SEQ ID NO 629
<211> LENGTH: 9
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: huCAN46G24 Codon Optimized; K, CDR2

<400> SEQUENCE: 629 gagacttcc                                                            9

<210> SEQ ID NO 630
<211> LENGTH: 27
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: huCAN46G24 Codon Optimized; K, CDR3

<400> SEQUENCE: 630
ttccagggtt ccggctaccc cttcacc                                       27

<210> SEQ ID NO 631
<211> LENGTH: 78
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: huCAN46G24 Codon Optimized; K, FR1

<400> SEQUENCE: 631
gagatcgtcc tgactcagtc cccttccagc ctgtctacca gtgtcggtga cagagtgaca   60
atctcatgct ccgcttct                                                 78

<210> SEQ ID NO 632
<211> LENGTH: 51
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: huCAN46G24 Codon Optimized; K, FR2

<400> SEQUENCE: 632
atgcactggt atcagcagaa gccaggcaaa gcccccaagc tgtggatcta c            51

<210> SEQ ID NO 633
<211> LENGTH: 108
<212> TYPE: DNA
<213> ORGANISM: Artificial Sequence
<220> FEATURE:
<223> OTHER INFORMATION: Description of Artificial Sequence: Synthetic
       polynucleotide <220> FEATURE:
<223> OTHER INFORMATION: huCAN46G24 Codon Optimized; K, FR3

<400> SEQUENCE: 633
aagctggcta gcggtgtgcc aggacgcttc agcggatctg aagtgggaa ctcttatacc    60 ttcaccatct ccagcctgca gccagaagat attgctacct actattgc               108

<210> SEQ ID NO 634
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24 Codon Optimized; K, FR4

<400> SEQUENCE: 634
tttggacagg ggacaaaagt ggagatcaag a                                  31

<210> SEQ ID NO 635
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G24 Codon Optimized; H, variable region

<400> SEQUENCE: 635
gaagtccagc tggtgcagag cggagcagag gtgaagaaac tggggaatc agtcaaagtg    60 tcctgtaagg catcaggata ctccttcacc gggtactata tccactgggt caagcaggca   120
cctggtcagg gactggagtg ggtgggtaga attttcccct acaatggcgc tgcaagctat   180
aaccagaatt ttaagggcaa agcaactctg accgtggaca gagctctag tacagcctac   240 atggagctgt catccctgcg ctctgaagac actgctgtct atttctgcgc aaggtggctg   300
cgggtgtact ttgattattg gggacagggg accacagtca cagtgagctc tg           352

<210> SEQ ID NO 636
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24 Codon Optimized; H, CDR1

<400> SEQUENCE: 636
ggatactcct tcaccgggta ctat                                          24

<210> SEQ ID NO 637
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G24 Codon Optimized; H, CDR2

<400> SEQUENCE: 637
attttcccct acaatggcgc tgca                                          24

<210> SEQ ID NO 638
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCAN46G24 Codon Optimized; H, CDR3

<400> SEQUENCE: 638
gcaaggtggc tgcgggtgta ctttgattat                                30

<210> SEQ ID NO 639
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCAN46G24 Codon Optimized; H, FR1

<400> SEQUENCE: 639
gaagtccagc tggtgcagag cggagcagag gtgaagaaac tggggaatc agtcaaagtg    60 tcctgtaagg catca                                                  75

<210> SEQ ID NO 640
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCAN46G24 Codon Optimized; H, FR2

<400> SEQUENCE: 640
atccactggg tcaagcaggc acctggtcag ggactggagt gggtgggtag a            51

<210> SEQ ID NO 641
<211> LENGTH: 114
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: huCAN46G24 Codon Optimized; H, FR3

<400> SEQUENCE: 641
agctataacc agaattttaa gggcaaagca actctgaccg tggacaagag ctctagtaca   60
gcctacatgg agctgtcatc cctgcgctct gaagacactg ctgtctattt ctgc        114

<210> SEQ ID NO 642
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCAN46G24 Codon Optimized; H, FR4

<400> SEQUENCE: 642
tggggacagg ggaccacagt cacagtgagc tctg                              34

<210> SEQ ID NO 643
<211> LENGTH: 319
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G24 Codon Optimized; K, variable
    region

<400> SEQUENCE: 643
gagatcgtgc tgactcagtc accctccagc atgtcaacct ccgtcggaga cagagtgaca    60
atgagctgct ctgcctctag ttcagtgacc tacatgcact ggtatcagca gaagccaggg   120
aaaagcccca agctgtggat ctacgagaca agcaagctgg cttctggtgt gcccagtcgc   180
ttcagtggct caggatccgg gaacgactat tccctgacca tttccagcat gcagccagaa   240
gatgtggcaa catactattg ctttcagggt agcggctacc ccttcacctt tggacagggg   300
acaaaactgg agatcaaga                                                319

<210> SEQ ID NO 644
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24 Codon Optimized; K, CDR1

<400> SEQUENCE: 644
agttcagtga cctac                                                     15

<210> SEQ ID NO 645
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24 Codon Optimized; K, CDR2

<400> SEQUENCE: 645 gagacaagc                                                             9

<210> SEQ ID NO 646
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G24 Codon Optimized; K, CDR3

<400> SEQUENCE: 646
tttcagggta gcggctaccc cttcacc                                        27

<210> SEQ ID NO 647
<211> LENGTH: 78
<212> TYPE: DNA
<213> ORGANISM: Artificial Sequence
<220> FEATURE:
<223> OTHER INFORMATION: Description of Artificial Sequence: Synthetic
    oligonucleotide <220> FEATURE:
<223> OTHER INFORMATION: rehuCAN46G24 Codon Optimized; K, FR1

<400> SEQUENCE: 647
gagatcgtgc tgactcagtc accctccagc atgtcaacct ccgtcggaga cagagtgaca    60
atgagctgct ctgcctct                                                 78

<210> SEQ ID NO 648
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; K, FR2

<400> SEQUENCE: 648
atgcactggt atcagcagaa gccagggaaa gccccaagc tgtggatcta c              51

<210> SEQ ID NO 649
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24 Codon Optimized; K, FR3

<400> SEQUENCE: 649
aagctggctt ctggtgtgcc cagtcgcttc agtggctcag gatccgggaa cgactattcc    60
ctgaccattt ccagcatgca gccagaagat gtggcaacat actattgc                108

<210> SEQ ID NO 650
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; K, FR4

<400> SEQUENCE: 650
tttggacagg ggacaaaact ggagatcaag a                                   31

<210> SEQ ID NO 651
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24 Codon Optimized; H, variable
      region

<400> SEQUENCE: 651
gaagtccagc tggtgcagtc cggagcagag gtggtcaaac tggggaaag cgtgaaaatc     60 tcttgtaagg ctagtggata tcattcaca gggtactata ttcactgggt caagcagact   120
ccaggccagt ctctggagtg ggtgggcaga atttttcccct acaatggagc tgcatcctat  180
aaccagaatt ttaagggcaa agcaaccctg acagtggaca gagcacttc taccgcctac   240 atggagctga gctctctgcg ctccgaagac agcgctgtct atttctgcgc aaggtggctg   300
cgggtgtact ttgattattg gggtcagggc accacactga cagtcagttc ag    352

<210> SEQ ID NO 652
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, CDR1

<400> SEQUENCE: 652
ggatactcat tcacagggta ctat    24

<210> SEQ ID NO 653
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, CDR2

<400> SEQUENCE: 653
attttcccct acaatggagc tgca    24

<210> SEQ ID NO 654
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, CDR3

<400> SEQUENCE: 654
gcaaggtggc tgcgggtgta ctttgattat    30

<210> SEQ ID NO 655
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, FR1

<400> SEQUENCE: 655
gaagtccagc tggtgcagtc cggagcagag gtggtcaaac tggggaaag cgtgaaaatc    60 tcttgtaagg ctagt    75

<210> SEQ ID NO 656
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, FR2

<400> SEQUENCE: 656
attcactggg tcaagcagac tccaggccag tctctggagt gggtgggcag a    51

<210> SEQ ID NO 657
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G24 Codon Optimized; H, FR3

<400> SEQUENCE: 657
tcctataacc agaattttaa gggcaaagca accctgacag tggacaagag cacttctacc      60
gcctacatgg agctgagctc tctgcgctcc gaagacagcg ctgtctattt ctgc           114

<210> SEQ ID NO 658
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G24 Codon Optimized; H, FR4

<400> SEQUENCE: 658
tggggtcagg gcaccacact gacagtcagt tcag                                 34

<210> SEQ ID NO 659
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G4 Codon Optimized; K, variable region

<400> SEQUENCE: 659
gaaattgtcc tgacccagtc ccctgctacc ctgtccctgt ccccggaga aagagcaacc      60 ctgtcctgtt cagcttcctc atctgtgtct tacatgcact ggtatcagca gaagccaggg    120
caggcaccca ggctgctgat ctacgagact agtaaactgg cattcggaat tcccgcacgc    180
ttttcaggca gcgggtccgg aaccgacttc accctgacaa tcagctccct ggagcctgaa    240
gatttcgccg tgtactattg ctttcagggc agcgggtatc cattcacatt tggacagggc    300
actcggctgg agatcaaga                                                 319

<210> SEQ ID NO 660
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; K, CDR1

<400> SEQUENCE: 660
tcatctgtgt cttac                                                     15

<210> SEQ ID NO 661
<211> LENGTH: 9
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: cdrCAN46G4 Codon Optimized; K, CDR2

<400> SEQUENCE: 661 gagactagt                                                                   9

<210> SEQ ID NO 662
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; K, CDR3

<400> SEQUENCE: 662
tttcagggca gcgggtatcc attcaca                                              27

<210> SEQ ID NO 663
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; K, FR1

<400> SEQUENCE: 663
gaaattgtcc tgacccagtc ccctgctacc ctgtccctgt ccccggaga aagagcaacc           60 ctgtcctgtt cagcttcc                                                        78

<210> SEQ ID NO 664
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; K, FR2

<400> SEQUENCE: 664
atgcactggt atcagcagaa gccagggcag gcacccaggc tgctgatcta c                  51

<210> SEQ ID NO 665
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G4 Codon Optimized; K, FR3

<400> SEQUENCE: 665
aaactggcat tcggaattcc cgcacgcttt tcaggcagcg ggtccggaac cgacttcacc          60
ctgacaatca gctccctgga gcctgaagat ttcgccgtgt actattgc                      108

<210> SEQ ID NO 666
<211> LENGTH: 31
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: cdrCAN46G4 Codon Optimized; K, FR4

<400> SEQUENCE: 666
tttggacagg gcactcggct ggagatcaag a                                    31

<210> SEQ ID NO 667
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G4 Codon Optimized; H, variable region

<400> SEQUENCE: 667
caggtccagc tggtccagtc tggggctgag gtcaaaaaac ccggctcttc cgtcaaagtc     60
tcctgcaaag catctggcta catttaccg ggtactata tgcactgggt gagacaggca     120
cctgggcagg gactggagtg gatcgggagg attttcccat acaacggagc cgccagctat   180
aaccagaact tcaaggacaa agccactatc accgctgatg aaagtacaaa tactgcctac    240
atggagctga gctccctgag gtctgaagac actgcagtct actattgcgc cggtggctg    300 agagtgtact tcgattattg gggccagggg acactggtca ccgtgagcag tg           352

<210> SEQ ID NO 668
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, CDR1

<400> SEQUENCE: 668
ggctatacat ttaccgggta ctat                                            24

<210> SEQ ID NO 669
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, CDR2

<400> SEQUENCE: 669
attttcccat acaacggagc cgcc                                            24

<210> SEQ ID NO 670
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, CDR3

<400> SEQUENCE: 670
gcccggtggc tgagagtgta cttcgattat                                      30

<210> SEQ ID NO 671
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, FR1

<400> SEQUENCE: 671
caggtccagc tggtccagtc tggggctgag gtcaaaaaac ccggctcttc cgtcaaagtc    60
tcctgcaaag catct                                                    75

<210> SEQ ID NO 672
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, FR2

<400> SEQUENCE: 672
atgcactggg tgagacaggc acctgggcag ggactggagt ggatcgggag g             51

<210> SEQ ID NO 673
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G4 Codon Optimized; H, FR3

<400> SEQUENCE: 673
agctataacc agaacttcaa ggacaaagcc actatcaccg ctgatgaaag tacaaatact    60
gcctacatgg agctgagctc cctgaggtct gaagacactg cagtctacta ttgc        114

<210> SEQ ID NO 674
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G4 Codon Optimized; H, FR4

<400> SEQUENCE: 674
tggggccagg ggacactggt caccgtgagc agtg                                34

<210> SEQ ID NO 675
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G4 Codon Optimized; K, variable region

<400> SEQUENCE: 675
gagaaggtcc tgacacagtc acccgctacc ctgtccctga gccctggcga gagagccact    60

```
atgacctgct cagcttccag ctctgtgtcc tacatgcact ggtatcagca gaagccagga    120
acctctccca aactgtggat ctacgaaacc agtaagctgg ctttcggggt gccagcacgc    180
ttttctggca gtggatcagg gaactcctat agcctgacca ttagttcact ggaaccagaa    240
gacttcgctg tgtactattg ctttcagggt agcggctacc ccttcacctt tggacagggg    300
acaagactgg agatcaagc                                                 319
```

<210> SEQ ID NO 676
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; K, CDR1

<400> SEQUENCE: 676

```
agctctgtgt cctac                                                     15
```

<210> SEQ ID NO 677
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; K, CDR2

<400> SEQUENCE: 677

```
gaaaccagt                                                             9
```

<210> SEQ ID NO 678
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; K, CDR3

<400> SEQUENCE: 678

```
tttcagggta gcggctaccc cttcacc                                        27
```

<210> SEQ ID NO 679
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; K, FR1

<400> SEQUENCE: 679

```
gagaaggtcc tgacacagtc acccgctacc ctgtccctga gccctggcga gagagccact    60
atgacctgct cagcttcc                                                  78
```

<210> SEQ ID NO 680
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCAN46G4 Codon Optimized; K, FR2

<400> SEQUENCE: 680
atgcactggt atcagcagaa gccaggaacc tctcccaaac tgtggatcta c    51

<210> SEQ ID NO 681
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G4 Codon Optimized; K, FR3

<400> SEQUENCE: 681
aagctggctt tcggggtgcc agcacgcttt tctggcagtg gatcagggaa ctcctatagc    60
ctgaccatta gttcactgga accagaagac ttcgctgtgt actattgc    108

<210> SEQ ID NO 682
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; K, FR4

<400> SEQUENCE: 682
tttggacagg ggacaagact ggagatcaag c    31

<210> SEQ ID NO 683
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G4 Codon Optimized; H, variable region

<400> SEQUENCE: 683
gaagtgcagc tgctgcagtc cggagctgag gtcaagaaac ccgggtcatc cgtgaagatt    60
agctgtaaag catctgatta cagttttacc ggctactata tgcactgggt gaagcaggca    120
cctggtcagg gactggagtg gatcggtaga attttcccct acaatggcgc tgcatcctat    180
aaccagaatt ttaaggacaa agctaccctg acagtggata gagctctag taccgcatat    240 atggagctgc attcactgcg ctccgaagac acagccgtct actattgcac taggtggctg    300
cgggtgtact tcgattattg gggacagggg accctggtca cagtgtcatc cg    352

<210> SEQ ID NO 684
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; H, CDR1

<400> SEQUENCE: 684
gattacagtt ttaccggcta ctat    24

<210> SEQ ID NO 685
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; H, CDR2

<400> SEQUENCE: 685 attttccccct acaatggcgc tgca                                           24

<210> SEQ ID NO 686
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; H, CDR3

<400> SEQUENCE: 686
actaggtggc tgcgggtgta cttcgattat                                      30

<210> SEQ ID NO 687
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; H, FR1

<400> SEQUENCE: 687
gaagtgcagc tgctgcagtc cggagctgag gtcaagaaac ccgggtcatc cgtgaagatt     60
agctgtaaag catct                                                      75

<210> SEQ ID NO 688
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCAN46G4 Codon Optimized; H, FR2

<400> SEQUENCE: 688
atgcactggg tgaagcaggc acctggtcag ggactggagt ggatcggtag a               51

<210> SEQ ID NO 689
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huCAN46G4 Codon Optimized; H, FR3

<400> SEQUENCE: 689
tcctataacc agaattttaa ggacaaagct accctgacag tggataagag ctctagtacc     60
gcatatatgg agctgcattc actgcgctcc gaagacacag ccgtctacta ttgc          114

<210> SEQ ID NO 690
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: huCAN46G4 Codon Optimized; H, FR4

<400> SEQUENCE: 690
tggggacagg ggaccctggt cacagtgtca tccg                              34

<210> SEQ ID NO 691
<211> LENGTH: 319
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G4 Codon Optimized; K, variable region

<400> SEQUENCE: 691
gaaaaggtcc tgactcagtc ccccgctact ctgtcagcat ccctggcga gagagtcacc     60 atgagctgct ctgcctccag ctctgtgtct tacatgcact ggtatcagca aaagcctggt    120
cagagtccca aactgtggat ctacgaaact tcaaagctgg cattcggcgt gccagcccgc    180
tttagtggct caggatccgg gaccgactat tccctgacaa ttagttcaat ggagccagaa    240
gatttcgcta catactattg ctttcagggt agcggctacc ccttcacttt tggacagggg    300
accagactgg agatcaagc                                                 319

<210> SEQ ID NO 692
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G4 Codon Optimized; K, CDR1

<400> SEQUENCE: 692
agctctgtgt cttac                                                    15

<210> SEQ ID NO 693
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G4 Codon Optimized; K, CDR2

<400> SEQUENCE: 693 gaaacttca                                                            9

<210> SEQ ID NO 694
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide <220> FEATURE:
<223> OTHER INFORMATION: rehuCAN46G4 Codon Optimized; K, CDR3

<400> SEQUENCE: 694
tttcagggta gcggctaccc cttcact                                            27

<210> SEQ ID NO 695
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; K, FR1

<400> SEQUENCE: 695
gaaaaggtcc tgactcagtc ccccgctact ctgtcagcat ccccctggcga gagagtcacc        60 atgagctgct ctgcctcc                                                      78

<210> SEQ ID NO 696
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; K, FR2

<400> SEQUENCE: 696
atgcactggt atcagcagaa gcctggtcag agtcccaaac tgtggatcta c                 51

<210> SEQ ID NO 697
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G4 Codon Optimized; K, FR3

<400> SEQUENCE: 697
aagctggcat tcggcgtgcc agcccgcttt agtggctcag gatccgggac cgactattcc        60
ctgacaatta gttcaatgga gccagaagat ttcgctacat actattgc                    108

<210> SEQ ID NO 698
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; K, FR4

<400> SEQUENCE: 698
tttggacagg ggaccagact ggagatcaag c                                       31

<210> SEQ ID NO 699
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: rehuCAN46G4 Codon Optimized; H, variable region

<400> SEQUENCE: 699
gaagtgcagc tgctgcagtc cggtgcagag gtggtcaagc caggatcatc cgtgaagatt      60
agctgtaaag ctagcggtta ctctttttacc ggctactata tgcactgggt gaagcaggca    120
cctggtcagg gcctggagtg gatcggaaga attttcccct acaacggggc tgcatcttat    180
aaccagaatt ttaaggacaa agccacactg actgctgata agtccaccaa tacagcatat    240
atggagctga gctctctgcg cagtgaagac tcagccgtct actattgcac caggtggctg    300
cgggtgtact cgattattg gggacagggg accctggtca cagtgagttc ag            352

<210> SEQ ID NO 700
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; H, CDR1

<400> SEQUENCE: 700
ggttactctt ttaccggcta ctat                                              24

<210> SEQ ID NO 701
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; H, CDR2

<400> SEQUENCE: 701
attttcccct acaacggggc tgca                                              24

<210> SEQ ID NO 702
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; H, CDR3

<400> SEQUENCE: 702
accaggtggc tgcgggtgta cttcgattat                                        30

<210> SEQ ID NO 703
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G4 Codon Optimized; H, FR1

<400> SEQUENCE: 703
gaagtgcagc tgctgcagtc cggtgcagag gtggtcaagc caggatcatc cgtgaagatt      60
agctgtaaag ctagc                                                        75
```

<210> SEQ ID NO 704
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G4 Codon Optimized; H, FR2

<400> SEQUENCE: 704
atgcactggg tgaagcaggc acctggtcag ggcctggagt ggatcggaag a           51

<210> SEQ ID NO 705
<211> LENGTH: 114
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: rehuCAN46G4 Codon Optimized; H, FR3

<400> SEQUENCE: 705
tcttataacc agaattttaa ggacaaagcc acactgactg ctgataagtc caccaataca    60
gcatatatgg agctgagctc tctgcgcagt gaagactcag ccgtctacta ttgc         114

<210> SEQ ID NO 706
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: rehuCAN46G4 Codon Optimized; H, FR4

<400> SEQUENCE: 706
tggggacagg ggaccctggt cacagtgagt tcag                               34

<210> SEQ ID NO 707
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Chimeric CAN46G13a; K, variable region

<400> SEQUENCE: 707
gagaatgtcc tgactcagtc ccctgctatt atggccgctt ccctggggca gaaagtgact    60
atgacctgtt ccgcttcctc ttccgtcagc tcctcttacc tgcactggta tcagcagaag   120
tctggcgcta gtccaaaacc cctgatccat cgaaccagca cactggcttc cggagtgcca   180
gcaagattct ctggcagtgg gtcaggaaca agctactccc tgactattag ttcagtcgag   240
gcagaagacg atgccaccta ctattgccag cagtggtctg gtaccccta taccttggc    300 ggggaacaa agctggagat caaa                                          324

<210> SEQ ID NO 708
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: K, variable region

<400> SEQUENCE: 708

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser Ser
            20                  25                  30

Tyr Leu His Trp Tyr Gln Gln Lys Ser Gly Ala Ser Pro Lys Pro Leu
        35                  40                  45

Ile His Arg Thr Ser Thr Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Tyr Thr Phe Gly Gly Gly Thr Lys Leu Glu Ile Lys
            100                 105

<210> SEQ ID NO 709
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: H, variable region

<400> SEQUENCE: 709
gacgtgcagc tgcaggaatc tgggcctggg ctggtgaaac ctagtcagtc tctgtctctg      60
acctgtaccg tgaccggata ctcaatcacc tccgattctg cctggaactg gatcaggcag     120
ttccctggca acaatctgga gtggatggga tacattagtt attcaggcag cacatcctac     180
aatccatccc tgaagtctag gatcagtatt acccgcgaca caagtaaaaa ccagttcttt     240
ctgcagctga attcagtgac cacagaagat accgctacat actattgcgc acggagatca     300
cgggtgagct tctactttga ctattggggg cagggaacta ccctgactgt cagctcc        357

<210> SEQ ID NO 710
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: H, variable region

<400> SEQUENCE: 710

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Ser Ala Trp Asn Trp Ile Arg Gln Phe Pro Gly Asn Asn Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

```
Leu Gln Leu Asn Ser Val Thr Thr Glu Asp Thr Ala Thr Tyr Tyr Cys
                85                  90                  95

Ala Arg Arg Ser Arg Val Ser Phe Tyr Phe Asp Tyr Trp Gly Gln Gly
            100                 105                 110

Thr Thr Leu Thr Val Ser Ser
        115
```

<210> SEQ ID NO 711
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; H, FR2

<400> SEQUENCE: 711
tggaactgga ttagacagcc acccggcaat ggactggagt ggatggggta c           51

<210> SEQ ID NO 712
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: rehuCAN46G13a Codon Optimized; H, FR3

<400> SEQUENCE: 712
tcttataatc caagtctgaa gtcaagaatc tccattactc gcgacacctc aaaaaaccag    60
ttctccctga agctgaatag cgtgactgct gcagatactg ctacctacta ttgc         114

<210> SEQ ID NO 713
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: rehuCAN46G13a Codon Optimized; H, FR4

<400> SEQUENCE: 713
tgggggcagg gtacactggt cactgtgtca tccg                               34

<210> SEQ ID NO 714
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19 Codon Optimized; K, variable region

<400> SEQUENCE: 714
gatattcaga tgacccagtc cccctcctcc ctgtcagctt ccgtcggcga tagagtcacc    60
attacctgtt ccgctagttc ctccgtcaca tacatgcact ggtatcagca gaagccaggg   120
aaagccccca agctgctgat ctacgagact agtaaactgg cttcaggagt gccaagcagg   180
ttctcaggca gcgggtccgg aactgactat acctttacaa tcagctccct gcagcctgaa   240
gatattgcca cctactattg cttccagggc agcgggtacc cattcacatt tggacagggc   300
```

```
actaaagtgg agatcaagc                                              319
```

<210> SEQ ID NO 715
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, CDR1

<400> SEQUENCE: 715

```
tcctccgtca catac                                                   15
```

<210> SEQ ID NO 716
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, CDR2

<400> SEQUENCE: 716

```
gagactagt                                                           9
```

<210> SEQ ID NO 717
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, CDR3

<400> SEQUENCE: 717

```
ttccagggca gcgggtaccc attcaca                                      27
```

<210> SEQ ID NO 718
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, FR1

<400> SEQUENCE: 718

```
gatattcaga tgacccagtc cccctcctcc ctgtcagctt ccgtcggcga tagagtcacc   60
attacctgtt ccgctagt                                                78
```

<210> SEQ ID NO 719
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: cdrCAN46G19 Codon Optimized; K, FR2

<400> SEQUENCE: 719

```
atgcactggt atcagcagaa gccagggaaa gcccccaagc tgctgatcta c            51
```

<210> SEQ ID NO 720
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cdrCAN46G19 Codon Optimized; K, FR3

<400> SEQUENCE: 720
aaactggctt caggagtgcc aagcaggttc tcaggcagcg ggtccggaac tgactatacc    60
tttacaatca gctccctgca gcctgaagat attgccacct actattgc                108

<210> SEQ ID NO 721
<211> LENGTH: 319
<212> TYPE: DNA
<213> ORGANISM: Mus musculus
<220> FEATURE:
<223> OTHER INFORMATION: CAN33G1; K, variable region

<400> SEQUENCE: 721
gacatccagc tgacacaatc ttcatcctcc tattctgtat ctctaggaga cagggtcacc    60
attacttgca aggcaagtga ggacatatat aatcggttag cctggtatca gcagagacca   120
ggaaatgctc ctaggctctt aatatctggt gcaaccagtt tggaaactgg gattccttca   180
agattcagtg gcagtggatc tggaaaggag tacactctca gcattgccag tcttcagact   240
gaagattttg ttacttatta ctgtcaacaa tattggaata ttccgacgtt cggtggaggc   300
accaggctgg aaatcaaac                                                319

<210> SEQ ID NO 722
<211> LENGTH: 18
<212> TYPE: DNA
<213> ORGANISM: Mus musculus
<220> FEATURE:
<223> OTHER INFORMATION: CAN33G1; K, CDR1

<400> SEQUENCE: 722
gaggacatat ataatcgg                                                  18

<210> SEQ ID NO 723
<211> LENGTH: 9
<212> TYPE: DNA
<213> ORGANISM: Mus musculus
<220> FEATURE:
<223> OTHER INFORMATION: CAN33G1; K, CDR2

<400> SEQUENCE: 723 ggtgcaacc                                                             9

<210> SEQ ID NO 724
<211> LENGTH: 24
<212> TYPE: DNA
<213> ORGANISM: Mus musculus
<220> FEATURE:
<223> OTHER INFORMATION: CAN33G1; K, CDR3

<400> SEQUENCE: 724
caacaatatt ggaatattcc gacg                                           24

<210> SEQ ID NO 725
<211> LENGTH: 78

<212> TYPE: DNA
<213> ORGANISM: Mus musculus
<220> FEATURE:
<223> OTHER INFORMATION: CAN33G1; K, FR1

<400> SEQUENCE: 725
gacatccagc tgacacaatc ttcatcctcc tattctgtat ctctaggaga cagggtcacc    60
attacttgca aggcaagt                                                  78

<210> SEQ ID NO 726
<211> LENGTH: 51
<212> TYPE: DNA
<213> ORGANISM: Mus musculus
<220> FEATURE:
<223> OTHER INFORMATION: CAN33G1; K, FR2

<400> SEQUENCE: 726
ttagcctggt atcagcagag accaggaaat gctcctaggc tcttaatatc t             51

<210> SEQ ID NO 727
<211> LENGTH: 108
<212> TYPE: DNA
<213> ORGANISM: Mus musculus
<220> FEATURE:
<223> OTHER INFORMATION: CAN33G1; K, FR3

<400> SEQUENCE: 727
agtttggaaa ctgggattcc ttcaagattc agtggcagtg gatctggaaa ggagtacact    60
ctcagcattg ccagtcttca gactgaagat tttgttactt attactgt                108

<210> SEQ ID NO 728
<211> LENGTH: 31
<212> TYPE: DNA
<213> ORGANISM: Mus musculus
<220> FEATURE:
<223> OTHER INFORMATION: CAN33G1; K, FR4

<400> SEQUENCE: 728
ttcggtggag gcaccaggct ggaaatcaaa c                                   31

<210> SEQ ID NO 729
<211> LENGTH: 355
<212> TYPE: DNA
<213> ORGANISM: Mus musculus
<220> FEATURE:
<223> OTHER INFORMATION: CAN33G1; H, variable region

<400> SEQUENCE: 729
gaggtccagc tgcagcagtc tggacctgac ctggtgaagc ctggggcttc agtgaagata    60
tcctgcaagg cttctggtta tcattcact ggctactaca tgcactgggt gaagcagagc   120
catggaaaga gccttgagtg gattggacgt gttaatcctt acaacggtga tactaattac   180
aaccagaatt tcaaggacaa ggccatatta actgtagaca gtcagccag tacagcctac   240 atggagttcc gcagcctgac atctgaggac tctgcggtct attactgtac aagatcaaac   300
tgggaaaact actttgacta ctggggccaa ggctccactc tcacagtctc ctcag        355

<210> SEQ ID NO 730
<211> LENGTH: 24
<212> TYPE: DNA
<213> ORGANISM: Mus musculus
<220> FEATURE:
<223> OTHER INFORMATION: CAN33G1; H, CDR1

```
<400> SEQUENCE: 730
ggttactcat tcactggcta ctac                                            24

<210> SEQ ID NO 731
<211> LENGTH: 24
<212> TYPE: DNA
<213> ORGANISM: Mus musculus
<220> FEATURE:
<223> OTHER INFORMATION: CAN33G1; H, CDR2

<400> SEQUENCE: 731
gttaatcctt acaacggtga tact                                            24

<210> SEQ ID NO 732
<211> LENGTH: 33
<212> TYPE: DNA
<213> ORGANISM: Mus musculus
<220> FEATURE:
<223> OTHER INFORMATION: CAN33G1; H, CDR3

<400> SEQUENCE: 732
acaagatcaa actgggaaaa ctactttgac tac                                  33

<210> SEQ ID NO 733
<211> LENGTH: 75
<212> TYPE: DNA
<213> ORGANISM: Mus musculus
<220> FEATURE:
<223> OTHER INFORMATION: CAN33G1; H, FR1

<400> SEQUENCE: 733
gaggtccagc tgcagcagtc tggacctgac ctggtgaagc ctggggcttc agtgaagata    60
tcctgcaagg cttct                                                      75

<210> SEQ ID NO 734
<211> LENGTH: 51
<212> TYPE: DNA
<213> ORGANISM: Mus musculus
<220> FEATURE:
<223> OTHER INFORMATION: CAN33G1; H, FR2

<400> SEQUENCE: 734
atgcactggg tgaagcagag ccatggaaag agccttgagt ggattggacg t              51

<210> SEQ ID NO 735
<211> LENGTH: 114
<212> TYPE: DNA
<213> ORGANISM: Mus musculus
<220> FEATURE:
<223> OTHER INFORMATION: CAN33G1; H, FR3

<400> SEQUENCE: 735
aattacaacc agaatttcaa ggacaaggcc atattaactg tagacaagtc agccagtaca    60
gcctacatgg agttccgcag cctgacatct gaggactctg cggtctatta ctgt          114

<210> SEQ ID NO 736
<211> LENGTH: 34
<212> TYPE: DNA
<213> ORGANISM: Mus musculus
<220> FEATURE:
<223> OTHER INFORMATION: CAN33G1; H, FR4

<400> SEQUENCE: 736
tggggccaag gctccactct cacagtctcc tcag                                 34
```

<210> SEQ ID NO 737
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cdrCAN46G4; K, variable region

<400> SEQUENCE: 737

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Glu Thr Ser Lys Leu Ala Phe Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Phe Thr
                85                  90                  95

Phe Gly Gln Gly Thr Arg Leu Glu Ile Lys
            100                 105

<210> SEQ ID NO 738
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: cdrCAN46G4; K, CDR1

<400> SEQUENCE: 738

Ser Ser Val Ser Tyr
1               5

<210> SEQ ID NO 739
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: cdrCAN46G4; K, CDR2

<400> SEQUENCE: 739

Glu Thr Ser
1

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: cdrCAN46G4; K, CDR3

<400> SEQUENCE: 740

```
Phe Gln Gly Ser Gly Tyr Pro Phe Thr
1               5
```

<210> SEQ ID NO 741
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; K, FR1

<400> SEQUENCE: 741

```
Glu Ile Val Leu Thr Gln Ser Pro Ala Thr Leu Ser Leu Ser Pro Gly
1               5                   10                  15
Glu Arg Ala Thr Leu Ser Cys Ser Ala Ser
            20                  25
```

<210> SEQ ID NO 742
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; K, FR2

<400> SEQUENCE: 742

```
Met His Trp Tyr Gln Gln Lys Pro Gly Gln Ala Pro Arg Leu Leu Ile
1               5                   10                  15
Tyr
```

<210> SEQ ID NO 743
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G4; K, FR3

<400> SEQUENCE: 743

```
Lys Leu Ala Phe Gly Ile Pro Ala Arg Phe Ser Gly Ser Gly Ser Gly
1               5                   10                  15
Thr Asp Phe Thr Leu Thr Ile Ser Ser Leu Glu Pro Glu Asp Phe Ala
            20                  25                  30
Val Tyr Tyr Cys
        35
```

<210> SEQ ID NO 744
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; K, FR4

<400> SEQUENCE: 744

```
Phe Gly Gln Gly Thr Arg Leu Glu Ile Lys
1               5                   10
```

```
<210> SEQ ID NO 745
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G4; H, variable region

<400> SEQUENCE: 745

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Arg Ile Phe Pro Tyr Asn Gly Ala Ala Ser Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Leu Arg Val Tyr Phe Asp Tyr Trp Gly Gln Gly Thr Leu
            100                 105                 110

Val Thr Val Ser Ser
        115

<210> SEQ ID NO 746
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, CDR1

<400> SEQUENCE: 746

Gly Tyr Thr Phe Thr Gly Tyr Tyr
1               5

<210> SEQ ID NO 747
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, CDR2

<400> SEQUENCE: 747

Ile Phe Pro Tyr Asn Gly Ala Ala
1               5

<210> SEQ ID NO 748
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, CDR3
```

<400> SEQUENCE: 748

Ala Arg Trp Leu Arg Val Tyr Phe Asp Tyr
1               5                   10

<210> SEQ ID NO 749
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, FR1

<400> SEQUENCE: 749

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 750
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, FR2

<400> SEQUENCE: 750

Met His Trp Val Arg Gln Ala Pro Gly Gln Gly Leu Glu Trp Ile Gly
1               5                   10                  15

Arg

<210> SEQ ID NO 751
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cdrCAN46G4; H, FR3

<400> SEQUENCE: 751

Ser Tyr Asn Gln Asn Phe Lys Asp Lys Ala Thr Ile Thr Ala Asp Glu
1               5                   10                  15

Ser Thr Asn Thr Ala Tyr Met Glu Leu Ser Ser Leu Arg Ser Glu Asp
            20                  25                  30

Thr Ala Val Tyr Tyr Cys
        35

<210> SEQ ID NO 752
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cdrCAN46G4; H, FR4

<400> SEQUENCE: 752

Trp Gly Gln Gly Thr Leu Val Thr Val Ser Ser

<210> SEQ ID NO 753
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: huCAN46G4; K, variable region

<400> SEQUENCE: 753

```
Glu Lys Val Leu Thr Gln Ser Pro Ala Thr Leu Ser Leu Ser Pro Gly
1               5                   10                  15

Glu Arg Ala Thr Met Thr Cys Ser Ala Ser Ser Val Ser Tyr Met
            20                  25                  30

His Trp Tyr Gln Gln Lys Pro Gly Thr Ser Pro Lys Leu Trp Ile Tyr
        35                  40                  45

Glu Thr Ser Lys Leu Ala Phe Gly Val Pro Ala Arg Phe Ser Gly Ser
    50                  55                  60

Gly Ser Gly Asn Ser Tyr Ser Leu Thr Ile Ser Ser Leu Glu Pro Glu
65                  70                  75                  80

Asp Phe Ala Val Tyr Tyr Cys Phe Gln Gly Ser Gly Tyr Pro Phe Thr
                85                  90                  95

Phe Gly Gln Gly Thr Arg Leu Glu Ile Lys
            100                 105
```

<210> SEQ ID NO 754
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: huCAN46G4; K, CDR1

<400> SEQUENCE: 754

```
Ser Ser Val Ser Tyr
1               5
```

<210> SEQ ID NO 755
<211> LENGTH: 3
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: huCAN46G4; K, CDR2

<400> SEQUENCE: 755

```
Glu Thr Ser
1
```

<210> SEQ ID NO 756
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: huCAN46G4; K, CDR3

<400> SEQUENCE: 756

Phe Gln Gly Ser Gly Tyr Pro Phe Thr
1               5

<210> SEQ ID NO 757
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; K, FR1

<400> SEQUENCE: 757

Glu Lys Val Leu Thr Gln Ser Pro Ala Thr Leu Ser Leu Ser Pro Gly
1               5                   10                  15

Glu Arg Ala Thr Met Thr Cys Ser Ala Ser
            20                  25

<210> SEQ ID NO 758
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; K, FR2

<400> SEQUENCE: 758

Met His Trp Tyr Gln Gln Lys Pro Gly Thr Ser Pro Lys Leu Trp Ile
1               5                   10                  15

Tyr

<210> SEQ ID NO 759
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G4; K, FR3

<400> SEQUENCE: 759

Lys Leu Ala Phe Gly Val Pro Ala Arg Phe Ser Gly Ser Gly Ser Gly
1               5                   10                  15

Asn Ser Tyr Ser Leu Thr Ile Ser Ser Leu Glu Pro Glu Asp Phe Ala
            20                  25                  30

Val Tyr Tyr Cys
        35

<210> SEQ ID NO 760
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; K, FR4

<400> SEQUENCE: 760

Phe Gly Gln Gly Thr Arg Leu Glu Ile Lys
1               5                   10

<210> SEQ ID NO 761
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G4; H, variable region

<400> SEQUENCE: 761

Glu Val Gln Leu Leu Gln Ser Gly Ala Glu Val Lys Lys Pro Gly Ser
1               5                   10                  15

Ser Val Lys Ile Ser Cys Lys Ala Ser Asp Tyr Ser Phe Thr Gly Tyr
                20                  25                  30

Tyr Met His Trp Val Lys Gln Ala Pro Gly Gln Gly Leu Glu Trp Ile
            35                  40                  45

Gly Arg Ile Phe Pro Tyr Asn Gly Ala Ala Ser Tyr Asn Gln Asn Phe
        50                  55                  60

Lys Asp Lys Ala Thr Leu Thr Val Asp Lys Ser Ser Thr Ala Tyr
65                  70                  75                  80

Met Glu Leu His Ser Leu Arg Ser Glu Asp Thr Ala Val Tyr Tyr Cys
                85                  90                  95

Thr Arg Trp Leu Arg Val Tyr Phe Asp Tyr Trp Gly Gln Gly Thr Leu
            100                 105                 110

Val Thr Val Ser Ser
        115

<210> SEQ ID NO 762
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; H, CDR1

<400> SEQUENCE: 762

Asp Tyr Ser Phe Thr Gly Tyr Tyr
1               5

<210> SEQ ID NO 763
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; H, CDR2

<400> SEQUENCE: 763

Ile Phe Pro Tyr Asn Gly Ala Ala
1               5

<210> SEQ ID NO 764
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: huCAN46G4; H, CDR3

<400> SEQUENCE: 764

Thr Arg Trp Leu Arg Val Tyr Phe Asp Tyr
1               5                   10

<210> SEQ ID NO 765
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; H, FR1

<400> SEQUENCE: 765

Glu Val Gln Leu Leu Gln Ser Gly Ala Glu Val Lys Lys Pro Gly Ser
1               5                   10                  15

Ser Val Lys Ile Ser Cys Lys Ala Ser
            20                  25

<210> SEQ ID NO 766
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; H, FR2

<400> SEQUENCE: 766

Met His Trp Val Lys Gln Ala Pro Gly Gln Gly Leu Glu Trp Ile Gly
1               5                   10                  15

Arg

<210> SEQ ID NO 767
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huCAN46G4; H, FR3

<400> SEQUENCE: 767

Ser Tyr Asn Gln Asn Phe Lys Asp Lys Ala Thr Leu Thr Val Asp Lys
1               5                   10                  15

Ser Ser Ser Thr Ala Tyr Met Glu Leu His Ser Leu Arg Ser Glu Asp
            20                  25                  30

Thr Ala Val Tyr Tyr Cys
        35

<210> SEQ ID NO 768
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCAN46G4; H, FR4

<400> SEQUENCE: 768

```
Trp Gly Gln Gly Thr Leu Val Thr Val Ser Ser
1               5                   10
```

<210> SEQ ID NO 769
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G4; K, variable region

<400> SEQUENCE: 769

```
Glu Lys Val Leu Thr Gln Ser Pro Ala Thr Leu Ser Ala Ser Pro Gly
1               5                   10                  15

Glu Arg Val Thr Met Ser Cys Ser Ala Ser Ser Val Ser Tyr Met
            20                  25                  30

His Trp Tyr Gln Gln Lys Pro Gly Gln Ser Pro Lys Leu Trp Ile Tyr
        35                  40                  45

Glu Thr Ser Lys Leu Ala Phe Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Phe Ala Thr Tyr Tyr Cys Phe Gln Gly Ser Gly Tyr Pro Phe Thr
                85                  90                  95

Phe Gly Gln Gly Thr Arg Leu Glu Ile Lys
            100                 105
```

<210> SEQ ID NO 770
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, CDR1

<400> SEQUENCE: 770

```
Ser Ser Val Ser Tyr
1               5
```

<210> SEQ ID NO 771
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, CDR2

<400> SEQUENCE: 771

```
Glu Thr Ser
1
```

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, CDR3

```
<400> SEQUENCE: 772

Phe Gln Gly Ser Gly Tyr Pro Phe Thr
 1               5

<210> SEQ ID NO 773
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, FR1

<400> SEQUENCE: 773

Glu Lys Val Leu Thr Gln Ser Pro Ala Thr Leu Ser Ala Ser Pro Gly
 1               5                  10                  15

Glu Arg Val Thr Met Ser Cys Ser Ala Ser
            20                  25

<210> SEQ ID NO 774
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, FR2

<400> SEQUENCE: 774

Met His Trp Tyr Gln Gln Lys Pro Gly Gln Ser Pro Lys Leu Trp Ile
 1               5                  10                  15

Tyr

<210> SEQ ID NO 775
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G4; K, FR3

<400> SEQUENCE: 775

Lys Leu Ala Phe Gly Val Pro Ala Arg Phe Ser Gly Ser Gly Ser Gly
 1               5                  10                  15

Thr Asp Tyr Ser Leu Thr Ile Ser Ser Met Glu Pro Glu Asp Phe Ala
            20                  25                  30

Thr Tyr Tyr Cys
        35

<210> SEQ ID NO 776
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; K, FR4

<400> SEQUENCE: 776

Phe Gly Gln Gly Thr Arg Leu Glu Ile Lys
```

```
1               5                   10
```

<210> SEQ ID NO 777

<400> SEQUENCE: 777

000

<210> SEQ ID NO 778
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G4; H, variable region

<400> SEQUENCE: 778

```
Glu Val Gln Leu Leu Gln Ser Gly Ala Glu Val Val Lys Pro Gly Ser
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ala Pro Gly Gln Gly Leu Glu Trp Ile
        35                  40                  45

Gly Arg Ile Phe Pro Tyr Asn Gly Ala Ala Ser Tyr Asn Gln Asn Phe
    50                  55                  60

Lys Asp Lys Ala Thr Leu Thr Ala Asp Lys Ser Thr Asn Thr Ala Tyr
65                  70                  75                  80

Met Glu Leu Ser Ser Leu Arg Ser Glu Asp Ser Ala Val Tyr Tyr Cys
                85                  90                  95

Thr Arg Trp Leu Arg Val Tyr Phe Asp Tyr Trp Gly Gln Gly Thr Leu
            100                 105                 110

Val Thr Val Ser Ser
        115
```

<210> SEQ ID NO 779
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; H, CDR1

<400> SEQUENCE: 779

```
Gly Tyr Ser Phe Thr Gly Tyr Tyr
1               5
```

<210> SEQ ID NO 780
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; H, CDR2

<400> SEQUENCE: 780

```
Ile Phe Pro Tyr Asn Gly Ala Ala
1               5
```

```
<210> SEQ ID NO 781
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; H, CDR3

<400> SEQUENCE: 781

Thr Arg Trp Leu Arg Val Tyr Phe Asp Tyr
1               5                   10

<210> SEQ ID NO 782
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; H, FR1

<400> SEQUENCE: 782

Glu Val Gln Leu Leu Gln Ser Gly Ala Glu Val Val Lys Pro Gly Ser
1               5                   10                  15

Ser Val Lys Ile Ser Cys Lys Ala Ser
            20                  25

<210> SEQ ID NO 783
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rehuCAN46G4; H, FR2

<400> SEQUENCE: 783

Met His Trp Val Lys Gln Ala Pro Gly Gln Gly Leu Glu Trp Ile Gly
1               5                   10                  15

Arg

<210> SEQ ID NO 784
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rehuCAN46G4; H, FR3

<400> SEQUENCE: 784

Ser Tyr Asn Gln Asn Phe Lys Asp Lys Ala Thr Leu Thr Ala Asp Lys
1               5                   10                  15

Ser Thr Asn Thr Ala Tyr Met Glu Leu Ser Ser Leu Arg Ser Glu Asp
            20                  25                  30

Ser Ala Val Tyr Tyr Cys
        35

<210> SEQ ID NO 785
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: rehuCAN46G4; H, FR4

<400> SEQUENCE: 785

Trp Gly Gln Gly Thr Leu Val Thr Val Ser Ser
1               5                   10

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 786
agrtycagct gcarcagtct                                                   20

<210> SEQ ID NO 787
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 787
aggtccaact gcagcagcc                                                    19

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 788
tctgcctggt gacwttccca                                                   20

<210> SEQ ID NO 789
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 789
gtgcagcttc aggagtcag                                                    19

<210> SEQ ID NO 790
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 790
gaggtgaagc ttctcgagtc                                                   20

<210> SEQ ID NO 791
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 791
gaagtgaagc tggtggagtc                                               20

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 792
atgkacttgg gactgarctg t                                             21

<210> SEQ ID NO 793
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 793
cagtgtgagg tgaagctggt                                               20

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 794
ccaggttact ctgaaagagt c                                             21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 795
tgtggacctt gctattcctg a                                             21

<210> SEQ ID NO 796
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 796
tgttggggct gaagtgggtt t                                             21

<210> SEQ ID NO 797
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 797
atggagtggg aactgagctt a         21

<210> SEQ ID NO 798
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 798
agcttcagga gtcaggacc         19

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 799
caggtgcagc ttgtagagac         20

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 800
atgcagctgg gtcatcttct t         21

<210> SEQ ID NO 801
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 801
gactggattt ggatcackct ct         22

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 802
tggagtttgg acttagttgg g         21

<210> SEQ ID NO 803
<211> LENGTH: 16
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 803
cagggatcca kagttc                                                        16

<210> SEQ ID NO 804
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 804
tgatgaccca ractccact                                                     19

<210> SEQ ID NO 805
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 805
gcttgtgctc tggatccc                                                      18

<210> SEQ ID NO 806
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 806
ctgctgctct gggttcc                                                       17

<210> SEQ ID NO 807
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 807
cagcttcctg ctaatcagtg                                                    20

<210> SEQ ID NO 808
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 808
ctcagatcct tggactthtg                                                    20

<210> SEQ ID NO 809
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 809
tggagtcaca gacycagg                                                  18

<210> SEQ ID NO 810
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 810
tggagtttca gacccagg                                                  18

<210> SEQ ID NO 811
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 811
ctgctmtggg tatctggt                                                  18

<210> SEQ ID NO 812
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 812
cwtcttgttg ctctggtttc                                                20

<210> SEQ ID NO 813
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 813
gatgtcctct gctcagttc                                                 19

<210> SEQ ID NO 814
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
cctgctgagt tccttggg                                                  18

<210> SEQ ID NO 815
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 815
ctgctgctgt ggcttaca                                              18

<210> SEQ ID NO 816
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 816
ccttctcaac ttctgctct                                             19

<210> SEQ ID NO 817
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 817
agggcccytg ctcagttt                                              18

<210> SEQ ID NO 818
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 818
atgagggtcc ttgctgag                                              18

<210> SEQ ID NO 819
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 819
gaggttccag gttcaggt                                              18

<210> SEQ ID NO 820
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 820
ccatgaccat gytctcact                                             19

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 821
atggaaactc cagcttcatt t                                                    21

<210> SEQ ID NO 822
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 822
atgagaccgt ctattcagtt                                                      20

<210> SEQ ID NO 823
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 823
tcaagaagca cacgac                                                          16

<210> SEQ ID NO 824
<211> LENGTH: 12
<212> TYPE: PRT
<213> ORGANISM: Mus musculus

<400> SEQUENCE: 824

Cys Thr Arg Trp Leu Arg Val Tyr Phe Asp Tyr Trp
1               5                   10

<210> SEQ ID NO 825
<211> LENGTH: 11
<212> TYPE: PRT
<213> ORGANISM: Mus musculus

<400> SEQUENCE: 825

Cys Phe Gln Gly Ser Gly Tyr Pro Phe Thr Phe
1               5                   10

<210> SEQ ID NO 826
<211> LENGTH: 14
<212> TYPE: PRT
<213> ORGANISM: Mus musculus

<400> SEQUENCE: 826

Cys Ala Arg Arg Ser Arg Val Ser Phe Tyr Phe Asp Tyr Trp
1               5                   10

<210> SEQ ID NO 827
<211> LENGTH: 10
<212> TYPE: PRT
<213> ORGANISM: Mus musculus

<400> SEQUENCE: 827

Cys Gln Gln Trp Ser Gly Tyr Pro Tyr Phe
1               5                   10

<210> SEQ ID NO 828
<211> LENGTH: 12
<212> TYPE: PRT
```

-continued

<213> ORGANISM: Mus musculus

<400> SEQUENCE: 828

Cys Ala Arg Trp Leu Arg Val Tyr Phe Asp Tyr Trp
1               5                   10

<210> SEQ ID NO 829
<211> LENGTH: 11
<212> TYPE: PRT
<213> ORGANISM: Mus musculus

<400> SEQUENCE: 829

Cys Phe Gln Gly Ser Gly Tyr Pro Phe Thr Phe
1               5                   10

<210> SEQ ID NO 830
<211> LENGTH: 12
<212> TYPE: PRT
<213> ORGANISM: Mus musculus

<400> SEQUENCE: 830

Cys Ala Arg Trp Leu Arg Val Tyr Phe Asp Tyr Trp
1               5                   10

<210> SEQ ID NO 831
<211> LENGTH: 11
<212> TYPE: PRT
<213> ORGANISM: Mus musculus

<400> SEQUENCE: 831

Cys Phe Gln Gly Ser Gly Tyr Pro Phe Thr Phe
1               5                   10

<210> SEQ ID NO 832
<211> LENGTH: 12
<212> TYPE: PRT
<213> ORGANISM: Mus musculus

<400> SEQUENCE: 832

Cys Ala Arg Trp Leu Arg Val Tyr Phe Asp Tyr Trp
1               5                   10

<210> SEQ ID NO 833
<211> LENGTH: 11
<212> TYPE: PRT
<213> ORGANISM: Mus musculus

<400> SEQUENCE: 833

Cys Phe Gln Gly Ser Gly Tyr Pro Phe Thr Phe
1               5                   10

<210> SEQ ID NO 834
<211> LENGTH: 13
<212> TYPE: PRT
<213> ORGANISM: Mus musculus

<400> SEQUENCE: 834

Cys Thr Arg Ser Asn Trp Glu Asn Tyr Phe Asp Tyr Trp
1               5                   10

<210> SEQ ID NO 835
<211> LENGTH: 10
<212> TYPE: PRT
<213> ORGANISM: Mus musculus

```
<400> SEQUENCE: 835

Cys Gln Gln Tyr Trp Asn Ile Pro Thr Phe
1               5                   10
```

ANTIBODIES AGAINST *CLOSTRIDIUM DIFFICILE*

CROSS-REFERENCE TO RELATED APPLICATIONS

This application is the U.S. National Stage of International Application PCT/US2013/072467, filed on Nov. 29, 2013, which claims benefit of U.S. Provisional Patent Application Ser. No. 61/730,790, filed on Nov. 28, 2012, the entire contents of both are hereby incorporated by reference for all purposes.

FIELD

The invention relates to monoclonal antibodies to *Clostridium difficile* toxin B. The invention further relates to compositions and methods for the diagnosis, treatment or prevention of infection by the bacteria, *Clostridium difficile*, in a vertebrate subject. Methods are provided for administering antibodies to the vertebrate subject in an amount effective to reduce, eliminate, or prevent relapse from infection.

INCORPORATION BY REFERENCE OF SEQUENCE LISTING

A sequence listing submitted as a text file via EFS-Web is incorporated herein by reference. The text file containing the sequence listing is named "57964_145483_Second Substitute Seq List.TXT"; its date of creation is Nov. 21, 2017; and its size is 317,939 bytes (as measured in MS-Windows®).

BACKGROUND

*Clostridium difficile* (*C. difficile*) is a common nosocomial pathogen and a major cause of morbidity and mortality among hospitalized patients throughout the world. Kelly et al., New Eng. J. Med., 330:257-62, 1994. The increased use of broad spectrum antibiotics and the emergence of unusually virulent strains of *C. difficile* have lead to the idea that immunotherapies may be well suited to reduce disease and death associated with this bacterium. *C. difficile* has few traditional antibiotic options and frequently causes a recurring disease (25% of cases). Even with medical intervention, *C. difficile* claims about 20,000 lives in the USA alone per year and causes around 500,000 confirmed infections. Recently, more virulent strains of *C. difficile* have emerged that produce elevated levels of toxin such as the B1/NAP1/027 strain, which also has a decreased susceptibility to metronidazole. Outbreaks of *C. difficile* have necessitated ward and partial hospital closure due to the persistence of the spores that facilitate the spread of the disease. With the increasing elderly population and the changing demographics of the population, *C. difficile* is set to become a major problem in the 21$^{st}$ century. The spectrum of *C. difficile* disease ranges from asymptomatic carriage to mild diarrhea to fulminant pseudomembranous colitis.

*C. difficile* has a dimorphic lifecycle whereby it exists both as an infectious and tough spore form and a metabolically active toxin-producing vegetative cell. *C. difficile*-associated disease (CDAD) is believed to be caused by the vegetative cells and more specifically the actions of two toxins, enterotoxin toxin A and cytotoxin toxin B. To date, vaccines and immune therapy for *C. difficile* have focused upon the toxins (A and B), toxoids of A and B, recombinant fragments of A and B, and vegetative cell surface layer proteins (SLPAs).

Toxin B (TcdB, ~269 kDa) is an approximately 2366 residue single polypeptide toxin encoded on a *C. difficile* pathogenicity locus (PaLoc) that also includes genes for two regulators (TcdC and TcdR) of toxin expression, a putative holin (TcdE), and Toxin A (TcdA). TcdB has at least four functional domains that contribute to cell entry and glucosylation of small-GTPases within the cytosol of the cell. TcdB's glucosyltransferase domain is included in the first 543 residues of the toxin and is the biologically active domain, which also includes a conserved DXD motif (Asp286/Asp288) and Trp102, which form a complex with $Mn^{2+}$ and UDP-Glucose. The cysteine protease domain at residues 544-955 is necessary for autoproteolytic activity and delivery of the enzymatic domain into the cytosol. Between the cysteine protease domain and the C-terminal binding domain, a delivery domain is suggested, which is responsible for toxin translocation across membranes and delivers the glucosyltransferase into the cytosol of target cells. Finally, the fourth functional domain of TcdB is located within the carboxy-terminal region of the toxin (1851-2366), and is predicted to interact with receptors on target cells. However, the precise toxin receptor in humans has not been identified. After binding, the toxins are endocytosed via clathrin- and dynamin-dependent pathways to reach acidic endosomal compartments from where the toxins are translocated into the cytosol. Most likely in the cytosol, the cysteine protease domain is activated by binding of InsP6, resulting in autocleavage and release of the glucosyltransferase domain, which then targets Rho proteins (RhoA, -B, and -C), Rac and Cdc42. The glycosylation of these small regulatory proteins, lead to disruption of vital signaling pathways in the cells, resulting in actin condensation and consequent rounding of the cells, membrane blebbing, and eventual apoptosis and death of the target cell. While both TcdA and TcdB exert their activities on a wide range of cell types, TcdB exhibits a higher rate of enzymatic activity than TcdA, leading to a quickened rate of cytopathic effects in some cell types. Depending on the cell type, TcdB ranged from 4-fold to 200-fold more cytotoxic than TcdA in different studies.

There is an unmet need for effective treatment and/or prevention of *C. difficile* associated infections including prevention from relapse of CDAD. The present invention provides both mouse and humanized antibodies to toxin B to satisfy these and other needs.

SUMMARY

The invention comprises in one embodiment an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 110, 111, and 112, respectively, and wherein the light chain variable region comprises three CDRs, CDR1, CDR2 and CDR3, having amino acid sequences about 80% to about 100% homologous to the amino acid sequences set forth in SEQ ID NOs: 102, 103 and 104, respectively.

In another embodiment, the invention comprises an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 126, 127 and 128, respectively, and wherein the light chain variable region comprises three CDRs, CDR1, CDR2 and CDR3, having amino acid sequences about 80% to about 100% homologous to the amino acid sequences set forth in SEQ ID NOs: 118, 119 and 120, respectively.

In a third embodiment, the invention comprises an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 142, 143 and 144, respectively, and wherein the light chain variable region comprises three CDRs, CDR1, CDR2 and CDR3, having amino acid sequences about 80% to about 100% homologous to the amino acid sequences set forth in SEQ ID NOs: 134, 135 and 136, respectively.

In a fourth embodiment, the invention comprises an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 206, 207 and 208, respectively, and wherein the light chain variable region comprises three CDRs, CDR1, CDR2 and CDR3, having amino acid sequences about 80% to about 100% homologous to the amino acid sequences set forth in SEQ ID NOs: 198, 199 and 200, respectively.

In a fifth embodiment, the invention comprises an isolated monoclonal antibody, or an antigen-binding portion thereof, comprising a heavy chain variable region and a light chain region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 222, 223 and 224, respectively, and wherein the light chain variable region comprises three CDRs, CDR1, CDR2 and CDR3, having amino acid sequences about 80% to about 100% homologous to the amino acid sequences set forth in SEQ ID NOs: 214, 215 and 216, respectively.

In a sixth embodiment, the invention comprises an isolated monoclonal antibody, or an antigen-binding portion thereof, comprising a heavy chain region and a light chain region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 238, 239 and 240, respectively, and wherein the light chain variable region comprises three CDRs, CDR1, CDR2 and CDR3, having amino acid sequences about 80% to about 100% homologous to the amino acid sequences set forth in SEQ ID NOs: 230, 231 and 232, respectively.

In a seventh embodiment, the invention comprises an isolated monoclonal antibody, or an antigen-binding portion thereof, comprising a heavy chain variable region and a light chain region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 238, 239 and 240, respectively, and wherein the light chain variable region comprises three CDRs, CDR1, CDR2 and CDR3, having amino acid sequences about 80% to about 100% homologous to the amino acid sequences set forth in SEQ ID NOs: 230, 231 and 232, respectively.

In an eighth embodiment the invention comprises an isolated monoclonal antibody, or an antigen-binding portion thereof, comprising a heavy chain variable region and a light chain region, wherein the heavy chain variable region comprises amino acid sequences about 80% to about 100% homologous to SEQ ID NO. 710 and the light chain variable region comprises amino acid sequences about 80% to about 100% homologous to SEQ ID NO. 708.

In a ninth embodiment, the invention comprises an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 76, 77 and 78, respectively, and wherein the light chain variable region comprises three CDRs, CDR1, CDR2 and CDR3, having amino acid sequences about 80% to about 100% homologous to the amino acid sequences set forth in SEQ ID NOs: 68, 69 and 70, respectively. In this embodiment, the heavy chain variable region comprises an amino acid sequence about 80% to about 100% homologous to the amino acid sequence set forth in SEQ ID NO: 75, and wherein the light chain variable region comprises an amino acid sequence about 80% to about 100% homologous to the amino acid sequence set forth in SEQ ID NO: 67.

In a tenth embodiment, the invention comprises an isolated monoclonal antibody, or an antigen-binding portion thereof, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 44, 45 and 46, respectively, and wherein the light chain variable region comprises three CDRs, CDR1, CDR2 and CDR3, having amino acid sequences about 80% to about 100% homologous to the amino acid sequences set forth in SEQ ID NOs: 36, 37 and 38, respectively. In this embodiment the heavy chain variable region comprises an amino acid sequence about 80% to about 100% homologous to the amino acid sequence set forth in SEQ ID NO: 43, and wherein the light chain variable region comprises an amino acid sequence about 80% to about 100% homologous to the amino acid sequence set forth in SEQ ID NO: 35.

In an eleventh embodiment, the isolated monoclonal antibody or an antigen-binding portion thereof, that binds to *C. difficile* toxin B, comprises a heavy chain variable region, wherein the heavy chain variable region comprises an amino acid sequence about 80% to about 100% homologous to the amino acid sequence set forth in SEQ ID NOs: 109, 125, 141, 157, 173, 189, 205, 221 and 237 and comprises a light chain variable region, wherein the light chain variable region having an amino acid sequence about 80% to about 100% homologous to the amino acid sequence set forth in SEQ ID NOs: 101, 117, 133, 149, 165, 181, 197, 213 and 229.

In a twelfth embodiment, the isolated monoclonal antibody or an antigen-binding portion thereof, that binds to *C.* difficile toxin B, comprises a heavy chain variable region, wherein the heavy chain variable region comprises a nucleic acid sequence about 80% to about 100% homologous to the nucleic acid sequence set forth in SEQ ID NOs: 389, 405, 421, 437, 453, 469, 485, 501, 517, 533, 549, 565, 571, 587, 603, 619, 635, 651 and 709, and wherein the light chain variable region comprises a nucleic acid sequence about 80% to about 100% homologous to the nucleic acid sequence set forth in SEQ ID NOs: 381, 397, 413, 429, 445, 461, 477, 493, 509, 525, 541, 557, 563, 579, 595, 611, 627, 643 and 707.

The present invention also provides for an isolated monoclonal antibody, or an antigen-binding portion, comprising a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 76, 77 and 78, respectively, and wherein the light chain variable region comprises three CDRs, CDR1, CDR2 and CDR3, having amino acid sequences about 80% to about 100% homologous to the amino acid sequences set forth in SEQ ID NOs: 68, 69 and 70, respectively.

The present invention provides for an isolated monoclonal antibody, or an antigen-binding portion, that binds to Clostridium difficile (C. difficile) toxin B and comprises: (1) a heavy chain variable region, wherein the heavy chain variable region comprises three CDRs, CDR1, CDR2 and CDR3, having amino acid sequences about 80% to about 100% homologous to the amino acid sequences set forth in SEQ ID NOs: 76, 77 and 78, respectively; (2) a light chain variable region, wherein the light chain variable region comprises three CDRs, CDR1, CDR2 and CDR3, having amino acid sequences about 80% to about 100% homologous to the amino acid sequences set forth in SEQ ID NOs: 68, 69 and 70, respectively; (3) a heavy chain variable region, wherein the heavy chain comprises an amino acid sequence about 80% to about 100% homologous to the amino acid sequence set forth in SEQ ID NO: 75, and wherein the light chain variable region comprises an amino acid sequence about 80% to about 100% homologous to the amino acid sequence set forth in SEQ ID NO: 67; (4) a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in SEQ ID NOs: 44, 45 and 46, respectively, and wherein the light chain variable region comprises three CDRs, CDR1, CDR2 and CDR3, having amino acid sequences about 80% to about 100% homologous to the amino acid sequences set forth in SEQ ID NOs: 36, 37 and 38, respectively; (5) a heavy chain variable region, wherein the heavy chain variable region comprises three CDRs, CDR1, CDR2 and CDR3, having amino acid sequences about 80% to about 100% homologous to the amino acid sequences set forth in SEQ ID NOs: 44, 45 and 46, respectively; (6) a light chain variable region, wherein the light chain variable region comprises three CDRs, CDR1, CDR2 and CDR3, having amino acid sequences about 80% to about 100% homologous to the amino acid sequences set forth in SEQ ID NOs: 36, 37 and 38, respectively; (7) a heavy chain variable region, wherein the heavy chain comprises an amino acid sequence about 80% to about 100% homologous to the amino acid sequence set forth in SEQ ID NO: 43, and wherein the light chain variable region comprises an amino acid sequence about 80% to about 100% homologous to the amino acid sequence set forth in SEQ ID NO: 35; (8) a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in (i) SEQ ID NOs: 110, 111 and 112 respectively; (ii) SEQ ID NOs: 126, 127 and 128, respectively; or (iii) SEQ ID NOs: 142, 143 and 144, respectively, and wherein the light chain variable region comprises three CDRs, CDR1, CDR2 and CDR3, having amino acid sequences about 80% to about 100% homologous to the amino acid sequences set forth in (i) SEQ ID NOs: 102, 103 and 104, respectively; (ii) SEQ ID NOs: 118, 119 and 120, respectively; or (iii) SEQ ID NOs: 134, 135 and 136, respectively; (9) a heavy chain variable region, wherein the heavy chain variable region comprises three CDRs, CDR1, CDR2 and CDR3, having amino acid sequences about 80% to about 100% homologous to the amino acid sequences set forth in (i) SEQ ID NOs: 110, 111 and 112 respectively; (ii) SEQ ID NOs: 126, 127 and 128, respectively; or (iii) SEQ ID NOs: 142, 143 and 144, respectively; (10) a light chain variable region, wherein the light chain variable region comprises three CDRs, CDR1, CDR2 and CDR3, having amino acid sequences about 80% to about 100% homologous to the amino acid sequences set forth in (i) SEQ ID NOs: 102, 103 and 104 respectively; (ii) SEQ ID NOs: 118, 119 and 120, respectively; or (iii) SEQ ID NOs: 134, 135 and 136, respectively; (11) a heavy chain variable region, wherein the heavy chain comprises an amino acid sequence about 80% to about 100% homologous to the amino acid sequence set forth in SEQ ID NOs: 109, 125 or 141, and wherein the light chain variable region comprises an amino acid sequence about 80% to about 100% homologous to the amino acid sequence set forth in SEQ ID NOs: 101, 117 or 133; (12) a heavy chain variable region and a light chain variable region, wherein the heavy chain variable region comprises three complementarity determining regions (CDRs), CDR1, CDR2 and CDR3, having amino acid sequences about 80% to about 100% homologous to the amino acid sequences set forth in (i) SEQ ID NOs: 206, 207 and 208, respectively; (ii) SEQ ID NOs: 222, 223 and 224, respectively; or (iii) SEQ ID NOs: 238, 239 and 240, respectively, and wherein the light chain variable region comprises three CDRs, CDR1, CDR2 and CDR3, having amino acid sequences about 80% to about 100% homologous to the amino acid sequences set forth in (i) SEQ ID NOs: 198, 199 and 200 respectively; (ii) SEQ ID NOs: 214, 215 and 216, respectively; or (iii) SEQ ID NOs: 230, 231 and 232, respectively; (13) a heavy chain variable region, wherein the heavy chain variable region comprises three CDRs, CDR1, CDR2 and CDR3, having amino acid sequences about 80% to about 100% homologous to the amino acid sequences set forth in (i) SEQ ID NOs: 206, 207 and 208 respectively; (ii) SEQ ID NOs: 222, 223 and 224, respectively; or (iii) SEQ ID NOs: 238, 239 and 240, respectively; (14) a light chain variable region, wherein the light chain variable region comprises three CDRs, CDR1, CDR2 and CDR3, having amino acid sequences about 80% to about 100% homologous to the amino acid sequences set forth in (i) SEQ ID NOs: 198, 199 and 200 respectively; (ii) SEQ ID NOs: 214, 215 and 216, respectively; or (iii) SEQ ID NOs: 230, 231 and 232, respectively; (15) a heavy chain variable region wherein the heavy chain comprises an amino acid sequence about 80% to about 100% homologous to the amino acid sequence set forth in SEQ ID NOs: 205, 221 or 237, and wherein the light chain variable region comprises an amino acid sequence about 80% to about 100% homologous to the amino acid sequence set forth in SEQ ID NOs: 197, 213 or 229; (16) a heavy chain variable region and a light chain variable region, wherein the heavy chain variable region comprises three complementarity determining regions (CDRs), CDR1, CDR2 and CDR3, encoded by nucleic acid sequences about 80% to about 100% homologous to the nucleic acid sequences set forth in (i) SEQ ID NOs: 486, 487 and 488, respectively; (ii) SEQ ID NOs: 502, 503 and 504, respectively; or (iii) SEQ ID NOs: 518, 519 and 520, respectively, and wherein the light chain variable region comprises three CDRs, CDR1, CDR2 and CDR3, encoded by nucleic acid sequences about 80% to about 100% homologous to the nucleic acid sequences set forth in (i) SEQ ID NOs: 478, 479 and 480, respectively; (ii) SEQ ID NOs: 494, 495 and 496, respectively; or (iii) SEQ ID NOs: 510, 511 and 512, respectively; (17) a heavy chain variable region, wherein the heavy chain variable region comprises three CDRs, CDR1, CDR2 and CDR3, encoded by nucleic acid sequences about 80% to about 100% homologous to the nucleic acid sequences set forth in (i) SEQ ID NOs: 486, 487 and 488, respectively; (ii) SEQ ID NOs: 502, 503 and 504, respectively; or (iii) SEQ ID NOs: 518, 519 and 520, respectively; (18) a light chain variable region, wherein the light chain variable region comprises three CDRs, CDR1, CDR2 and CDR3, encoded by nucleic acid sequences about 80% to about 100% homologous to the nucleic acid sequences set forth in (i) SEQ ID NOs: 478, 479 and 480, respectively; (ii) SEQ ID NOs: 494, 495 and 496, respectively; or (iii) SEQ ID NOs: 510, 511 and 512, respectively; (19) a heavy chain variable region and a light chain variable region, wherein the heavy chain variable region comprises three complementarity determining regions (CDRs), CDR1, CDR2 and CDR3, encoded by nucleic acid sequences about 80% to about 100% homologous to the nucleic acid sequences set forth in (i) SEQ ID NOs: 390, 391 and 392, respectively; (ii) SEQ ID NOs: 406, 407 and 408, respectively; or (iii) SEQ ID NOs: 422, 423 and 424, respectively, and wherein the light chain variable region comprises three CDRs, CDR1, CDR2 and CDR3, encoded by nucleic acid sequences about 80% to about 100% homologous to the nucleic acid sequences set forth in (i) SEQ ID NOs: 382, 383 and 384, respectively; (ii) SEQ ID NOs: 398, 399 and 400, respectively; or (iii) SEQ ID NOs: 414, 415 and 416, respectively; (20) a heavy chain variable region, wherein the heavy chain variable region comprises three CDRs, CDR1, CDR2 and CDR3, encoded by nucleic acid sequences about 80% to about 100% homologous to the nucleic acid sequences set forth in (i) SEQ ID NOs: 390, 391 and 392, respectively; (ii) SEQ ID NOs: 406, 407 and 408, respectively; or (iii) SEQ ID NOs: 422, 423 and 424, respectively; (21) a light chain variable region, wherein the light chain variable region comprises three CDRs, CDR1, CDR2 and CDR3, encoded by nucleic acid sequences about 80% to about 100% homologous to the nucleic acid sequences set forth in (i) SEQ ID NOs: 382, 383 and 384, respectively; (ii) SEQ ID NOs: 398, 399 and 400, respectively; or (iii) SEQ ID NOs: 414, 415 and 416, respectively; (22) a heavy chain variable region and a light chain variable region, wherein the heavy chain variable region comprises three complementarity determining regions (CDRs), CDR1, CDR2 and CDR3, encoded by nucleic acid sequences about 80% to about 100% homologous to the nucleic acid sequences set forth in (i) SEQ ID NOs: 620, 621 and 622 respectively; (ii) SEQ ID NOs: 636, 637 and 638, respectively; or (iii) SEQ ID NOs: 652, 653 and 654, respectively, and wherein the light chain variable region comprises three CDRs, CDR1, CDR2 and CDR3, encoded by nucleic acid sequences about 80% to about 100% homologous to the nucleic acid sequences set forth in (i) SEQ ID NOs: 612, 613 and 614, respectively; (ii) SEQ ID NOs: 628, 629 and 630, respectively; or (iii) SEQ ID NOs: 644, 645 and 646, respectively; (23) a heavy chain variable region, wherein the heavy chain variable region comprises three CDRs, CDR1, CDR2 and CDR3, encoded by nucleic acid sequences about 80% to about 100% homologous to the nucleic acid sequences set forth in (i) SEQ ID NOs: 620, 621 and 622 respectively; (ii) SEQ ID NOs: 636, 637 and 638, respectively; or (iii) SEQ ID NOs: 652, 653 and 654, respectively; (24) a light chain variable region, wherein the light chain variable region comprises three CDRs, CDR1, CDR2 and CDR3, encoded by nucleic acid sequences about 80% to about 100% homologous to the nucleic acid sequences set forth in (i) SEQ ID NOs: 612, 613 and 614, respectively; (ii) SEQ ID NOs: 628, 629 and 630, respectively; or (iii) SEQ ID NOs: 644, 645 and 646, respectively; (25) a heavy chain variable region and a light chain variable region, wherein the heavy chain variable region comprises three complementarity determining regions (CDRs), CDR1, CDR2 and CDR3, encoded by nucleic acid sequences about 80% to about 100% homologous to the nucleic acid sequences set forth in (i) SEQ ID NOs: 534, 535 and 536, respectively; (ii) SEQ ID NOs: 550, 551 and 552, respectively; or (iii) SEQ ID NOs: 566, 567 and 568, respectively, and wherein the light chain variable region comprises three CDRs, CDR1, CDR2 and CDR3, encoded by nucleic acid sequences about 80% to about 100% homologous to the nucleic acid sequences set forth in (i) SEQ ID NOs: 526, 527 and 528, respectively; (ii) SEQ ID NOs: 542, 543 and 544, respectively; or (iii) SEQ ID NOs: 558, 559 and 560, respectively; (26) a heavy chain variable region, wherein the heavy chain variable region comprises three CDRs, CDR1, CDR2 and CDR3, encoded by nucleic acid sequences about 80% to about 100% homologous to the nucleic acid sequences set forth in (i) SEQ ID NOs: 534, 535 and 536, respectively; (ii) SEQ ID NOs: 550, 551 and 552, respectively; or (iii) SEQ ID NOs: 566, 567 and 568, respectively; (27) a light chain variable region, wherein the light chain variable region comprises three CDRs, CDR1, CDR2 and CDR3, encoded by nucleic acid sequences about 80% to about 100% homologous to the nucleic acid sequences set forth in (i) SEQ ID NOs: 526, 527 and 528, respectively; (ii) SEQ ID NOs: 542, 543 and 544, respectively; or (iii) SEQ ID NOs: 558, 559 and 560, respectively; (28) a heavy chain variable region encoded by a nucleic acid sequence about 80% to about 100% homologous to the nucleic acid sequence set forth in SEQ ID NO: 485, 501 and 517 wherein the light chain variable region is encoded by an nucleic acid sequence about 80% to about 100% homologous to the nucleic acid sequence set forth in SEQ ID NO: 477, 493 and 509; (29) a heavy chain variable region is encoded by a nucleic acid sequence about 80% to about 100% homologous to the nucleic acid sequence set forth in SEQ ID NO: 389, 405 or 421, and wherein the light chain variable region is encoded by a nucleic acid sequence about 80% to about 100% homologous to the nucleic acid sequence set forth in SEQ ID NO: 381, 397 or 413; (30) a heavy chain variable region is encoded by a nucleic acid sequence about 80% to about 100% homologous to the nucleic acid sequence set forth in SEQ ID NO: 619, 635 or 651, and wherein the light chain variable region is encoded by a nucleic acid sequence about 80% to about 100% homologous to the nucleic acid sequence set forth in SEQ ID NO: 611, 627 or 643; (31) a heavy chain variable region is encoded by a nucleic acid sequence about 80% to about 100% homologous to the nucleic acid sequence set forth in SEQ ID NO: 533, 549 or 565, and wherein the light chain variable region is encoded by a nucleic acid sequence about 80% to about 100% homologous to the nucleic acid sequence set forth in SEQ ID NO: 525, 541 or 557; (32) a heavy chain variable region, wherein the heavy chain variable region comprises an amino acid sequence about 80% to about 100% homologous to the amino acid sequence set forth in SEQ ID NOs: 11, 27, 43, 59, 75 or 93; (33) a light chain variable region, wherein the light chain variable region comprises an amino acid sequence about 80% to about 100% homologous to the amino acid sequence set forth in SEQ ID NOs: 3, 19, 35, 51, 67 or 85; (34) a heavy chain variable region, wherein the heavy chain variable region comprises an amino acid sequence about 80% to about 100% homologous to the amino acid sequence set forth in SEQ ID NOs: 109, 125, 141, 157, 173, 189, 205, 221, 237 or 710; (35) a light chain variable region, wherein the light chain variable region comprises an amino acid sequence about 80% to about 100% homologous to the amino acid sequence set forth in SEQ ID NOs: 101, 117, 133, 149, 165, 181, 197, 213, 229 or 708; (36) a heavy chain variable region, wherein the heavy chain variable region is encoded by a nucleic acid sequence about 80% to about 100% homologous to the nucleic acid sequence set forth in SEQ ID NOs: 253, 269, 285, 301, 317, 341, 357 or 373; (37) a light chain variable region, wherein the light chain variable region is encoded by a nucleic acid sequence about 80% to about 100% homologous to the nucleic acid sequence set forth in SEQ ID NOs: 245, 261, 277, 293, 309, 325, 333, 349 or 365; (38) a heavy chain variable region, wherein the heavy chain variable region is encoded by a nucleic acid sequence about 80% to about 100% homologous to the nucleic acid sequence set forth in SEQ ID NOs: 389, 405, 421, 437, 453, 469, 485, 501, 517, 533, 549, 565, 571, 587, 603, 619, 635 or 651; (39) a light chain variable region, wherein the light chain variable region is encoded by a nucleic acid sequence about 80% to about 100% homologous to the nucleic acid sequence set forth in SEQ ID NOs: 381, 397, 413, 429, 445, 461, 477, 493, 509, 525, 541, 557, 579, 595, 611, 627, 643 or 714; or (40) a heavy chain variable region and a light chain variable region comprising amino acid sequences about 80% to about 100% homologous to the amino acid sequences set forth in SEQ ID NOs: 75 and 67, respectively.

The isolated monoclonal antibody or antigen-binding portion thereof binds to C. difficile toxin B, and may have a dissociation constant ($K_D$) less than about $1 \times 10^{-8}$ M.

The isolated monoclonal antibody or antigen-binding portion may be humanized or chimeric, e.g., mouse-human, and may be: (a) a whole immunoglobulin molecule; (b) an scFv; (c) a Fab fragment; (d) an F(ab')$_2$; or (e) a disulfide linked Fv and may contain at least one constant domain, e.g., (a) an IgG constant domain; (b) IgM constant domain; (c) IgD constant domain; (d) IgE constant domain; or (e) an IgA constant domain. The present antibody or antigen-binding portion may be fused in-frame to fusion partners or incorporate domains for post-translational modifications to facilitate stability in vitro to affect formulation/shelf life (e.g. encapsulation, acylated) or in vivo to affect PK/PD (e.g. pegylation, sialyation, glycosylation). The fusion partner may act as a ligand for therapeutic or diagnostic applications. The antibody or antigen-binding portion may be engineered to increase avidity through valency (multivalent) or complimented with specificity, by fusion or association with antibody or antigen-binding portions against other antigens (e.g. different domains of TcdA, TcdB, binary toxin).

The isolated monoclonal antibody or antigen-binding portion may bind to: (i) fragment 4 of C. difficile toxin B; and/or, (ii) fragment 1 of C. difficile toxin B.

The present invention provides for an isolated monoclonal antibody, or an antigen-binding portion, wherein the antibody, or antigen-binding portion thereof, binds to the same or antigenically similar epitope of C. difficile toxin B recognized by an antibody comprising: (1) a heavy chain variable region and a light chain variable region comprising amino acid sequences about 80% to about 100% homologous to the amino acid sequences set forth in SEQ ID NOs: 43 and 35, respectively; (2) a heavy chain variable region and a light chain variable region comprising amino acid sequences about 80% to about 100% homologous to the amino acid sequences set forth in (i) SEQ ID NOs: 109 and 101, respectively; (ii) SEQ ID NOs: 125 and 117, respectively; (iii) SEQ ID NOs: 141 and 133, respectively; (3) a heavy chain variable region and a light chain variable region comprising amino acid sequences about 80% to about 100% homologous to the amino acid sequences set forth in (i) SEQ ID NOs: 205 and 197, respectively; (ii) SEQ ID NOs: 221 and 213, respectively; or (iii) SEQ ID NOs: 237 and 229, respectively; (4) a heavy chain variable region and a light chain variable region comprising nucleic acid sequences about 80% to about 100% homologous to the nucleic acid sequences set forth in (i) SEQ ID NOs: 389 and 381, respectively; (ii) SEQ ID NOs: 405 and 397, respectively; (iii) SEQ ID NOs: 421 and 413, respectively; or (iv) SEQ ID NOs: 709 and 707, respectively; or, (5) a heavy chain variable region and a light chain variable region encoded by nucleic acid sequences about 80% to about 100% homologous to the nucleic acid sequences set forth in (i) SEQ ID NOs: 485 and 477, respectively; (ii) SEQ ID NOs: 501 and 493, respectively; or (iii) SEQ ID NOs: 517 and 509, respectively.

The present invention provides for an isolated monoclonal antibody produced by hybridoma designated CAN33G1, CAN46G4, CAN46G13, CAN46G13a, CAN46G19 or CAN46G24 or for a hybridoma which is designated CAN33G1, CAN46G4, CAN46G13, CAN46G13a, CAN46G19 or CAN46G24.

The present invention provides for an isolated monoclonal antibody, or an antigen-binding portion thereof, wherein, in an in vivo toxin B challenge experiment, when the antibody, or an antigen-binding portion thereof, is administered to a mammal at a dosage ranging from about 8 mg/kg body weight to about 13 mg/kg body weight about 24 hours before the mammal is exposed to about 75 ng or greater than about 75 ng of C. difficile toxin B, the chance of survival for the mammal is greater than about 80% within about 4 days after the exposure to toxin B. Lethal dose or lethal concentration is dependent on the toxicity of the toxin. The amount of antibody required to neutralize the toxin may vary accordingly.

The present invention provides for an isolated monoclonal antibody, or an antigen-binding portion thereof, wherein the antibody, or antigen-binding portion thereof, at a concentration ranging from about 25 µg/ml to about 100 µg/ml, neutralizes greater than about 40% of about 5 ng/ml C. difficile toxin B in an in vitro neutralization assay. The toxicity of the toxin is dependent on the strain from which it was isolated, as it varies between strains. Accordingly, the concentration of antibody required to neutralize the toxin is dependent on the source of the toxin.

Cells that may be used with the present invention, include, but are not limited to, bacterial cell, a eukaryotic cell, or a mammalian cell. For example, the cells can be COS-1, COS-7, HEK293, BHK21, CHO, CHOK1SV, Per.C6, BSC-1, Hep G2, SP2/0, HeLa, myeloma or lymphoma cells.

The present invention provides for an antibody produced by a hybridoma designated: (1) CAN46G13-1-8, wherein the hybridoma is deposited with the American Type Culture Collection having the ATCC Patent Deposit Designation PTA-13257. The deposit for PTA-13257 was made on Aug. 23, 2012. As used herein, CAN46G13a refers to the hybridoma clone CAN46G13-1-8 or the monoclonal antibodies generated by the corresponding clone; (2) CAN46G4-1-2, wherein the hybridoma is deposited with the American Type Culture Collection having the ATCC Patent Deposit Designation PTA-13258. The deposit for PTA-13258 was made on Aug. 23, 2012. As used herein, CAN46G4 refers to the clone CAN46G4-1-2 or the monoclonal antibodies generated by the corresponding clone; (3) CAN46G19-3-2, wherein the hybridoma is deposited with the American Type Culture Collection having the ATCC Patent Deposit Designation PTA-13259. The deposit for PTA-13259 was made on Aug. 23, 2012. As used herein, CAN46G19 refers to the clone CAN46G19-3-2 or the monoclonal antibodies generated by the corresponding clone; (4) CAN46G13-1-5, wherein the hybridoma is deposited with the American Type Culture Collection having the ATCC Patent Deposit Designation PTA-13260. The deposit for PTA-13260 was made on Aug. 23, 2012. As used herein, CAN46G13 and CAN46G24 refer to the clone CAN46G13-1-5 or the monoclonal antibodies generated by the corresponding clone. The sequences for the monoclonal antibodies generated by CAN46G13 and CAN46G24 are identical.

The present invention provides for a composition comprising the isolated monoclonal antibody or antigen-binding portion thereof, and at least one pharmaceutically acceptable carrier. This composition may be used as a method of preventing or treating *C. difficile*-associated disease comprising administering to a subject an effective amount of the present antibody or antigen-binding portion thereof. The antibody or antigen-binding portion thereof may be administered intravenously, subcutaneously, intramuscularly or transdermally. The present method may further comprise the step of administering to the subject a second agent, or multiple agents (e.g., third, fourth, fifth and sixth) such as a different antibody or fragment thereof (e.g., an antibody or antigen-binding portion thereof that binds *C. difficile* toxin A), an antiparasitic (e.g. nitrazoxanide), an antibiotic (e.g., vancomycin, metronidazole, rifaximin, or fidaxomicin), probiotics (compositions with *saccharomyces boulardi*, bifidobacteria, or *lactobacillus*), or fecal transplant. The present method may further comprise the step of administering to the subject one or more additional agents such as a different antibody or fragment thereof (e.g., and antibody or antigen-bind portion thereof that binds a different fragment of *C. difficile* toxin B).

BRIEF DESCRIPTION OF THE DRAWINGS

FIG. 4 shows a Western immunoblot of purified murine CAN46G4 and CAN46G19 mAbs.

FIG. 5 shows a Western immunoblot of purified murine CAN46G13 and CAN46G13a mAbs.

FIG. 6 shows a Western immunoblot of purified murine CAN46G24 mAb.

FIG. 10 shows primers useful for variable (V) chain gene amplification from RNA. (RT-VH1-1, SEQ ID NO: 786; RT-VH1-2, SEQ ID NO: 787; RT-VH2, SEQ ID NO: 788: RT-VH3, SEQ ID NO: 789; RT-VH4, SEQ ID NO: 790; RT-VHS, SEQ ID NO: 791; RT-VH6, SEQ ID NO: 792; RT-VH7, SEO ID NO: 793; RT-VH8, SEQ ID NO: 794; RT-VH9, SEQ ID NO: 795: RT-VH10, SEQ ID NO: 796; RT-VH11, SEO ID NO: 797; RT-VH12, SEQ ID NO: 798; RT-VH13, SEQ ID NO: 799; RT-VH14, SEQ ID NO: 800; RT-VH15, SEQ ID NO: 801; RT-VH16, SEQ ID NO: 802; RTCGamma, SEQ ID NO: 803; RT-VK1, SEQ ID NO: 804; RT-VK2, SEQ ID NO: 805; RT-VK3, SEQ ID NO: 806; RT-VK4, SEQ ID NO: 807; RT-VKS, SEO ID NO: 808; RT-VK6, SEQ ID NO: 809; RT-VK7, SEQ ID NO: 810; RT-VK8, SEQ ID NO: 811, RT-VK9, SEQ ID NO: 812; RT-VK10, SEQ ID NO: 813; RT-VK11, SEQ ID NO: 814; RT-VK12, SEQ ID NO: 815; RT-VK13, SEQ ID NO: 816; RT-VK14, SEQ ID NO: 817; RT-VK15, SEQ ID NO: 818; RT-VK16, SEQ ID NO: 819; RT-VK17, SEQ ID NO: 820; RT-VK18, SEQ ID NO: 821; RT-VK19, SEQ ID NO: 822; RTCK, SEQ ID NO: 823).

FIG. 11 shows variable (V) gene sequencing results for murine CAN46G4(CAN46G4 HEAVY. SEQ ID NO: 11; CTRWLRVYFDYW, SEQ ID NO: 824; CAN46G4KAPPA, SEQ ID NO: 3; CFQGSGYPFTF, SEQ ID NO: 825), CAN46G13a(CAN46G13a HEAVY, SEQ ID NO: 43; CARRSRVSFYFDYW, SEQ ID NO: 826; CAN46G13KAPPA, SEQ ID NO: 35; CQQWSGYPYF, SEQ ID NO: 827), CAN46G19(CAN46G19 HEAVY, SEQ ID NO: 59; CARWLRVYFDYW, SEQ ID NO: 828; CAN46G19KAPPA, SEQ ID NO: 51; CFQGSGYPFTF, SEQ ID NO: 829), CAN46G24(CAN46G24 HEAVY, SEQ ID NO: 75; CARWLRVYFDYW, SEQ ID NO: 830; CAN46G24KAPPA, SEQ ID NO: 67; CFQGSGYPFTF, SEQ ID NO: 831), CAN46G13(CAN46G13HEAVY SEQ ID NO: 27; CARWLRVYFDYW, SEQ ID NO: 832; CAN46G13KAPPA, SEQ ID NO: 19, CFQGSGYPFTF, SEQ ID NO: 833), and CAN33G1(CAN33G1HEAVY, SEQ ID NO: 93, CTRSNWENYFDYW, SEQ ID NO: 834; CAN33G1KAPPA, SEQ ID NO: 85, CQQYWNIPTF, SEQ ID NO: 835) that includes, both VH and VL sequences from the murine CAN46and CAN33G1parental clones.

FIG. 12 shows amino acid variable V-region sequence of humanized CDR Grafted CAN46mAbs. (cdrCAN46G4KAPPA, SEQ ID NO: 737; cdrCAN46G4 HEAVY, SEQ ID NO: 745; cdrCAN46G13a KAPPA, SEQ ID NO: 101; cdrCAN46G13 HEAVY, SEQ ID NO: 109; cdrCAN46G19KAPPA, SEQ ID NO: 149; cdrCAN46G19 HEAVY, SEQ ID NO: 157; cdrCAN46G24KAPPA, SEQ ID NO: 197; cdrCAN46G24 HEAVY, SEQ ID NO: 205).

FIG. 13 shows amino acid variable V-region sequence of humanized huCAN46G mAbs. (huCAN46G4KAPPA, SEQ ID NO: 753; huCAN46G4 HEAVY, SEQ ID NO: 761; huCAN46G13a KAPPA, SEQ ID NO: 117; huCAN46G13a HEAVY, SEQ ID NO: 125; huCAN46G19KAPPA. SEQ ID NO: 165; huCAN46G19 HEAVY, SEQ ID NO: 173; huCAN46G24KAPPA, SEQ ID NO: 213; huCAN46G24 HEAVY. SEQ ID NO: 221).

FIG. 14 shows amino acid variable V-region sequence of resurfaced, humanized rehuCAN46G mAbs. (rehuCAN46G4KAPPA, SEQ ID NO: 769: rehuCAN46G4 HEAVY, SEQ ID NO: 778; rehuCAN46G13a KAPPA, SEQ ID NO: 133; rehuCAN46G13a HEAVY, SEQ ID NO: 141; rehuCAN46G19KAPPA, SEQ ID NO: 181; rehuCAN46G19 HEAVY, SEQ ID NO: 189; rehuCAN46G24KAPPA, SEQ ID NO: 229; rehuCAN46G24 HEAVY, SEQ ID NO: 237).

FIG. 15a shows a bar graph depicting in vitro neutralization data for purified humanized CAN46G4 variants in Per.C6 construct expressed in HEK293F cells at 250 pg/ml depicted as a bar graph.

FIG. 18 is a table showing the total Human IgG ELISA results from mice injected with humanized CAN46 mAb pre- (−12 hours) and post- (72 hours after challenge) Toxin B challenge.

FIG. 24 is a table showing the affinity analysis of humanized CAN46G4, CAN46G13a, and CAN46G19 Tcd B mAbs.

FIG. 25 is a line graph showing the in vitro Toxin B neutralization of the humanized CAN46G mAbs purified from CHOK1 SV cells expressing the CHO-based construct FIG. 26 includes multiple bar graphs showing the EC50 of the humanized CAN46 mAbs against various C. difficile clinical isolates.

FIG. 29 is a table showing the immunoreactive responses in vitro measured by direct ELISA of different mAbs purified from HEK293F cells expressing the Per.C6-based constructs against partially purified toxins from different C. difficile strains. (H =high binding, M =medium binding, L =low binding).

FIG. 31 contains graphs showing the binding characteristics of humanized CAN46 mAbs to captured toxins from different C. difficile non-NAP1 and NAP1 strains by sandwich ELISA.

DETAILED DESCRIPTION

Figure 1:
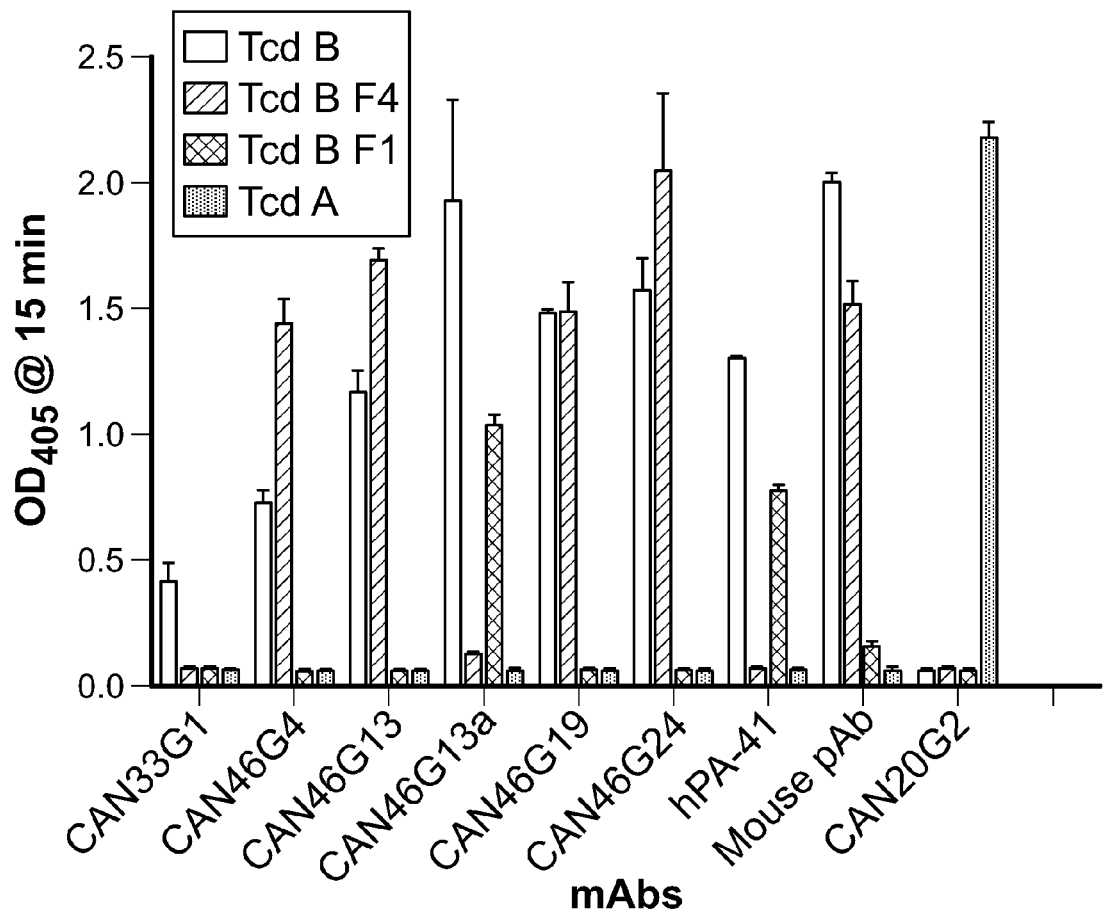
FIG. 1 is an ELISA showing the binding specificity of murine CAN33 and CAN46 monoclonal antibodies (mAbs) to whole toxin B (TcdB), fragment 4 of toxin B (TcdB F4), and fragment 1 of toxin B (TcdB F1). TcdA (toxin A) negative control is shown, along with control antibodies hPA-41, mouse anti-toxin B polyclonal (mouse pAB), and anti-toxin B (CAN20G2).

The present invention provides for compositions and methods for the diagnosis, prevention or treatment of Clostridium difficile (C. difficile) bacterial infection or bacterial carriage. The compositions contain antibodies (or an antigen-binding portion) that recognize toxin B of C. difficile, including mouse monoclonal antibodies, humanized antibodies, chimeric antibodies (murine/human), or antigen-binding portions of any of the foregoing. These antibodies (or antigen-binding portion thereof) can neutralize toxin B in vitro, in vivo, and/or inhibit binding of toxin B to mammalian cells. Therefore, the present antibodies or antigen-binding portion can be used in a passive immunization manner or protocol to prevent or treat C. difficile-associated disease (CDAD).

In one embodiment, the present antibodies or antigen-binding portion provide one or more of the following effects: protect from or treat C. difficile-mediated colitis, antibiotic-associated colitis, pseudomembranous colitis (PMC) or other intestinal disease in a subject; protect from or treat diarrhea in a subject; and/or treat or inhibit relapse of C. difficile-mediated disease. When administered to a mammal, the present antibodies or antigen-binding portion may protect the mammal against toxin B administered in an amount that would otherwise be fatal to the mammal had the antibody or antigen-binding portion not administered.

The present antibodies or antigen-binding portions include murine antibodies produced by hybridomas CAN46G4, CAN46G13, CAN46G13a, CAN46G19, CAN46G24 and CAN33G1 as well as humanized antibodies derived from the same hybridomas described herein.

Also encompassed by the present invention are antibodies or antigen-binding portions that include an antigen-binding portion of the antibody produced by hybridomas CAN46G4, CAN46G13, CAN46G13a, CAN46G19, CAN46G24 or CAN33G1; as used herein, CAN46G4, CAN46G13, CAN46G13a, CAN46G19, CAN46G24 and CAN33G1 refer to the hybridoma clones or the monoclonal antibodies generated by the corresponding hybridoma clones.

The antibodies or antigen-binding portions can specifically bind to an epitope: (i) within fragment 1 of toxin B, e.g., an epitope between amino acid residues 1-592 of toxin B (CAN46G13a); or an epitope within fragment 4 of toxin B, e.g., an epitope between amino acid residues 1777-2366 of toxin B (CAN46G4, CAN46G13, CAN46G19, CAN46G24 or CAN33G1). Babcock, G. J. et al., Infection and Immunity, 74: 6339-6347 (2006).

In other embodiments, the antibodies or antigen-binding portions specifically bind to an epitope within fragment 2 (amino acid residues 593-1183) or fragment 3 (amino acid residues 1184-1776) of toxin B. In certain embodiments, the antibodies or antigen-binding portions specifically bind an epitope within amino acid residues 1-600, 400-600, 415-540, 1-100, 100-200, 200-300, 300-400, 400-500, 500-600, 600-700, 700-800, 900-1000, 1100-1200, 1200-1300, 1300-1400, 1400-1500, 1500-1600, 1600-1700, 1800-1900, 1900-2000, 2000-2100, 2100-2200 or 2200-2366 of toxin B, or any interval, portion or range thereof.

The present antibodies, or antigen-binding portions, include, but are not limited to, monoclonal antibodies, chimeric antibodies, humanized antibodies, polyclonal antibodies, recombinant antibodies, as well as antigen-binding portions of the foregoing. An antigen-binding portion of an antibody may include a portion of an antibody that specifically binds to a toxin of *C. difficile* (e.g., toxin B) and may comprise the heavy or light chain alone of the antibody molecule.

CDRs and Variable Regions

The CDRs of the present antibodies or antigen-binding portions can be from a non-human, e.g., murine (*Mus musculus*) or a human source (*Homo Saipian*). The framework of the present antibodies or antigen-binding portions can be human, humanized, non-human (e.g., a murine framework modified to decrease antigenicity in humans), or a synthetic framework (e.g., a consensus sequence).

In one embodiment, the present antibodies, or antigen-binding portions, contain at least one heavy chain variable region and/or at least one light chain variable region. The heavy chain variable region (or light chain variable region) contains three CDRs and four framework regions (FRs), arranged from amino-terminus to carboxyl-terminus in the following order: FR1, CDR1, FR2, CDR2, FR3, CDR3, FR4. Kabat, E. A., et al. Sequences of Proteins of Immunological Interest, Fifth Edition, U.S. Department of Health and Human Services, NIH Publication No. 91-3242, 1991. Chothia, C. et al., J. Mol. Biol. 196:901-917, 1987.

The present antibodies or antigen-binding portions can specifically bind to toxin B with a dissociation constant ($K_D$) of less than about $10^{-7}$ M, less than about $10^{-8}$ M, less than about $10^{-9}$ M, less than about $10^{-10}$ M, less than about $10^{-11}$ M, or less than about $10^{-12}$ M.

Antibodies with a heavy chain variable region and a light chain variable region that are at least about 70%, at least about 75%, at least about 80%, at least about 85%, at least about 90%, at least about 95%, at least about 99%, about 70% to about 100%, about 80% to about 100%, about 90% to about 100%, about 95% to about 100%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the heavy chain variable region and light chain variable region of the antibody produced by clone CAN46G4, CAN46G13, CAN46G13a, CAN46G19, CAN46G24 or CAN33G1 can also bind to toxin B and are encompassed by the invention.

In related embodiments, anti-toxin B antibodies or antigen-binding portions include, for example, the CDRs of variable heavy chains and/or variable light chains of CAN46G4, CAN46G13, CAN46G13a, CAN46G19, CAN46G24 or CAN33G1. The CDRs of the heavy chain variable regions from these clones, as well as the CDRs of the light chain variable regions from these clones, are shown in Table 1.

TABLE 1

Sequence ID NOs

| Name | Chain, Region | Origin | Sequence | Seq ID No: |
|---|---|---|---|---|
| Fragment 1 of Toxin B | TcdB, Frag 1, aa 1-546 | *Clostridium difficile* | MSLVNRKQLEKMANVRFRTQEDEYV AILDALEEYHNMSENTVVEKYLKLKDI NSLTDIYIDTYKKSGRNKALKKFKEYL VTEVLELKNNNLTPVEKNLHFVWIGG QINDTAINYINQWKDVNSDYNVNVFY DSNAFLINTLKKTVVESAINDTLESFRE NLNDPRFDYNKFFRKRMEIIYDKQKNF INYYKAQREENPELIIDDIVKTYLSNEY SKEIDELNTYIEESLNKITQNSGNDVRN FEEFKNGESFNLYEQELVERWNLAAAS DILRISALKEIGGMYLDVDMLPGIQPDL FESIEKPSSVTVDFWEMTKLEAIMKYK EYIPEYTSEHFDMLDEEVQSSFESVLAS KSDKSEIFSSLGDMEASPLEVKIAFNSK GIINQGLISVKDSYCSNLIVKQIENRYKI LNNSLNPAISEDNDFNTTTNTFIDSIMA EANADNGRFMMELGKYLRVGFFPDV KTTINLSGPEAYAAAYQDLLMFKEGS MNIHLIEADLRNFEISKTNISQSTEQEM | 1 |

TABLE 1-continued

Sequence ID NOs

| Name | Chain, Region | Origin | Sequence | Seq ID No: |
|---|---|---|---|---|
| | | | ASLWSFDDARAKAQFEEYKRNYFEGS LGED | |
| Fragment 4 of Toxin B | TcdB, Frag 4, aa 1777-2366 | Clostridium difficile | ANKLSFNFSDKQDVPVSEIILSFTPSYY EDGLIGYDLGLVSLYNEKFYINNFGM MVSGLIYINDSLYYFKPPVNNLITGFVT VGDDKYYFNPINGGAASIGETIIDDKN YYFNQSGVLQTGVFSTEDGFKYFAPA NTLDENLEGEAIDFTGKLIIDENIYYFD DNYRGAVEWKELDGEMHYFSPETGK AFKGLNQIGDYKYYFNSDGVMQKGFV SINDNKHYFDDSGVMKVGYTEIDGKH FYFAENGEMQIGVFNTEDGFKYFAHH NEDLGNEEGEEISYSGILNFNNKIYYFD DSFTAVVGWKDLEDGSKYYFDEDTAE AYIGLSLINDGQYYFNDDGIMQVGFVT INDKVFYFSDSGIIESGVQNIDDNYFYI DDNGIVQIGVFDTSDGYKYFAPANTVN DNIYGQAVEYSGLVRVGEDVYYFGET YTIETGWIYDMENESDKYYFNPETKKA CKGINLIDDIKYYFDEKGIMRTGLISFE NNNYYFNENGEMQFGYINIEDKMFYF GEDGVMQIGVFNTPDGFKYFAHQNTL DENFEGESINYTGWLDLDEKRYYFTDE YIAATGSVIIDGEEYYFDPDTAQLVISE | 2 |
| CAN46G4 | K, variable region | Mus musculus | EKVLTQSPAIMSASPGEEVTMTCSASSS VSYMHWYQQKSSTSPKLWIYETSKLA FGVPGRFSGSGSGNSYSLTISSMEAEDV ATYYCFQGSGYPFTFGSGTKLEVK | 3 |
| CAN46G4 | K, CDR1 | Mus musculus | SSVSY | 4 |
| CAN46G4 | K, CDR2 | Mus musculus | ETS | 5 |
| CAN46G4 | K, CDR3 | Mus musculus | FQGSGYPFT | 6 |
| CAN46G4 | K, FR1 | Mus musculus | EKVLTQSPAIMSASPGEEVTMTCSAS | 7 |
| CAN46G4 | K, FR2 | Mus musculus | MHWYQQKSSTSPKLWIY | 8 |
| CAN46G4 | K, FR3 | Mus musculus | KLAFGVPGRFSGSGSGNSYSLTISSMEA EDVATYYC | 9 |
| CAN46G4 | K, FR4 | Mus musculus | FGSGTKLEVK | 10 |
| CAN46G4 | H, variable region | Mus musculus | EVQLLQSGPELVKPGASVKISCKASDY SFTGYYMHWVKQSHVKSLEWIGRIFP YNGAASYNQNFKDKATLTVDKSSSTA YMELHSLTSEDSAVYYCTRWLRVYFD YWGQGTTLTVSS | 11 |
| CAN46G4 | H, CDR1 | Mus musculus | DYSFTGYY | 12 |
| CAN46G4 | H, CDR2 | Mus musculus | IFPYNGAA | 13 |
| CAN46G4 | H, CDR3 | Mus musculus | TRWLRVYFDY | 14 |
| CAN46G4 | H, FR1 | Mus musculus | EVQLLQSGPELVKPGASVKISCKAS | 15 |
| CAN46G4 | H, FR2 | Mus musculus | MHWVKQSHVKSLEWIGR | 16 |
| CAN46G4 | H, FR3 | Mus musculus | SYNQNFKDKATLTVDKSSSTAYMELH SLTSEDSAVYYC | 17 |

TABLE 1-continued

Sequence ID NOs

| Name | Chain, Region | Origin | Sequence | Seq ID No: |
|---|---|---|---|---|
| CAN46G4 | H, FR4 | Mus musculus | WGQGTTLTVSS | 18 |
| CAN46G13 | K, variable region | Mus musculus | EIVLTQSPAIMSTSPGEKVTMSCSAS<u>SS VTY</u>MHWYQQKSITSPKLWIY<u>ETS</u>KLAS GVPGRFSGSGSGNSYSLTISSMEAEDV ATYYC<u>FQGSGYPFT</u>FGSGTKLEIK | 19 |
| CAN46G13 | K, CDR1 | Mus musculus | SSVTY | 20 |
| CAN46G13 | K, CDR2 | Mus musculus | ETS | 21 |
| CAN46G13 | K, CDR3 | Mus musculus | FQGSGYPFT | 22 |
| CAN46G13 | K, FR1 | Mus musculus | EIVLTQSPAIMSTSPGEKVTMSCSAS | 23 |
| CAN46G13 | K, FR2 | Mus musculus | MHWYQQKSITSPKLWIY | 24 |
| CAN46G13 | K, FR3 | Mus musculus | KLASGVPGRFSGSGSGNSYSLTISSMEA EDVATYYC | 25 |
| CAN46G13 | K, FR4 | Mus musculus | FGSGTKLEIK | 26 |
| CAN46G13 | H, variable region | Mus musculus | EVQLLQSGPELVKPGTSVKISCKAS<u>GY SFTGYY</u>IHWVKQTHVKSLEWVGR<u>IFPY NGAA</u>SYNQNFKGKATLTVDKSSTAY MELHSLTSEDSAVYFC<u>ARWLRVYFDY</u> WGQGTTLTVSS | 27 |
| CAN46G13 | H, CDR1 | Mus musculus | GYSFTGYY | 28 |
| CAN46G13 | H, CDR2 | Mus musculus | IFPYNGAA | 29 |
| CAN46G13 | H, CDR3 | Mus musculus | ARWLRVYFDY | 30 |
| CAN46G13 | H, FR1 | Mus musculus | EVQLLQSGPELVKPGTSVKISCKAS | 31 |
| CAN46G13 | H, FR2 | Mus musculus | IHWVKQTHVKSLEWVGR | 32 |
| CAN46G13 | H, FR3 | Mus musculus | SYNQNFKGKATLTVDKSSTAYMELH SLTSEDSAVYFC | 33 |
| CAN46G13 | H, FR4 | Mus musculus | WGQGTTLTVSS | 34 |
| CAN46G13a | K, variable region | Mus musculus | ENVLTQSPAIMAASLGQKVTMTCSAS<u>S SVSSSY</u>LHWYQQKSGASPKPLIH<u>RTS</u>T LASGVPARFSGSGSGTSYSLTISSVEAE DDATYYC<u>QQWSGYPYT</u>FGGGTKLEIK | 35 |
| CAN46G13a | K, CDR1 | Mus musculus | SSVSSSY | 36 |
| CAN46G13a | K, CDR2 | Mus musculus | RTS | 37 |
| CAN46G13a | K, CDR3 | Mus musculus | QQWSGYPYT | 38 |
| CAN46G13a | K, FR1 | Mus musculus | ENVLTQSPAIMAASLGQKVTMTCSAS | 39 |

TABLE 1-continued

Sequence ID NOs

| Name | Chain, Region | Origin | Sequence | Seq ID No: |
|---|---|---|---|---|
| CAN46G13a | K, FR2 | Mus musculus | LHWYQQKSGASPKPLIH | 40 |
| CAN46G13a | K, FR3 | Mus musculus | TLASGVPARFSGSGSGTSYSLTISSVEA EDDATYYC | 41 |
| CAN46G13a | K, FR4 | Mus musculus | FGGGTKLEIK | 42 |
| CAN46G13a | H, variable region | Mus musculus | DVQLQESGPGLVKPSQSLSLTCTVT<u>GY SITSDSA</u>WNWIRQFPGNNLEWMGY<u>ISY SGST</u>SYNPSLKSRISITRDTSKNQFFLQL NSVTTEDTATYYC<u>ARRSRVSFYFDY</u>W GQGTTLTVSS | 43 |
| CAN46G13a | H, CDR1 | Mus musculus | GYSITSDSA | 44 |
| CAN46G13a | H, CDR2 | Mus musculus | ISYSGST | 45 |
| CAN46G13a | H, CDR3 | Mus musculus | ARRSRVSFYFDY | 46 |
| CAN46G13a | H, FR1 | Mus musculus | DVQLQESGPGLVKPSQSLSLTCTVT | 47 |
| CAN46G13a | H, FR2 | Mus musculus | WNWIRQFPGNNLEWMGY | 48 |
| CAN46G13a | H, FR3 | Mus musculus | SYNPSLKSRISITRDTSKNQFFLQLNSV TTEDTATYYC | 49 |
| CAN46G13a | H, FR4 | Mus musculus | WGQGTTLTVSS | 50 |
| CAN46G19 | K, variable region | Mus musculus | ENVLTQSPTIMSASPGEEVTMTCSAS<u>SS VTYM</u>HWYQQKSITSPKLWIY<u>ETS</u>KLAS GVPGRFSGSGSGNSYSLTISSMEAEDV ATYYC<u>FQGSGYPFT</u>FGSGTKLEIK | 51 |
| CAN46G19 | K, CDR1 | Mus musculus | SSVTY | 52 |
| CAN46G19 | K, CDR2 | Mus musculus | ETS | 53 |
| CAN46G19 | K, CDR3 | Mus musculus | FQGSGYPFT | 54 |
| CAN46G19 | K, FR1 | Mus musculus | ENVLTQSPTIMSASPGEEVTMTCSAS | 55 |
| CAN46G19 | K, FR2 | Mus musculus | MHWYQQKSITSPKLWIY | 56 |
| CAN46G19 | K, FR3 | Mus musculus | KLASGVPGRFSGSGSGNSYSLTISSMEA EDVATYYC | 57 |
| CAN46G19 | K, FR4 | Mus musculus | FGSGTKLEIK | 58 |
| CAN46G19 | H, variable region | Mus musculus | EVQLLQSGPELVKPGTSVKISCKAS<u>GY SFTGYY</u>IHWVKQTHVKSLEWVGR<u>IFPY NGAA</u>SYNQNFKGKATLTVDKSSTTAY MELHSLTSEDSAVYFC<u>ARWLRVYFDY</u> WGQGTTLTVSS | 59 |
| CAN46G19 | H, CDR1 | Mus musculus | GYSFTGYY | 60 |
| CAN46G19 | H, CDR2 | Mus musculus | IFPYNGAA | 61 |

TABLE 1-continued

Sequence ID NOs

| Name | Chain, Region | Origin | Sequence | Seq ID No: |
|---|---|---|---|---|
| CAN46G19 | H, CDR3 | Mus musculus | ARWLRVYFDY | 62 |
| CAN46G19 | H, FR1 | Mus musculus | EVQLLQSGPELVKPGTSVKISCKAS | 63 |
| CAN46G19 | H, FR2 | Mus musculus | IHWVKQTHVKSLEWVGR | 64 |
| CAN46G19 | H, FR3 | Mus musculus | SYNQNFKGKATLTVDKSSTTAYMELHSLTSEDSAVYFC | 65 |
| CAN46G19 | H, FR4 | Mus musculus | WGQGTTLTVSS | 66 |
| CAN46G24 | K, variable region | Mus musculus | EIVLTQSPAIMSTSPGEKVTMSCSAS<u>SSVTY</u>MHWYQQKSITSPKLWIY<u>ETS</u>KLASGVPGRFSGSGSGNSYSLTISSMEAEDVATYYC<u>FQGSYPFT</u>FGSGTKLEIK | 67 |
| CAN46G24 | K, CDR1 | Mus musculus | SSVTY | 68 |
| CAN46G24 | K, CDR2 | Mus musculus | ETS | 69 |
| CAN46G24 | K, CDR3 | Mus musculus | FQGSYPFT | 70 |
| CAN46G24 | K, FR1 | Mus musculus | EIVLTQSPAIMSTSPGEKVTMSCSAS | 71 |
| CAN46G24 | K, FR2 | Mus musculus | MHWYQQKSITSPKLWIY | 72 |
| CAN46G24 | K, FR3 | Mus musculus | KLASGVPGRFSGSGSGNSYSLTISSMEAEDVATYYC | 73 |
| CAN46G24 | K, FR4 | Mus musculus | FGSGTKLEIK | 74 |
| CAN46G24 | H, variable region | Mus musculus | EVQLLQSGPELVKPGTSVKISCKAS<u>GYSFTGYY</u>IHWVKQTHVKSLEWVGR<u>IFPYNGAA</u>SYNQNFKGKATLTVDKSSTAYMELHSLTSEDSAVYFC<u>ARWLRVYFDY</u>WGQGTTLTVSS | 75 |
| CAN46G24 | H, CDR1 | Mus musculus | GYSFTGYY | 76 |
| CAN46G24 | H, CDR2 | Mus musculus | IFPYNGAA | 77 |
| CAN46G24 | H, CDR3 | Mus musculus | ARWLRVYFDY | 78 |
| CAN46G24 | H, FR1 | Mus musculus | EVQLLQSGPELVKPGTSVKISCKAS | 79 |
| CAN46G24 | H, FR2 | Mus musculus | IHWVKQTHVKSLEWVGR | 80 |
| CAN46G24 | H, FR3 | Mus musculus | SYNQNFKGKATLTVDKSSTAYMELHSLTSEDSAVYFC | 81 |
| CAN46G24 | H, FR4 | Mus musculus | WGQGTTLTVSS | 82 |
| CAN33G1 | K, variable region | Mus musculus | DIQLTQSSSSFSVSLGDRVTITCKAS<u>EDIYNR</u>LAWYQQRPGNAPRLLIS<u>GATSLET</u>GIPSRFSGSGSGKEYTLSIASLQTEDFVTYYC<u>QQYWNIPT</u>FGGGTRLEIK | 85 |
| CAN33G1 | K, CDR1 | Mus musculus | EDIYNR | 86 |

TABLE 1-continued

Sequence ID NOs

| Name | Chain, Region | Origin | Sequence | Seq ID No: |
|---|---|---|---|---|
| CAN33G1 | K, CDR2 | Mus musculus | GAT | 87 |
| CAN33G1 | K, CDR3 | Mus musculus | QQYWNIPT | 88 |
| CAN33G1 | K, FR1 | Mus musculus | DIQLTQSSSSFSVSLGDRVTITCKAS | 89 |
| CAN33G1 | K, FR2 | Mus musculus | LAWYQQRPGNAPRLLIS | 90 |
| CAN33G1 | K, FR3 | Mus musculus | SLETGIPSRFSGSGSGKEYTLSIASLQTEDFVTYYC | 91 |
| CAN33G1 | K, FR4 | Mus musculus | FGGGTRLEIK | 92 |
| CAN33G1 | H, variable region | Mus musculus | EVQLQQSGPDLVKPGASVKISCKASGYSFTGYYMHWVKQSHGKSLEWIGRVNPYNGDTNYNQNFKDKAILTVDKSASTAYMEFRSLTSEDSAVYYCTRSNWENYFDYWGQGSTLTVSS | 93 |
| CAN33G1 | H, CDR1 | Mus musculus | GYSFTGYY | 94 |
| CAN33G1 | H, CDR2 | Mus musculus | VNPYNGDT | 95 |
| CAN33G1 | H, CDR3 | Mus musculus | TRSNWENYFDY | 96 |
| CAN33G1 | H, FR1 | Mus musculus | EVQLQQSGPDLVKPGASVKISCKAS | 97 |
| CAN33G1 | H, FR2 | Mus musculus | MHWVKQSHGKSLEWIGR | 98 |
| CAN33G1 | H, FR3 | Mus musculus | NYNQNFKDKAILTVDKSASTAYMEFRSLTSEDSAVYYC | 99 |
| CAN33G1 | H, FR4 | Mus musculus | WGQGSTLTVSS | 100 |
| cdrCAN46G4 | K, variable region | Artificial sequence | EIVLTQSPATLSLSPGERATLSCSASSSVSYMHWYQQKPGQAPRLLIYETSKLAFGIPARFSGSGSGTDFTLTISSLEPEDFAVYYCFQGSGYPFTFGQGTRLEIK | 737 |
| cdrCAN46G4 | K, CDR1 | Artificial sequence | SSVSY | 738 |
| cdrCAN46G4 | K, CDR2 | Artificial sequence | ETS | 739 |
| cdrCAN46G4 | K, CDR3 | Artificial sequence | FQGSGYPFT | 740 |
| cdrCAN46G4 | K, FR1 | Artificial sequence | EIVLTQSPATLSLSPGERATLSCSAS | 741 |
| cdrCAN46G4 | K, FR2 | Artificial sequence | MHWYQQKPGQAPRLLIY | 742 |
| cdrCAN46G4 | K, FR3 | Artificial sequence | KLAFGIPARFSGSGSGTDFTLTISSLEPEDFAVYYC | 743 |
| cdrCAN46G4 | K, FR4 | Artificial sequence | FGQGTRLEIK | 744 |
| cdrCAN46G4 | H, variable sequence | Artificial sequence | QVQLVQSGAEVKKPGSSVKVSCKASGYTFTGYYMHWVRQAPGQGLEWIGRIF | 745 |

TABLE 1-continued

Sequence ID NOs

| Name | Chain, Region | Origin | Sequence | Seq ID No: |
|---|---|---|---|---|
| | region | | PYNGAASYNQNFKDKATITADESTNT AYMELSSLRSEDTAVYYCARWLRVYF DYWGQGTLVTVSS | |
| cdrCAN46G4 | H, CDR1 | Artificial sequence | GYTFTGYY | 746 |
| cdrCAN46G4 | H, CDR2 | Artificial sequence | IFPYNGAA | 747 |
| cdrCAN46G4 | H, CDR3 | Artificial sequence | ARWLRVYFDY | 748 |
| cdrCAN46G4 | H, FR1 | Artificial sequence | QVQLVQSGAEVKKPGSSVKVSCKAS | 749 |
| cdrCAN46G4 | H, FR2 | Artificial sequence | MHWVRQAPGQGLEWIGR | 750 |
| cdrCAN46G4 | H, FR3 | Artificial sequence | SYNQNFKDKATITADESTNTAYMELSS LRSEDTAVYYC | 751 |
| cdrCAN46G4 | H, FR4 | Artificial sequence | WGQGTLVTVSS | 752 |
| huCAN46G4 | K, variable region | Artificial sequence | EKVLTQSPATLSLSPGERATMTCSASSS VSYMHWYQQKPGTSPKLWIYETSKLA FGVPARFSGSGSGNSYSLTISSLEPEDF AVYYCFQGSGYPFTFGQGTRLEIK | 753 |
| huCAN46G4 | K, CDR1 | Artificial sequence | SSVSY | 754 |
| huCAN46G4 | K, CDR2 | Artificial sequence | ETS | 755 |
| huCAN46G4 | K, CDR3 | Artificial sequence | FQGSGYPFT | 756 |
| huCAN46G4 | K, FR1 | Artificial sequence | EKVLTQSPATLSLSPGERATMTCSAS | 757 |
| huCAN46G4 | K, FR2 | Artificial sequence | MHWYQQKPGTSPKLWIY | 758 |
| huCAN46G4 | K, FR3 | Artificial sequence | KLAFGVPARFSGSGSGNSYSLTISSLEP EDFAVYYC | 759 |
| huCAN46G4 | K, FR4 | Artificial sequence | FGQGTRLEIK | 760 |
| huCAN46G4 | H, variable region | Artificial sequence | EVQLLQSGAEVKKPGSSVKISCKASDY SFTGYYMHWVKQAPGQGLEWIGRIFP YNGAASYNQNFKDKATLTVDKSSSTA YMELHSLRSEDTAVYYCTRWLRVYFD YWGQGTLVTVSS | 761 |
| huCAN46G4 | H, CDR1 | Artificial sequence | DYSFTGYY | 762 |
| huCAN46G4 | H, CDR2 | Artificial sequence | IFPYNGAA | 763 |
| huCAN46G4 | H, CDR3 | Artificial sequence | TRWLRVYFDY | 764 |
| huCAN46G4 | H, FR1 | Artificial sequence | EVQLLQSGAEVKKPGSSVKISCKAS | 765 |
| huCAN46G4 | H, FR2 | Artificial sequence | MHWVKQAPGQGLEWIGR | 766 |
| huCAN46G4 | H, FR3 | Artificial sequence | SYNQNFKDKATLTVDKSSSTAYMELH SLRSEDTAVYYC | 767 |

TABLE 1-continued

Sequence ID NOs

| Name | Chain, Region | Origin | Sequence | Seq ID No: |
|---|---|---|---|---|
| huCAN46G4 | H, FR4 | Artificial sequence | WGQGTLVTVSS | 768 |
| rehuCAN46G4 | K, variable region | Artificial sequence | EKVLTQSPATLSASPGERVTMSCSASSS VSYMHWYQQKPGQSPKLWIYETSKLA FGVPARFSGSGSGTDYSLTISSMEPEDF ATYYCFQGSGYPFTFGQGTRLEIK | 769 |
| rehuCAN46G4 | K, CDR1 | Artificial sequence | SSVSY | 770 |
| rehuCAN46G4 | K, CDR2 | Artificial sequence | ETS | 771 |
| rehuCAN46G4 | K, CDR3 | Artificial sequence | FQGSGYPFT | 772 |
| rehuCAN46G4 | K, FR1 | Artificial sequence | EKVLTQSPATLSASPGERVTMSCSAS | 773 |
| rehuCAN46G4 | K, FR2 | Artificial sequence | MHWYQQKPGQSPKLWIY | 774 |
| rehuCAN46G4 | K, FR3 | Artificial sequence | KLAFGVPARFSGSGSGTDYSLTISSMEP EDFATYYC | 775 |
| rehuCAN46G4 | K, FR4 | Artificial sequence | FGQGTRLEIK | 776 |
| rehuCAN46G4 | H, variable region | Artificial sequence | EVQLLQSGAEVVKPGSSVKISCKASGY SFTGYYMHWVKQAPGQGLEWIGRIFP YNGAASYNQNFKDKATLTADKSTNTA YMELSSLRSEDSAVYYCTRWLRVYFD YWGQGTLVTVSS | 778 |
| rehuCAN46G4 | H, CDR1 | Artificial sequence | GYSFTGYY | 779 |
| rehuCAN46G4 | H, CDR2 | Artificial sequence | IFPYNGAA | 780 |
| rehuCAN46G4 | H, CDR3 | Artificial sequence | TRWLRVYFDY | 781 |
| rehuCAN46G4 | H, FR1 | Artificial sequence | EVQLLQSGAEVVKPGSSVKISCKAS | 782 |
| rehuCAN46G4 | H, FR2 | Artificial sequence | MHWVKQAPGQGLEWIGR | 783 |
| rehuCAN46G4 | H, FR3 | Artificial sequence | SYNQNFKDKATLTADKSTNTAYMELS SLRSEDSAVYYC | 784 |
| rehuCAN46G4 | H, FR4 | Artificial sequence | WGQGTLVTVSS | 785 |
| cdrCAN46G13a | K, variable region | Artificial Sequence | DIQMTQSPSSLSASVGDRVTITCSAS<u>SS VSSSY</u>LHWYQQKPGKAPKLLIY<u>RTSTL</u> ASGVPSRFSGSGSGTDFTFTISSLQPEDI ATYYC<u>QQWSGYPYT</u>FGQGTKVEIK | 101 |
| cdrCAN46G13a | K, CDR1 | Mus Musculus | SSVSSSY | 102 |
| cdrCAN46G13a | K, CDR2 | Mus Musculus | RTS | 103 |
| cdrCAN46G13a | K, CDR3 | Mus Musculus | QQWSGYPYT | 104 |
| cdrCAN46G13a | K, FR1 | Homo sapiens | DIQMTQSPSSLSASVGDRVTITCSAS | 105 |

TABLE 1-continued

Sequence ID NOs

| Name | Chain, Region | Origin | Sequence | Seq ID No: |
|---|---|---|---|---|
| cdrCAN46G13a | K, FR2 | Homo sapiens | LHWYQQKPGKAPKLLIY | 106 |
| cdrCAN46G13a | K, FR3 | Homo sapiens | TLASGVPSRFSGSGSGTDFTFTISSLQPE DIATYYC | 107 |
| cdrCAN46G13a | K, FR4 | Mus musculus | FGQGTKVEIK | 108 |
| cdrCAN46G13a | H, variable region | Artificial Sequence | QVQLQESGPGLVKPSQTLSLTCTVS<u>GG SISSDSA</u>WNWIRQPPGKGLEWIGY<u>ISYS GST</u>SYNPSLKSRVTMSVDTSKNQFSLK VNSVTAADTAVYYC<u>ARRSRVSFYFDY</u> WGQGTLVTVSS | 109 |
| cdrCAN46G13a | H, CDR1 | Mus Musculus | GGSISSDSA | 110 |
| cdrCAN46G13a | H, CDR2 | Mus Musculus | ISYSGST | 111 |
| cdrCAN46G13a | H, CDR3 | Mus Musculus | ARRSRVSFYFDY | 112 |
| cdrCAN46G13a | H, FR1 | Homo sapiens | QVQLQESGPGLVKPSQTLSLTCTVS | 113 |
| cdrCAN46G13a | H, FR2 | Homo sapiens | WNWIRQPPGKGLEWIGY | 114 |
| cdrCAN46G13a | H, FR3 | Homo sapiens | SYNPSLKSRVTMSVDTSKNQFSLKVNS VTAADTAVYYC | 115 |
| cdrCAN46G13a | H, FR4 | Mus musculus | WGQGTLVTVSS | 116 |
| huCAN46G13a | K, variable region | Artificial sequence | ENVLTQSPSSLSASVGDRVTMTCSASS <u>SVSSSY</u>LHWYQQKPGKSPKPLIH<u>RTST</u> LASGVPSRFSGSGSGTSYSLTISSLQPED IATYYC<u>QQWSGYPYT</u>FGGGTKVEIK | 117 |
| huCAN46G13a | K, CDR1 | Mus musculus | SSVSSSY | 118 |
| huCAN46G13a | K, CDR2 | Mus musculus | RTS | 119 |
| huCAN46G13a | K, CDR3 | Mus musculus | QQWSGYPYT | 120 |
| huCAN46G13a | K, FR1 | Artificial sequence | ENVLTQSPSSLSASVGDRVTMTCSAS | 121 |
| huCAN46G13a | K, FR2 | Artificial sequence | LHWYQQKPGKSPKPLIH | 122 |
| huCAN46G13a | K, FR3 | Artificial sequence | TLASGVPSRFSGSGSGTSYSLTISSLQPE DIATYYC | 123 |
| huCAN46G13a | K, FR4 | Mus musculus | FGGGTKVEIK | 124 |
| huCAN46G13a | H, variable region | Artificial sequence | QVQLQESGPGLVKPSQTLSLTCTVT<u>GY SITSDSA</u>WNWIRQFPGNNLEWMGY<u>ISY SGST</u>SYNPSLKSRISITRDTSKNQFSLKV NSVTAADTAVYYC<u>ARRSRVSFYFDY</u>W GQGTLVTVSS | 125 |
| huCAN46G13a | H, CDR1 | Artificial sequence | GYSITSDSA | 126 |
| huCAN46G13a | H, CDR2 | Mus musculus | ISYSGST | 127 |

TABLE 1-continued

Sequence ID NOs

| Name | Chain, Region | Origin | Sequence | Seq ID No: |
|---|---|---|---|---|
| huCAN46G13a | H, CDR3 | Mus musculus | ARRSRVSFYFDY | 128 |
| huCAN46G13a | H, FR1 | Artificial sequence | QVQLQESGPGLVKPSQTLSLTCTVT | 129 |
| huCAN46G13a | H, FR2 | Artificial sequence | WNWIRQFPGNNLEWMGY | 130 |
| huCAN46G13a | H, FR3 | Artificial sequence | SYNPSLKSRISITRDTSKNQFSLKVNSV TAADTAVYYC | 131 |
| huCAN46G13a | H, FR4 | Mus musculus | WGQGTLVTVSS | 132 |
| rehuCAN46G13a | K, variable region | Artificial sequence | ENVLTQSPSSMSASVGDRVTMTCSAS<u>S SVSSSY</u>LHWYQQKPGKAPKPLIH<u>RTST</u> LASGVPSRFSGSGSGTSYSLTISSVQPE DIATYYC<u>QQWSGYPYT</u>FGGGTKVEIK | 133 |
| rehuCAN46G13a | K, CDR1 | Mus musculus | SSVSSSY | 134 |
| rehuCAN46G13a | K, CDR2 | Mus musculus | RTS | 135 |
| rehuCAN46G13a | K, CDR3 | Mus musculus | QQWSGYPYT | 136 |
| rehuCAN46G13a | K, FR1 | Artificial sequence | ENVLTQSPSSMSASVGDRVTMTCSAS | 137 |
| rehuCAN46G13a | K, FR2 | Artificial sequence | LHWYQQKPGKAPKPLIH | 138 |
| rehuCAN46G13a | K, FR3 | Artificial sequence | TLASGVPSRFSGSGSGTSYSLTISSVQPE DIATYYC | 139 |
| rehuCAN46G13a | K, FR4 | Mus musculus | FGGGTKVEIK | 140 |
| rehuCAN46G13a | H, variable region | Artificial sequence | QVQLQESGPGLVKPSQTLSLTCTVT<u>GY SITSDSA</u>WNWIRQPPGNGLEWMGY<u>ISY SGST</u>SYNPSLKSRISITRDTSKNQFSLKL NSVTAADTATYYC<u>ARRSRVSFYFDY</u>W GQGTLVTVSS | 141 |
| rehuCAN46G13a | H, CDR1 | Artificial sequence | GYSITSDSA | 142 |
| rehuCAN46G13a | H, CDR2 | Mus musculus | ISYSGST | 143 |
| rehuCAN46G13a | H, CDR3 | Mus musculus | ARRSRVSFYFDY | 144 |
| rehuCAN46G13a | H, FR1 | Artificial sequence | QVQLQESGPGLVKPSQTLSLTCTVT | 145 |
| rehuCAN46G13a | H, FR2 | Artificial sequence | WNWIRQPPGNGLEWMGY | 146 |
| rehuCAN46G13a | H, FR3 | Artificial sequence | SYNPSLKSRISITRDTSKNQFSLKLNSV TAADTATYYC | 147 |
| rehuCAN46G13a | H, FR4 | Mus musculus | WGQGTLVTVSS | 148 |
| cdrCAN46G19 | K, variable region | Artificial sequence | DIQMTQSPSSLSASVGDRVTITCSAS<u>SS VTYMH</u>WYQQKPGKAPKLLIY<u>ETSKLA</u> SGVPSRFSGSGSGTDYTFTISSLQPEDIA TYYC<u>FQGSGYPFT</u>FGQGTKVEIK | 149 |

TABLE 1-continued

Sequence ID NOs

| Name | Chain, Region | Origin | Sequence | Seq ID No: |
|---|---|---|---|---|
| cdrCAN46G19 | K, CDR1 | Mus musculus | SSVTY | 150 |
| cdrCAN46G19 | K, CDR2 | Mus musculus | ETS | 151 |
| cdrCAN46G19 | K, CDR3 | Mus musculus | FQGSGYPFT | 152 |
| cdrCAN46G19 | K, FR1 | Homo sapiens | DIQMTQSPSSLSASVGDRVTITCSAS | 153 |
| cdrCAN46G19 | K, FR2 | Homo sapiens | MHWYQQKPGKAPKLLIY | 154 |
| cdrCAN46G19 | K, FR3 | Homo sapiens | KLASGVPSRFSGSGSGTDYTFTISSLQP EDIATYYC | 155 |
| cdrCAN46G19 | K, FR4 | Homo sapiens | FGQGTKVEIK | 156 |
| cdrCAN46G19 | H, variable region | Artificial sequence | QVQLVQSGAEVKKPGESVKVSCKASG YTFTGYYIHWVRQAPGQGLEWMGRIF PYNGAASYNQNFKGRVTITADKSTSTA YMELSSLRSEDTAVYYCARWLRVYFD YWGQGTTVTVSS | 157 |
| cdrCAN46G19 | H, CDR1 | Artificial sequence | GYTFTGYY | 158 |
| cdrCAN46G19 | H, CDR2 | Mus musculus | IFPYNGAA | 159 |
| cdrCAN46G19 | H, CDR3 | Mus musculus | ARWLRVYFDY | 160 |
| cdrCAN46G19 | H, FR1 | Homo sapiens | QVQLVQSGAEVKKPGESVKVSCKAS | 161 |
| cdrCAN46G19 | H, FR2 | Homo sapiens | IHWVRQAPGQGLEWMGR | 162 |
| cdrCAN46G19 | H, FR3 | Homo sapiens | SYNQNFKGRVTITADKSTSTAYMELSS LRSEDTAVYYC | 163 |
| cdrCAN46G19 | H, FR4 | Homo sapiens | WGQGTTVTVSS | 164 |
| huCAN46G19 | K, variable region | Artificial sequence | ENVLTQSPSSLSASVGDRVTITCSASSS VTYMHWYQQKPGKAPKLWIYETSKL ASGVPGRFSGSGSGNSYTFTISSLQPEDI ATYYCFQGSGYPFTFGQGTKVEIK | 165 |
| huCAN46G19 | K, CDR1 | Mus musculus | SSVTY | 166 |
| huCAN46G19 | K, CDR2 | Mus musculus | ETS | 167 |
| huCAN46G19 | K, CDR3 | Mus musculus | FQGSGYPFT | 168 |
| huCAN46G19 | K, FR1 | Artificial sequence | ENVLTQSPSSLSASVGDRVTITCSAS | 169 |
| huCAN46G19 | K, FR2 | Artificial sequence | MHWYQQKPGKAPKLWIY | 170 |
| huCAN46G19 | K, FR3 | Artificial sequence | KLASGVPGRFSGSGSGNSYTFTISSLQP EDIATYYC | 171 |
| huCAN46G19 | K, FR4 | Homo sapiens | FGQGTKVEIK | 172 |

TABLE 1-continued

Sequence ID NOs

| Name | Chain, Region | Origin | Sequence | Seq ID No: |
|---|---|---|---|---|
| huCAN46G19 | H, variable region | Artificial sequence | EVQLVQSGAEVKKPGESVKVSCKAS<u>G YSFTGYY</u>IHWVKQAPGQGLEWVGR<u>IF PYNGAA</u>SYNQNFKGKATLTVDKSTT AYMELSSLRSEDTAVYFC<u>ARWLRVYF DY</u>WGQGTTVTVSS | 173 |
| huCAN46G19 | H, CDR1 | Mus musculus | GYSFTGYY | 174 |
| huCAN46G19 | H, CDR2 | Mus musculus | IFPYNGAA | 175 |
| huCAN46G19 | H, CDR3 | Mus musculus | ARWLRVYFDY | 176 |
| huCAN46G19 | H, FR1 | Artificial sequence | EVQLVQSGAEVKKPGESVKVSCKAS | 177 |
| huCAN46G19 | H, FR2 | Artificial sequence | IHWVKQAPGQGLEWVGR | 178 |
| huCAN46G19 | H, FR3 | Artificial sequence | SYNQNFKGKATLTVDKSSTTAYMELS SLRSEDTAVYFC | 179 |
| huCAN46G19 | H, FR4 | Homo sapiens | WGQGTTVTVSS | 180 |
| rehuCAN46G19 | K, variable region | Artificial sequence | ENVLTQSPSSMSASVGDRVTMTCSAS<u>S SVTY</u>MHWYQQKPGKSPKLWIY<u>ETS</u>KL ASGVPSRFSGSGSGNDYSLTISSMQPED VATYYC<u>QGSGYPFT</u>FGQGTKLEIK | 181 |
| rehuCAN46G19 | K, CDR1 | Mus musculus | SSVTY | 182 |
| rehuCAN46G19 | K, CDR2 | Mus musculus | ETS | 183 |
| rehuCAN46G19 | K, CDR3 | Mus musculus | FQGSGYPFT | 184 |
| rehuCAN46G19 | K, FR1 | Artificial sequence | ENVLTQSPSSMSASVGDRVTMTCSAS | 185 |
| rehuCAN46G19 | K, FR2 | Artificial sequence | MHWYQQKPGKSPKLWIY | 186 |
| rehuCAN46G19 | K, FR3 | Artificial sequence | KLASGVPSRFSGSGSGNDYSLTISSMQP EDVATYYC | 187 |
| rehuCAN46G19 | K, FR4 | Homo sapiens | FGQGTKLEIK | 188 |
| rehuCAN46G19 | H, variable region | Artificial sequence | EVQLVQSGAEVVKPGESVKISCKAS<u>GY SFTGYY</u>IHWVKQTPGQSLEWVGR<u>IFPY NGAA</u>SYNQNFKGKATLTVDKSTTTAY MELSSLRSEDSAVYFC<u>ARWLRVYFDY</u> WGQGTTLTVSS | 189 |
| rehuCAN46G19 | H, CDR1 | Mus musculus | GYSFTGYY | 190 |
| rehuCAN46G19 | H, CDR2 | Mus musculus | IFPYNGAA | 191 |
| rehuCAN46G19 | H, CDR3 | Mus musculus | ARWLRVYFDY | 192 |
| rehuCAN46G19 | H, FR1 | Artificial sequence | EVQLVQSGAEVVKPGESVKISCKAS | 193 |
| rehuCAN46G19 | H, FR2 | Artificial sequence | IHWVKQTPGQSLEWVGR | 194 |

TABLE 1-continued

Sequence ID NOs

| Name | Chain, Region | Origin | Sequence | Seq ID No: |
|---|---|---|---|---|
| rehuCAN46G19 | H, FR3 | Artificial sequence | SYNQNFKGKATLTVDKSTTTAYMELS SLRSEDSAVYFC | 195 |
| rehuCAN46G19 | H, FR4 | Mus musculus | WGQGTTLTVSS | 196 |
| cdrCAN46G24 | K, variable region | Artificial sequence | DIQMTQSPSSLSASVGDRVTITCSAS<u>SS VTY</u>MHWYQQKPGKAPKLLIY<u>ETS</u>KLA SGVPSRFSGSGSGTDYTFTISSLQPEDIA TYYC<u>FQGSGYPFT</u>FGQGTKVEIK | 197 |
| cdrCAN46G24 | K, CDR1 | Mus musculus | SSVTY | 198 |
| cdrCAN46G24 | K, CDR2 | Mus musculus | ETS | 199 |
| cdrCAN46G24 | K, CDR3 | Mus musculus | FQGSGYPFT | 200 |
| cdrCAN46G24 | K, FR1 | Homo sapiens | DIQMTQSPSSLSASVGDRVTITCSAS | 201 |
| cdrCAN46G24 | K, FR2 | Homo sapiens | MHWYQQKPGKAPKLLIY | 202 |
| cdrCAN46G24 | K, FR3 | Homo sapiens | KLASGVPSRFSGSGSGTDYTFTISSLQP EDIATYYC | 203 |
| cdrCAN46G24 | K, FR4 | Homo sapiens | FGQGTKVEIK | 204 |
| cdrCAN46G24 | H, variable region | Artificial sequence | QVQLVQSGAEVKKPGESVKVSCKAS<u>G YTFTGYY</u>IHWVRQAPGQGLEWMGR<u>IF PYNGAA</u>SYNQNFKGRVTITADKSTSTA YMELSSLRSEDTAVYYC<u>ARWLRVYFD Y</u>WGQGTTVTVSS | 205 |
| cdrCAN46G24 | H, CDR1 | Mus musculus | GYTFTGYY | 206 |
| cdrCAN46G24 | H, CDR2 | Mus musculus | IFPYNGAA | 207 |
| cdrCAN46G24 | H, CDR3 | Mus musculus | ARWLRVYFDY | 208 |
| cdrCAN46G24 | H, FR1 | Homo sapiens | QVQLVQSGAEVKKPGESVKVSCKAS | 209 |
| cdrCAN46G24 | H, FR2 | Homo sapiens | IHWVRQAPGQGLEWMGR | 210 |
| cdrCAN46G24 | H, FR3 | Homo sapiens | SYNQNFKGRVTITADKSTSTAYMELSS LRSEDTAVYYC | 211 |
| cdrCAN46G24 | H, FR4 | Homo sapiens | WGQGTTVTVSS | 212 |
| huCAN46G24 | K, variable region | Artificial sequence | EIVLTQSPSSLSTSVGDRVTISCSAS<u>SSV TY</u>MHWYQQKPGKAPKLWIY<u>ETS</u>KLAS GVPGRFSGSGSGNSYTFTISSLQPEDIA TYYC<u>FQGSGYPFT</u>FGQGTKVEIK | 213 |
| huCAN46G24 | K, CDR1 | Mus musculus | SSVTY | 214 |
| huCAN46G24 | K, CDR2 | Mus musculus | ETS | 215 |
| huCAN46G24 | K, CDR3 | Mus musculus | FQGSGYPFT | 216 |

TABLE 1-continued

Sequence ID NOs

| Name | Chain, Region | Origin | Sequence | Seq ID No: |
|---|---|---|---|---|
| huCAN46G24 | K, FR1 | Artificial sequence | EIVLTQSPSSLSTSVGDRVTISCSAS | 217 |
| huCAN46G24 | K, FR2 | Artificial sequence | MHWYQQKPGKAPKLWIY | 218 |
| huCAN46G24 | K, FR3 | Artificial sequence | KLASGVPGRFSGSGSGNSYTFTISSLQP EDIATYYC | 219 |
| huCAN46G24 | K, FR4 | *Homo sapiens* | FGQGTKVEIK | 220 |
| huCAN46G24 | H, variable region | Artificial sequence | EVQLVQSGAEVKKPGESVKVSCKASGYSFTGYYIHWVKQAPGQGLEWVGRIFPYNGAASYNQNFKGKATLTVDKSSSTAYMELSSLRSEDTAVYFCARWLRVYFDYWGQGTTVTVSS | 221 |
| huCAN46G24 | H, CDR1 | *Mus musculus* | GYSFTGYY | 222 |
| huCAN46G24 | H, CDR2 | *Mus musculus* | IFPYNGAA | 223 |
| huCAN46G24 | H, CDR3 | *Mus musculus* | ARWLRVYFDY | 224 |
| huCAN46G24 | H, FR1 | Artificial sequence | EVQLVQSGAEVKKPGESVKVSCKAS | 225 |
| huCAN46G24 | H, FR2 | Artificial sequence | IHWVKQAPGQGLEWVGR | 226 |
| huCAN46G24 | H, FR3 | Artificial sequence | SYNQNFKGKATLTVDKSSSTAYMELSS LRSEDTAVYFC | 227 |
| huCAN46G24 | H, FR4 | *Homo sapiens* | WGQGTTVTVSS | 228 |
| rehuCAN46G24 | K, variable region | Artificial sequence | EIVLTQSPSSMSTSVGDRVTMSCSASSSVTYMHWYQQKPGKSPKLWIYETSKLASGVPSRFSGSGSGNDYSLTISSMQPEDVATYYCFQGSGYPFTFGQGTKLEIK | 229 |
| rehuCAN46G24 | K, CDR1 | *Mus musculus* | SSVTY | 230 |
| rehuCAN46G24 | K, CDR2 | *Mus musculus* | ETS | 231 |
| rehuCAN46G24 | K, CDR3 | *Mus musculus* | FQGSGYPFT | 232 |
| rehuCAN46G24 | K, FR1 | Artificial sequence | EIVLTQSPSSMSTSVGDRVTMSCSAS | 233 |
| rehuCAN46G24 | K, FR2 | Artificial sequence | MHWYQQKPGKSPKLWIY | 234 |
| rehuCAN46G24 | K, FR3 | Artificial sequence | KLASGVPSRFSGSGSGNDYSLTISSMQP EDVATYYC | 235 |
| rehuCAN46G24 | K, FR4 | Artificial sequence | FGQGTKLEIK | 236 |
| rehuCAN46G24 | H, variable region | Artificial sequence | EVQLVQSGAEVVKPGESVKISCKASGYSFTGYYIHWVKQTPGQSLEWVGRIFPYNGAASYNQNFKGKATLTVDKSTSTAYMELSSLRSEDSAVYFCARWLRVYFDYWGQGTTLTVSS | 237 |
| rehuCAN46G24 | H, CDR1 | Artificial sequence | GYSFTGYY | 238 |

TABLE 1-continued

Sequence ID NOs

| Name | Chain, Region | Origin | Sequence | Seq ID No: |
|---|---|---|---|---|
| rehuCAN46G24 | H, CDR2 | Mus musculus | IFPYNGAA | 239 |
| rehuCAN46G24 | H, CDR3 | Artificial sequence | ARWLRVYFDY | 240 |
| rehuCAN46G24 | H, FR1 | Artificial sequence | EVQLVQSGAEVVKPGESVKISCKAS | 241 |
| rehuCAN46G24 | H, FR2 | Artificial sequence | IHWVKQTPGQSLEWVGR | 242 |
| rehuCAN46G24 | H, FR3 | Artificial sequence | SYNQNFKGKATLTVDKSTSTAYMELS SLRSEDSAVYFC | 243 |
| rehuCAN46G24 | H, FR4 | Mus musculus | WGQGTTLTVSS | 244 |
| CAN46G4 | K, variable region | Mus musculus | gaaaaggttctcacccagtctccagcaatcatgtctgcatctc caggggaagaggtcaccatgacctgcagtgccagctcaag tgtaagttacatgcattggtaccagcagaagtcaagcacctc ccccaaactctggatttatgaaacatccaaactggcttttgga gtcccaggtcgcttcagtggcagtggatctggaaactcttact ctctcacgatcagcagcatggaggctgaagatgttgccactt attactgtttttcaggggagtgggtacccattcacgttcggctc ggggacaaagttggaagtaaaa | 245 |
| CAN46G4 | K, CDR1 | Mus musculus | tcaagtgtaagttac | 246 |
| CAN46G4 | K, CDR2 | Mus musculus | gaaacatcc | 247 |
| CAN46G4 | K, CDR3 | Mus musculus | tttcaggggagtgggtacccattcacg | 248 |
| CAN46G4 | K, FR1 | Mus musculus | gaaaaggttctcacccagtctccagcaatcatgtctgcatctc caggggaagaggtcaccatgacctgcagtgccagc | 249 |
| CAN46G4 | K, FR2 | Mus musculus | atgcattggtaccagcagaagtcaagcacctcccccaaact ctggatttat | 250 |
| CAN46G4 | K, FR3 | Mus musculus | aaactggcttttggagtcccaggtcgcttcagtggcagtgga tctggaaactcttactctctcacgatcagcagcatggaggctg aagatgttgccacttattactgt | 251 |
| CAN46G4 | K, FR4 | Mus musculus | ttcggctcggggacaaagttggaagtaaaa | 252 |
| CAN46G4 | H, variable region | Mus musculus | gaggtccagctgctacagtctggccctgagctggtgaagcc tggggcttcagtgaagatatcctgcaaggcttctgattactcat tcactggctacatgcactgggtgaagcaaagccatgtaa agagccttgagtggattggacgtatttttccttacaatggtgct gctagctacaaccagaatttcaaggacaaggccaccttgact gtagataagtcttccagcacagcctacatggagctccacagc ctgacatctgaggactctgcagtctattattgtacaagatggtt aagggtctactttgactactggggccaaggcaccactctcac agtctcctca | 253 |
| CAN46G4 | H, CDR1 | Mus musculus | gattactcattcactggctactac | 254 |
| CAN46G4 | H, CDR2 | Mus musculus | atttttccttacaatggtgctgct | 255 |
| CAN46G4 | H, CDR3 | Mus musculus | acaagatggttaagggtctactttgactac | 256 |
| CAN46G4 | H, FR1 | Mus musculus | gaggtccagctgctacagtctggccctgagctggtgaagcc tggggcttcagtgaagatatcctgcaaggcttct | 257 |
| CAN46G4 | H, FR2 | Mus musculus | atgcactgggtgaagcaaagccatgtaaagagccttgagtg gattggacgt | 258 |

TABLE 1-continued

Sequence ID NOs

| Name | Chain, Region | Origin | Sequence | Seq ID No: |
|---|---|---|---|---|
| CAN46G4 | H, FR3 | Mus musculus | agctacaaccagaatttcaaggacaaggccaccttgactgta gataagtcttccagcacagcctacatggagctccacagcctg acatctgaggactctgcagtctattattgt | 259 |
| CAN46G4 | H, FR4 | Mus musculus | tggggccaaggcaccactctcacagtctcctca | 260 |
| CAN46G13 | K, variable region | Mus musculus | gaaattgttctcacccagtctccagcaatcatgtctacatctcc aggggaaaaggtcaccatgtcctgcagtgccagctcaagtg taacttacatgcactggtaccagcagaagtcaatcacctccc ccaaactctggatttatgaaacatccaaactggcttctggagt ccccggtcgcttcagtggcagtgggtctggaaactcttactct ctcacgatcagcagcatggaggctgaagatgttgccacttat tactgttttcaggggagtgggtacccattcacgttcggctcgg ggacaaagttggaaataaaac | 261 |
| CAN46G13 | K, CDR1 | Mus musculus | tcaagtgtaacttac | 262 |
| CAN46G13 | K, CDR2 | Mus musculus | gaaacatcc | 263 |
| CAN46G13 | K, CDR3 | Mus musculus | tttcaggggagtgggtacccattcacg | 264 |
| CAN46G13 | K, FR1 | Mus musculus | gaaattgttctcacccagtctccagcaatcatgtctacatctcc aggggaaaaggtcaccatgtcctgcagtgccagc | 265 |
| CAN46G13 | K, FR2 | Mus musculus | atgcactggtaccagcagaagtcaatcacctcccccaaactc tggatttat | 266 |
| CAN46G13 | K, FR3 | Mus musculus | aaactggcttctggagtccccggtcgcttcagtggcagtggg tctggaaactcttactctctcacgatcagcagcatggaggctg aagatgttgccacttattactgt | 267 |
| CAN46G13 | K, FR4 | Mus musculus | ttcggctcggggacaaagttggaaataaaac | 268 |
| CAN46G13 | H, variable region | Mus musculus | gaggtccagctgctacagtctggccctgagctggtgaagcc tgggacttcagtgaagatatcctgcaaggcttctggttactcat tcactggctactacatacactgggtgaagcagacccatgtaa agagccttgagtggggttggacgtattttccttacaatggtgct gctagctacaatcagaatttcaagggcaaggccaccttgact gtagataagtcctccagcacagcctacatggagctccacag cctgacatctgaggactctgcagtctatttctgtgcaagatggt taagggtctactttgactactggggccaaggcaccactctca cagtctcctcag | 269 |
| CAN46G13 | H, CDR1 | Mus musculus | ggttactcattcactggctactac | 270 |
| CAN46G13 | H, CDR2 | Mus musculus | atttttccttacaatggtgctgct | 271 |
| CAN46G13 | H, CDR3 | Mus musculus | gcaagatggttaagggtctactttgactac | 272 |
| CAN46G13 | H, FR1 | Mus musculus | gaggtccagctgctacagtctggccctgagctggtgaagcc tgggacttcagtgaagatatcctgcaaggcttct | 273 |
| CAN46G13 | H, FR2 | Mus musculus | atacactgggtgaagcagacccatgtaaagagccttgagtg ggttggacgt | 274 |
| CAN46G13 | H, FR3 | Mus musculus | agctacaatcagaatttcaagggcaaggccaccttgactgta gataagtcctccagcacagcctacatggagctccacagcct gacatctgaggactctgcagtctatttctgt | 275 |
| CAN46G13 | H, FR4 | Mus musculus | tggggccaaggcaccactctcacagtctcctcag | 276 |
| CAN46G13a | K, variable region | Mus musculus | gaaaatgtgctcacccagtctccagcaataatggctgcctct ctggggcagaaggtcaccatgacctgcagtgccagctcaa gtgtaagttccagttacttgcactggtaccagcagaagtcag gcgcttcccccaaaccccttgattcataggacatccacccctgg | 277 |

TABLE 1-continued

Sequence ID NOs

| Name | Chain, Region | Origin | Sequence | Seq ID No: |
|---|---|---|---|---|
| | | | cttctggcgtcccagctcgcttcagtggcagtgggtctgga cctcttactctctcacaatcagcagcgtggaggctgaagatg atgcaacttattactgccagcagtggagtggttacccgtacac gttcggagggggaccaagctggaaataaaa | |
| CAN46G13a | K, CDR1 | Mus musculus | tcaagtgtaagttccagttac | 278 |
| CAN46G13a | K, CDR2 | Mus musculus | aggacatcc | 279 |
| CAN46G13a | K, CDR3 | Mus musculus | cagcagtggagtggttacccgtacacg | 280 |
| CAN46G13a | K, FR1 | Mus musculus | gaaaatgtgctcacccagtctccagcaataatggctgcctct ctggggcagaaggtcaccatgacctgcagtgccagc | 281 |
| CAN46G13a | K, FR2 | Mus musculus | ttgcactggtaccagcagaagtcaggcgcttcccccaaacc cttgattcat | 282 |
| CAN46G13a | K, FR3 | Mus musculus | accctggcttctggcgtcccagctcgcttcagtggcagtggg tctgggacctcttactctctcacaatcagcagcgtggaggct gaagatgatgcaacttattactgc | 283 |
| CAN46G13a | K, FR4 | Mus musculus | ttcggagggggaccaagctggaaataaaa | 284 |
| CAN46G13a | H, variable region | Mus musculus | gatgtgcagcttcaggagtcaggacctggcctggtgaaacc ttctcagtctctgtccctcacctgcactgtcactggctactcaat caccagtgattctgcctggaactggatccggcagtttccagg aaacaacctggagtggatgggctacataagctacagtggta gcactagctacaacccatctctcaaaagtcgaatctctatcac tcgagacacatccaagaaccagttcttcctgcagttgaattct gtgactactgaggacacagccacatattactgtgcaagaag gagtagggtctcattctactttgactactggggccaaggcac cactctcacagtctcctcag | 285 |
| CAN46G13a | H, CDR1 | Mus musculus | ggctactcaatcaccagtgattctgcc | 286 |
| CAN46G13a | H, CDR2 | Mus musculus | ataagctacagtggtagcact | 287 |
| CAN46G13a | H, CDR3 | Mus musculus | gcaagaaggagtagggtctcattctactttgactac | 288 |
| CAN46G13a | H, FR1 | Mus musculus | gatgtgcagcttcaggagtcaggacctggcctggtgaaacc ttctcagtctctgtccctcacctgcactgtcact | 289 |
| CAN46G13a | H, FR2 | Mus musculus | tggaactggatccggcagtttccaggaaacaacctggagtg gatgggctac | 290 |
| CAN46G13a | H, FR3 | Mus musculus | agctacaacccatctctcaaaagtcgaatctctatcactcgag acacatccaagaaccagttcttcctgcagttgaattctgtgact actgaggacacagccacatattactgt | 291 |
| CAN46G13a | H, FR4 | Mus musculus | tggggccaaggcaccactctcacagtctcctcag | 292 |
| CAN46G19 | K, variable region | Mus musculus | gaaaatgttctcacccagtctccaacaatcatgtctgcatctcc aggggaagaggtcaccatgacctgcagtgccagctcaagt gtaacttacatgcactggtaccagcagaagtcaatcacctcc cccaaactctggatttatgaaacatccaaactggcttctggag tcccaggtcgcttcagtggcagtgggtctggaaactcttactc tctcacgatcagcagcatggaggctgaagatgttgccactta ttactgttttcaggggagtgggtacccattcacgttcggctcg gggacaaagttggaaataaaac | 293 |
| CAN46G19 | K, CDR1 | Mus musculus | tcaagtgtaacttac | 294 |
| CAN46G19 | K, CDR2 | Mus musculus | gaaacatcc | 295 |

TABLE 1-continued

Sequence ID NOs

| Name | Chain, Region | Origin | Sequence | Seq ID No: |
|---|---|---|---|---|
| CAN46G19 | K, CDR3 | Mus musculus | tttcaggggagtgggtacccattcacg | 296 |
| CAN46G19 | K, FR1 | Mus musculus | gaaaatgttctcacccagtctccaacaatcatgtctgcatctcc aggggaagaggtcaccatgacctgcagtgccagc | 297 |
| CAN46G19 | K, FR2 | Mus musculus | atgcactggtaccagcagaagtcaatcacctcccccaaactc tggatttat | 298 |
| CAN46G19 | K, FR3 | Mus musculus | aaactggcttctggagtcccaggtcgcttcagtggcagtggg tctggaaactcttactctctcacgatcagcagcatggaggctg aagatgttgccacttattactgt | 299 |
| CAN46G19 | K, FR4 | Mus musculus | ttcggctcggggacaaagttggaaataaaac | 300 |
| CAN46G19 | H, variable region | Mus musculus | gaggtccagctgctacagtctggccctgagctggtgaagcc tgggacttcagtgaagatatcctgcaaggcttctggttactcat tcactggctacattcactgggtgaagcagacccatgtaa agagccttgagtgggttggacgtattttccttacaatggtgct gctagctacaaccagaatttcaagggcaaggccaccttgact gtagataagtcctccaccacagcctacatggagctccacag cctgacatctgaggactctgcagtctatttctgtgcaagatggt taagggtctactttgactactggggccaaggcaccactctca cagtctcctcag | 301 |
| CAN46G19 | H, CDR1 | Mus musculus | ggttactcattcactggctactac | 302 |
| CAN46G19 | H, CDR2 | Mus musculus | attttccttacaatggtgctgct | 303 |
| CAN46G19 | H, CDR3 | Mus musculus | gcaagatggttaagggtctactttgactac | 304 |
| CAN46G19 | H, FR1 | Mus musculus | gaggtccagctgctacagtctggccctgagctggtgaagcc tgggacttcagtgaagatatcctgcaaggcttct | 305 |
| CAN46G19 | H, FR2 | Mus musculus | attcactgggtgaagcagacccatgtaaagagccttgagtg ggttggacgt | 306 |
| CAN46G19 | H, FR3 | Mus musculus | agctacaaccagaatttcaagggcaaggccaccttgactgta gataagtcctccaccacagcctacatggagctccacagcct gacatctgaggactctgcagtctatttctgt | 307 |
| CAN46G19 | H, FR4 | Mus musculus | tggggccaaggcaccactctcacagtctcctcag | 308 |
| CAN46G24 | K, variable region | Mus musculus | gaaattgttctcacccagtctccagcaatcatgtctacatctcc aggggaaaaggtcaccatgtcctgcagtgccagctcaagtg taacttacatgcactggtaccagcagaagtcaatcacctccc ccaaactctggatttatgaaacatccaaactggcttctggagt ccccggtcgcttcagtggcagtgggtctggaaactcttactct ctcacgatcagcagcatggaggctgaagatgttgccacttat tactgttttcaggggagtgggtacccattcacgttcggctcgg ggacaaagttggaaataaaac | 309 |
| CAN46G24 | K, CDR1 | Mus musculus | tcaagtgtaacttac | 310 |
| CAN46G24 | K, CDR2 | Mus musculus | gaaacatcc | 311 |
| CAN46G24 | K, CDR3 | Mus musculus | tttcaggggagtgggtacccattcacg | 312 |
| CAN46G24 | K, FR1 | Mus musculus | gaaattgttctcacccagtctccagcaatcatgtctacatctcc aggggaaaaggtcaccatgtcctgcagtgccagc | 313 |
| CAN46G24 | K, FR2 | Mus musculus | atgcactggtaccagcagaagtcaatcacctcccccaaactc tggatttat | 314 |
| CAN46G24 | K, FR3 | Mus musculus | aaactggcttctggagtccccggtcgcttcagtggcagtggg tctggaaactcttactctctcacgatcagcagcatggaggctg aagatgttgccacttattactgt | 315 |

TABLE 1-continued

Sequence ID NOs

| Name | Chain, Region | Origin | Sequence | Seq ID No: |
|---|---|---|---|---|
| CAN46G24 | K, FR4 | Mus musculus | ttcggctcggggacaaagttggaaataaaac | 316 |
| CAN46G24 | H, variable region | Mus musculus | gaggtccagctgctacagtctggccctgagctggtgaagcc tgggacttcagtgaagatatcctgcaaggcttctggttactcat tcactggctactacatacactgggtgaagcagacccatgtaa agagccttgagtgggttggacgtattttccttacaatggtgct gctagctacaatcagaatttcaagggcaaggccaccttgact gtagataagtcctccagcacagcctacatggagctccacag cctgacatctgaggactctgcagtctatttctgtgcaagatggt taagggtctactttgactactggggccaaggcaccactctca cagtctcctcag | 317 |
| CAN46G24 | H, CDR1 | Mus musculus | ggttactcattcactggctactac | 318 |
| CAN46G24 | H, CDR2 | Mus musculus | attttccttacaatggtgctgct | 319 |
| CAN46G24 | H, CDR3 | Mus musculus | gcaagatggttaagggtctactttgactac | 320 |
| CAN46G24 | H, FR1 | Mus musculus | gaggtccagctgctacagtctggccctgagctggtgaagcc tgggacttcagtgaagatatcctgcaaggcttct | 321 |
| CAN46G24 | H, FR2 | Mus musculus | atacactgggtgaagcagacccatgtaaagagccttgagtg ggttggacgt | 322 |
| CAN46G24 | H, FR3 | Mus musculus | agctacaatcagaatttcaagggcaaggccaccttgactgta gataagtcctccagcacagcctacatggagctccacagcct gacatctgaggactctgcagtctatttctgt | 323 |
| CAN46G24 | H, FR4 | Mus musculus | tggggccaaggcaccactctcacagtctcctcag | 324 |
| CAN33G1 | K, variable region | Mus musculus | gacatccagctgacacaatcttcatcctcctattctgtatctcta ggagacagggtcaccattacttgcaaggcaagtgaggacat atataatcggttagcctggtatcagcagagaccaggaaatgc tcctaggctcttaatatctggtgcaaccagtttggaaactggg attccttcaagattcagtggcagtggatctggaaaggagtac actctcagcattgccagtcttcagactgaagattttgttactt-att actgtcaacaatattggaatattccgacgttcggtggaggca ccaggctggaaatcaaac | 721 |
| CAN33G1 | K, CDR1 | Mus musculus | gaggacatatataatcgg | 722 |
| CAN33G1 | K, CDR2 | Mus musculus | ggtgcaacc | 723 |
| CAN33G1 | K, CDR3 | Mus musculus | caacaatattggaatattccgacg | 724 |
| CAN33G1 | K, FR1 | Mus musculus | gacatccagctgacacaatcttcatcctcctattctgtatctcta ggagacagggtcaccattacttgcaaggcaagt | 725 |
| CAN33G1 | K, FR2 | Mus musculus | ttagcctggtatcagcagagaccaggaaatgctcctaggctc ttaatatct | 726 |
| CAN33G1 | K, FR3 | Mus musculus | agtttggaaactgggattccttcaagattcagtggcagtggat ctggaaaggagtacactctcagcattgccagtcttcagactg aagattttgttacttattactgt | 727 |
| CAN33G1 | K, FR4 | Mus musculus | ttcggtggaggcaccaggctggaaatcaaac | 728 |
| CAN33G1 | H, variable region | Mus musculus | gaggtccagctgcagcagtctggacctgacctggtgaagcc tggggcttcagtgaagatatcctgcaaggcttctggttactca ttcactggctactacatgcactgggtgaagcagagccatgga aagagccttgagtggattggacgtgttaatccttacaacggtg atactaattacaaccagaatttcaaggacaaggccatattaac tgtagacaagtcagccagtacagcctacatggagttccgca | 729 |

TABLE 1-continued

Sequence ID NOs

| Name | Chain, Region | Origin | Sequence | Seq ID No: |
|---|---|---|---|---|
| | | | gcctgacatctgaggactctgcggtctattactgtacaagatc aaactgggaaaactactttgactactggggccaaggctcca ctctcacagtctcctcag | |
| CAN33G1 | H, CDR1 | Mus musculus | ggttactcattcactggctactac | 730 |
| CAN33G1 | H, CDR2 | Mus musculus | gttaatccttacaacggtgatact | 731 |
| CAN33G1 | H, CDR3 | Mus musculus | acaagatcaaactgggaaaactactttgactac | 732 |
| CAN33G1 | H, FR1 | Mus musculus | gaggtccagctgcagcagtctggacctgacctggtgaagcc tggggcttcagtgaagatatcctgcaaggcttct | 733 |
| CAN33G1 | H, FR2 | Mus musculus | atgcactgggtgaagcagagccatggaaagagccttgagt ggattggacgt | 734 |
| CAN33G1 | H, FR3 | Mus musculus | aattacaaccagaatttcaaggacaaggccatattaactgtag acaagtcagccagtacagcctacatggagttccgcagcctg acatctgaggactctgcggtctattactgt | 735 |
| CAN33G1 | H, FR4 | Mus musculus | tggggccaaggctccactctcacagtctcctcag | 736 |
| CAN46G4 Codon optimized | K, variable region | Artificial sequence | gaaaaggttctcacccagtctccagcaatcatgtctgcatctc caggggaagaggtcaccatgacctgcagtgccagctcaag tgtaagttacatgcattggtaccagcagaagtcaagcacctc ccccaaactctggatttatgaaacatccaaactggcttttgga gtcccagtcgcttcagtggcagtggatctggaaactcttact ctctcacgatcagcagcatggaggctgaagatgttgccactt attactgttttcaggggagtgggtacccattcacgttcggctc ggggacaaagttggaagtaaaac | 325 |
| CAN46G4 Codon optimized | K, CDR1 | Artificial sequence | tcaagtgtaagttac | 326 |
| CAN46G4 Codon optimized | K, CDR2 | Artificial sequence | gaaacatcc | 327 |
| CAN46G4 Codon optimized | K, CDR3 | Artificial sequence | tttcaggggagtgggtacccattcacg | 328 |
| CAN46G4 Codon optimized | K, FR1 | Artificial sequence | gaaaaggttctcacccagtctccagcaatcatgtctgcatctc caggggaagaggtcaccatgacctgcagtgccagc | 329 |
| CAN46G4 Codon optimized | K, FR2 | Artificial sequence | atgcattggtaccagcagaagtcaagcacctcccccaaact ctggatttat | 330 |
| CAN46G4 Codon optimized | K, FR3 | Artificial sequence | aaactggcttttggagtcccagtcgcttcagtggcagtgga tctggaaactcttactctctcacgatcagcagcatggaggctg aagatgttgccacttattactgt | 331 |
| CAN46G4 Codon optimized | K, FR4 | Artificial sequence | ttcggctcggggacaaagttggaagtaaaac | 332 |
| CAN46G13a Codon optimized | K, variable region | Artificial sequence | gaaaatgtgctcacccagtctccagcaataatggctgcctct ctggggcagaaggtcaccatgacctgcagtgccagctcaa gtgtaagttccagttacttgcactggtaccagcagaagtcag gcgcttcccccaaaccccttgattcataggacatccaccctgg cttctggcgtcccagctcgcttcagtggcagtgggtctggga cctcttactctctcacaatcagcagcgtggaggctgaagatg atgcaacttattactgccagcagtggagtggttacccgtacac gttcggagggggggaccaagctggaaataaaac | 333 |
| CAN46G13a Codon optimized | K, CDR1 | Artificial sequence | tcaagtgtaagttccagttac | 334 |
| CAN46G13a Codon optimized | K, CDR2 | Artificial sequence | aggacatcc | 335 |

TABLE 1-continued

Sequence ID NOs

| Name | Chain, Region | Origin | Sequence | Seq ID No: |
|---|---|---|---|---|
| CAN46G13a Codon optimized | K, CDR3 | Artificial sequence | cagcagtggagtggttacccgtacacg | 336 |
| CAN46G13a Codon optimized | K, FR1 | Artificial sequence | gaaaatgtgctcacccagtctccagcaataatggctgcctct ctggggcagaaggtcaccatgacctgcagtgccagc | 337 |
| CAN46G13a Codon optimized | K, FR2 | Artificial sequence | ttgcactggtaccagcagaagtcaggcgcttcccccaaacc cttgattcat | 338 |
| CAN46G13a Codon optimized | K, FR3 | Artificial sequence | accctggcttctggcgtcccagctcgcttcagtggcagtggg tctgggacctcttactctctcacaatcagcagcgtggaggct gaagatgatgcaacttattactgc | 339 |
| CAN46G13a Codon optimized | K, FR4 | Artificial sequence | ttcggaggggggaccaagctggaaataaaac | 340 |
| CAN46G13a Codon optimized | H, variable region | Artificial sequence | gatgtgcagcttcaggagtcaggacctggcctggtgaaacc ttctcagtctctgtccctcacctgcactgtcactggctactcaat caccagtgattctgcctggaactggattcggcagtttccagg aaacaacctggagtggatgggctacataagctacagtggta gcactagctacaacccatctctcaaaagtcgaatctctatcac tcgagacacatccaagaaccagttcttcctgcagttgaactct gtgactactgaggacacagccacatattactgtgcaagaag gagtagggtctcattctactttgactactggggccaaggcac cactctcacagtctcctcag | 341 |
| CAN46G13a Codon optimized | H, CDR1 | Artificial sequence | ggctactcaatcaccagtgattctgcc | 342 |
| CAN46G13a Codon optimized | H, CDR2 | Artificial sequence | ataagctacagtggtagcact | 343 |
| CAN46G13a Codon optimized | H, CDR3 | Artificial sequence | gcaagaaggagtagggtctcattctactttgactac | 344 |
| CAN46G13a Codon optimized | H, FR1 | Artificial sequence | gatgtgcagcttcaggagtcaggacctggcctggtgaaacc ttctcagtctctgtccctcacctgcactgtcact | 345 |
| CAN46G13a Codon optimized | H, FR2 | Artificial sequence | tggaactggattcggcagtttccaggaaacaacctggagtg gatgggctac | 346 |
| CAN46G13a Codon optimized | H, FR3 | Artificial sequence | agctacaacccatctctcaaaagtcgaatctctatcactcgag acacatccaagaaccagttcttcctgcagttgaactctgtgac tactgaggacacagccacatattactgt | 347 |
| CAN46G13a Codon optimized | H, FR4 | Artificial sequence | tggggccaaggcaccactctcacagtctcctcag | 348 |
| CAN46G19 Codon optimized | K, variable region | Artificial sequence | gaaaatgttctcacccagtctccaacaatcatgtctgcatctcc aggggaagaggtcaccatgacctgcagtgccagctcaagt gtaacttacatgcactggtaccagcagaagtcaatcacctcc cccaaactctggatttatgaaacatccaaactggcttctggag tcccaggtcgcttcagtggcagtgggtctggaaactcttactc tctcacgatcagcagcatggaggctgaagatgttgccactta ttactgttttcaggggagtgggtacccattcacgttcggctcg gggacaaagttggaaataaaac | 349 |
| CAN46G19 Codon optimized | K, CDR1 | Artificial sequence | tcaagtgtaacttac | 350 |
| CAN46G19 Codon optimized | K, CDR2 | Artificial sequence | gaaacatcc | 351 |

TABLE 1-continued

Sequence ID NOs

| Name | Chain, Region | Origin | Sequence | Seq ID No: |
|---|---|---|---|---|
| CAN46G19 Codon optimized | K, CDR3 | Artificial sequence | tttcaggggagtgggtacccattcacg | 352 |
| CAN46G19 Codon optimized | K, FR1 | Artificial sequence | gaaaatgttctcacccagtctccaacaatcatgtctgcatctcc aggggaagaggtcaccatgacctgcagtgccagc | 353 |
| CAN46G19 Codon optimized | K, FR2 | Artificial sequence | atgcactggtaccagcagaagtcaatcacctcccccaaactc tggatttat | 354 |
| CAN46G19 Codon optimized | K, FR3 | Artificial sequence | aaactggcttctggagtcccaggtcgcttcagtggcagtggg tctggaaactcttactctctcacgatcagcagcatggaggctg aagatgttgccacttattactgt | 355 |
| CAN46G19 Codon optimized | K, FR4 | Artificial sequence | ttcggctcggggacaaagttggaaataaaac | 356 |
| CAN46G19 Codon optimized | H, variable region | Artificial sequence | gaggtccagctgctacagtctggccctgagctggtgaagcc tgggacttcagtgaagatatcctgcaaggcttctggttactcat tcactggctactacattcactgggtgaagcagacccatgtaa agagccttgagtgggttggacgtattttccttacaatggtgct gcaagctacaaccagaatttcaagggcaaggccaccttgac tgtagataagtcctccaccacagcctacatggagctccacag cctgacatctgaggactctgcagtctatttctgtgcaagatggt taagggtctactttgactactggggccaaggcaccactctca cagtctcctcag | 357 |
| CAN46G19 Codon optimized | H, CDR1 | Artificial sequence | ggttactcattcactggctactac | 358 |
| CAN46G19 Codon optimized | H, CDR2 | Artificial sequence | attttccttacaatggtgctgca | 359 |
| CAN46G19 Codon optimized | H, CDR3 | Artificial sequence | gcaagatggttaagggtctactttgactac | 360 |
| CAN46G19 Codon optimized | H, FR1 | Artificial sequence | gaggtccagctgctacagtctggccctgagctggtgaagcc tgggacttcagtgaagatatcctgcaaggcttct | 361 |
| CAN46G19 Codon optimized | H, FR2 | Artificial sequence | attcactgggtgaagcagacccatgtaaagagccttgagtg ggttggacgt | 362 |
| CAN46G19 Codon optimized | H, FR3 | Artificial sequence | agctacaaccagaatttcaagggcaaggccaccttgactgta gataagtcctccaccacagcctacatggagctccacagcct gacatctgaggactctgcagtctatttctgt | 363 |
| CAN46G19 Codon optimized | H, FR4 | Artificial sequence | tggggccaaggcaccactctcacagtctcctcag | 364 |
| CAN46G24 Codon optimized | K, variable region | Artificial sequence | gaaattgttctcacccagtctccagcaatcatgtctacatctcc aggggaaaaggtcaccatgtcctgcagtgccagctcaagtg taacttacatgcactggtaccagcagaagtcaatcacctccc ccaaactctggatttatgaaacatccaaactggcttctggagt ccccggtcgcttcagtggcagtgggtctggaaactcttactct ctcacgatcagcagcatggaggctgaagatgttgccacttat tactgttttcaggggagtgggtacccattcacgttcggctcgg ggacaaagttggaaataaaac | 365 |
| CAN46G24 Codon optimized | K, CDR1 | Artificial sequence | tcaagtgtaacttac | 366 |

TABLE 1-continued

Sequence ID NOs

| Name | Chain, Region | Origin | Sequence | Seq ID No: |
|---|---|---|---|---|
| CAN46G24 Codon optimized | K, CDR2 | Artificial sequence | gaaacatcc | 367 |
| CAN46G24 Codon optimized | K, CDR3 | Artificial sequence | tttcaggggagtgggtacccattcacg | 368 |
| CAN46G24 Codon optimized | K, FR1 | Artificial sequence | gaaattgttctcacccagtctccagcaatcatgtctacatctcc aggggaaaaggtcaccatgtcctgcagtgccagc | 369 |
| CAN46G24 Codon optimized | K, FR2 | Artificial sequence | atgcactggtaccagcagaagtcaatcacctcccccaaactc tggatttat | 370 |
| CAN46G24 Codon optimized | K, FR3 | Artificial sequence | aaactggcttctggagtccccggtcgcttcagtggcagtggg tctggaaactcttactctctcacgatcagcagcatggaggctg aagatgttgccacttattactgt | 371 |
| CAN46G24 Codon optimized | K, FR4 | Artificial sequence | ttcggctcggggacaaagttggaaataaaac | 372 |
| CAN46G24 Codon optimized | H, variable region | Artificial sequence | gaggtccagctgctacagtctggccctgagctggtgaagcc tgggacttcagtgaagatatcctgcaaggcttctggttactcat tcactggctactacatacactgggtgaagcagacccatgtaa agagccttgagtgggttggacgtattttccttacaatggtgct gctagctacaatcagaatttcaagggcaaggccaccttgact gtagataagtcctccagcacagcctacatggagctccacag cctgacatctgaggactctgcagtctatttctgtgcaagatggt taagggtctactttgactactggggccaaggcaccactctca cagtctcctcag | 373 |
| CAN46G24 Codon optimized | H, CDR1 | Artificial sequence | ggttactcattcactggctactac | 374 |
| CAN46G24 Codon optimized | H, CDR2 | Artificial sequence | attttccttacaatggtgctgct | 375 |
| CAN46G24 Codon optimized | H, CDR3 | Artificial sequence | gcaagatggttaagggtctactttgactac | 376 |
| CAN46G24 Codon optimized | H, FR1 | Artificial sequence | gaggtccagctgctacagtctggccctgagctggtgaagcc tgggacttcagtgaagatatcctgcaaggcttct | 377 |
| CAN46G24 Codon optimized | H, FR2 | Artificial sequence | atacactgggtgaagcagacccatgtaaagagccttgagtg ggttggacgt | 378 |
| CAN46G24 Codon optimized | H, FR3 | Artificial sequence | agctacaatcagaatttcaagggcaaggccaccttgactgta gataagtcctccagcacagcctacatggagctccacagcct gacatctgaggactctgcagtctatttctgt | 379 |
| CAN46G24 Codon optimized | H, FR4 | Artificial sequence | tggggccaaggcaccactctcacagtctcctcag | 380 |
| cdrCAN46G13a | K, variable region | Artificial sequence | gacatccagatgacccagtcccctcctccctgtccgcctcc gtgggcgaccgcgtgaccatcacctgtccgcctcctcctc cgtgtcctcctcctacctgcactggtaccagcagaagcccg gcaaggccccccaagctgctgatctaccgcacctccaccctg gcctccggcgtgcctcccgcttctccggctccggctccgg caccgacttcaccttcaccatctctcccctgcagcccgagga catcgccacctactactgccagcagtggtccggctacccta cccttcggccagggcaccaaggtggagatcaagc | 381 |
| cdrCAN46G13a | K, CDR1 | Artificial sequence | tcctccgtgtcctcctcctac | 382 |

TABLE 1-continued

Sequence ID NOs

| Name | Chain, Region | Origin | Sequence | Seq ID No: |
|---|---|---|---|---|
| cdrCAN46G13a | K, CDR2 | Artificial sequence | cgcacctcc | 383 |
| cdrCAN46G13a | K, CDR3 | Artificial sequence | cagcagtggtccggctacccctacacc | 384 |
| cdrCAN46G13a | K, FR1 | Artificial sequence | gacatccagatgacccagtcccctcctccctgtccgcctcc gtgggcgaccgcgtgaccatcacctgctccgcctcc | 385 |
| cdrCAN46G13a | K, FR2 | Artificial sequence | ctgcactggtaccagcagaagcccggcaaggcccccaag ctgctgatctac | 386 |
| cdrCAN46G13a | K, FR3 | Artificial sequence | accctggcctccggcgtgccctcccgcttctccggctccgg ctccggcaccgacttcaccttcaccatctctcctgcagcc cgaggacatcgccacctactactgc | 387 |
| cdrCAN46G13a | K, FR4 | Artificial sequence | ttcggccagggcaccaaggtggagatcaagc | 388 |
| cdrCAN46G13a | H, variable region | Artificial sequence | caggtgcagctgcaggagtccggccccggcctggtgaagc cctcccagaccctgtccctgacctgcaccgtgtccggcggc tccatctcctccgactccgcctggaactggatccgccagccc cccggcaagggcctggagtggatcggctacatctcctactc cggctccacctcctacaacccctccctgaagtcccgcgtga ccatgtccgtggacacctccaagaaccagttctccctgaagg tgaactccgtgaccgccgccgacaccgccgtgtactactgc gcccgccgctcccgcgtgtccttctacttcgactactggggc cagggcaccctggtgaccgtgtcctccg | 389 |
| cdrCAN46G13a | H, CDR1 | Artificial sequence | ggcggctccatctcctccgactccgcc | 390 |
| cdrCAN46G13a | H, CDR2 | Artificial sequence | atctcctactccggctccacc | 391 |
| cdrCAN46G13a | H, CDR3 | Artificial sequence | gcccgccgctcccgcgtgtccttctacttcgactac | 392 |
| cdrCAN46G13a | H, FR1 | Artificial sequence | caggtgcagctgcaggagtccggccccggcctggtgaagc cctcccagaccctgtccctgacctgcaccgtgtcc | 393 |
| cdrCAN46G13a | H, FR2 | Artificial sequence | tggaactggatccgccagccccccggcaagggcctggagt ggatcggctac | 394 |
| cdrCAN46G13a | H, FR3 | Artificial sequence | tcctacaacccctccctgaagtcccgcgtgaccatgtccgtg gacacctccaagaaccagttctccctgaaggtgaactccgtg accgccgccgacaccgccgtgtactactgc | 395 |
| cdrCAN46G13a | H, FR4 | Artificial sequence | tggggccagggcaccctggtgaccgtgtcctccg | 396 |
| huCAN46G13a | K, variable region | Artificial sequence | gagaacgtgctgacccagtcccctcctccctgtccgcctcc gtgggcgaccgcgtgaccatgacctgctccgcctcctcctc cgtgtcctcctcctacctgcactggtaccagcagaagcccg gcaagtcccccaagcccctgatccaccgcacctccaccctg gctccggcgtgccctcccgcttctccggctccggctccgg cacctcctactccctgaccatctctcctgcagcccgagga catcgccacctactactgccagcagtggtccggctacccta caccttcggcggcggcaccaaggtggagatcaagc | 397 |
| huCAN46G13a | K, CDR1 | Artificial sequence | tcctccgtgtcctcctcctac | 398 |
| huCAN46G13a | K, CDR2 | Artificial sequence | cgcacctcc | 399 |
| huCAN46G13a | K, CDR3 | Artificial sequence | cagcagtggtccggctacccctacacc | 400 |
| huCAN46G13a | K, FR1 | Artificial sequence | gagaacgtgctgacccagtcccctcctccctgtccgcctcc gtgggcgaccgcgtgaccatgacctgctccgcctcc | 401 |

TABLE 1-continued

Sequence ID NOs

| Name | Chain, Region | Origin | Sequence | Seq ID No: |
|---|---|---|---|---|
| huCAN46G13a | K, FR2 | Artificial sequence | ctgcactggtaccagcagaagcccggcaagtcccccaagc ccctgatccac | 402 |
| huCAN46G13a | K, FR3 | Artificial sequence | accctggcctccggcgtgccctcccgcttctccggctccgg ctccggcacctcctactccctgaccatctcctccctgcagcc cgaggacatcgccacctactactgc | 403 |
| huCAN46G13a | K, FR4 | Artificial sequence | ttcggcggcggcaccaaggtggagatcaagc | 404 |
| huCAN46G13a | H, variable region | Artificial sequence | caggtgcagctgcaggagtccggccccggcctggtgaagc cctcccagaccctgtccctgacctgcaccgtgaccggctact ccatcacctccgactccgcctggaactggatccgccagttcc ccggcaacaacctggagtggatgggctacatctcctactcc ggctccacctcctacaaccctccctgaagtcccgcatctcc atcacccgcgacacctccaagaaccagttctccctgaaggt gaactccgtgaccgccgccgacaccgccgtgtactactgcg cccgccgctcccgcgtgtccttctacttcgactactggggcc agggcaccctggtgaccgtgtcctccg | 405 |
| huCAN46G13a | H, CDR1 | Artificial sequence | ggctactccatcacctccgactccgcc | 406 |
| huCAN46G13a | H, CDR2 | Artificial sequence | atctcctactccggctccacc | 407 |
| huCAN46G13a | H, CDR3 | Artificial sequence | gcccgccgctcccgcgtgtccttctacttcgactac | 408 |
| huCAN46G13a | H, FR1 | Artificial sequence | caggtgcagctgcaggagtccggccccggcctggtgaagc cctcccagaccctgtccctgacctgcaccgtgacc | 409 |
| huCAN46G13a | H, FR2 | Artificial sequence | tggaactggatccgccagttccccggcaacaacctggagtg gatgggctac | 410 |
| huCAN46G13a | H, FR3 | Artificial sequence | tcctacaaccctccctgaagtcccgcatctccatcacccgc gacacctccaagaaccagttctccctgaaggtgaactccgtg accgccgccgacaccgccgtgtactactgc | 411 |
| huCAN46G13a | H, FR4 | Artificial sequence | tggggccagggcaccctggtgaccgtgtcctccg | 412 |
| rehuCAN46G13a | K, variable region | Artificial sequence | gagaacgtgctgacccagtcccccctcctccatgtccgcctcc gtgggcgaccgcgtgaccatgacctgctccgcctcctcctc cgtgtcctcctcctacctgcactggtaccagcagaagcccg gcaaggcccccaagcccctgatccaccgcacctccaccct ggcctccggcgtgccctcccgcttctccggctccggctccg gcacctcctactccctgaccatctcctccgtgcagcccgagg acatcgccacctactactgccagcagtggtccggctaccccct acaccttcggcggcggcaccaaggtggagatcaagc | 413 |
| rehuCAN46G13a | K, CDR1 | Artificial sequence | tcctccgtgtcctcctcctac | 414 |
| rehuCAN46G13a | K, CDR2 | Artificial sequence | cgcacctcc | 415 |
| rehuCAN46G13a | K, CDR3 | Artificial sequence | cagcagtggtccggctaccccctacacc | 416 |
| rehuCAN46G13a | K, FR1 | Artificial sequence | gagaacgtgctgacccagtcccccctcctccatgtccgcctcc gtgggcgaccgcgtgaccatgacctgctccgcctcc | 417 |
| rehuCAN46G13a | K, FR2 | Artificial sequence | ctgcactggtaccagcagaagcccggcaaggcccccaag cccctgatccac | 418 |
| rehuCAN46G13a | K, FR3 | Artificial sequence | accctggcctccggcgtgccctcccgcttctccggctccgg ctccggcacctcctactccctgaccatctcctccgtgcagcc cgaggacatcgccacctactactgc | 419 |
| rehuCAN46G13a | K, FR4 | Artificial sequence | ttcggcggcggcaccaaggtggagatcaagc | 420 |

TABLE 1-continued

Sequence ID NOs

| Name | Chain, Region | Origin | Sequence | Seq ID No: |
|---|---|---|---|---|
| rehuCAN46G13a | H, variable region | Artificial sequence | caggtgcagctgcaggagtccggccccggcctggtgaagc cctcccagaccctgtccctgacctgcaccgtgaccggctact ccatcacctccgactccgcctggaactggatccgccagcc ccggcaacggcctggagtggatgggctacatctcctactc cggctccacctcctacaaccctccctgaagtcccgcatctc catcacccgcgacacctccaagaaccagttctccctgaagct gaactccgtgaccgccgccgacaccgccacctactactgc gcccgccgctcccgcgtgtccttctacttcgactactggggc cagggcaccctggtgaccgtgtcctccg | 421 |
| rehuCAN46G13a | H, CDR1 | Artificial sequence | ggctactccatcacctccgactccgcc | 422 |
| rehuCAN46G13a | H, CDR2 | Artificial sequence | atctcctactccggctccacc | 423 |
| rehuCAN46G13a | H, CDR3 | Artificial sequence | gcccgccgctcccgcgtgtccttctacttcgactac | 424 |
| rehuCAN46G13a | H, FR1 | Artificial sequence | caggtgcagctgcaggagtccggccccggcctggtgaagc cctcccagaccctgtccctgacctgcaccgtgacc | 425 |
| rehuCAN46G13a | H, FR2 | Artificial sequence | tggaactggatccgccagccccccggcaacggcctggagt ggatgggctac | 426 |
| rehuCAN46G13a | H, FR3 | Artificial sequence | tcctacaaccctccctgaagtcccgcatctccatcacccgc gacacctccaagaaccagttctccctgaagctgaactccgtg accgccgccgacaccgccacctactactgc | 427 |
| rehuCAN46G13a | H, FR4 | Artificial sequence | tggggccagggcaccctggtgaccgtgtcctccg | 428 |
| cdrCAN46G19 | K, variable region | Artificial sequence | gacatccagatgacccagtcccccctcctccctgtccgcctcc gtgggcgaccgcgtgaccatcacctgctccgcctcctcctc cgtgacctacatgcactggtaccagcagaagcccggcaag gcccccaagctgctgatctacgagacctccaagctggcctc cggcgtgccctcccgcttctccggctccggctccggcaccg actacaccttcaccatctcctccctgcagcccgaggacatcg ccacctactactgcttccagggctccggctaccccttcacctt cggccagggcaccaaggtggagatcaagc | 429 |
| cdrCAN46G19 | K, CDR1 | Artificial sequence | tcctccgtgacctac | 430 |
| cdrCAN46G19 | K, CDR2 | Artificial sequence | gagacctcc | 431 |
| cdrCAN46G19 | K, CDR3 | Artificial sequence | ttccagggctccggctaccccttcacc | 432 |
| cdrCAN46G19 | K, FR1 | Artificial sequence | gacatccagatgacccagtcccccctcctccctgtccgcctcc gtgggcgaccgcgtgaccatcacctgctccgcctcc | 433 |
| cdrCAN46G19 | K, FR2 | Artificial sequence | atgcactggtaccagcagaagcccggcaaggcccccaag ctgctgatctac | 434 |
| cdrCAN46G19 | K, FR3 | Artificial sequence | aagctggcctccggcgtgccctcccgcttctccggctccgg ctccggcaccgactacaccttcaccatctcctccctgcagcc cgaggacatcgccacctactactgc | 435 |
| cdrCAN46G19 | K, FR4 | Artificial sequence | ttcggccagggcaccaaggtggagatcaagc | 436 |
| cdrCAN46G19 | H, variable region | Artificial sequence | Caggtgcagctggtgcagtccggcgccgaggtgaagaag cccggcgagtccgtgaaggtgtcctgcaaggcctccggcta caccttcaccggctactacatccactgggtgcgccaggccc ccggccagggcctggagtggatgggccgcatcttccctac aacggcgccgcctcctacaaccagaacttcaagggccgcg tgaccatcaccgccgacaagtccacctccaccgcctacatg gagctgtcctccctgcgctccgaggacaccgccgtgtacta ctgcgcccgctggctgcgcgtgtacttcgactactggggcc agggcaccaccgtgaccgtgtcctccg | 437 |
| cdrCAN46G19 | H, CDR1 | Artificial sequence | ggctacaccttcaccggctactac | 438 |

TABLE 1-continued

Sequence ID NOs

| Name | Chain, Region | Origin | Sequence | Seq ID No: |
|---|---|---|---|---|
| cdrCAN46G19 | H, CDR2 | Artificial sequence | atcttcccctacaacggcgccgcc | 439 |
| cdrCAN46G19 | H, CDR3 | Artificial sequence | gcccgctggctgcgcgtgtacttcgactac | 440 |
| cdrCAN46G19 | H, FR1 | Artificial sequence | caggtgcagctggtgcagtccggcgccgaggtgaagaag cccggcgagtccgtgaaggtgtcctgcaaggcctcc | 441 |
| cdrCAN46G19 | H, FR2 | Artificial sequence | atccactgggtgcgccaggcccccggccagggcctggagt ggatgggccgc | 442 |
| cdrCAN46G19 | H, FR3 | Artificial sequence | tcctacaaccagaacttcaagggccgcgtgaccatcaccgc cgacaagtccacctccaccgcctacatggagctgtcctccct gcgctccgaggacaccgccgtgtactactgc | 443 |
| cdrCAN46G19 | H, FR4 | Artificial sequence | tggggccagggcaccaccgtgaccgtgtcctccg | 444 |
| huCAN46G19 | K, variable region | Artificial sequence | gagaacgtgctgacccagtcccccctcctccctgtccgcctcc gtgggcgaccgcgtgaccatcacctgctccgcctcctcctc cgtgacctacatgcactggtaccagcagaagcccggcaag gcccccaagctgtggatctacgagacctccaagctggcctc cggcgtgcccggccgcttctccggctccggctccggcaact cctacaccttcaccatctcctccctgcagcccgaggacatcg ccacctactactgcttccagggctccggctacccccttcacctt cggccagggcaccaaggtggagatcaag | 445 |
| huCAN46G19 | K, CDR1 | Artificial sequence | tcctccgtgacctac | 446 |
| huCAN46G19 | K, CDR2 | Artificial sequence | gagacctcc | 447 |
| huCAN46G19 | K, CDR3 | Artificial sequence | ttccagggctccggctacccccttcacc | 448 |
| huCAN46G19 | K, FR1 | Artificial sequence | gagaacgtgctgacccagtcccccctcctccctgtccgcctcc gtgggcgaccgcgtgaccatcacctgctccgcctcc | 449 |
| huCAN46G19 | K, FR2 | Artificial sequence | atgcactggtaccagcagaagcccggcaaggcccccaag ctgtggatctac | 450 |
| huCAN46G19 | K, FR3 | Artificial sequence | aagctggcctccggcgtgcccggccgcttctccggctccgg ctccggcaactcctacaccttcaccatctcctccctgcagccc gaggacatcgccacctactactgc | 451 |
| huCAN46G19 | K, FR4 | Artificial sequence | ttcggccagggcaccaaggtggagatcaag | 452 |
| huCAN46G19 | H, variable region | Artificial sequence | Gaggtgcagctggtgcagtccggcgccgaggtgaagaag cccggcgagtccgtgaaggtgtcctgcaaggcctccggcta ctccttcaccggctactacatccactgggtgaagcaggcccc cggccaggcctggagtgggtgggccgcatcttcccctac aacggcgccgcctcctacaaccagaacttcaagggccaagg ccaccctgaccgtggacaagtcctccaccaccgcctacatg gagctgtcctccctgcgctccgaggacaccgccgtgtacttc tgcgcccgctggctgcgcgtgtacttcgactactggggcca gggcaccaccgtgaccgtgtcctccg | 453 |
| huCAN46G19 | H, CDR1 | Artificial sequence | ggctactccttcaccggctactac | 454 |
| huCAN46G19 | H, CDR2 | Artificial sequence | atcttcccctacaacggcgccgcc | 455 |
| huCAN46G19 | H, CDR3 | Artificial sequence | gcccgctggctgcgcgtgtacttcgactac | 456 |
| huCAN46G19 | H, FR1 | Artificial sequence | gaggtgcagctggtgcagtccggcgccgaggtgaagaag cccggcgagtccgtgaaggtgtcctgcaaggcctcc | 457 |

TABLE 1-continued

Sequence ID NOs

| Name | Chain, Region | Origin | Sequence | Seq ID No: |
|---|---|---|---|---|
| huCAN46G19 | H, FR2 | Artificial sequence | atccactgggtgaagcaggcccccggccagggcctggagt gggtgggccgc | 458 |
| huCAN46G19 | H, FR3 | Artificial sequence | tcctacaaccagaacttcaagggcaaggccaccctgaccgt ggacaagtcctccaccaccgcctacatggagctgtcctccct gcgctccgaggacaccgccgtgtacttctgc | 459 |
| huCAN46G19 | H, FR4 | Artificial sequence | tggggccagggcaccaccgtgaccgtgtcctccg | 460 |
| rehuCAN46G19 | K, variable region | Artificial sequence | gagaacgtgctgacccagtcccctcctccatgtccgcctcc gtgggcgaccgcgtgaccatgacctgctccgcctcctcctc cgtgacctacatgcactggtaccagcagaagcccggcaagt cccccaagctgtggatctacgagacctccaagctggcctcc ggcgtgccctccgcttctccggctccggctccggcaacga ctactccctgaccatctcctccatgcagcccgaggacgtggc cacctactactgcttccagggctccggctacccccttccttc ggccagggcaccaagctggagatcaagc | 461 |
| rehuCAN46G19 | K, CDR1 | Artificial sequence | tcctccgtgacctac | 462 |
| rehuCAN46G19 | K, CDR2 | Artificial sequence | gagacctcc | 463 |
| rehuCAN46G19 | K, CDR3 | Artificial sequence | ttccagggctccggctacccccttcacc | 464 |
| rehuCAN46G19 | K, FR1 | Artificial sequence | gagaacgtgctgacccagtcccctcctccatgtccgcctcc gtgggcgaccgcgtgaccatgacctgctccgcctcc | 465 |
| rehuCAN46G19 | K, FR2 | Artificial sequence | atgcactggtaccagcagaagcccggcaagtcccccaagc tgtggatctac | 466 |
| rehuCAN46G19 | K, FR3 | Artificial sequence | aagctggcctccggcgtgccctccgcttctccggctccgg ctccggcaacgactactccctgaccatctcctccatgcagcc cgaggacgtggccacctactactgc | 467 |
| rehuCAN46G19 | K, FR4 | Artificial sequence | ttcggccagggcaccaagctggagatcaagc | 468 |
| rehuCAN46G19 | H, variable region | Artificial sequence | Gaggtgcagctggtgcagtccggcgccgaggtggtgaag cccggcgagtccgtgaagatctcctgcaaggcctccggcta ctccttcaccggctactacatccactgggtgaagcagacccc cggccagtccctggagtgggtgggccgcatcttcccctaca acggcgccgcctcctacaaccagaacttcaagggcaaggc caccctgaccgtggacaagtccaccaccaccgcctacatgg agctgtcctccctgcgctccgaggactccgccgtgtacttct gcgcccgctggctgcgcgtgtacttcgactactggggccag ggcaccaccctgaccgtgtcctccg | 469 |
| rehuCAN46G19 | H, CDR1 | Artificial sequence | ggctactccttcaccggctactac | 470 |
| rehuCAN46G19 | H, CDR2 | Artificial sequence | atcttcccctacaacggcgccgcc | 471 |
| rehuCAN46G19 | H, CDR3 | Artificial sequence | gcccgctggctgcgcgtgtacttcgactac | 472 |
| rehuCAN46G19 | H, FR1 | Artificial sequence | gaggtgcagctggtgcagtccggcgccgaggtggtgaagc ccggcgagtccgtgaagatctcctgcaaggcctcc | 473 |
| rehuCAN46G19 | H, FR2 | Artificial sequence | atccactgggtgaagcagacccccggccagtccctggagt gggtgggccgc | 474 |
| rehuCAN46G19 | H, FR3 | Artificial sequence | tcctacaaccagaacttcaagggcaaggccaccctgaccgt ggacaagtccaccaccaccgcctacatggagctgtcctccc tgcgctccgaggactccgccgtgtacttctgc | 475 |
| rehuCAN46G19 | H, FR4 | Artificial sequence | tggggccagggcaccaccctgaccgtgtcctccg | 476 |

TABLE 1-continued

Sequence ID NOs

| Name | Chain, Region | Origin | Sequence | Seq ID No: |
|---|---|---|---|---|
| cdrCAN46G24 | K, variable region | Artificial sequence | gacatccagatgacccagtcccctcctccctgtccgcctcc gtgggcgaccgcgtgaccatcacctgctccgcctcctcctc cgtgacctacatgcactggtaccagcagaagcccggcaag gcccccaagctgctgatctacgagacctccaagctggcctc cggcgtgccctcccgcttctccggctccggctccggcaccg actacaccttcaccatctcctccctgcagccgaggacatcg ccacctactactgcttccagggctccggctacccttcacctt cggccagggcaccaaggtggagatcaagc | 477 |
| cdrCAN46G24 | K, CDR1 | Artificial sequence | tcctccgtgacctac | 478 |
| cdrCAN46G24 | K, CDR2 | Artificial sequence | gagacctcc | 479 |
| cdrCAN46G24 | K, CDR3 | Artificial sequence | ttccagggctccggctacccttcacc | 480 |
| cdrCAN46G24 | K, FR1 | Artificial sequence | gacatccagatgacccagtcccctcctccctgtccgcctcc gtgggcgaccgcgtgaccatcacctgctccgcctcctcctc | 481 |
| cdrCAN46G24 | K, FR2 | Artificial sequence | atgcactggtaccagcagaagcccggcaaggcccccaag ctgctgatctac | 482 |
| cdrCAN46G24 | K, FR3 | Artificial sequence | aagctggcctccggcgtgccctcccgcttctccggctccgg ctccggcaccgactacaccttcaccatctcctccctgcagcc cgaggacatcgccacctactactgc | 483 |
| cdrCAN46G24 | K, FR4 | Artificial sequence | ttcggccagggcaccaaggtggagatcaagc | 484 |
| cdrCAN46G24 | H, variable region | Artificial sequence | caggtgcagctggtgcagtccggcgccgaggtgaagaag cccggcgagtccgtgaaggtgtcctgcaaggcctccggcta caccttcaccggctactacatccactgggtgcgccaggccc ccggccagggcctggagtggatgggccgcatcttcccctac aacggcgccgcctcctacaaccagaacttcaagggccgcg tgaccatcaccgccgacaagtccacctccaccgcctacatg gagctgtcctccctgcgctccgaggacaccgccgtgtacta ctgcgcccgctggctgcgcgtgtacttcgactactggggcc agggcaccaccgtgaccgtgtcctccg | 485 |
| cdrCAN46G24 | H, CDR1 | Artificial sequence | ggctacaccttcaccggctactac | 486 |
| cdrCAN46G24 | H, CDR2 | Artificial sequence | atcttcccctacaacggcgccgcc | 487 |
| cdrCAN46G24 | H, CDR3 | Artificial sequence | gcccgctggctgcgcgtgtacttcgactac | 488 |
| cdrCAN46G24 | H, FR1 | Artificial sequence | caggtgcagctggtgcagtccggcgccgaggtgaagaag cccggcgagtccgtgaaggtgtcctgcaaggcctcc | 489 |
| cdrCAN46G24 | H, FR2 | Artificial sequence | atccactgggtgcgccaggcccccggccagggcctggagt ggatgggccgc | 490 |
| cdrCAN46G24 | H, FR3 | Artificial sequence | tcctacaaccagaacttcaagggccgcgtgaccatcaccgc cgacaagtccacctccaccgcctacatggagctgtcctccct gcgctccgaggacaccgccgtgtactactgc | 491 |
| cdrCAN46G24 | H, FR4 | Artificial sequence | tggggccagggcaccaccgtgaccgtgtcctccg | 492 |
| huCAN46G24 | K, variable region | Artificial sequence | gagatcgtgctgacccagtcccctcctccctgtccacctcc gtgggcgaccgcgtgaccatcacctgctccgcctcctcctc gtgacctacatgcactggtaccagcagaagcccggcaagg cccccaagctgtggatctacgagacctccaagctggcctcc ggcgtgccgggcggcttctccggctccggctccggcaactc ctacaccttcaccatctcctccctgcagccgaggacatcgc cacctactactgcttccagggctccggctacccttcaccttc ggccagggcaccaaggtggagatcaagc | 493 |
| huCAN46G24 | K, CDR1 | Artificial sequence | tcctccgtgacctac | 494 |

TABLE 1-continued

Sequence ID NOs

| Name | Chain, Region | Origin | Sequence | Seq ID No: |
|---|---|---|---|---|
| huCAN46G24 | K, CDR2 | Artificial sequence | gagacctcc | 495 |
| huCAN46G24 | K, CDR3 | Artificial sequence | ttccagggctccggctacccccttcacc | 496 |
| huCAN46G24 | K, FR1 | Artificial sequence | gagatcgtgctgacccagtcccccctcctccctgtccacctcc gtgggcgaccgcgtgaccatctcctgctccgcctcc | 497 |
| huCAN46G24 | K, FR2 | Artificial sequence | atgcactggtaccagcagaagcccggcaaggccccccaag ctgtggatctac | 498 |
| huCAN46G24 | K, FR3 | Artificial sequence | aagctggcctccggcgtgcccggccgcttctccggctccgg ctccggcaactcctacaccttcaccatctcctccctgcagccc gaggacatcgccacctactactgc | 499 |
| huCAN46G24 | K, FR4 | Artificial sequence | ttcggccagggcaccaaggtggagatcaagc | 500 |
| huCAN46G24 | H, variable region | Artificial sequence | gaggtgcagctggtgcagtccggcgccgaggtgaagaag cccggcgagtccgtgaaggtgtcctgcaaggcctccggcta ctccttcaccggctactacatccactgggtgaagcaggcccc cggccagggcctggagtgggtgggccgcatcttcccctac aacggcgccgcctcctacaaccagaacttcaagggcaagg ccaccctgaccgtggacaagtcctcctccaccgcctacatg gagctgtcctcctgcgctccgaggacaccgccgtgtacttc tgcgcccgctggctgcgcgtgtacttcgactactggggcca gggcaccaccgtgaccgtgtcctccg | 501 |
| huCAN46G24 | H, CDR1 | Artificial sequence | ggctactccttcaccggctactac | 502 |
| huCAN46G24 | H, CDR2 | Artificial sequence | atcttcccctacaacggcgccgcc | 503 |
| huCAN46G24 | H, CDR3 | Artificial sequence | gcccgctggctgcgcgtgtacttcgactac | 504 |
| huCAN46G24 | H, FR1 | Artificial sequence | gaggtgcagctggtgcagtccggcgccgaggtgaagaag cccggcgagtccgtgaaggtgtcctgcaaggcctcc | 505 |
| huCAN46G24 | H, FR2 | Artificial sequence | atccactgggtgaagcaggccccccggccagggcctggagt gggtgggccgc | 506 |
| huCAN46G24 | H, FR3 | Artificial sequence | tcctacaaccagaacttcaagggcaaggccaccctgaccgt ggacaagtcctcctccaccgcctacatggagctgtcctccct gcgctccgaggacaccgccgtgtacttctgc | 507 |
| huCAN46G24 | H, FR4 | Artificial sequence | tggggccagggcaccaccgtgaccgtgtcctccg | 508 |
| rehuCAN46G24 | K, variable region | Artificial sequence | gagatcgtgctgacccagtcccccctcctccatgtccacctcc gtgggcgaccgcgtgaccatgtcctgctccgcctcctcctcc gtgacctacatgcactggtaccagcagaagcccggcaagtc ccccaagctgtggatctacgagacctccaagctggccgccg gcgtgccctcccgcttctccggctccggctccggcaacgac tactccctgaccatctcctccatgcagcccgaggacgtggcc acctactactgcttccagggctccggctacccccttcaccttcg gccagggcaccaagctggagatcaagc | 509 |
| rehuCAN46G24 | K, CDR1 | Artificial sequence | tcctccgtgacctac | 510 |
| rehuCAN46G24 | K, CDR2 | Artificial sequence | gagacctcc | 511 |
| rehuCAN46G24 | K, CDR3 | Artificial sequence | ttccagggctccggctacccccttcacc | 512 |
| rehuCAN46G24 | K, FR1 | Artificial sequence | gagatcgtgctgacccagtcccccctcctccatgtccacctcc gtgggcgaccgcgtgaccatgtcctgctccgcctcc | 513 |

TABLE 1-continued

Sequence ID NOs

| Name | Chain, Region | Origin | Sequence | Seq ID No: |
|---|---|---|---|---|
| rehuCAN46G24 | K, FR2 | Artificial sequence | atgcactggtaccagcagaagcccggcaagtcccccaagc tgtggatctac | 514 |
| rehuCAN46G24 | K, FR3 | Artificial sequence | aagctggcctccggcgtgccctcccgcttctccggctccgg ctccggcaacgactactccctgaccatctcctccatgcagcc cgaggacgtggccacctactactgc | 515 |
| rehuCAN46G24 | K, FR4 | Artificial sequence | ttcggccagggcaccaagctggagatcaagc | 516 |
| rehuCAN46G24 | H, variable region | Artificial sequence | Gaggtgcagctggtgcagtccggcgccgaggtggtgaag cccggcgagtccgtgaagatctcctgcaaggcctccggcta ctccttcaccggctacatccactgggtgaagcagaccccc cggccagtccctggagtgggtgggccgcatcttccctaca acggcgccgcctcctacaaccagaacttcaagggcaaggc caccctgaccgtggacaagtccacctccaccgcctacatgg agctgtcctccctgcgctccgaggactccgccgtgtacttct gcgcccgctggctgcgcgtgtacttcgactactggggccag ggcaccaccctgaccgtgtcctccg | 517 |
| rehuCAN46G24 | H, CDR1 | Artificial sequence | ggctactccttcaccggctactac | 518 |
| rehuCAN46G24 | H, CDR2 | Artificial sequence | atcttccctacaacggcgccgcc | 519 |
| rehuCAN46G24 | H, CDR3 | Artificial sequence | gcccgctggctgcgcgtgtacttcgactac | 520 |
| rehuCAN46G24 | H, FR1 | Artificial sequence | gaggtgcagctggtgcagtccggcgccgaggtggtgaagc ccggcgagtccgtgaagatctcctgcaaggcctcc | 521 |
| rehuCAN46G24 | H, FR2 | Artificial sequence | atccactgggtgaagcagacccccggccagtccctggagt gggtgggccgc | 522 |
| rehuCAN46G24 | H, FR3 | Artificial sequence | tcctacaaccagaacttcaagggcaaggccaccctgaccgt ggacaagtccacctccaccgcctacatggagctgtcctccct gcgctccgaggactccgccgtgtacttctgc | 523 |
| rehuCAN46G24 | H, FR4 | Artificial sequence | tggggccagggcaccaccctgaccgtgtcctccg | 524 |
| cdrCAN46G13a Codon Optimized | K, variable region | Artificial sequence | gacattcagatgactcagtctccctcctccctgtctgcttccgt gggggaccgcgtcactattacctgttccgcttcctcctccgtc agctcctcttacctgcactggtatcagcagaagccaggaaaa gcccccaagctgctgatctaccggacctccacactggcttct ggcgtgcccagtagattctctggcagtgggtcaggaacaga cttcacttttaccatcagttcactgcagcctgaggatattgcca cttactattgccagcagtggagcggctacccatataccttgg ccaggggacaaaagtggagatcaaga | 525 |
| cdrCAN46G13a Codon Optimized | K, CDR1 | Artificial sequence | tcctccgtcagctcctcttac | 526 |
| cdrCAN46G13a Codon Optimized | K, CDR2 | Artificial sequence | cggacctcc | 527 |
| cdrCAN46G13a Codon Optimized | K, CDR3 | Artificial sequence | cagcagtggagcggctacccatatacc | 528 |
| cdrCAN46G13a Codon Optimized | K, FR1 | Artificial sequence | gacattcagatgactcagtctccctcctccctgtctgcttccgt gggggaccgcgtcactattacctgttccgcttcc | 529 |
| cdrCAN46G13a Codon Optimized | K, FR2 | Artificial sequence | ctgcactggtatcagcagaagccaggaaaagcccccaagc tgctgatctac | 530 |

TABLE 1-continued

Sequence ID NOs

| Name | Chain, Region | Origin | Sequence | Seq ID No: |
|---|---|---|---|---|
| cdrCAN46G13a Codon Optimized | K, FR3 | Artificial sequence | acactggcttctggcgtgcccagtagattctctggcagtggg tcaggaacagacttcacttttaccatcagttcactgcagcctg aggatattgccacttactattgc | 531 |
| cdrCAN46G13a Codon Optimized | K, FR4 | Artificial sequence | tttggccaggggacaaaagtggagatcaaga | 532 |
| cdrCAN46G13a Codon Optimized | H, variable region | Artificial sequence | caggtgcagctgcaggaatctgggcctggactggtcaaacc ctctcagactctgtctctgacttgtactgtgtccggggggagc atcagctccgatagcgcctggaactggatcagacagcccc tgggaagggactggagtggatcgggtacattagttattcagg aagcacctcctacaatccctccctgaaatctagggtcactatg tcagtggacaccagcaagaaccagttctccctgaaagtcaat tctgtgactgccgctgataccgccgtgtactattgcgctcgga gaagtagggtgtcattctactttgactattggggccaggggga ccctggtcacagtgtctagtg | 533 |
| cdrCAN46G13a Codon Optimized | H, CDR1 | Artificial sequence | gggggagcatcagctccgatagcgcc | 534 |
| cdrCAN46G13a Codon Optimized | H, CDR2 | Artificial sequence | attagttattcaggaagcacc | 535 |
| cdrCAN46G13a Codon Optimized | H, CDR3 | Artificial sequence | gctcggagaagtagggtgtcattctactttgactat | 536 |
| cdrCAN46G13a Codon Optimized | H, FR1 | Artificial sequence | caggtgcagctgcaggaatctgggcctggactggtcaaacc ctctcagactctgtctctgacttgtactgtgtcc | 537 |
| cdrCAN46G13a Codon Optimized | H, FR2 | Artificial sequence | tggaactggatcagacagcccctgggaagggactggagt ggatcgggtac | 538 |
| cdrCAN46G13a Codon Optimized | H, FR3 | Artificial sequence | tcctacaatccctccctgaaatctagggtcactatgtcagtgg acaccagcaagaaccagttctccctgaaagtcaattctgtga ctgccgctgataccgccgtgtactattgc | 539 |
| cdrCAN46G13a Codon Optimized | H, FR4 | Artificial sequence | tggggccaggggaccctggtcacagtgtctagtg | 540 |
| huCAN46G13a Codon Optimized | K, variable region | Artificial sequence | gaaaatgtgctgactcagtccccttccagcctgtccgcaagc gtcggcgacagggtgactatgacctgcagcgcctctagttc agtgtccagctcttacctgcactggtatcagcagaagcccgg gaaatctcctaagccactgatccataggacatctactctggct agtggtgtgccttcacggttctctggtagtggctcaggaacat cctacagcctgactatcagttcactgcagccagaggacattg caacctactattgccagcagtggtctggataccctataccttt ggcggagggacaaaagtggagatcaagc | 541 |
| huCAN46G13a Codon Optimized | K, CDR1 | Artificial sequence | agttcagtgtccagctcttac | 542 |
| huCAN46G13a Codon Optimized | K, CDR2 | Artificial sequence | aggacatct | 543 |
| huCAN46G13a Codon Optimized | K, CDR3 | Artificial sequence | cagcagtggtctggataccctatacc | 544 |
| huCAN46G13a Codon Optimized | K, FR1 | Artificial sequence | gaaaatgtgctgactcagtccccttccagcctgtccgcaagc gtcggcgacagggtgactatgacctgcagcgcctct | 545 |

TABLE 1-continued

Sequence ID NOs

| Name | Chain, Region | Origin | Sequence | Seq ID No: |
|---|---|---|---|---|
| huCAN46G13a Codon Optimized | K, FR2 | Artificial sequence | ctgcactggtatcagcagaagcccgggaaatctcctaagcc actgatccat | 546 |
| huCAN46G13a Codon Optimized | K, FR3 | Artificial sequence | actctggctagtggtgtgccttcacggttctctggtagtggctc aggaacatcctacagcctgactatcagttcactgcagccaga ggacattgcaacctactattgc | 547 |
| huCAN46G13a Codon Optimized | K, FR4 | Artificial sequence | tttggcggagggacaaaagtggagatcaagc | 548 |
| huCAN46G13a Codon Optimized | H, variable region | Artificial sequence | caggtccagctgcaggaatccgggcctggtctggtgaagc catctcagaccctgagtctgacttgtaccgtgacagggtaca gcatcacatctgacagtgcctggaactggattagacagttcc ctggtaacaatctggagtggatgggctacatttcatattccgg aagcacctcttataatcccagtctgaagtcaagaatctccatta cccgcgacacatcaaaaaaccagttttccctgaaggtcaata gcgtgacagctgcagatactgctgtctactattgcgcaaggc ggagccgcgtgtctttctactttgactattggggccagggaa ctctggtcaccgtgtcatccg | 549 |
| huCAN46G13a Codon Optimized | H, CDR1 | Artificial sequence | gggtacagcatcacatctgacagtgcc | 550 |
| huCAN46G13a Codon Optimized | H, CDR2 | Artificial sequence | atttcatattccggaagcacc | 551 |
| huCAN46G13a Codon Optimized | H, CDR3 | Artificial sequence | gcaaggcggagccgcgtgtctttctactttgactat | 552 |
| huCAN46G13a Codon Optimized | H, FR1 | Artificial sequence | caggtccagctgcaggaatccgggcctggtctggtgaagc catctcagaccctgagtctgacttgtaccgtgaca | 553 |
| huCAN46G13a Codon Optimized | H, FR2 | Artificial sequence | tggaactggattagacagttccctggtaacaatctggagtgg atgggctac | 554 |
| huCAN46G13a Codon Optimized | H, FR3 | Artificial sequence | tcttataatcccagtctgaagtcaagaatctccattacccgcg acacatcaaaaaaccagttttccctgaaggtcaatagcgtga cagctgcagatactgctgtctactattgc | 555 |
| huCAN46G13a Codon Optimized | H, FR4 | Artificial sequence | tggggccagggaactctggtcaccgtgtcatccg | 556 |
| rehuCAN46G13a Codon Optimized | K, variable region | Artificial sequence | gagaacgtcctgacacagtccccttccagcatgtccgcaag cgtcggcgacagggtgactatgacctgctccgcctctagttc agtgtccagctcttacctgcactggtatcagcagaagccagg caaagctcccaagcctctgatccataggacatctactctggc aagtggagtgccctcacggttctctggtagtggctcaggaac atcctacagcctgactatcagttcagtgcagcctgaggacatt gctacctactattgccagcagtggagcggctacccatatacc tttggcggagggacaaaagtggagatcaagc | 557 |
| rehuCAN46G13a Codon Optimized | K, CDR1 | Artificial sequence | agttcagtgtccagctcttac | 558 |
| rehuCAN46G13a Codon Optimized | K, CDR2 | Artificial sequence | aggacatct | 559 |
| rehuCAN46G13a Codon Optimized | K, CDR3 | Artificial sequence | cagcagtggagcggctacccatatacc | 560 |

TABLE 1-continued

Sequence ID NOs

| Name | Chain, Region | Origin | Sequence | Seq ID No: |
|---|---|---|---|---|
| rehuCAN46G13a Codon Optimized | K, FR1 | Artificial sequence | gagaacgtcctgacacagtccccttccagcatgtccgcaag cgtcggcgacagggtgactatgacctgctccgcctct | 561 |
| rehuCAN46G13a Codon Optimized | K, FR2 | Artificial sequence | ctgcactggtatcagcagaagccaggcaaagctcccaagc ctctgatccat | 562 |
| rehuCAN46G13a Codon Optimized | K, FR3 | Artificial sequence | actctggcaagtggagtgccctcacggttctctggtagtggc tcaggaacatcctacagcctgactatcagttcagtgcagcct gaggacattgctacctactattgc | 563 |
| rehuCAN46G13a Codon Optimized | K, FR4 | Artificial sequence | tttggcggagggacaaaagtggagatcaagc | 564 |
| rehuCAN46G13a Codon Optimized | H, variable region | Artificial sequence | caggtccagctgcaggaaagcgggcccggtctggtgaagc cttctcagaccctgagtctgacttgtaccgtgacaggatactc tatcacatctgacagtgcctggaactggattagacagccacc cggcaatggactggagtggatggggtacatttcatattccgg tagcacatcttataatccaagtctgaagtcaagaatctccatta ctcgcgacacctcaaaaaaccagttctccctgaagctgaata gcgtgactgctgcagatactgctacctactattgcgcaaggc ggagccgcgtgtctttctactttgactattgggggcagggtac actggtcactgtgtcatccg | 565 |
| rehuCAN46G13a Codon Optimized | H, CDR1 | Artificial sequence | ggatactctatcacatctgacagtgcc | 566 |
| rehuCAN46G13a Codon Optimized | H, CDR2 | Artificial sequence | atttcatattccggtagcaca | 567 |
| rehuCAN46G13a Codon Optimized | H, CDR3 | Artificial sequence | gcaaggcggagccgcgtgtctttctactttgactat | 568 |
| rehuCAN46G13a Codon Optimized | H, FR1 | Artificial sequence | caggtccagctgcaggaaagcgggcccggtctggtgaagc cttctcagaccctgagtctgacttgtaccgtgaca | 569 |
| rehuCAN46G13a Codon Optimized | H, FR2 | Artificial sequence | tggaactggattagacagccacccggcaatggactggagtg gatggggtac | 711 |
| rehuCAN46G13a Codon Optimized | H, FR3 | Artificial sequence | tcttataatccaagtctgaagtcaagaatctccattactcgcga cacctcaaaaaaccagttctccctgaagctgaatagcgtgac tgctgcagatactgctacctactattgc | 712 |
| rehuCAN46G13a Codon Optimized | H, FR4 | Artificial sequence | tgggggcagggtacactggtcactgtgtcatccg | 713 |
| cdrCAN46G19 Codon Optimized | K, variable region | Artificial sequence | gatattcagatgacccagtcccctcctccctgtcagcttccg tcggcgatagagtcaccattacctgttccgctagttcctccgt cacatacatgcactggtatcagcagaagccagggaaagcc cccaagctgctgatctacgagactagtaaactggcttcagga gtgccaagcaggttctcaggcagcgggtccggaactgacta tacctttacaatcagctccctgcagcctgaagatattgccacc tactattgcttccagggcagcgggtacccattcacatttggac agggcactaaagtggagatcaagc | 714 |
| cdrCAN46G19 Codon Optimized | K, CDR1 | Artificial sequence | tcctccgtcacatac | 715 |
| cdrCAN46G19 Codon Optimized | K, CDR2 | Artificial sequence | gagactagt | 716 |

TABLE 1-continued

Sequence ID NOs

| Name | Chain, Region | Origin | Sequence | Seq ID No: |
|---|---|---|---|---|
| cdrCAN46G19 Codon Optimized | K, CDR3 | Artificial sequence | ttccagggcagcgggtacccattcaca | 717 |
| cdrCAN46G19 Codon Optimized | K, FR1 | Artificial sequence | gatattcagatgacccagtcccctcctccctgtcagcttccg tcggcgatagagtcaccattacctgttccgctagt | 718 |
| cdrCAN46G19 Codon Optimized | K, FR2 | Artificial sequence | atgcactggtatcagcagaagccagggaaagcccccaagc tgctgatctac | 719 |
| cdrCAN46G19 Codon Optimized | K, FR3 | Artificial sequence | aaactggcttcaggagtgccaagcaggttctcaggcagcgg gtccggaactgactataccttacaatcagctccctgcagcct gaagatattgccacctactattgc | 720 |
| cdrCAN46G19 Codon Optimized | K, FR4 | Artificial sequence | tttggacagggcactaaagtggagatcaagc | 570 |
| cdrCAN46G19 Codon Optimized | H, variable region | Artificial sequence | caggtgcagctggtccagtccggggccgaggtcaaaaagc ctggggagtccgtcaaagtgtcttgtaaagcatctgggtatac atttaccgggtactatatccactgggtgagacaggcacctgg acagggactggagtggatggggaggattttcccatacaacg gagccgccagctataaccagaacttcaagggccgcgtgac aatcactgcagacaaaagtacctcaacagcctacatggagc tgagctccctgcgaagcgaagacacagccgtctactattgc gctcggtggctgagagtgtacttcgattattggggccagggg accacagtcaccgtgtctagtg | 571 |
| cdrCAN46G19 Codon Optimized | H, CDR1 | Artificial sequence | gggtatacatttaccgggtactat | 572 |
| cdrCAN46G19 Codon Optimized | H, CDR2 | Artificial sequence | attttcccatacaacggagccgcc | 573 |
| cdrCAN46G19 Codon Optimized | H, CDR3 | Artificial sequence | gctcggtggctgagagtgtacttcgattat | 574 |
| cdrCAN46G19 Codon Optimized | H, FR1 | Artificial sequence | caggtgcagctggtccagtccggggccgaggtcaaaaagc ctggggagtccgtcaaagtgtcttgtaaagcatct | 575 |
| cdrCAN46G19 Codon Optimized | H, FR2 | Artificial sequence | atccactgggtgagacaggcacctggacagggactggagt ggatggggagg | 576 |
| cdrCAN46G19 Codon Optimized | H, FR3 | Artificial sequence | agctataaccagaacttcaagggccgcgtgacaatcactgc agacaaaagtacctcaacagcctacatggagctgagctccc tgcgaagcgaagacacagccgtctactattgc | 577 |
| cdrCAN46G19 Codon Optimized | H, FR4 | Artificial sequence | tggggccaggggaccacagtcaccgtgtctagtg | 578 |
| huCAN46G19 Codon Optimized | K, variable region | Artificial sequence | gagaacgtcctgacacagtcaccttccagcctgagcgcctct gtcggtgacagagtgaccatcacatgctctgcttctagttcag tgcatacatgcactggtatcagcagaagccaggcaaagca cccaagctgtggatctacgagacttctaagctggcaagtggt gtgccaggacgcttcagtggatcaggatccgggaactcttat actttaccatctccagcctgcagccagaagatattgctacct actattgcttccagggttccggctaccccttcacatttggaca ggggactaaagtggagatcaaga | 579 |
| huCAN46G19 Codon Optimized | K, CDR1 | Artificial sequence | agttcagtgacatac | 580 |

TABLE 1-continued

Sequence ID NOs

| Name | Chain, Region | Origin | Sequence | Seq ID No: |
|---|---|---|---|---|
| huCAN46G19 Codon Optimized | K, CDR2 | Artificial sequence | gagacttct | 581 |
| huCAN46G19 Codon Optimized | K, CDR3 | Artificial sequence | ttccagggttccggctacccccttcaca | 582 |
| huCAN46G19 Codon Optimized | K, FR1 | Artificial sequence | gagaacgtcctgacacagtcaccttccagcctgagcgcctct gtcggtgacagagtgaccatcacatgctctgcttct | 583 |
| huCAN46G19 Codon Optimized | K, FR2 | Artificial sequence | atgcactggtatcagcagaagccaggcaaagcacccaagc tgtggatctac | 584 |
| huCAN46G19 Codon Optimized | K, FR3 | Artificial sequence | aagctggcaagtggtgtgccaggacgcttcagtggatcagg atccgggaactctttatacttttaccatctccagcctgcagcca gaagatattgctacctactattgc | 585 |
| huCAN46G19 Codon Optimized | K, FR4 | Artificial sequence | tttggacaggggactaaagtggagatcaaga | 586 |
| huCAN46G19 Codon Optimized | H, variable region | Artificial sequence | gaagtccagctggtgcagagcggagcagaggtgaagaaa cctggggaaagcgtcaaagtgtcttgtaaggctagcggata ctctttcaccgggtactatatccactgggtcaagcaggcacct ggtcagggactggagtgggtgggtagaattttcccctacaat ggcgctgcaagctataaccagaattttaagggcaaagcaac cctgacagtggacaagagctctaccacagcctacatggagc tgagttcactgcgctctgaagacaccgctgtctatttctgcgc aaggtggctgcgggtgtactttgattattggggacaggggac taccgtcactgtgtccagcg | 587 |
| huCAN46G19 Codon Optimized | H, CDR1 | Artificial sequence | ggatactctttcaccgggtactat | 588 |
| huCAN46G19 Codon Optimized | H, CDR2 | Artificial sequence | attttcccctacaatggcgctgca | 589 |
| huCAN46G19 Codon Optimized | H, CDR3 | Artificial sequence | gcaaggtggctgcgggtgtactttgattat | 590 |
| huCAN46G19 Codon Optimized | H, FR1 | Artificial sequence | gaagtccagctggtgcagagcggagcagaggtgaagaaa cctggggaaagcgtcaaagtgtcttgtaaggctagc | 591 |
| huCAN46G19 Codon Optimized | H, FR2 | Artificial sequence | atccactgggtcaagcaggcacctggtcagggactggagt gggtgggtaga | 592 |
| huCAN46G19 Codon Optimized | H, FR3 | Artificial sequence | agctataaccagaattttaagggcaaagcaaccctgacagtg gacaagagctctaccacagcctacatggagctgagttcact gcgctctgaagacaccgctgtctatttctgc | 593 |
| huCAN46G19 Codon Optimized | H, FR4 | Artificial sequence | tggggacaggggactaccgtcactgtgtccagcg | 594 |
| rehuCAN46G19 Codon Optimized | K, variable region | Artificial sequence | gagaacgtcctgacacagagtccttccagcatgtcagcctcc gtcggagacagagtgacaatgacttgctctgcttctagttcag tgacatacatgcactggtatcagcagaagccagggaaatcc cccaagctgtggatctacagagacttctaagctggcaagtggt gtgccctcacgcttcagcggctctggaagtgggaacgacta tagcctgacaatttccagcatgcagcagaagatgtggcca cttactattgctttcagggttctggctacccccttcacctttggac aggggacaaaaactggagatcaaga | 595 |

TABLE 1-continued

Sequence ID NOs

| Name | Chain, Region | Origin | Sequence | Seq ID No: |
|---|---|---|---|---|
| rehuCAN46G19 Codon Optimized | K, CDR1 | Artificial sequence | agttcagtgacatac | 596 |
| rehuCAN46G19 Codon Optimized | K, CDR2 | Artificial sequence | gagacttct | 597 |
| rehuCAN46G19 Codon Optimized | K, CDR3 | Artificial sequence | tttcagggttctggctacccttcacc | 598 |
| rehuCAN46G19 Codon Optimized | K, FR1 | Artificial sequence | gagaacgtcctgacacagagtccttccagcatgtcagcctcc gtcggagacagagtgacaatgacttgctctgcttct | 599 |
| rehuCAN46G19 Codon Optimized | K, FR2 | Artificial sequence | atgcactggtatcagcagaagccagggaaatcccccaagct gtggatctac | 600 |
| rehuCAN46G19 Codon Optimized | K, FR3 | Artificial sequence | aagctggcaagtggtgtgccctcacgcttcagcggctctgg aagtgggaacgactatagcctgacaatttccagcatgcagc cagaagatgtggccacttactattgc | 601 |
| rehuCAN46G19 Codon Optimized | K, FR4 | Artificial sequence | tttggacaggggacaaaactggagatcaaga | 602 |
| rehuCAN46G19 Codon Optimized | H, variable region | Artificial sequence | gaagtccagctggtgcagtccggagcagaggtggtcaaac ctggggaatctgtgaaaatcagttgtaaggcctcaggatact ccttcactgggtactatattcactgggtcaagcagacccctgg tcagagcctggagtgggtgggcagaattttcccctacaatgg agctgcatcttataaccagaattttaagggcaaagcaactctg accgtggacaagagcaccacaactgcctacatggagctga gctctctgcgcagcgaagactctgctgtctatttctgcgcaag gtggctgcgggtgtactttgattattggggtcagggcaccac actgacagtcagttcag | 603 |
| rehuCAN46G19 Codon Optimized | H, CDR1 | Artificial sequence | ggatactccttcactgggtactat | 604 |
| rehuCAN46G19 Codon Optimized | H, CDR2 | Artificial sequence | attttcccctacaatggagctgca | 605 |
| rehuCAN46G19 Codon Optimized | H, CDR3 | Artificial sequence | gcaaggtggctgcgggtgtactttgattat | 606 |
| rehuCAN46G19 Codon Optimized | H, FR1 | Artificial sequence | gaagtccagctggtgcagtccggagcagaggtggtcaaac ctggggaatctgtgaaaatcagttgtaaggcctca | 607 |
| rehuCAN46G19 Codon Optimized | H, FR2 | Artificial sequence | attcactgggtcaagcagacccctggtcagagcctggagtg ggtgggcaga | 608 |
| rehuCAN46G19 Codon Optimized | H, FR3 | Artificial sequence | tcttataaccagaattttaagggcaaagcaactctgaccgtgg acaagagcaccacaactgcctacatggagctgagctctctg cgcagcgaagactctgctgtctatttctgc | 609 |
| rehuCAN46G19 Codon Optimized | H, FR4 | Artificial sequence | tggggtcagggcaccacactgacagtcagttcag | 610 |
| cdrCAN46G24 Codon Optimized | K, variable region | Artificial sequence | gatattcagatgacccagtcccctcctccctgtcagcttccg tcggcgatagagtcaccattacctgttccgctagttcctccgt cacatacatgcactggtatcagcagaagccagggaaagcc cccaagctgctgatctacgagactagtaaactggcttcagga gtgccaagcaggttctcaggcagcgggtccggaactgacta taccttacaatcagctccctgcagcctgaagatattgccacc | 611 |

TABLE 1-continued

Sequence ID NOs

| Name | Chain, Region | Origin | Sequence | Seq ID No: |
|---|---|---|---|---|
| | | | tactattgcttccagggcagcgggtacccattcacatttggac agggcactaaagtggagatcaagc | |
| cdrCAN46G24 Codon Optimized | K, CDR1 | Artificial sequence | tcctccgtcacatac | 612 |
| cdrCAN46G24 Codon Optimized | K, CDR2 | Artificial sequence | gagactagt | 613 |
| cdrCAN46G24 Codon Optimized | K, CDR3 | Artificial sequence | ttccagggcagcgggtacccattcaca | 614 |
| cdrCAN46G24 Codon Optimized | K, FR1 | Artificial sequence | gatattcagatgacccagtcccctcctccctgtcagcttccg tcggcgatagagtcaccattacctgttccgctagt | 615 |
| cdrCAN46G24 Codon Optimized | K, FR2 | Artificial sequence | atgcactggtatcagcagaagccagggaaagcccccaagc tgctgatctac | 616 |
| cdrCAN46G24 Codon Optimized | K, FR3 | Artificial sequence | aaactggcttcaggagtgccaagcaggttctcaggcagcgg gtccggaactgactataccttacaatcagctccctgcagcct gaagatattgccacctactattgc | 617 |
| cdrCAN46G24 Codon Optimized | K, FR4 | Artificial sequence | tttggacagggcactaaagtggagatcaagc | 618 |
| cdrCAN46G24 Codon Optimized | H, variable region | Artificial sequence | caggtgcagctggtccagtccggggccgaggtcaaaaagc ctggggagtccgtcaaagtgtcttgtaaagcatctgggtatac atttaccgggtactatatccactgggtgagacaggcacctgg acagggactggagtggatggggaggattttcccatacaacg gagccgccagctataaccagaacttcaagggccgcgtgac aatcactgcagacaaaagtacctcaacagcctacatggagc tgagctccctgcgaagcgaagacacagccgtctactattgc gctcggtggctgagagtgtacttcgattattggggccagggg accacagtcaccgtgtctagtg | 619 |
| cdrCAN46G24 Codon Optimized | H, CDR1 | Artificial sequence | gggtatacatttaccgggtactat | 620 |
| cdrCAN46G24 Codon Optimized | H, CDR2 | Artificial sequence | attttcccatacaacggagccgcc | 621 |
| cdrCAN46G24 Codon Optimized | H, CDR3 | Artificial sequence | gctcggtggctgagagtgtacttcgattat | 622 |
| cdrCAN46G24 Codon Optimized | H, FR1 | Artificial sequence | caggtgcagctggtccagtccggggccgaggtcaaaaagc ctggggagtccgtcaaagtgtcttgtaaagcatct | 623 |
| cdrCAN46G24 Codon Optimized | H, FR2 | Artificial sequence | atccactgggtgagacaggcacctggacagggactggagt ggatggggagg | 624 |
| cdrCAN46G24 Codon Optimized | H, FR3 | Artificial sequence | agctataaccagaacttcaagggccgcgtgacaatcactgc agacaaaagtacctcaacagcctacatggagctgagctccc tgcgaagcgaagacacagccgtctactattgc | 625 |
| cdrCAN46G24 Codon Optimized | H, FR4 | Artificial sequence | tggggccaggggaccacagtcaccgtgtctagtg | 626 |
| huCAN46G24 Codon Optimized | K, variable region | Artificial sequence | gagatcgtcctgactcagtccccttccagcctgtctaccagtg tcggtgacagagtgacaatctcatgctccgcttctagttcagt gacatacatgcactggtatcagcagaagccaggcaaagcc cccaagctgtggatctacgagacttccaagctggctagcggt gtgccaggacgcttcagcggatctggaagtgggaactcttat | 627 |

| Name | Chain, Region | Origin | Sequence | Seq ID No: |
|---|---|---|---|---|
| | | | accttcaccatctccagcctgcagccagaagatattgctacct actattgcttccagggttccggctaccccttcacctttggaca ggggacaaaagtggagatcaaga | |
| huCAN46G24 Codon Optimized | K, CDR1 | Artificial sequence | agttcagtgacatac | 628 |
| huCAN46G24 Codon Optimized | K, CDR2 | Artificial sequence | gagacttcc | 629 |
| huCAN46G24 Codon Optimized | K, CDR3 | Artificial sequence | ttccagggttccggctaccccttcacc | 630 |
| huCAN46G24 Codon Optimized | K, FR1 | Artificial sequence | gagatcgtcctgactcagtccccttccagcctgtctaccagtg tcggtgacagagtgacaatctcatgctccgcttct | 631 |
| huCAN46G24 Codon Optimized | K, FR2 | Artificial sequence | atgcactggtatcagcagaagccaggcaaagcccccaagc tgtggatctac | 632 |
| huCAN46G24 Codon Optimized | K, FR3 | Artificial sequence | aagctggctagcggtgtgccaggacgcttcagcggatctgg aagtgggaactcttataccttcaccatctccagcctgcagcca gaagatattgctacctactattgc | 633 |
| huCAN46G24 Codon Optimized | K, FR4 | Artificial sequence | tttggacaggggacaaaagtggagatcaaga | 634 |
| huCAN46G24 Codon Optimized | H, variable region | Artificial sequence | gaagtccagctggtgcagagcggagcagaggtgaagaaa cctggggaatcagtcaaagtgtcctgtaaggcatcaggatac tccttcaccgggtactatatccactgggtcaagcaggcacct ggtcagggactggagtgggtgggtagaattttcccctacaat ggcgctgcaagctataaccagaattttaagggcaaagcaac tctgaccgtggacaagagctctagtacagcctacatggagct gtcatccctgcgctctgaagacactgctgtctatttctgcgca aggtggctgcgggtgtactttgattattggggacagggggacc acagtcacagtgagctctg | 635 |
| huCAN46G24 Codon Optimized | H, CDR1 | Artificial sequence | ggatactccttcaccgggtactat | 636 |
| huCAN46G24 Codon Optimized | H, CDR2 | Artificial sequence | attttcccctacaatggcgctgca | 637 |
| huCAN46G24 Codon Optimized | H, CDR3 | Artificial sequence | gcaaggtggctgcgggtgtactttgattat | 638 |
| huCAN46G24 Codon Optimized | H, FR1 | Artificial sequence | gaagtccagctggtgcagagcggagcagaggtgaagaaa cctggggaatcagtcaaagtgtcctgtaaggcatca | 639 |
| huCAN46G24 Codon Optimized | H, FR2 | Artificial sequence | atccactgggtcaagcaggcacctggtcagggactggagt gggtgggtaga | 640 |
| huCAN46G24 Codon Optimized | H, FR3 | Artificial sequence | agctataaccagaattttaagggcaaagcaactctgaccgtg gacaagagctctagtacagcctacatggagctgtcatccctg cgctctgaagacactgctgtctatttctgc | 641 |
| huCAN46G24 Codon Optimized | H, FR4 | Artificial sequence | tggggacaggggaccacagtcacagtgagctctg | 642 |
| rehuCAN46G24 Codon Optimized | K, variable region | Artificial sequence | gagatcgtgctgactcagtcaccctccagcatgtcaacctcc gtcggagacagagtgacaatgagctgctctgcctctagttca gtgacctacatgcactggtatcagcagaagccagggaaaa gccccaagctgtggatctacgagacaagcaagctggcttct | 643 |

TABLE 1-continued

Sequence ID NOs

| Name | Chain, Region | Origin | Sequence | Seq ID No: |
|---|---|---|---|---|
| | | | ggtgtgcccagtcgcttcagtggctcaggatccgggaacga ctattccctgaccatttccagcatgcagccagaagatgtggc aacatactattgctttcagggtagcggctaccccttcaccttg gacaggggacaaaactggagatcaaga | |
| rehuCAN46G24 Codon Optimized | K, CDR1 | Artificial sequence | agttcagtgacctac | 644 |
| rehuCAN46G24 Codon Optimized | K, CDR2 | Artificial sequence | gagacaagc | 645 |
| rehuCAN46G24 Codon Optimized | K, CDR3 | Artificial sequence | tttcagggtagcggctaccccttcacc | 646 |
| rehuCAN46G24 Codon Optimized | K, FR1 | Artificial sequence | gagatcgtgctgactcagtcaccctccagcatgtcaacctcc gtcggagacagagtgacaatgagctgctctgcctct | 647 |
| rehuCAN46G24 Codon Optimized | K, FR2 | Artificial sequence | atgcactggtatcagcagaagccagggaaaagccccaagc tgtggatctac | 648 |
| rehuCAN46G24 Codon Optimized | K, FR3 | Artificial sequence | aagctggcttctggtgtgcccagtcgcttcagtggctcagga tccgggaacgactattccctgaccatttccagcatgcagcca gaagatgtggcaacatactattgc | 649 |
| rehuCAN46G24 Codon Optimized | K, FR4 | Artificial sequence | tttggacaggggacaaaactggagatcaaga | 650 |
| rehuCAN46G24 Codon Optimized | H, variable region | Artificial sequence | gaagtccagctggtgcagtccggagcagaggtggtcaaac ctggggaaagcgtgaaaatctcttgtaaggctagtggatact cattcacagggtactatattcactgggtcaagcagactccag gccagtctctggagtgggtgggcagaattttccccctacaatg gagctgcatcctataaccagaattttaagggcaaagcaaccc tgacagtggacaagagcacttctaccgcctacatggagctg agctctctgcgctccgaagacagcgctgtctatttctgcgcaa ggtggctgcgggtgtactttgattattggggtcagggcacca cactgacagtcagttcag | 651 |
| rehuCAN46G24 Codon Optimized | H, CDR1 | Artificial sequence | ggatactcattcacagggtactat | 652 |
| rehuCAN46G24 Codon Optimized | H, CDR2 | Artificial sequence | attttccccctacaatggagctgca | 653 |
| rehuCAN46G24 Codon Optimized | H, CDR3 | Artificial sequence | gcaaggtggctgcgggtgtactttgattat | 654 |
| rehuCAN46G24 Codon Optimized | H, FR1 | Artificial sequence | gaagtccagctggtgcagtccggagcagaggtggtcaaac ctggggaaagcgtgaaaatctcttgtaaggctagt | 655 |
| rehuCAN46G24 Codon Optimized | H, FR2 | Artificial sequence | attcactgggtcaagcagactccaggccagtctctggagtg ggtgggcaga | 656 |
| rehuCAN46G24 Codon Optimized | H, FR3 | Artificial sequence | tcctataaccagaattttaagggcaaagcaaccctgacagtg gacaagagcacttctaccgcctacatggagctgagctctctg cgctccgaagacagcgctgtctatttctgc | 657 |
| rehuCAN46G24 Codon Optimized | H, FR4 | Artificial sequence | tggggtcagggcaccacactgacagtcagttcag | 658 |
| cdrCAN46G4 Codon Optimized | K, variable region | Artificial sequence | gaaattgtcctgacccagtccctgctaccctgtccctgtccc ccggagaaagagcaaccctgtcctgttcagcttcctcatctgt gtcttacatgcactggtatcagcagaagccagggcaggcac | 659 |

TABLE 1-continued

Sequence ID NOs

| Name | Chain, Region | Origin | Sequence | Seq ID No: |
|---|---|---|---|---|
| | | | ccaggctgctgatctacgagactagtaaactggcattcggaa ttcccgcacgcttttcaggcagcgggtccggaaccgacttca ccctgacaatcagctccctggagcctgaagatttcgccgtgt actattgctttcagggcagcgggtatccattcacatttggaca gggcactcggctggagatcaaga | |
| cdrCAN46G4 Codon Optimized | K, CDR1 | Artificial sequence | tcatctgtgtcttac | 660 |
| cdrCAN46G4 Codon Optimized | K, CDR2 | Artificial sequence | gagactagt | 661 |
| cdrCAN46G4 Codon Optimized | K, CDR3 | Artificial sequence | tttcagggcagcgggtatccattcaca | 662 |
| cdrCAN46G4 Codon Optimized | K, FR1 | Artificial sequence | gaaattgtcctgacccagtcccctgctaccctgtccctgtccc ccggagaaagagcaaccctgtcctgttcagcttcc | 663 |
| cdrCAN46G4 Codon Optimized | K, FR2 | Artificial sequence | atgcactggtatcagcagaagccagggcaggcacccaggc tgctgatctac | 664 |
| cdrCAN46G4 Codon Optimized | K, FR3 | Artificial sequence | aaactggcattcggaattcccgcacgcttttcaggcagcggg tccggaaccgacttcaccctgacaatcagctccctggagcct gaagatttcgccgtgtactattgc | 665 |
| cdrCAN46G4 Codon Optimized | K, FR4 | Artificial sequence | tttggacagggcactcggctggagatcaaga | 666 |
| cdrCAN46G4 Codon Optimized | H, variable region | Artificial sequence | caggtccagctggtccagtctggggctgaggtcaaaaaacc cggctcttccgtcaaagtctcctgcaaagcatctggctataca tttaccgggtactatatgcactgggagacaggcacctggg cagggactggagtggatcgggaggattttcccatacaacgg agccgccagctataaccagaacttcaaggacaaagccacta tcaccgctgatgaaagtacaaatactgcctacatggagctga gctccctgaggtctgaagacactgcagtctactattgcgccc ggtggctgagagtgtacttcgattattggggccaggggaca ctggtcaccgtgagcagtg | 667 |
| cdrCAN46G4 Codon Optimized | H, CDR1 | Artificial sequence | ggctatacatttaccgggtactat | 668 |
| cdrCAN46G4 Codon Optimized | H, CDR2 | Artificial sequence | attttcccatacaacggagccgcc | 669 |
| cdrCAN46G4 Codon Optimized | H, CDR3 | Artificial sequence | gcccggtggctgagagtgtacttcgattat | 670 |
| cdrCAN46G4 Codon Optimized | H, FR1 | Artificial sequence | Caggtccagctggtccagtctggggctgaggtcaaaaaac ccggctcttccgtcaaagtctcctgcaaagcatct | 671 |
| cdrCAN46G4 Codon Optimized | H, FR2 | Artificial sequence | atgcactgggtgagacaggcacctgggcagggactggagt ggatcgggagg | 672 |
| cdrCAN46G4 Codon Optimized | H, FR3 | Artificial sequence | agctataaccagaacttcaaggacaaagccactatcaccgct gatgaaagtacaaatactgcctacatggagctgagctccctg aggtctgaagacactgcagtctactattgc | 673 |
| cdrCAN46G4 Codon Optimized | H, FR4 | Artificial sequence | tggggccaggggacactggtcaccgtgagcagtg | 674 |
| huCAN46G4 Codon | K, variable sequence | Artificial | gagaaggtcctgacacagtcacccgctaccctgtccctgag ccctggcgagagagccactatgacctgctcagcttccagct | 675 |

TABLE 1-continued

Sequence ID NOs

| Name | Chain, Region | Origin | Sequence | Seq ID No: |
|---|---|---|---|---|
| Optimized | region | | ctgtgtcctacatgcactggtatcagcagaagccaggaacct ctcccaaactgtggatctacgaaaccagtaagctggctttcg gggtgccagcacgcttttctggcagtggatcagggaactcct atagcctgaccattagttcactggaaccagaagacttcgctgt gtactattgctttcagggtagcggctaccccttcacctttggac aggggacaagactggagatcaagc | |
| huCAN46G4 Codon Optimized | K, CDR1 | Artificial sequence | agctctgtgtcctac | 676 |
| huCAN46G4 Codon Optimized | K, CDR2 | Artificial sequence | gaaaccagt | 677 |
| huCAN46G4 Codon Optimized | K, CDR3 | Artificial sequence | tttcagggtagcggctaccccttcacc | 678 |
| huCAN46G4 Codon Optimized | K, FR1 | Artificial sequence | gagaaggtcctgacacagtcacccgctaccctgtccctgag ccctggcgagagagccactatgacctgctcagcttcc | 679 |
| huCAN46G4 Codon Optimized | K, FR2 | Artificial sequence | atgcactggtatcagcagaagccaggaacctctcccaaact gtggatctac | 680 |
| huCAN46G4 Codon Optimized | K, FR3 | Artificial sequence | aagctggctttcggggtgccagcacgcttttctggcagtgga tcagggaactcctatagcctgaccattagttcactggaacca gaagacttcgctgtgtactattgc | 681 |
| huCAN46G4 Codon Optimized | K, FR4 | Artificial sequence | tttggacaggggacaagactggagatcaagc | 682 |
| huCAN46G4 Codon Optimized | H, variable region | Artificial sequence | gaagtgcagctgctgcagtccggagctgaggtcaagaaac ccgggtcatccgtgaagattagctgtaaagcatctgattaca gtttaccggctactatatgcactgggtgaagcaggcacctg gtcagggactggagtggatcggtagaattttcccctacaatg gcgctgcatcctataaccagaattttaaggacaaagctaccct gacagtggataagagctctagtaccgcatatatggagctgca ttcactgcgctccgaagacacagccgtctactattgcactag gtggctgcgggtgtacttcgattattggggacaggggaccct ggtcacagtgtcatccg | 683 |
| huCAN46G4 Codon Optimized | H, CDR1 | Artificial sequence | gattacagttttaccggctactat | 684 |
| huCAN46G4 Codon Optimized | H, CDR2 | Artificial sequence | attttcccctacaatggcgctgca | 685 |
| huCAN46G4 Codon Optimized | H, CDR3 | Artificial sequence | actaggtggctgcgggtgtacttcgattat | 686 |
| huCAN46G4 Codon Optimized | H, FR1 | Artificial sequence | gaagtgcagctgctgcagtccggagctgaggtcaagaaac ccgggtcatccgtgaagattagctgtaaagcatct | 687 |
| huCAN46G4 Codon Optimized | H, FR2 | Artificial sequence | atgcactgggtgaagcaggcacctggtcagggactggagt ggatcggtaga | 688 |
| huCAN46G4 Codon Optimized | H, FR3 | Artificial sequence | tcctataaccagaattttaaggacaaagctaccctgacagtg gataagagctctagtaccgcatatatggagctgcattcactgc gctccgaagacacagccgtctactattgc | 689 |
| huCAN46G4 Codon Optimized | H, FR4 | Artificial sequence | tggggacaggggaccctggtcacagtgtcatccg | 690 |

TABLE 1-continued

Sequence ID NOs

| Name | Chain, Region | Origin | Sequence | Seq ID No: |
|---|---|---|---|---|
| rehuCAN46G4 Codon Optimized | K, variable region | Artificial sequence | gaaaaggtcctgactcagtcccccgctactctgtcagcatcc cctggcgagagagtcaccatgagctgctctgcctccagctct gtgtcttacatgcactggtatcagcagaagcctggtcagagt cccaaactgtggatctacgaaacttcaaagctggcattcggc gtgccagcccgctttagtggctcaggatccgggaccgacta ttccctgacaattagttcaatggagccagaagatttcgctacat actattgctttcagggtagcggctaccccttcacttttggacag gggaccagactggagatcaagc | 691 |
| rehuCAN46G4 Codon Optimized | K, CDR1 | Artificial sequence | agctctgtgtcttac | 692 |
| rehuCAN46G4 Codon Optimized | K, CDR2 | Artificial sequence | gaaacttca | 693 |
| rehuCAN46G4 Codon Optimized | K, CDR3 | Artificial sequence | tttcagggtagcggctaccccttcact | 694 |
| rehuCAN46G4 Codon Optimized | K, FR1 | Artificial sequence | gaaaaggtcctgactcagtcccccgctactctgtcagcatcc cctggcgagagagtcaccatgagctgctctgcctcc | 695 |
| rehuCAN46G4 Codon Optimized | K, FR2 | Artificial sequence | atgcactggtatcagcagaagcctggtcagagtcccaaact gtggatctac | 696 |
| rehuCAN46G4 Codon Optimized | K, FR3 | Artificial sequence | aagctggcattcggcgtgccagcccgctttagtggctcagg atccgggaccgactattccctgacaattagttcaatggagcc agaagatttcgctacatactattgc | 697 |
| rehuCAN46G4 Codon Optimized | K, FR4 | Artificial sequence | tttggacaggggaccagactggagatcaagc | 698 |
| rehuCAN46G4 Codon Optimized | H, variable region | Artificial sequence | gaagtgcagctgctgcagtccggtgcagaggtggtcaagc caggatcatccgtgaagattagctgtaaagctagcggttact cttttaccggctactatatgcactgggtgaagcaggcacctg gtcagggcctggagtggatcggaagaatttttcccctacaac ggggctgcatcttataaccagaattttaaggacaaagccaca ctgactgctgataagtccaccaatacagcatatatggagctg agctctctgcgcagtgaagactcagccgtctactattgcacc aggtggctgcgggtgtacttcgattattggggacaggggac cctggtcacagtgagttcag | 699 |
| rehuCAN46G4 Codon Optimized | H, CDR1 | Artificial sequence | ggttactcttttaccggctactat | 700 |
| rehuCAN46G4 Codon Optimized | H, CDR2 | Artificial sequence | attttcccctacaacggggctgca | 701 |
| rehuCAN46G4 Codon Optimized | H, CDR3 | Artificial sequence | accaggtggctgcgggtgtacttcgattat | 702 |
| rehuCAN46G4 Codon Optimized | H, FR1 | Artificial sequence | Gaagtgcagctgctgcagtccggtgcagaggtggtcaagc caggatcatccgtgaagattagctgtaaagctagc | 703 |
| rehuCAN46G4 Codon Optimized | H, FR2 | Artificial sequence | atgcactgggtgaagcaggcacctggtcagggcctggagt ggatcggaaga | 704 |
| rehuCAN46G4 Codon Optimized | H, FR3 | Artificial sequence | tcttataaccagaattttaaggacaaagccacactgactgctg ataagtccaccaatacagcatatatggagctgagctctctgc gcagtgaagactcagccgtctactattgc | 705 |

TABLE 1-continued

Sequence ID NOs

| Name | Chain, Region | Origin | Sequence | Seq ID No: |
|---|---|---|---|---|
| rehuCAN46G4 Codon Optimized | H, FR4 | Artificial sequence | tggggacaggggaccctggtcacagtgagttcag | 706 |
| Chimeric CAN46G13a | K, variable region | Artificial sequence | gagaatgtcctgactcagtcccctgctattatggccgcttccc tggggcagaaagtgactatgacctgttccgcttcctcttccgt cagctcctcttacctgcactggtatcagcagaagtctggcgct agtccaaaaccoctgatccatcgaaccagcacactggcttcc ggagtgccagcaagattctctggcagtgggtcaggaacaa gctactccctgactattagttcagtcgaggcagaagacgatg ccacctactattgccagcagtggtctgggtacccttatacctttggcgggggaacaaagctggagatcaaa | 707 |
| | K, variable region | Artificial sequence | ENVLTQSPAIMAASLGQKVTMTCSASS SVSSSYLHWYQQKSGASPKPLIHRTST LASGVPARFSGSGSGTSYSLTISSVEAE DDATYYCQQWSGYPYTFGGGTKLEIK | 708 |
| | H, variable region | Artificial sequence | gacgtgcagctgcaggaatctgggcctgggctggtgaaac ctagtcagtctctgtctctgacctgtaccgtgaccggatactc aatcacctccgattctgcctggaactggatcaggcagttccct ggcaacaatctggagtggatgggatacattagttattcaggc agcacatcctacaatccatccctgaagtctaggatcagtatta cccgcgacacaagtaaaaaccagttctttctgcagctgaattc agtgaccacagaagataccgctacatactattgcgcacgga gatcacgggtgagcttctactttgactattgggggcagggaa ctaccctgactgtcagctcc | 709 |
| | H, variable region | Artificial sequence | DVQLQESGPGLVKPSQSLSLTCTVTGY SITSDSAWNWIRQFPGNNLEWMGYISY SGSTSYNPSLKSRISITRDTSKNQFFLQL NSVTTEDTATYYCARRSRVSFYFDYW GQGTTLTVSS | 710 |

In Table 1, for amino acid sequences the CDRs are underlined and for nucleotide sequences the CDRs are IMGT numbering. H: heavy chain; K: kappa chain. The CDR regions can be identified using Kabat, IMGT, Honnegger, and Chothia and can vary accordingly.

As used herein, "homologous to" means "at least about 70%, at least about 75%, at least about 80%, at least about 85%, at least about 90%, at least about 95%, at least about 99%, about 70% to about 100%, about 80% to about 100%, about 90% to about 100%, about 95% to about 100%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous" to a defined sequence, amino acid or nucleotide. If a range if specified, e.g., about 80% to about 100%, then the term homologous as used in therein refers to that range particularly.

The antibodies or antigen-binding portions can comprise: (1) a heavy chain variable region comprising an amino acid sequence homologous to a heavy chain variable region amino acid sequence of the antibody produced by clone CAN33G1 (SEQ ID NO. 93), CAN46G4 (SEQ ID NO: 11), CAN46G13 (SEQ ID NO: 27), CAN46G13a (SEQ ID NO: 43), CAN46G19 (SEQ ID NO: 59), or CAN46G24 (SEQ ID NO: 75); and/or, (2) a light chain variable region comprising an amino acid sequence homologous to a light chain variable region amino acid sequence of the antibodies produced by clones CAN33G1 (SEQ ID NO. 85), CAN46G4 (SEQ ID NO: 3), CAN46G13 (SEQ ID NO: 19), CAN46G13a (SEQ ID NO: 35), CAN46G19 (SEQ ID NO: 51), or CAN46G24 (SEQ ID NO: 67). The antibodies or antigen-binding portions can comprise any combination of the amino acid sequences set forth for the heavy chain variable region (1) and light chain variable region (2) listed in the preceeding paragraph.

The antibodies or antigen-binding portions can specifically bind to an epitope that overlaps with, is antigenically similar to, or is homologous to, either at the amino acid or nucleotide sequence level, an epitope bound by an antibody produced by clones, including, but not limited to, humanized antibodies derived from these clones, CAN46G4, CAN46G13, CAN46G13a, CAN46G19, CAN46G24 or CAN33G1 and can compete for binding to toxin B with an antibody produced by clones CAN46G4, CAN46G13, CAN46G13a, CAN46G19, CAN46G24 or CAN33G1.

In one embodiment, the antibodies or antigen-binding portions of the present invention comprises: (1) a heavy chain variable region comprising one, two, three or more complementarity determining regions (CDRs) that are homologous to one, two, three or more CDRs of the antibodies produced by clones, CAN33G1 (SEQ ID NOs: 94, 95 and/or 96), CAN46G4 (SEQ ID NOs: 12, 13 and/or 14), CAN46G13 (SEQ ID NOs: 28, 29 and/or 30), CAN46G13a (SEQ ID NOs: 44, 45 and/or 46), CAN46G19 (SEQ ID NOs: 60, 61 and/or 62), or CAN46G24 (SEQ ID NOs: 76, 77 and/or 78); or, (2) a light chain variable region comprising one, two, three or more CDRs that are homologous to one, two, three or more CDRs of the antibodies produced by clones, CAN33G1 (SEQ ID NOs: 86, 87 and/or 88), CAN46G4 (SEQ ID NOs: 4, 5 and/or 6), CAN46G13 (SEQ ID NOs: 20, 21 and/or 22), CAN46G13a (SEQ ID NOs: 36, 37 and/or 38), CAN46G19 (SEQ ID NOs: 52, 53 and/or 54), or CAN46G24 (SEQ ID NOs: 68, 69 and/or 70). The antibodies or antigen-binding portions can comprise any combination of the amino acid sequences set forth for the heavy chain variable region (1) and light chain variable region (2) listed in the preceeding paragraph.

In another embodiment, the antibodies or antigen-binding portions can comprise: (i) a heavy chain variable region of the antibodies or antigen-binding portion comprising one, two, three or more complementarity determining regions (CDRs) that are homologous to one, two, three or more CDRs of the antibodies produced by clones cdrCAN46G13a (SEQ ID NOs:110, 111 and/or 112), huCAN46G13a (SEQ ID NOs: 126, 127 and/or 128), rehuCAN46G13a (SEQ ID NOs: 142, 143 and/or 144), cdrCAN46G19 (SEQ ID NOs: 158, 159 and/or 160), huCAN46G19 (SEQ ID NOs: 174, 175 and/or 176), rehuCAN46G19 (SEQ ID NOs: 190, 191 and/or 192), cdrCAN46G24 (SEQ ID NOs: 206, 207 and/or 208), huCAN46G24 (SEQ ID NOs: 222, 223 and/or 224) or rehuCAN46G24 (SEQ ID NOs: 238, 239 and/or 240); or (ii) a light chain variable region of the antibodies or antigen-binding portion comprising one, two, three or more CDRs that are homologous to one, two, three or more CDRs of a light chain variable region of the antibodies produced by the clones cdrCAN46G13a (SEQ ID NOs: 102, 103 and/or 104), huCAN46G13a (SEQ ID NOs: 118, 119 and/or 120), rehuCAN46G13a (SEQ ID NOs: 134, 135 and/or 136), cdrCAN46G19 (SEQ ID NOs: 150, 151 and/or 152), huCAN46G19 (SEQ ID NOs: 166, 167 and/or 168), rehuCAN46G19 (SEQ ID NOs: 182, 183 and/or 184), cdrCAN46G24 (SEQ ID NOs: 198, 199 and/or 200), huCAN46G24 (SEQ ID NOs: 214, 215 and/or 216) or rehuCAN46G24 (SEQ ID NOs: 230, 231 and/or 232). The antibodies or antigen-binding portions can comprise any combination of the amino acid sequences set forth for the CDRs for heavy chain variable region and light chain variable region listed in the preceeding paragraph.

In a third embodiment, the antibodies or antigen-binding portion comprise: (i) a heavy chain variable region of the antibodies or antigen-binding portion which comprises one, two, three or more complementarity determining regions (CDRs) that are homologous to one, two, three or more CDRs of the antibodies produced by clones, cdrCAN46G13a (SEQ ID NOs:110, 111 and/or 112), huCAN46G13a (SEQ ID NOs: 126, 127 and/or 128), rehuCAN46G13a (SEQ ID NOs: 142, 143 and/or 144), cdrCAN46G19 (SEQ ID NOs: 158, 159 and/or 160), huCAN46G19 (SEQ ID NOs: 174, 175 and/or 176), rehuCAN46G19 (SEQ ID NOs: 190, 191 and/or 192), cdrCAN46G24 (SEQ ID NOs: 206, 207 and/or 208), huCAN46G24 (SEQ ID NOs: 222, 223 and/or 224) or rehuCAN46G24 (SEQ ID NOs: 238, 239 and/or 240); or (ii) a light chain variable region of the antibodies or antigen-binding portion comprising one, two, three or more CDRs that are homologous to one, two, three or more CDRs of a light chain variable region of the antibody produced by clones, cdrCAN46G13a (SEQ ID NOs: 102, 103 and/or 104), huCAN46G13a (SEQ ID NOs: 118, 119 and/or 120), rehuCAN46G13a (SEQ ID NOs: 134, 135 and/or 136), cdrCAN46G19 (SEQ ID NOs: 150, 151 and/or 152), huCAN46G19 (SEQ ID NOs: 166, 167 and/or 168), rehuCAN46G19 (SEQ ID NOs: 182, 183 and/or 184), cdrCAN46G24 (SEQ ID NOs: 198, 199 and/or 200), huCAN46G24 (SEQ ID NOs: 214, 215 and/or 216) or rehuCAN46G24 (SEQ ID NOs: 230, 231 and/or 232).

In certain embodiments, the antibody or antigen-binding portion comprises a light chain variable region and heavy chain variable region homologous to a light chain variable region and heavy chain variable region of the antibodies produced by clones cdrCAN46G13a (SEQ ID NOs: 101 and 109, light chain variable region—heavy chain variable region, respectively), huCAN46G13a (SEQ ID NOs: 117 and 125, light chain variable region—heavy chain variable region, respectively), rehuCAN46G13a (SEQ ID NOs: 133 and 141, light chain variable region—heavy chain variable region, respectively), chimeric CAN46G13a (SEQ ID NOs: 708 and 710, light chain variable region—heavy chain variable region, respectively), cdrCAN46G19 (SEQ ID NOs: 149 and 157, light chain variable region—heavy chain variable region, respectively), huCAN46G19 (SEQ ID NOs: 165 and 173, light chain variable region—heavy chain variable region, light chain variable region—heavy chain variable region, respectively), rehuCAN46G19 (SEQ ID NOs: 181 and 189, respectively), cdrCAN46G24 (SEQ ID NOs: 197 and 205, respectively), huCAN46G24 (SEQ ID NOs: 213 and 221, light chain variable region—heavy chain variable region, respectively) or rehuCAN46G24 (SEQ ID NOs: 229 and 237, light chain variable region—heavy chain variable region, respectively).

The antibody or antigen-binding portion can comprise: (i) a light chain variable region homologous to a light chain variable region as set forth in SEQ ID NOs: 101, 117, 133, 708, 149, 165 or 181, 197, 213 or 229; or (ii) a heavy chain variable region homologous to a heavy chain variable region as set forth in SEQ ID NOs: 109, 125, 141, 710, 157, 173, 189, 205, 221 or 237. In certain embodiments, the antibody or antigen-binding portions comprise both heavy chain variable regions (i) and light chain variable regions (ii).

The antibodies or antigen-binding portion can comprise: (i) a heavy chain variable region encoded by a nucleic acid sequence homologous to a nucleic acid sequence as set forth in SEQ ID NOs: 667, 683, 699, 389, 405, 421, 533, 549, 565, 709, 437, 453, 469, 571, 587, 603, 485, 501, 517, 619, 635, or 651; (ii) a light chain variable region encoded by a nucleic acid sequence homologous to a nucleic acid sequence as set forth in SEQ ID NOs: 659, 675, 691, 381, 397, 413, 525, 541, 557, 707, 429, 445, 461, 557, 579, 595, 477, 493, 509, 611, 627, or 643; and/or, (iii) both a heavy chain variable region encoded by a nucleic acid sequence homologous to a nucleic acid sequence as set forth in SEQ ID NOs: 667, 683, 699, 389, 405, 421, 533, 549, 565, 709, 437, 453, 469, 571, 587, 603, 485, 501, 517, 619, 635, or 651, and a light chain variable region encoded by a nucleic acid sequence homologous to a nucleic acid sequence as set forth in SEQ ID NOs: 659, 675, 691, 381, 397, 413, 525, 541, 557, 707, 429, 445, 461, 557, 579, 595, 477, 493, 509, 611, 627, or 643.

The antibodies or antigen-binding portion can comprise one, two, three or more complementarity determining regions (CDRs) encoded by nucleic acid sequences that are homologous to one, two, three or more CDRs encoded by the nucleic acid sequence of: (i) the cdrs of the heavy chain variable region as set forth in, cdrCAN46G4 (SEQ ID NOs: 668, 669 and/or 670), huCAN46G4 (SEQ ID NOs: 684, 685 and/or 686), rehuCAN46G4 (SEQ ID NOs: 700, 701 and/or 702), cdrCAN46G13a (SEQ ID NOs: (a) 390, 391 and/or 392, or (b) 534, 535 and/or 536), huCAN46G13a (SEQ ID NOs: (a) 406, 407 and/or 408, or (b) 550, 551 and/or 552), rehuCAN46G13a (SEQ ID NOs: (a) 422, 423 and/or 424, or (b) 566, 567 and/or 568), cdrCAN46G19 (SEQ ID NOs: (a) 438, 439 and 440, or (b) 572, 573 and/or 574), huCAN46G19 (SEQ ID NOs: (a) 454, 455 and/or 456, or (b) 588, 589 and/or 590), rehuCAN46G19 (SEQ ID NOs: (a)

470, 471 and/or 472, or (b) 604, 605 and/or 606), cdrCAN46G24 (SEQ ID NOs: (a) 486, 487 and/or 488, or (b) 620, 621 and/or 622), huCAN46G24 (SEQ ID NOs: (a) 502, 503 and/or 504, or (b) 636, 637 and/or 638) or rehuCAN46G24 (SEQ ID NOs: (a) 518, 519 and/or 520, or (b) 652, 653 and/or 654); or, (ii) the cdrs of the light chain variable region as set forth in cdrCAN46G4 (SEQ ID NOs: 660, 661 and/or 662), huCAN46G4 (SEQ ID NOs: 676, 677 and/or 678), rehuCAN46G4 (SEQ ID NOs: 692, 693 and/or 694), cdrCAN46G13a (SEQ ID NOs: (a) 382 383 and/or 384, or (b) 526, 527 and/or 528), huCAN46G13a (SEQ ID NOs: (a) 398, 399 and/or 400, or (b) 542, 543 and/or 544), rehuCAN46G13a (SEQ ID NOs: (a) 414, 415 and/or 416, or (b) 558, 559 and/or 560), cdrCAN46G19 (SEQ ID NOs: (a) 430, 431 and/or 432, or (b) 715, 716 and/or 717), huCAN46G19 (SEQ ID NOs: (a) 446, 447 and/or 448, or (b) 580, 581 and 582), rehuCAN46G19 (SEQ ID NOs: (a) 462, 463 and/or 464, or (b) 596, 597 and/or 598), cdrCAN46G24 (SEQ ID NOs: (a) 478, 479 and/or 480, or (b) 612, 613 and/or 614), huCAN46G24 (SEQ ID NOs: (a) 494, 495 and/or 496 or (b) 628, 629 and/or 630) or rehuCAN46G24 (SEQ ID NOs: (a) 510, 511 and 512, or (b) 644, 645 and/or 646).

In certain embodiments, the antibody or antigen-binding portions comprise both heavy chain variable regions (i) and light chain variable regions (ii). Specifically, The antibodies or antigen-binding portion can comprise one, two, three or more complementarity determining regions (CDRs) encoded by nucleic acid sequences that are homologous to one, two, three or more CDRs encoded by the nucleic acid sequence of: (i) the cdrs of the heavy chain variable region as set forth in, cdrCAN46G4 (SEQ ID NOs: 668, 669 and/or 670), huCAN46G4 (SEQ ID NOs: 684, 685 and/or 686), rehuCAN46G4 (SEQ ID NOs: 700, 701 and/or 702), cdrCAN46G13a (SEQ ID NOs: (a) 390, 391 and/or 392, or (b) 534, 535 and/or 536), huCAN46G13a (SEQ ID NOs: (a) 406, 407 and/or 408, or (b) 550, 551 and/or 552), rehuCAN46G13a (SEQ ID NOs: (a) 422, 423 and/or 424, or (b) 566, 567 and/or 568), cdrCAN46G19 (SEQ ID NOs: (a) 438, 439 and 440, or (b) 572, 573 and/or 574), huCAN46G19 (SEQ ID NOs: (a) 454, 455 and/or 456, or (b) 588, 589 and/or 590), rehuCAN46G19 (SEQ ID NOs: (a) 470, 471 and/or 472, or (b) 604, 605 and/or 606), cdrCAN46G24 (SEQ ID NOs: (a) 486, 487 and/or 488, or (b) 620, 621 and/or 622), huCAN46G24 (SEQ ID NOs: (a) 502, 503 and/or 504, or (b) 636, 637 and/or 638) or rehuCAN46G24 (SEQ ID NOs: (a) 518, 519 and/or 520, or (b) 652, 653 and/or 654); and, (ii) the cdrs of the light chain variable region as set forth in cdrCAN46G4 (SEQ ID NOs: 660, 661 and/or 662), huCAN46G4 (SEQ ID NOs: 676, 677 and/or 678), rehuCAN46G4 (SEQ ID NOs: 692, 693 and/or 694), cdrCAN46G13a (SEQ ID NOs: (a) 382 383 and/or 384, or (b) 526, 527 and/or 528), huCAN46G13a (SEQ ID NOs: (a) 398, 399 and/or 400, or (b) 542, 543 and/or 544), rehuCAN46G13a (SEQ ID NOs: (a) 414, 415 and/or 416, or (b) 558, 559 and/or 560), cdrCAN46G19 (SEQ ID NOs: (a) 430, 431 and/or 432, or (b) 715, 716 and/or 717), huCAN46G19 (SEQ ID NOs: (a) 446, 447 and/or 448, or (b) 580, 581 and 582), rehuCAN46G19 (SEQ ID NOs: (a) 462, 463 and/or 464, or (b) 596, 597 and/or 598), cdrCAN46G24 (SEQ ID NOs: (a) 478, 479 and/or 480, or (b) 612, 613 and/or 614), huCAN46G24 (SEQ ID NOs: (a) 494, 495 and/or 496 or (b) 628, 629 and/or 630) or rehuCAN46G24 (SEQ ID NOs: (a) 510, 511 and 512, or (b) 644, 645 and/or 646). The antibodies or antigen-binding portion can comprise any combination, one, two, three or more, of the CDRs encoded by nucleic acid sequences for the heavy chain variable and light chain variable set forth in the preceeding paragraph.

The antibodies or antigen-binding portion can comprise: (i) a heavy chain variable region comprising three CDRs that are encoded by nucleic acid sequences homologous to nucleic acid sequences as set forth in cdrCAN46G4 (SEQ ID NOs: 668, 669 and 670), huCAN46G4 (SEQ ID NOs: 684, 685 and 686), rehuCAN46G4 (SEQ ID NOs: 700, 701 and 702), cdrCAN46G13a (SEQ ID NOs: (a) 390, 391 and 392; or (b) 534, 535 and 536), huCAN46G13a (SEQ ID NOs: (a) 406, 407 and 408, or (b) 550, 551 and 552), rehuCAN46G13a (SEQ ID NOs: (a) 422, 423 and 424, or (b) 566, 567 and 568), cdrCAN46G19 (SEQ ID NOs: (a) 438, 439 and 440, or (b) 572, 573 and 574), huCAN46G19 (SEQ ID NOs: (a) 454, 455 and 456, or (b) 588, 589 and 590), rehuCAN46G19 (SEQ ID NOs: (a) 470, 471 and 472, or (b) 604, 605 and 606), cdrCAN46G24 (SEQ ID NOs: (a) 486, 487 and 488, or (b) 620, 621 and 622), huCAN46G24 (SEQ ID NOs: (a) 502, 503 and 504, or (b) 636, 637 and 638) or rehuCAN46G24 (SEQ ID NOs: (a) 518, 519 and 520, or (b) 652, 653 and 654); or, (ii) a light chain variable region comprising three CDRs that are encoded by nucleic acid sequences homologous to nucleic acid sequences as set forth in cdrCAN46G4 (SEQ ID NOs: 660, 661 and 662), huCAN46G4 (SEQ ID NOs: 676, 677 and 678), rehuCAN46G4 (SEQ ID NOs: 692, 693 and 694), cdrCAN46G13a (SEQ ID NOs: (a) 382 383 and 384, or (b) 526, 527 and 528), huCAN46G13a (SEQ ID NOs: (a) 398, 399 and 400, or (b) 542, 543 and 544), rehuCAN46G13a (SEQ ID NOs: (a) 414, 415 and 416, or (b) 558, 559 and 560), cdrCAN46G19 (SEQ ID NOs: (a) 430, 431 and 432, or (b) 715, 716 and 717), huCAN46G19 (SEQ ID NOs: (a) 446, 447 and 448, or (b) 580, 581 and 582), rehuCAN46G19 (SEQ ID NOs: (a) 462, 463 and 464, or (b) 596, 597 and 598), cdrCAN46G24 (SEQ ID NOs: (a) 478, 479 and 480, or (b) 612, 613 and 614), huCAN46G24 (SEQ ID NOs: (a) 494, 495 and 496, or (b) 628, 629 and 630) or rehuCAN46G24 (SEQ ID NOs: (a) 510, 511 and 512, or (b) 644, 645 and 646).

In certain embodiments, the antibody or antigen-binding portions comprise both heavy chain variable regions (i) and light chain variable regions (ii). Specifically, the heavy and light chain variable regions comprise three CDRs that are encoded by nucleic acid sequences homologous to nucleic acid sequences as set forth in: (i) a heavy chain variable region comprising three CDRs that are encoded by nucleic acid sequences homologous to nucleic acid sequences as set forth in cdrCAN46G4 (SEQ ID NOs: 668, 669 and 670), huCAN46G4 (SEQ ID NOs: 684, 685 and 686), rehuCAN46G4 (SEQ ID NOs: 700, 701 and 702), cdrCAN46G13a (SEQ ID NOs: (a) 390, 391 and 392; or (b) 534, 535 and 536), huCAN46G13a (SEQ ID NOs: (a) 406, 407 and 408, or (b) 550, 551 and 552), rehuCAN46G13a (SEQ ID NOs: (a) 422, 423 and 424, or (b) 566, 567 and 568), cdrCAN46G19 (SEQ ID NOs: (a) 438, 439 and 440, or (b) 572, 573 and 574), huCAN46G19 (SEQ ID NOs: (a) 454, 455 and 456, or (b) 588, 589 and 590), rehuCAN46G19 (SEQ ID NOs: (a) 470, 471 and 472, or (b) 604, 605 and 606), cdrCAN46G24 (SEQ ID NOs: (a) 486, 487 and 488, or (b) 620, 621 and 622), huCAN46G24 (SEQ ID NOs: (a) 502, 503 and 504, or (b) 636, 637 and 638) or rehuCAN46G24 (SEQ ID NOs: (a) 518, 519 and 520, or (b) 652, 653 and 654); or, (ii) a light chain variable region comprising three CDRs that are encoded by nucleic acid sequences homologous to nucleic acid sequences as set forth in cdrCAN46G4 (SEQ ID NOs: 660, 661 and 662), huCAN46G4 (SEQ ID NOs: 676, 677 and 678), rehuCAN46G4 (SEQ ID NOs: 692, 693 and 694), cdrCAN46G13a (SEQ ID NOs: (a) 382 383 and 384, or (b) 526, 527 and 528), huCAN46G13a (SEQ ID NOs: (a) 398, 399 and 400, or (b) 542, 543 and 544), rehuCAN46G13a (SEQ ID NOs: (a) 414, 415 and 416, or (b) 558, 559 and 560), cdrCAN46G19 (SEQ ID NOs: (a) 430, 431 and 432, or (b) 715, 716 and 717), huCAN46G19 (SEQ ID NOs: (a) 446, 447 and 448, or (b) 580, 581 and 582), rehuCAN46G19 (SEQ ID NOs: (a) 462, 463 and 464, or (b) 596, 597 and 598), cdrCAN46G24 (SEQ ID NOs: (a) 478, 479 and 480, or (b) 612, 613 and 614), huCAN46G24 (SEQ ID NOs: (a) 494, 495 and 496, or (b) 628, 629 and 630) or rehuCAN46G24 (SEQ ID NOs: (a) 510, 511 and 512, or (b) 644, 645 and 646). The antibodies or antigen-binding portions can comprise any combination of the CDRS encoded for by the nucleic acid sequences set forth for the heavy chain variable region and light chain variable region listed in the preceeding paragraph.

In one embodiment, the antibody or antigen-binding portion contains a light chain variable region and heavy chain variable region encoded by nucleic acid sequences homologous to nucleic acid sequences as set forth in cdrCAN46G4 (SEQ ID NOs: 659 and 667, light chain variable and heavy chain variable region, respectively), huCAN46G4 (SEQ ID NOs: 675 and 683, light chain variable and heavy chain variable region, respectively), rehuCAN46G4 (691 and 699, light chain variable and heavy chain variable region, respectively), cdrCAN46G13a (SEQ ID NOs: (a) 381 and 389, or (b) 525 and 533, respectively), huCAN46G13a (SEQ ID NOs: (a) 397 and 405, or (b) 541 and 549, light chain variable and heavy chain variable region, respectively), rehuCAN46G13a (SEQ ID NOs: (a) 413 and 421, or (b) 557 and 565, light chain variable and heavy chain variable region, respectively), cdrCAN46G19 (SEQ ID NOs: (a) 429 and 437, or (b) 714 and 571 light chain variable and heavy chain variable region, respectively), huCAN46G19 (SEQ ID NOs: (a) 445 and 453, or (b) 579 and 587, light chain variable and heavy chain variable region, respectively), rehuCAN46G19 (SEQ ID NOs: (a) 461 and 469, or (b) 595 and 603, light chain variable and heavy chain variable region, respectively), cdrCAN46G24 (SEQ ID NOs: (a) 477 and 485, or (b) 611 and 619, light chain variable and heavy chain variable region, respectively), huCAN46G24 (SEQ ID NOs: (a) 493 and 501, or (b) 627 and 635, light chain variable and heavy chain variable region, respectively) or rehuCAN46G24 (SEQ ID NOs: (a) 509 and 517, or (b) 643 and 651, light chain variable and heavy chain variable region, respectively). The antibodies or antigen-binding portions can comprise any combination of the nucleic sequences set forth for the heavy chain variable region (1) and light chain variable region (2) listed in the preceeding paragraph.

In another embodiment, the antibody or antigen-binding portion contains a light chain variable region encoded by nucleic acid sequences homologous to nucleic acid sequences as set forth in CAN46G4 (SEQ ID NOs: 659, 675, or 691), CAN46G13a (SEQ ID NOs: 381, 397, 413, 525, 541, 557, or 707), CAN46G19 (SEQ ID NOs: 429, 445, 461, 714, 579, or 595), or CAN46G24 (SEQ ID NOs: 477, 493, 509, 611, 627, or 643).

The antibody or antigen-binding portion comprises a heavy chain variable region encoded by nucleic acid sequences homologous to nucleic acid sequences as set forth in CAN46G4 (SEQ ID NOs: 667, 683, or 699), CAN46G13a (SEQ ID NOs: 389, 405, 421, 533, 549, 565, or 709), CAN46G19 (SEQ ID NOs: 437, 453, 469, 571, 587, or 603), or CAN46G24 (SEQ ID NOs: 485, 501, 517, 619, 635, or 651).

Humanized Antibodies

The humanized antibody of the present invention is an antibody from a non-human species where the amino acid sequence in the non-antigen-binding regions (and/or the antigen-binding regions) has been altered so that the antibody more closely resembles a human antibody, and still retains comparable specificity and affinity.

Humanized antibodies can be generated by replacing sequences of the variable region that are not directly involved in antigen-binding with equivalent sequences from human variable regions. Those methods include isolating, manipulating, and expressing the nucleic acid sequences that encode all or part of variable regions from at least one of a heavy or light chain. Sources of such nucleic acid are well known to those skilled in the art and, for example, may be obtained from a hybridoma producing an antibody against toxin B. The recombinant DNA encoding the humanized antibody, or fragment, can then be cloned into an appropriate expression vector.

An antibody light or heavy chain variable region consists of a framework region interrupted by three hypervariable regions, referred to as complementarity determining regions (CDRs). In one embodiment, humanized antibodies are antibody molecules from non-human species having one, two or all CDRs from the non-human species and a framework region from a human immunoglobulin molecule.

The humanized antibodies of the present invention can be produced by methods known in the art. For example, once non-human (e.g., murine) antibodies are obtained, variable regions can be sequenced, and the location of the CDRs and framework residues determined. Kabat, E. A., et al. (1991) Sequences of Proteins of Immunological Interest, Fifth Edition, U.S. Department of Health and Human Services, NIH Publication No. 91-3242. Chothia, C. et al. (1987) J. Mol. Biol., 196:901-917. The light and heavy chain variable regions can, optionally, be ligated to corresponding constant regions. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in Table 1) or only some of the CDRs may be replaced. It is only necessary to keep the CDRs required for binding of the antibody to a predetermined antigen (e.g., toxin B of *C. difficile*). Morrison, S. L., 1985, Science, 229:1202-1207. Oi et al., 1986, BioTechniques, 4:214. U.S. Pat. Nos. 5,585,089; 5,225,539; 5,693,761 and 5,693,762. EP 519596. Jones et al., 1986, Nature, 321:552-525. Verhoeyan et al., 1988, Science, 239:1534. Beidler et al., 1988, J. Immunol., 141:4053-4060.

Also encompassed by the present invention are antibodies or antigen-binding portion containing one, two, or all CDRs as disclosed herein, with the other regions replaced by sequences from at least one different species including, but not limited to, human, rabbits, sheep, dogs, cats, cows, horses, goats, pigs, monkeys, apes, gorillas, chimpanzees, ducks, geese, chickens, amphibians, reptiles and other animals.

Chimeric Antibodies

A chimeric antibody is a molecule in which different portions are derived from different animal species. For example, an antibody may contain a variable region derived from a murine mAb and a human immunoglobulin constant region. Chimeric antibodies can be produced by recombinant DNA techniques. Morrison, et al., Proc Natl Acad Sci, 81:6851-6855 (1984). For example, a gene encoding a murine (or other species) monoclonal antibody molecule is digested with restriction enzymes to remove the region encoding the murine Fc, and the equivalent portion of a gene encoding a human Fc constant region is substituted. Chimeric antibodies can also be created by recombinant DNA techniques where DNA encoding murine V regions can be ligated to DNA encoding the human constant regions. Better et al., Science, 1988, 240:1041-1043. Liu et al. PNAS, 1987 84:3439-3443. Liu et al., J. Immunol., 1987, 139:3521-3526. Sun et al. PNAS, 1987, 84:214-218. Nishimura et al., Canc. Res., 1987, 47:999-1005. Wood et al. Nature, 1985, 314:446-449. Shaw et al., J. Natl. Cancer Inst., 1988, 80:1553-1559. International Patent Publication Nos. WO1987002671 and WO 86/01533. European Patent Application Nos. 184, 187; 171,496; 125,023; and 173,494. U.S. Pat. No. 4,816,567.

Types of Antibodies

The antibodies can be full-length or can include a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al., Proc. Natl. Acad. Sci. USA, 1988, 85:5879-5883.

The antibodies or antigen-binding portion of the present invention may be monospecific, bi-specific or multispecific. Multispecific or bi-specific antibodies or fragments thereof may be specific for different epitopes of one target polypeptide (e.g., toxin B) or may contain antigen-binding domains specific for more than one target polypeptide (e.g., antigen-binding domains specific for toxin A and toxin B; antigen-binding domains specific for toxin B and other antigen of C. difficile; or antigen-binding domains specific for toxin B and other kind of bacterium or virus). In one embodiment, a multispecific antibody or antigen-binding portion thereof comprises at least two different variable domains, wherein each variable domain is capable of specifically binding to a separate antigen or to a different epitope on the same antigen. Tutt et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for toxin B, and the other arm of the immunoglobulin is specific for a second therapeutic target or is conjugated to a therapeutic moiety such as a trypsin inhibitor.

All antibody isotypes are encompassed by the present invention, including IgG (e.g., IgG1, IgG2, IgG3, IgG4), IgM, IgA (IgA1, IgA2), IgD or IgE. The antibodies or antigen-binding portion may be mammalian (e.g., mouse, human) antibodies or antigen-binding portion. The light chains of the antibody may be of kappa or lambda type. The antibodies or antigen-binding portion may also be based on camelid (Bactrian camels, dromedaries and llamas) antibodies devoid of light chains also referred to as Nanobody®.

Variations of the Antibodies

The antibodies or antigen-binding portion are peptides. The peptides may also include variants, analogs, orthologs, homologs and derivatives of peptides, that exhibit a biological activity, e.g., binding of an antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portion in which specific amino acids have been substituted, deleted or added. These alternations do not have a substantial effect on the peptide's biological properties such as binding activity. For example, antibodies may have amino acid substitutions in the framework region, such as to improve binding to the antigen, modify solubility and/or influence pharmacokinetics/pharmacodynamics. In another example, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

The antibody, or antigen-binding portion can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

The present peptides may be the functionally active variant of antibodies of antigen-binding portion disclosed herein, e.g., with less than about 30%, about 25%, about 20%, about 15%, about 10%, about 5% or about 1% amino acid residues substituted or deleted but retain essentially the same immunological properties including, but not limited to, binding to toxin B.

The antibody, or antigen-binding portion thereof, can be codon optimized. For example, codons within the cloned gene that are generally not used by the host cell translation system are changed by in vitro mutagenesis to the preferred codons of the host cell system without changing the amino acid sequence of the synthesized antibody.

Nucleic Acids Encoding Antibody Variable Regions

The invention also encompasses a nucleic acid encoding the present antibody or antigen-binding portion thereof that specifically binds to toxin B of C. difficile. The nucleic acid may be expressed in a cell to produce the present antibody or antigen-binding portion thereof. The isolated nucleic acid of the present invention comprises a sequence encoding a peptide homologous to SEQ ID NOs: 3, 11, 19, 27, 35, 43, 51, 59, 67, 75, 85 or 93.

The invention also encompasses expression vectors including: (i) a nucleic acid encoding a peptide homologous to amino acid sequences SEQ ID NOs: 3, 11, 19, 27, 35, 43, 51, 59, 67, 75, 85 or 93; (ii) a nucleic acid encoding a peptide homologous to amino acid SEQ ID NOs: 101, 109, 117, 125, 133, 141, 149, 157, 165, 173, 181, 189, 197, 205, 213, 221, 229, 237, 708 and 710; or (iii) a nucleic acid encoding a peptide homologous to nucleic acid sequences SEQ ID NOs: 381, 389, 397, 405, 413, 421, 429, 437, 445, 453, 461, 469, 477, 485, 493, 501, 509, 517, 525, 533, 541, 549, 565, 557, 714, 571, 579, 587, 595, 603, 611, 619, 627, 635, 643 and 651. The nucleic acid may be expressed in a cell to produce the present antibody or antigen-binding portion thereof.

Nucleic acid molecules encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al., Proc Natl Acad Sci USA, 86:10029-10033 (1989).

Anti-toxin antibodies or portions can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

The present nucleic acids can be expressed in various suitable cells, including prokaryotic and eukaryotic cells, e.g., bacterial cells, (e.g., E. coli), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO, e.g. CHO-SKV1), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant. The types of the cells are discussed above.

The present antibody or antigen-binding portion can be expressed in various cells. The types of the cells are discussed above.

The present antibody or antigen-binding portion thereof can be expressed in cell-free translation systems, viral infection constructs or transgenic animals.

Alternatively, the present antibody or antigen-binding portion can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

C. difficile Toxins

The present invention provides for methods for making an antibody or antigen-binding portion thereof that specifically binds to toxin B of C. difficile. For example, a non-human animal is immunized with a composition that includes an inactivated toxin B, toxoid B, fragment of ToxinB, modified fragment of toxinB (synthetic variant), and then a specific antibody is isolated from the animal. The method can further include evaluating binding of the antibody to toxin B.

Any of a variety of Clostridium difficile toxin proteins, particularly toxin B, may be used in the practice of the present invention. In one embodiment toxin B is isolated from strain VPI10463. Toxin A and toxin B of C. difficile are high molecular mass proteins (280 to 310 kDa) that possess multiple functional domains, also referred to as fragments or domains. The N-terminal domains of both toxins contain glucosyltransferase activity that modifies Rho-like GTPases. This modification leads to cytoskeletal dysregulation in the toxified cells and disruption of colonic epithelial tight junctions. The central domain is predicted to be involved in membrane transport given the presence of hydrophobic regions and caveolin binding sites. The C-terminal third of the toxins contains repeating subunits believed to interact with carbohydrate receptors expressed on the target cell surface. The interaction of toxin A with carbohydrates also induces the hemagglutination of rabbit erythrocytes and provides a model for the study of toxin A receptor binding. Both toxins are cytotoxic, with toxin B being 1000 times more potent than toxin A when tested in in vitro cytotoxicity assays, and both are lethal when injected intravenously or intraperitoneally (i.p.) into a mouse. Toxin A is also a potent enterotoxin, as demonstrated by the induction of fluid accumulation in the mouse ligated intestinal loop diarrhea model. See, e.g., Babcock, G. J. et al., Infection and Immunity, 74: 6339-6347 (2006) and references contained therein for background.

Table 2 provides amino acid sequences of *Clostridium difficile* toxin B. Variants and fragments of the sequences provided below can also be used as an antigen to generate antibodies.

TABLE 2

| SEQ ID NO | Accession Number And Protein Name | Amino acid Sequence |
|---|---|---|
| 83 | NC_009089, Toxin B (tcdB) | MSLVNRKQLEKMANVRFRTQEDEYVAILDALEEYHNMSEN TVVEKYLKLKDINSLTDIYIDTYKKSGRNKALKKFKEYLVTE VLELKNNNLTPVEKNLHFVWIGGQINDTAINYINQWKDVNS DYNVNVFYDSNAFLINTLKKTVVESAINDTLESFRENLNDPR FDYNKFFRKRMEIIYDKQKNFINYYKAQREENPELIIDDIVKT YLSNEYSKEIDELNTYIEESLNKITQNSGNDVRNFEEFKNGES FNLYEQELVERWNLAAASDILRISALKEIGGMYLDVDMLPGI QPDLFESIEKPSSVTVDFWEMTKLEAIMKYKEYIPEYTSEHFD MLDEEVQSSFESVLASKSDKSEIFSSLGDMEASPLEVKIAFNS KGIINQGLISVKDSYCSNLIVKQIENRYKILNNSLNPAISEDND FNTTTNTFIDSIMAEANADNGRFMMELGKYLRVGFFPDVKT TINLSGPEAYAAAYQDLLMFKEGSMNIHLIEADLRNFEISKTN ISQSTEQEMASLWSFDDARAKAQFEEYKRNYFEGSLGEDDN LDFSQNIVVDKEYLLEKISSLARSSERGYIHYIVQLQGDKISYE AACNLFAKTPYDSVLFQKNIEDSEIAYYYNPGDGEIQEIDKY KIPSIISDRPKIKLTFIGHGKDEFNTDIFAGFDVDSLSTEIEAAID LAKEDISPKSIEINLLGCNMFSYSINVEETYPGKLLLKVKDKIS ELMPSISQDSIIVSANQYEVRINSEGRRELLDHSGEWINKEESII KDISSKEYISFNPKENKITVKSKNLPELSTLLQEIRNNSNSSDIE LEEKVMLTECEINVISNIDTQIVEERIEEAKNLTSDSINYIKDEF KLIESISDALCDLKQQNELEDSHFISFEDISETDEGFSIRFINKE TGESIFVETEKTIFSEYANHITEEISKIKGTIFDTVNGKLVKKV NLDTTHEVNTLNAAFFIQSLIEYNSSKESLSNLSVAMKVQVY AQLFSTGLNTITDAAKVVELVSTALDETIDLLPTLSEGLPIIATI IDGVSLGAAIKELSETSDPLLRQEIEAKIGIMAVNLTTATTAIIT SSLGIASGFSILLVPLAGISAGIPSLVNNELVLRDKATKVVDYF KHVSLVETEGVFTLLDDKIMMPQDDLVISEIDFNNNSIVLGK CEIWRMEGGSGHTVTDDIDHFFSAPSITYREPHLSIYDVLEVQ KEELDLSKDLMVLPNAPNRVFAWETGWTPGLRSLENDGTKL LDRIRDNYEGEFYWRYFAFIADALITTLKPRYEDTNIRINLDS NTRSFIVPIITTEYIREKLSYSFYGSGGTYALSLSQYNMGINIEL |

TABLE 2-continued

| SEQ ID NO | Accession Number And Protein Name | Amino acid Sequence |
|---|---|---|
| | | SESDVWIIDVDNVVRDVTIESDKIKKGDLIEGILSTLSIEENKII |
| | | LNSHEINFSGEVNGSNGFVSLTFSILEGINAIIEVDLLSKSYKLL |
| | | ISGELKILMLNSNHIQQKIDYIGFNSELQKNIPYSFVDSEGKEN |
| | | GFINGSTKEGLFVSELPDVVLISKVYMDDSKPSFGYYSNNLK |
| | | DVKVITKDNVNILTGYYLKDDIKISLSLTLQDEKTIKLNSVHL |
| | | DESGVAEILKFMNRKGNTNTSDSLMSFLESMNIKSIFVNFLQS |
| | | NIKFILDANFIISGTTSIGQFEFICDENDNIQPYFIKFNTLETNYT |
| | | LYVGNRQNMIVEPNYDLDDSGDISSTVINFSQKYLYGIDSCV |
| | | NKVVISPNIYTDEINITPVYETNNTYPEVIVLDANYINEKINVN |
| | | INDLSIRYVWSNDGNDFILMSTSEENKVSQVKIRFVNVFKDK |
| | | TLANKLSFNFSDKQDVPVSEIILSFTPSYYEDGLIGYDLGLVSL |
| | | YNEKFYINNFGMMVSGLIYINDSLYYFKPPVNNLITGFVTVG |
| | | DDKYYFNPINGGAASIGETIIDDKNYYFNQSGVLQTGVFSTE |
| | | DGFKYFAPANTLDENLEGEAIDFTGKLIIDENIYYFDDNYRG |
| | | AVEWKELDGEMHYFSPETGKAFKGLNQIGDYKYYFNSDGV |
| | | MQKGFVSINDNKHYFDDSGVMKVGYTEIDGKHFYFAENGE |
| | | MQIGVFNTEDGFKYFAHHNEDLGNEEGEEISYSGILNFNNKI |
| | | YYFDDSFTAVVGWKDLEDGSKYYFDEDTAEAYIGLSLINDG |
| | | QYYFNDDGIMQVGFVTINDKVFYFSDSGIIESGVQNIDDNYF |
| | | YIDDNGIVQIGVFDTSDGYKYFAPANTVNDNIYGQAVEYSGL |
| | | VRVGEDVYYFGETYTIETGWIYDMENESDKYYFNPETKKAC |
| | | KGINLIDDIKYYFDEKGIMRTGLISFENNNYYFNENGEMQFG |
| | | YINIEDKMFYFGEDGVMQIGVFNTPDGFKYFAHQNTLDENFE |
| | | GESINYTGWLDLDEKRYYFTDEYIAATGSVIIDGEEYYFDPD |
| | | TAQLVISE |

Table 3 provides nucleic acid sequences encoding the proteins of Table 2.

TABLE 3

| SEQ ID NO | Accession Number And Gene Name | Nucleotide Sequence |
|---|---|---|
| 84 | NC_009089, | atgagtttagttaatagaaaacagttagaaaaaatggcaaatgtaagatttcgtactcaagaagatg |
| | Toxin B | aatatgttgcaatattggatgctttagaagaatatcataatatgtcagagaatactgtagtcgaaaaat |
| | tcdB | atttaaaattaaaagatataaatagtttaacagatatttatatagatacatataaaaaatctggtagaaat |
| | | aaagccttaaaaaaatttaaggaatatctagttacagaagtattagagctaaagaataataatttaact |
| | | ccagttgagaaaaatttacattttgtttggattggaggtcaaataaatgacactgctattaattatataa |

TABLE 3-continued

| SEQ ID NO | Accession Number And Gene Name | Nucleotide Sequence |
|---|---|---|
| | | atcaatggaaagatgtaaatagtgattataatgttaatgttttttatgatagtaatgcattttttgataaaca |
| | | cattgaaaaaaactgtagtagaatcagcaataaatgatacacttgaatcatttagagaaaacttaaat |
| | | gaccctagatttgactataataaattcttcagaaaacgtatggaaataatttatgataaacagaaaat |
| | | ttcataaactactataaagctcaaagagaagaaaatcctgaacttataattgatgatattgtaaagac |
| | | atatctttcaaatgagtattcaaaggagatagatgaacttaatacctatattgaagaatccttaaataaa |
| | | attacacagaatagtggaaatgatgttagaaactttgaagaatttaaaaatggagagtcattcaactt |
| | | atatgaacaagagttggtagaaaggtggaatttagctgctgcttctgacatattaagaatatctgcatt |
| | | aaaagaaattggtggtatgtatttagatgttgatatgttaccaggaatacaaccagacttatttgagtct |
| | | atagagaaacctagttcagtaacagtggattttgggaaatgacaaagttagaagctataatgaaat |
| | | acaaagaatatataccagaatatacctcgaaacattttgacatgttagacgaagaagttcaaagtag |
| | | ttttgaatctgttctagcttctaagtcagataaatcagaaatattctcatcacttggtgatatggaggcat |
| | | caccactagaagttaaaattgcatttaatagtaagggtattataaatcaagggctaatttctgtgaaag |
| | | actcatattgtagcaatttaatagtaaaacaaatcgagaatagatataaaatattgaataatagtttaaa |
| | | tccagctattagcgaggataatgattttaatactacaacgaatacctttattgatagtataatggctgaa |
| | | gctaatgcagataatggtagatttatgatggaactaggaaagtatttaagagttggtttcttcccagat |
| | | gttaaaactactattaacttaagtggccctgaagcatatgcggcagcttatcaagatttattaatgttta |
| | | aagaaggcagtatgaatatccatttgatagaagctgatttaagaaactttgaaatctctaaaactaa |
| | | tatttctcaatcaactgaacaagaaatggctagcttatggtcatttgacgatgcaagagctaaagctc |
| | | aatttgaagaatataaaaggaattattttgaaggttctcttggtgaagatgataatcttgattttttctcaa |
| | | aatatagtagttgacaaggagtatcttttagaaaaaatatcttcattagcaagaagttcagagagagg |
| | | atatatacactatattgttcagttacaaggagataaaattagttatgaagcagcatgtaacttatttgca |
| | | aagactccttatgatagtgtactgtttcagaaaaatatagaagattcagaaattgcatattattataatc |
| | | ctggagatggtgaaatacaagaaatagacaagtataaaattccaagtataatttctgatagacctaa |
| | | gattaaaattaacatttattggtcatggtaaagatgaatttaatactgatatatttgcaggttttgatgtaga |
| | | ttcattatccacagaaatagaagcagcaatagatttagctaaagaggatatttctcctaagtcaatag |
| | | aaataaatttattaggatgtaatatgtttagctactctatcaacgtagaggagacttatcctggaaaatt |
| | | attacttaaagttaaagataaaatatcagaattaatgccatctataagtcaagactctattatagtaagt |
| | | gcaaatcaatatgaagttagaataaaatagtgaaggaagaagagaattattggatcattctggtgaat |
| | | ggataaataaagaagaaagtattataaaggatatttcatcaaaagaatatatatcatttaatcctaaag |
| | | aaaataaaattacagtaaaatctaaaaatttacctgagctatctacattattacaagaaattagaaata |
| | | attctaattcaagtgatattgaactagaagaaaaagtaatgttaacagaatgtgagataaatgttatttc |
| | | aaatatagatacgcaaattgttgaggaaaggattgaagaagctaagaatttaacttctgactctatta |
| | | attatataaaagatgaatttaaactaatagaatctatttctgatgcactatgtgacttaaaaacaacagaa |
| | | tgaattagaagattctcatttttatatcttttgaggacatatcagagactgatgagggatttagtataaga |
| | | tttattaataaagaaactggagaatctatatttgtagaaactgaaaaaacaatattctctgaatatgcta |
| | | atcatataactgaagagatttctaagataaaaggtactatatttgatactgtaaatggtaagttagtaaa |
| | | aaaagtaaatttagatactacacacgaagtaaatactttaaatgctgcattttttatacaatcattaatag |
| | | aatataatagttctaaagaatctcttagtaatttaagtgtagcaatgaaagtccaagtttacgctcaatt |

TABLE 3-continued

| SEQ ID NO | Accession Number And Gene Name | Nucleotide Sequence |
|---|---|---|
| | | atttagtactggtttaaatactattacagatgcagccaaagttgttgaattagtatcaactgcattagat gaaactatagacttacttectacattatctgaaggattacctataattgcaactattatagatggtgtaa gtttaggtgcagcaatcaaagagctaagtgaaacgagtgacccattattaagacaagaaatagaa gctaagataggtataatggcagtaaatttaacaacagctacaactgcaatcattacttcatctttggg gatagctagtggatttagtatacttttagttcctttagcaggaatttcagcaggtataccaagcttagta aacaatgaacttgtacttcgagataaggcaacaaaggttgtagattattttaaacatgtttcattagttg aaactgaaggagtatttactttattagatgataaaataatgatgccacaagatgatttagtgatatcag aaatagattttaataataattcaatagtttaggtaaatgtgaaatctggagaatggaaggtggttcag gtcatactgtaactgatgatatagatcacttcttttcagcaccatcaataacatatagagagccacact tatctatatgacgtattggaagtacaaaaagaagaacttgatttgtcaaaagatttaatggtattacc taatgctccaaatagagtatttgcttgggaaacaggatggacaccaggtttaagaagcttagaaaat gatggcacaaaactgttagaccgtataagagataactatgaaggtgagttttattggagatattttgct tttatagctgatgctttaataacaacattaaaaccaagatatgaagatactaatataagaataaatttag atagtaatactagaagtttatagttccaataataactacagaatatataagagaaaaattatcatattct ttctatggttcaggaggaacttatgcattgtctctttctcaatataatatgggtataaatatagaattaag tgaaagtgatgtttggattatagatgttgataatgttgtgagagatgtaactatagaatctgataaaatt aaaaaaggtgatttaatagaaggtattttatctacactaagtattgaagagaataaaattatcttaaata gccatgagattaattttctggtgaggtaaatggaagtaatggatttgtttctttaacattttcaattttag aaggaataaatgcaattatagaagttgatttattatctaaatcatataaattacttatttctggcgaatta aaaatattgatgttaaattcaaatcatattcaacagaaaatagattatataggattcaatagcgaattac agaaaaatataccatatagctttgtagatagtgaaggaaaagagaatggttttattaatggttcaaca aaagaaggtttatttgtatctgaattacctgatgtagttcttataagtaaggtttatatggatgatagtaa gccttcatttggatattatagtaataatttgaaagatgtcaaagttataactaaagataatgttaatatatt aacaggttattatcttaaggatgatataaaaatctctctttctttgactctacaagatgaaaaaactata aagttaaatagtgtgcatttagatgaaagtggagtagctgagattttgaagttcatgaatagaaaagg taatacaaatacttcagattctttaatgagcttttagaaagtatgaatataaaaagtattttcgttaatttc ttacaatctaatattaagtttatattagatgctaattttataataagtggtactacttctattggccaatttg agtttatttgtgatgaaaatgataatatacaaccatatttcattaagtttaatacactagaaactaattata ctttatatgtaggaaatagacaaaatatgatagtggaaccaaattatgatttagatgattctggagata tatcttcaactgttatcaatttctctcaaaagtatctttatggaatagacagttgtgttaataaagttgtaa tttcaccaaatatttatacagatgaaataaatataacgcctgtatatgaaacaaataatacttatccaga agttattgtattagatgcaaattatataaatgaaaaaataaatgttaatatcaatgatctatctatacgat atgtatggagtaatgatggtaatgattttattcttatgtcaactagtgaagaaaataaggtgtcacaag ttaaaataagattcgttaatgttttttaaagataagactttggcaaataagctatctttttaacttagtgata aacaagatgtacctgtaagtgaaataatcttatcatttacaccttcatattatgaggatggattgattgg ctatgatttgggtctagttctttatataatgagaaattttatattaataacttggaatgatggtatctgga ttaatatatattaatgattcattatattattttaaaccaccagtaaataatttgataactggatttgtgactg |

TABLE 3-continued

| SEQ ID NO | Accession Number And Gene Name | Nucleotide Sequence |
|---|---|---|
| | | taggcgatgataaatactactttaatccaattaatggtggagctgcttcaattggagagacaataatt |
| | | gatgacaaaaattattatttcaaccaaagtggagtgttacaaacaggtgtatttagtacagaagatgg |
| | | atttaaatattttgccccagctaatacacttgatgaaaacctagaaggagaagcaattgattttactgg |
| | | aaaattaattattgacgaaaatatttattattttgatgataattatagaggagctgtagaatggaaagaa |
| | | ttagatggtgaaatgcactattttagcccagaaacaggtaaagcttttaaaggtctaaatcaaatagg |
| | | tgattataaatactatttcaattctgatggagttatgcaaaaaggatttgttagtataaatgataataaac |
| | | actattttgatgattctggtgttatgaaagtaggttacactgaaatagatggcaagcatttctactttgct |
| | | gaaaacggagaaatgcaaataggagtatttaatacagaagatggatttaaatattttgctcatcataa |
| | | tgaagatttaggaaatgaagaaggtgaagaaatctcatattctggtatattaaatttcaataataaaatt |
| | | tactattttgatgattcatttacagctgtagtggatggaaagatttagaggatggttcaaagtattatttt |
| | | gatgaagatacagcagaagcatatataggtttgtcattaaataaatgatggtcaatattattttaatgatg |
| | | atggaattatgcaagttggatttgtcactataaatgataaagtcttctacttctctgactctggaattata |
| | | gaatctggagtacaaaacatagatgacaattatttctatatagatgataatggtatagttcaaattggt |
| | | gtatttgatacttcagatggatataaatattttgcacctgctaatactgtaaatgataatatttacggaca |
| | | agcagttgaatatagtggtttagttagagttggtgaagatgtatattattttggagaaacatatacaatt |
| | | gagactggatggatatatgatatggaaaatgaaagtgataaatattatttcaatccagaaactaaaaa |
| | | agcatgcaaaggtattaatttaattgatgatataaaatattattttgatgagaagggcataatgagaac |
| | | gggtcttatatcatttgaaaataataattattacttttaatgagaatggtgaaatgcaatttggttatataa |
| | | atatagaagataagatgttctattttggtgaagatggtgtcatgcagattggagtatttaatacaccag |
| | | atggatttaaatactttgcacatcaaaatactttggatgagaattttgagggagaatcaataaactata |
| | | ctggttggttagatttagatgaaaagagatattattttacagatgaatatattgcagcaactggttcagt |
| | | tattattgatggtgaggagtattattttgatcctgatacagctcaattagtgattagtgaatag |

Antibody Preparation

In one embodiment, the present invention provides for a method for making a hybridoma that expresses an antibody that specifically binds to toxin B of *C. difficile*. The method contains the following steps: immunizing an animal with a composition that includes inactivated toxin B (e.g., toxoid B); isolating splenocytes from the animal; generating hybridomas from the splenocytes; and selecting a hybridoma that produces an antibody that specifically binds to toxin B. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

Toxins can be inactivated, for example, by treatment with formaldehyde, glutaraldehyde, UDP-dialdehyde, peroxide, oxygen or by mutation (e.g., using recombinant methods). Relyveld et al., Methods in Enzymology, 93:24, 1983. Woodrow and Levine, eds., New Generation Vaccines, Marcel Dekker, Inc., New York, 1990. Genth et al., Inf. and Immun., 68(3):1094-1101, 2000. Mutant *C. difficile* toxins with reduced toxicity can be produced using recombinant methods. U.S. Pat. Nos. 5,085,862; 5,221,618; 5,244,657; 5,332,583; 5,358,868; and 5,433,945. A full-length or fragment of the toxins or toxoids can be used as immunogens.

In one embodiment, inactivated toxin B is used to immunize mice intraperitoneally or intravenously. One or more boosts may or may not be given. The titers of the antibodies in the plasma can be monitored by, e.g., ELISA (enzyme-linked immunosorbent assay) or flow cytometry. Mice with sufficient titers of anti-toxin B antibodies are used for fusions. Mice may or may not be boosted with the antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-toxin monoclonal antibodies. The antibody secreting hybridomas are replated, screened again, and if still positive for anti-toxin monoclonal antibodies, can be subcloned by limiting dilution. For example, the hybridoma clones CAN46G4, CAN46G13, CAN46G13a and CAN46G19 of the present invention have been subcloned. The subclones include, e.g., CAN46G4-1-2, CAN46G13-1-5, CAN46G13-1-8 and CAN46G19-3-2. The hybridomas CAN46G13-1-8, CAN46G4-1-2, CAN46G13-1-5 and CAN46G19-3-2 have been deposited with the American Type Culture Collection, Manassas, Va. (deposited on Aug. 23, 2012). The ATCC Patent Deposit Designation for each of the hybridomas is as follows: PTA-13257

(CAN46G13-1-8), PTA-13258 (CAN46G4-1-2), PTA-13259 (CAN46G19-3-2) and PTA-13260 (CAN46G13-1-5).

Adjuvants that may be used to increase the immunogenicity of one or more of the *Clostridium difficile* toxin antigens, particularly toxin B include any compound or compounds that act to increase an immune response to peptides or combination of peptides. Non-limiting examples of adjuvants include alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid, QS21 (saponin adjuvant), MPL (Monophosphoryl Lipid A), 3DMPL (3-O-deacylated MPL), extracts from Aquilla, ISCOMS (see, e.g., Sjolander et al. (1998) J. Leukocyte Biol. 64:713; WO90/03184; WO96/11711; WO 00/48630; WO98/36772; WO00/41720; WO06/134423 and WO07/026190), LT/CT mutants, poly (D,L-lactide-co-glycolide) (PLG) microparticles, Quil A, interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The immunized animal can be any animal that is capable of producing recoverable antibodies when administered an immunogen, such as, but not limited to, mice, rabbits, rats, hamsters, goats, horses, monkeys, baboons and humans. The host may be transgenic, but produce human antibodies/U.S. Pat. Nos. 8,236,311; 7,625,559 and 5,770,429, the disclosure of each of which is incorporated herein by reference in its entirety. Lonberg et al., Nature 368(6474): 856-859, 1994. Lonberg, N., Handbook of Experimental Pharmacology 113: 49-101, 1994. Lonberg, N. and Huszar, D., Intern. Rev. Immunol., 13: 65-93, 1995. Harding, F. and Lonberg, N., Ann. N.Y. Acad. Sci., 764:536-546, 1995.

Antibody Assays

After the host is immunized and the antibodies are produced, the antibodies are assayed to confirm that they are specific for the antigen of interest and to determine whether they exhibit any cross reactivity with other antigens. One method of conducting such assays is a sera screen assay as described in U.S. Patent Publication No. 2004/0126829. Anti-toxin antibodies can be characterized for binding to the toxin by a variety of known techniques. For example, in an ELISA, microtiter plates are coated with the toxin or toxoid antigen in PBS, and then blocked with irrelevant proteins such as bovine serum albumin (BSA) diluted in PBS. Dilutions of plasma from toxin-immunized mice are added to each well and incubated. The plates are washed and then incubated with a secondary antibody conjugated to an enzyme (e.g., alkaline phosphatase). After washing, the plates are developed with the enzyme's substrate (e.g., ABTS), and analyzed at a specific OD. In other embodiments, to determine if the selected monoclonal antibodies bind to unique epitopes, the antibody can be biotinylated which can then be detected with a streptavidin labeled probe. Anti-toxin antibodies can be tested for reactivity with the toxin by Western blotting.

Neutralization assays can also be used to measure activity of the anti-toxin antibodies. For example, in vitro neutralization assays can be used to measure the ability of an antibody to inhibit a cytopathic effect on cells in culture (see Example 7 below). In one embodiment, in an in vitro neutralization assay, the present antibody, or antigen-binding portion thereof, at a concentration ranging from about 0.01 μM to about 50 μM, from about 0.2 μM to about 40 μM, from about 0.6 μM to about 30 μM, from about 2 μM to about 20 μM, from about 4 μM to about 10 μM, from about 0.2 μM to about 7 μM, from about 0.2 μM to about 10 μM, from about 4 μM to about 7 μM, from about 5 μM to about 15 μM, about 10 μM, about 0.01 μg/ml to about 200 μg/ml, about 0.01 μg/ml to about 150 μg/ml, about 0.01 μg/ml to about 100 μg/ml, about 0.01 μg/ml to about 50 μg/ml, about 0.01 μg/ml to about 25 μg/ml, about 0.01 μg/ml to about 10 μg/ml, about 0.01 μg/ml to about 5 μg/ml, about 0.1 μg/ml to about 2 μg/ml, about 1 μg/ml to about 2 μg/ml, about 0.5 μg/ml to about 2 μg/ml, about 0.25 μg/ml to about 2 μg/ml, about 0.1 μg/ml to about 2 μg/ml, about 0.06 μg/ml to about 2 μg/ml, or about 0.03 μg/ml to about 2 μg/ml, neutralizes a percentage of about 5 ng/ml, about 200 pg/ml, about 250 pg/ml, or about 200-250 pg/ml *C. difficile* toxin B. The percentages of toxin B neutralized by the present antibody, or antigen-binding portion thereof, may be greater than about 20%, greater than about 30%, greater than about 40%, greater than about 50%, greater than about 60%, greater than about 70%, greater than about 80%, greater than about 90%, greater than about 95%, or greater than about 99%.

In vivo assays can be used to measure toxin neutralization as well. In another embodiment, in an in vivo toxin B challenge experiment (e.g., procedures as described in Example 8, as well as Babcock et al., Human Monoclonal Antibodies Directed against Toxins A and B prevent *Clostridium difficile*-Induced Mortality in Hamsters. Infection and Immunity (2006) 74(11):6339), when the antibody, or an antigen-binding portion thereof, is administered to a mammal at a dosage ranging from about 1 mg/kg body weight to about 50 mg/kg body weight, from about 2 mg/kg body weight to about 40 mg/kg body weight, from about 3 mg/kg body weight to about 30 mg/kg body weight, from about 5 mg/kg body weight to about 20 mg/kg body weight, from about 8 mg/kg body weight to about 13 mg/kg body weight, or about 10 mg/kg body weight about 24 hours before the mammal is exposed to greater than about 75 ng, or about 75 ng of *C. difficile* toxin B, the mammal has a chance to survive. The chance of survival for the mammal may be greater than about 40%, greater than about 50%, greater than about 60%, greater than about 70%, greater than about 80%, greater than about 90%, greater than about 95%, or greater than about 99% within about 7 days or within about 4 days.

Hybridomas that produce antibodies that bind, preferably with high affinity, to the toxin can than be subcloned and further characterized. One clone from each hybridoma, which retains the reactivity of the parent cells (by ELISA), can then be chosen for making a cell bank, and for antibody purification.

To purify the anti-toxin antibodies, supernatants from the cultured hybridomas can be filtered and concentrated before affinity chromatography with protein A-Sepharose (Pharmacia, Piscataway, N.J.).

Antibodies, or antigen-binding fragments, variants or derivatives thereof of the present disclosure can also be described or specified in terms of their binding affinity to an antigen. The affinity of an antibody for an antigen can be determined experimentally using any suitable method (see, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

Pharmaceutical Compositions

The present invention also provides compositions containing an antibody or antigen-binding portion thereof described herein, and a pharmaceutically acceptable carrier. The composition may contain an isolated nucleic acid encoding the present antibody or antigen-binding portion thereof, and a pharmaceutically acceptable carrier. Pharmaceutically acceptable carriers include any and all solvents, dispersion media, isotonic and absorption delaying agents, and the like that are physiologically compatible. In one embodiment, the composition is effective to reduce, eliminate, or prevent *Clostridium difficile* bacterial infection in a subject.

The invention also features methods of treating *C. difficile* disease in a subject by administering to the subject the present antibody or antigen-binding portion thereof in an amount effective to inhibit *C. difficile* disease. Routes of administration of the present compositions include, but are not limited to, intravenous, intramuscular, subcutaneous, oral, topical, subcutaneous, intradermal, transdermal, subdermal, parenteral, rectal, spinal, or epidermal administration.

The compositions of the present invention can be prepared as injectables, either as liquid solutions or suspensions, or as solid forms which are suitable for solution or suspension in liquid vehicles prior to injection. The composition can also be prepared in solid form, emulsified or the active ingredient encapsulated in liposome vehicles or other particulate carriers used for sustained delivery. For example, the composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain poly-acids or polyesters such as those used to make resorbable sutures, that allow for sustained release of the vaccine.

The present antibodies or antigen-binding portion are formulated into compositions for delivery to a mammalian subject. The composition is administered alone, and/or mixed with a pharmaceutically acceptable vehicle or excipient. Suitable vehicles are, for example, water, saline, dextrose, glycerol, ethanol, or the like, and combinations thereof. In addition, the vehicle can contain minor amounts of auxiliary substances such as wetting or emulsifying agents, pH buffering agents, or adjuvants. The compositions of the present invention can also include ancillary substances, such as pharmacological agents, cytokines, or other biological response modifiers. Methods of preparing the formulations are known, or will be apparent, to those skilled in the art. See, e.g., Remington's Pharmaceutical Sciences, Mack Publishing Company, Easton, Pa., 21st edition.

Compositions can be administered in a single dose treatment or in multiple dose treatments on a schedule and over a time period appropriate to the age, weight and condition of the subject, the particular composition used, and the route of administration.

In one embodiment, a single dose of the composition according to the invention is administered. In other embodiments, multiple doses are administered. The frequency of administration can vary depending on any of a variety of factors, e.g., severity of the symptoms, degree of immuno-protection desired, whether the composition is used for prophylactic or curative purposes, etc. For example, in one embodiment, the composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a polypeptide according to the invention, e.g., the period of time over which the composition is administered, can vary, depending on any of a variety of factors, e.g., subject response, etc. For example, the composition can be administered over a period of time ranging from about 10 minutes to about 1 day, from about 30 minutes to about 20 hours, from about 1 hour to about 15 hours, from about 2 hours to about 10 hours, from about 3 hours to about 8 hours, from about 4 hours to about 6 hours, from about 1 day to about 1 week, from about 2 weeks to about 4 weeks, from about 1 month to about 2 months, from about 2 months to about 4 months, from about 4 months to about 6 months, from about 6 months to about 8 months, from about 8 months to about 1 year, from about 1 year to about 2 years, or from about 2 years to about 4 years, or more.

The present antibodies or antigen-binding portion thereof can be combined with a pharmaceutically acceptable carrier. Pharmaceutically acceptable carriers can contain a physiologically acceptable compound that acts to, e.g., stabilize, or increase or decrease the absorption or clearance rates of the present antibodies or antigen-binding portion thereof. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's").

In one aspect, the present antibodies or antigen-binding portion thereof are dissolved in a pharmaceutically acceptable carrier, e.g., an aqueous carrier. Examples of aqueous solutions include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate.

Solid formulations can be used in the present invention. They can be formulated as, e.g., pills, tablets, powders or capsules. For solid compositions, conventional solid carriers can be used which include, e.g., mannitol, lactose, starch, magnesium stearate, sodium saccharin, talcum, cellulose, glucose, sucrose, magnesium carbonate, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. Sayani, Crit. Rev. Ther. Drug Carrier Syst. 13: 85-184, 1996. For topical, transdermal administration, the agents are formulated into ointments, creams, salves, powders and gels. Transdermal delivery systems can also include, e.g., patches.

The present compositions can also be administered in sustained delivery or sustained release mechanisms. For example, biodegradeable microspheres or capsules or other biodegradeable polymer configurations capable of sustained delivery of a peptide can be included in the formulations of the invention (see, e.g., Putney, Nat. Biotechnol. 16: 153-157, 1998).

For inhalation, the present compositions can be delivered using any system known in the art, including dry powder aerosols, liquids delivery systems, air jet nebulizers, propellant systems, and the like. Patton, Biotechniques 16: 141-143, 1998. Also can be used in the present invention are product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

Compositions or nucleic acids, polypeptides, or antibodies of the invention can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for preparing parenterally administrable compositions will be known or apparent to those skilled in the art and are described in detail. Bai, J. Neuroimmunol. 80: 65-75, 1997. Warren, J. Neurol. Sci. 152: 31-38, 1997. Tonegawa, J. Exp. Med. 186: 507-515, 1997.

In one aspect, the pharmaceutical formulations comprising nucleic acids, polypeptides, or antibodies of the invention are incorporated in lipid monolayers or bilayers, e.g., liposomes. U.S. Pat. Nos. 6,110,490; 6,096,716; 5,283,185 and 5,279,833. Aspects of the invention also provide formulations in which nucleic acids, peptides or polypeptides of the invention have been attached to the surface of the monolayer or bilayer. For example, peptides can be attached to hydrazide-PEG-(distearoylphosphatidyl) ethanolamine-containing liposomes (see, e.g., Zalipsky, Bioconjug. Chem. 6: 705-708, 1995). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla, J. Pharm. Sci. 85: 5-8, 1996), transmucosally, or orally. The invention also provides pharmaceutical preparations in which the nucleic acid, peptides and/or polypeptides of the invention are incorporated within micelles and/or liposomes (see, e.g., Suntres, J. Pharm. Pharmacol. 46: 23-28, 1994; Woodle, Pharm. Res. 9: 260-265, 1992). Liposomes and liposomal formulations can be prepared according to standard methods and are also well known in the art. Akimaru, Cytokines Mol. Ther. 1: 197-210, 1995. Alving, Immunol. Rev. 145: 5-31, 1995. Szoka, Ann. Rev. Biophys. Bioeng. 9: 467, 1980. U.S. Pat. Nos. 4,235,871; 4,501,728 and 4,837,028.

In one aspect, the compositions are prepared with carriers that will protect the peptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. U.S. Pat. No. 4,522,811.

It is advantageous to formulate parenteral or oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. In one embodiment, the dosage of such compounds lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

An exemplary, non-limiting range for a therapeutically or prophylactically effective amount of an antibody or antigen-binding portion of the invention is from about 0.001 to about 60 mg/kg body weight, about 0.01 to about 30 mg/kg body weight, about 0.01 to about 25 mg/kg body weight, about 0.5 to about 25 mg/kg body weight, about 0.1 to about 20 mg/kg body weight, about 10 to about 20 mg/kg body weight, about 0.75 to about 10 mg/kg body weight, about 1 to about 10 mg/kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight.

The composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging from about 0.01 mg to about 10 g, from about 0.1 mg to about 9 g, from about 1 mg to about 8 g, from about 1 mg to about 7 g, from about 5 mg to about 6 g, from about 10 mg to about 5 g, from about 20 mg to about 1 g, from about 50 mg to about 800 mg, from about 100 mg to about 500 mg, from about 0.01 mg to about 10 g, from about 0.05 µg to about 1.5 mg, from about 10 µg to about 1 mg protein, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

In therapeutic applications, the present compositions are administered to a subject at risk for *Clostridium difficile* bacterial infection or suffering from active infection in an amount sufficient to at least partially arrest or prevent the condition or a disease and/or its complications.

Use of Antibodies

The present antibodies or antigen-binding portion have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose *C. difficile* and disease associated with *C. difficile*.

The antibodies or antigen-binding portion can be used on cells in culture, e.g., in vitro or ex vivo. For example, cells can be cultured in vitro in culture medium and contacted by the anti-toxin antibody or fragment thereof. The methods can be performed on cells present in a subject, as part of an in vivo (e.g., therapeutic or prophylactic) protocol. For in vivo embodiments, the contacting step is effected in a subject and includes administering an anti-toxin antibody or portion thereof to the subject under conditions effective to permit binding of the antibody, or portion thereof, to a toxin (e.g., toxin B) expressed by *C. difficile* in the subject, e.g., in the gut.

The antibody or antigen-binding portion thereof can be administered alone or in combination with another therapeutic agent, e.g., a second monoclonal or polyclonal antibody or antigen-binding portion thereof. In one example, the antibody or antigen-binding portion thereof specifically binds to *C. difficile* toxin B is combined with an antibody (monoclonal or polyclonal) or antigen-binding portion thereof specifically binds to *C. difficile* toxin A. In another example, the second agent is an antibiotic, e.g., vancomycin, bacitracin or metronidazole. The antibodies can be used in combination with probiotic agents such as *Saccharomyces boulardii*. The antibodies can also be administered in combinations with a *C. difficile* vaccine, e.g., a toxoid vaccine.

The antibody or antigen-binding portion thereof can also be administered in combination with one or more additional therapeutic agents, e.g., a second and third monoclonal or polyclonal antibody or antigen-binding portion thereof. In one example, the antibody or antigen-binding portion thereof specifically binds to *C. difficile* toxin B is combined with an antibody (monoclonal or polyclonal) or antigen-binding portion thereof which specifically binds to *C. difficile* toxin A and another antibody (monoclonal or polyclonal) or antigen-binding portion thereof which specifically binds to a different region of the *C. difficile* toxin B from the first *C. difficile* Toxin B antibody. In another example, the second or third monoclonal or polyclonal antibody or antigen-binding portion thereof is specific against binary toxin, or *C difficile* spore. In another example, the second agent is an antibiotic, e.g., vancomycin, bacitracin or metronidazole. In another example, the second agent is an antiparasitic, e.g. nitrazoxanide. The antibodies can be used in combination with probiotic agents such as *Saccharomyces boulardii*. The antibodies can also be administered in combinations with a *C. difficile* vaccine, e.g., a toxoid vaccine. In yet another use, the antibody or antigen-binding portion thereof can also be administered in combination with fecal transplants.

An anti-toxin antibody (e.g., monoclonal antibody) can also be used to isolate toxins by standard techniques, such as affinity chromatography or immunoprecipitation. Moreover, an anti-toxin antibody can be used to detect the toxin, e.g., to screen samples (e.g., in a stool sample, blood sample, culture sample, food samples) for the presence of *C. difficile*. Anti-toxin antibodies can be used diagnostically to monitor levels of the toxin in tissue as part of a clinical testing procedure to, for example, determine the efficacy of a given treatment regimen.

Vaccines

The present invention further encompasses vaccines and immunogen-containing compositions. The vaccines or immunogen-containing compositions may comprise one or more epitope recognized and/or bound by one or more of the present antibodies or antigen-binding portion thereof. In one embodiment, the vaccines or immunogen-containing compositions comprises one or more epitope recognized and/or bound by one or more of CAN46G4, CAN46G13, CAN46G13a, CAN46G19, CAN46G24, CAN33G1, antigen-binding portion of any of these antibodies, humanized form of any of these antibodies, or chimeric form of any of these antibodies. The vaccines or immunogen-containing compositions may contain the epitope, or may contain a peptide or protein having the epitope. In one embodiment, the epitope-containing portions, fragments, or peptides are derived from toxin B. For example, the epitope-containing portions, fragments, or peptides of toxin B are derived from the toxin B protein by proteolytic cleavage (e.g., by enterokinase, caspase, etc.). The epitope-containing portions, fragments, or peptides may also be chemically or recombinantly synthesized.

Such epitope-containing portions, fragments, or peptides of the toxins, when administered in the form of a vaccine or immunogen to a subject infected with *C. difficile* or afflicted with *C. difficile*-associated disease, may elicit a humoral response in the subject, i.e., antibodies having specificities for toxin B, thereby allowing the subject to mount an immune response against the toxins and to neutralize, block, reduce, ameliorate, cure, or treat the *C. difficile*-associated disease, infection, or CDAD in the subject. Accordingly, another embodiment provides a method of neutralizing, blocking, reducing, ameliorating, curing, or treating *C. difficile* infection or a *C. difficile*-associated disease in a subject in need thereof, comprising administering to the subject an effective amount of the above-described vaccine or immunogen. In an embodiment, the subject elicits a humoral response to toxin B of *C. difficile*, thereby neutralizing, blocking, reducing, ameliorating, curing, or treating *C. difficile*-associated disease, infection, or CDAD in the subject. In another embodiment, the subject elicits a cellular immune response to toxin B of *C. difficile*. In another embodiment, the subject elicits both a humoral and a cellular immune response to toxin B of *C. difficile*. International Patent Publication No. WO2011130650.

Kits

The invention also provides kits containing an anti-toxin antibody or antigen-binding portion thereof. Additional components of the kits may include one or more of the following: instructions for use; another therapeutic agent, an agent useful for coupling an antibody to a label or therapeutic agent, other reagents, or other materials for preparing the antibody for administration; pharmaceutically acceptable carriers; and devices or other materials for administration to a subject.

Various combinations of antibodies can be packaged together. For example, a kit can include antibodies that bind to toxin B and antibodies that bind to toxin A (e.g., monoclonal anti-toxin A antibodies, or polyclonal antisera reactive with toxin A). The antibodies can be mixed together, or packaged separately within the kit.

Instructions for use can include instructions for therapeutic application including suggested dosages and/or modes of administration, e.g., in a patient with a symptom of CDAD. Other instructions can include instructions on coupling of the antibody to a label or a therapeutic agent, or for purification of a conjugated antibody, e.g., from unreacted conjugation components. The kits can be for diagnostic use, e.g., to detect the toxin, to screen samples (e.g., in a stool sample) for the presence of *C. difficile*. The kits can be used diagnostically to monitor levels of the toxin in tissue as part of a clinical testing procedure to, for example, determine the efficacy of a given treatment regimen.

The kit may or may not contain at least one nucleic acid encoding anti-toxin antibodies or fragment thereof, and instructions for expression of the nucleic acids. Other possible components of the kit include expression vectors and cells.

The present antibodies or antigen-binding portion, compositions and methods can be used in all vertebrates, e.g., mammals and non-mammals, including human, mice, rats, guinea pigs, hamsters, dogs, cats, cows, horses, goats, sheep, pigs, monkeys, apes, gorillas, chimpanzees, rabbits, ducks, geese, chickens, amphibians, reptiles and other animals.

The following examples of specific aspects for carrying out the present invention are offered for illustrative purposes only, and are not intended to limit the scope of the present invention in any way.

EXAMPLES

Example 1

Hybridoma Fusion

Methods and reagents for generating monoclonal antibodies are well known and encompass immunization protocols as well as techniques for isolating and fusing splenocytes. A classical hybridoma fusion was performed using the standard somatic cell hybridization technique of Kohler and Milstein, *Nature*, 256: 495, 1975. See generally, Harlow, E and Lane, D. *Antibodies: A Laboratory Manual*, Cold Spring Harbor Laboratory Press, Cold Spring Harbor, N.Y. 1988. In general, mice are immunized with inactivated toxin, or toxoids, fragments of the toxin, or whole toxin. Mice received their first immunization with antigen using Complete Freund's Adjuvant (CFA) or other adjuvants, followed by subsequent boosters every other week (up to a total of 4) with antigen and Incomplete Freund's Adjuvant (IFA). A trial bleed from the medial saphenous vein was performed, and the serum tested to check for titers of anti-toxin B antibody. If IgG titers were sufficient, fusions were performed using 1 or 2 mice at a time. Mice were given a final push intraperitoneally (IP) with a toxoid B/toxin B combination in PBS three days prior to the fusion.

On the day of the fusion, mice are sacrificed and their spleens removed. Splenocytes are washed from the spleen using a syringe and needle and collected in a 50 ml tube for fusion with myeloma cells. Myelomas are an immortal tumor cell line used as fusion partners, grown in the presence of 8-azaguanine(8-aza), a toxic nucleotide analog which blocks the salvage pathway. Cells grown in the presence of 8-aza survive only by incurring defective mutations in the hypoxanthine-guanine phosphoribosyl transferase (HGPRT) gene. B cells are fused with the myeloma cells using Polyethylene Glycol 1500. Fused cells are mixed into semi-solid agarose with drug selection and plated out into petri dishes. HAT media containing Hypoxanthine, Aminopterin, and Thymidine is used for drug selection. Aminopterin is a drug which inhibits the de novo pathway for nucleotide metabolism which is absolutely required for survival/cell growth in myeloma lines defective in HGPRT, and allows selection usually within 24-48 hours.

Example 2

Hybridoma Screening

The next step is screening of the growing hybridomas. A commercial semisolid agarose within which the cells grow as a mass of cells in the 3-D matrix was used. This facilitates picking clusters by hand (by visual inspection) and transferring these clonal clusters into a 96 well plate containing suitable media. The cells were allowed to grow for 3-7 days and then the supernatant removed for screening and replaced with fresh media. Positive binding in ELISA (or other tests) resulted in continuing to grow the hybridomas by transferring them into larger tissue culture vessels with increasing volume. The mAbs were isotyped using a suitable commercial isotyping kit for murine mAbs using the spent supernatant. The decision to move a clone to the next stage of selection is based on its reactivity to native toxin B using an ELISA and its survival, usually based upon serial dilutions and reactivity of at least 1/8 or 1/16 or higher, as well as IgG class; therefore the number of clones decreased throughout the selection procedure. The murine mAbs that underwent further characterization were: CAN33G1, CAN46G4, CAN46G13, CAN46G13a, CAN46G19 and CAN46G24.

Example 3

ELISA Assay of Mouse Monoclonal Antibodies

An ELISA was used to test the binding of the mAbs against whole toxin B and recombinant toxin B fragments 1 and 4 as well as to determine if they were cross-reactive to whole toxin A. The mAb clones were compared to purified anti-toxoid B mouse pAb (polyclonal Ab). The ELISA plate was coated with 100 ng of toxin B fragment 1, fragment 4, or 400 ng of whole toxin B so that the coatings were equimolar. The wells were blocked with 5% skim milk then probed with serially diluted CAN46 series mAbs (0.1 µg/ml to 1 µg/ml) and binding was detected with a commercial goat anti-mouse IgG-HRP antibody. Negative and positive controls were also run. The polyclonal toxoid B antibody (pAb) served as the positive control, and is derived from immunized mice. The murine anti-toxin A mAb CAN20G2 is specific for Toxin A and was used as the negative control. The secondary antibody control is for the murine secondary antibody. The plate was read at 405 nm after 15 min incubation with substrate. The titration data for each antibody is shown in FIG. 1.

Results: As shown in FIG. 1, CAN46 series mAbs bind to whole toxin B and toxin B fragments at a similar level to the mouse pAb, with the exception of reduced binding with CAN33G1. CAN46G4, CAN46G19 and CAN46G24 bind to toxin B fragment 4 at a similar level to the mouse pAb. CAN46G13a binds to toxin B fragment 1 at a similar level to the mouse pAb. None of the CAN46 mAbs showed cross-reactivity to toxin A.

Example 4

Competition ELISA Assay of Mouse Monoclonal Antibodies

An ELISA was performed to test if the CAN33 or CAN46 mAbs compete with MDX 1388 (Medarex, US Patent Publication No. US 2005/0287150 A1) or hPA-41 (Progenics Pharmaceuticals, Inc., International Patent Publication No. WO 2011/130650; Marozsan et al., Protection Against Clostridium difficile Infection With Broadly Neutralizing Antitoxin Monoclonal Antibodies, J. Infect. Dis. 2012 September; 206(5):706-13) for binding to Toxin B. The ELISA plate was coated with 400 ng of whole Toxin B. The wells were blocked with 5% skim milk and then probed with the mAb mixtures as follows: the murine CAN33 and CAN46 mAbs were prepared at 1 µg/ml and serially diluted two-fold. In order to provide a baseline OD of approximately 1.0, a dilution of 1/1,650,000 was prepared for MDX1388 anti-toxin B mAb used as a control, dilution based on previous data generated in house and mixed with the CAN33 and CAN46 mAbs 1:1. Similarly, hPA-41 was diluted to 1/335,000 and mixed 1:1 with the serially diluted CAN33 and CAN46 mAbs as above. Binding for CAN33 and CAN46 mAbs was detected with a commercial goat anti-mouse IgG-HRP antibody. Binding for MDX1388 and hPA-41 was detected with a commercial goat anti-human IgG-HRP antibody. Negative and positive controls were also run. Excess Toxin B mixed 1:1 with either MDX1388 or hPA-41 served as the positive control. MDX1388 and hPA-41 were also diluted with just phosphate buffered saline for a negative control with no competitive mAb. The plate was read at 405 nm after 15 min incubation with substrate.

Figure 2:
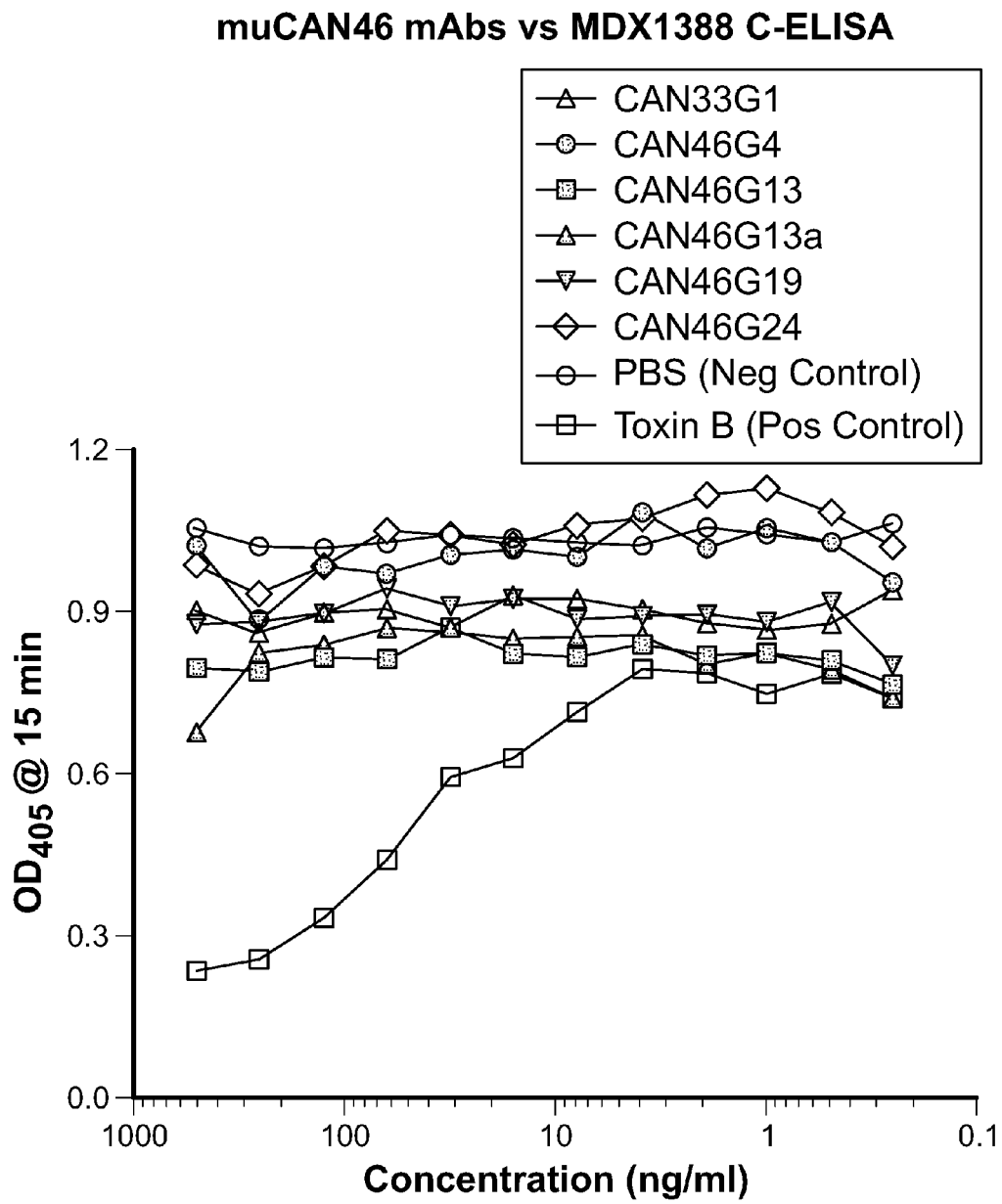
FIG. 2 is a competition ELISA showing the murine CAN33 and CAN46 mAbs bind distinct epitopes and do not compete with mAb MDX-1388 (Medarex) on toxin B.
Figure 3:
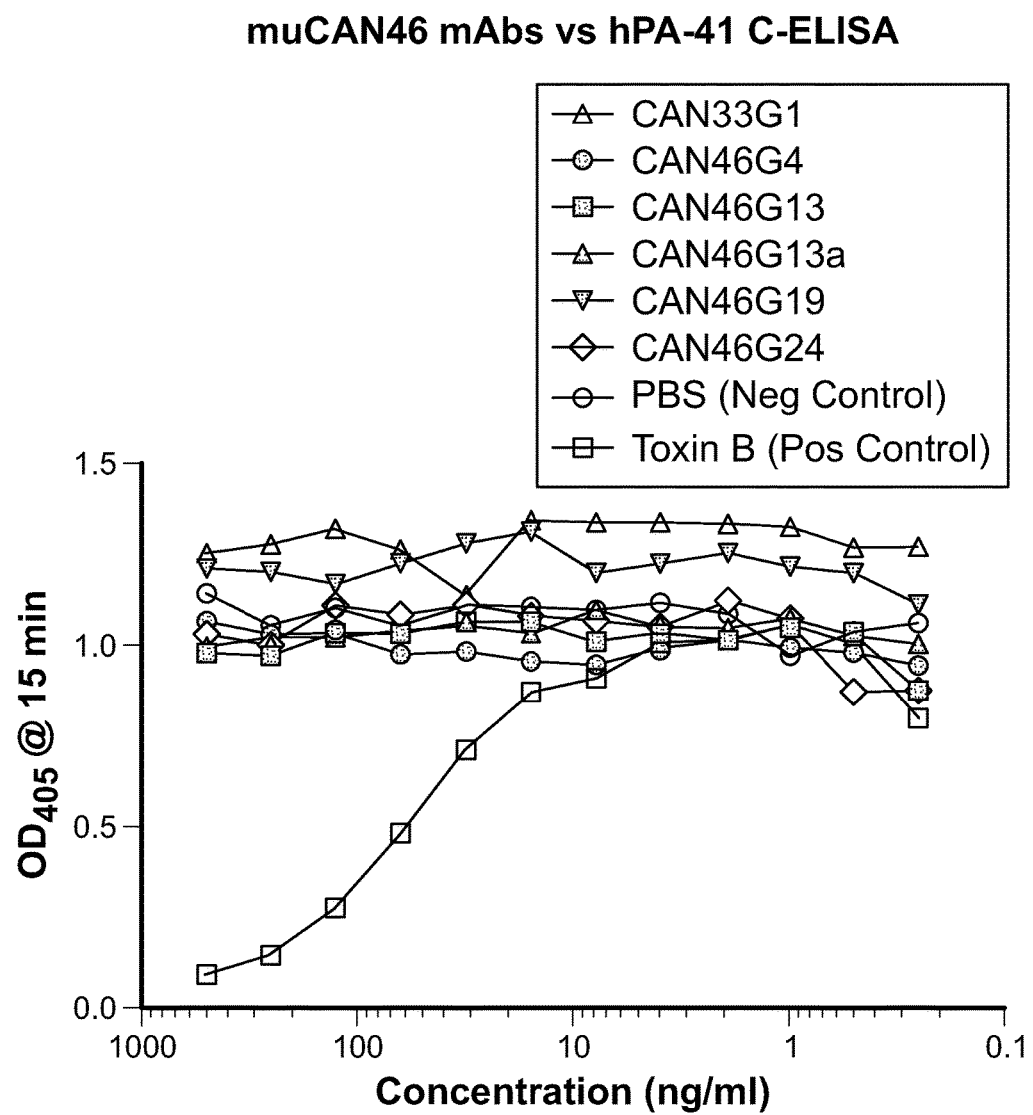
FIG. 3 is a competition ELISA showing the murine CAN33 and CAN46 mAbs bind distinct epitopes and do not compete with mAb hPA-41 (Progenics Pharmaceuticals, Inc.) on toxin B.

Results: As shown in FIGS. 2 and 3, CAN33 and CAN46 mAbs do not compete with MDX-13-88 or hPA-41 for binding to whole toxin B. All of the mAbs show similar binding patterns to those for the negative control containing no competitive mAb. None of the mAbs showed competition with either MDX-1388 or hPA-41 indicating they bind different epitopes on whole toxin B.

Example 5

Western Blot of Mouse Monoclonal Antibodies

A 4-12% gradient SDS-PAGE gel was run for 1.5 hours at 200 volts with a combination of C. difficile proteins: recombinant toxin B fragment 1, (82 kDa), recombinant toxin B fragment 4 (85 kDa), whole toxin B (280 kDa), and commercial BSA. The gel was then transferred to a nitrocellulose membrane for 1 hour 15 min at 45 volts. The membrane was blocked overnight at 4° C. with 5% skim milk in 1×TBST. The next day the mAbs (1° Ab) were diluted in 2.5% skim milk in 1×TBST at concentrations ranging from 2 µg/ml to 5 µg/ml depending on the antibody and used to probe the membrane containing the transferred products for 2 hours at room temperature (RT) on a shaker. The membranes were then washed with 1×TBST to remove unbound 1° Ab and probed with anti-mouse IgG-HRP (2° Ab) at a dilution of 1:4000 to 1:5000 for 1.5 hours at RT on a shaker.

Results: As shown in FIGS. 4, 5 and 6, CAN46G4, CAN46G13, CAN46G19 and CAN46G24 showed binding to recombinant toxin B fragment 4 and whole toxin B. CAN46G13a showed binding to recombinant toxin B fragment 1 and whole toxin B. They all showed no cross-reactivity to the negative control (BSA).

Example 6

Affinity Analysis of Mouse Monoclonal Antibodies

Biolayer interferometry was used to measure the interactions between whole toxin B and the anti-toxin B antibodies. The Octet QKe instrument (ForteBio) was equipped with Streptavidin (SA) biosensors. 40 µg/ml of biotinylated antibody was coupled to SA sensors and toxin B, in a dilution series from 50 nM to 0.78 nM, were reacted on the antibody-coated pins followed by a dissociation step in PBS-Triton. The results were then analyzed using ForteBio Data Analysis software to determine the dissociation constant ($K_D$), which is the measure used to describe the binding strength between antibody and antigen, $k_{on}$(1/Ms), the on-rate at which antibody antigen complexes form, and $k_{dis}$(1/s), the off-rate at which the antibody antigen complexes dissociate. Table 4 shows affinity (equilibrium dissociation constant ($K_D$) ratio of $k_{dis}/k_{on}$ between antibody and antigen is inversely related to affinity whereby the lower the $K_D$ the higher the affinity) of purified murine CAN33 and CAN46 mAbs.

TABLE 4

Affinity data for CAN46G and CAN33G versions, hPA-41 and MDX1388

| Antibody | $K_D$ (M) | $k_{on}$(1/Ms) | $k_{dis}$(1/s) |
|---|---|---|---|
| CAN46G4 | 1.41E−09 | 7.18E+04 | 1.01E−04 |
| CAN46G13 | 1.17E−09 | 1.28E+05 | 1.49E−04 |
| CAN46G13a | 8.57E−09 | 8.08E+05 | 6.93E−03 |
| CAN46G19 | 1.27E−09 | 1.14E+05 | 1.45E−04 |
| CAN46G24 | 1.89E−09 | 1.49E+05 | 2.80E−04 |
| hPA-41 | 9.83E−11 | 5.38E+05 | 5.30E−05 |
| CAN33G1 | 1.09E−08 | 5.44E+04 | 5.91E−04 |
| MDX1388 | 3.84E−09 | 3.62E+04 | 1.39E−04 |

Example 7

Epitope Binning of Mouse Monoclonal Antibodies

The Octet QKe is a label free real-time biosensor that uses disposable fiber-optic sensors that detect biomolecular interactions via biolayer interferometry. The epitope binning assay was performed against the previously characterized MDX1388 mAb to examine whether the present toxin B mAbs share a similar or a different epitope with MDX1388. Secondly, the assay was used to confirm shared single or potentially multiple epitope bins between the toxin B mAbs. The classical sandwich method was used and involves coupling the mAb to sensor, binding antigen, and then binding to another mAb. The second mAb can bind the captured Ag only if its epitope does not overlap that of the immobilized mAb. For example, biotinylated CAN46G24 antibody is coupled to a Streptavidin (SA) biosensor. The bound antibody is then incubated with free Toxin B and free CAN46G24. The CAN46G24-toxin B complex is again incubated with free antibody. A large nm shift in wavelength indicates binding of the analyte indicating that CAN46G24 and the free antibody have different epitopes. 1 Biotinylated CAN46G24 to SA biosensors; 2 Free whole toxin B forming a complex with CAN46G24; 3 Free CAN46G24 associating with biotinylated CAN46G24-Toxin B complex; 4 Association sample curves; 5 Dissociation step.

Figure 7:
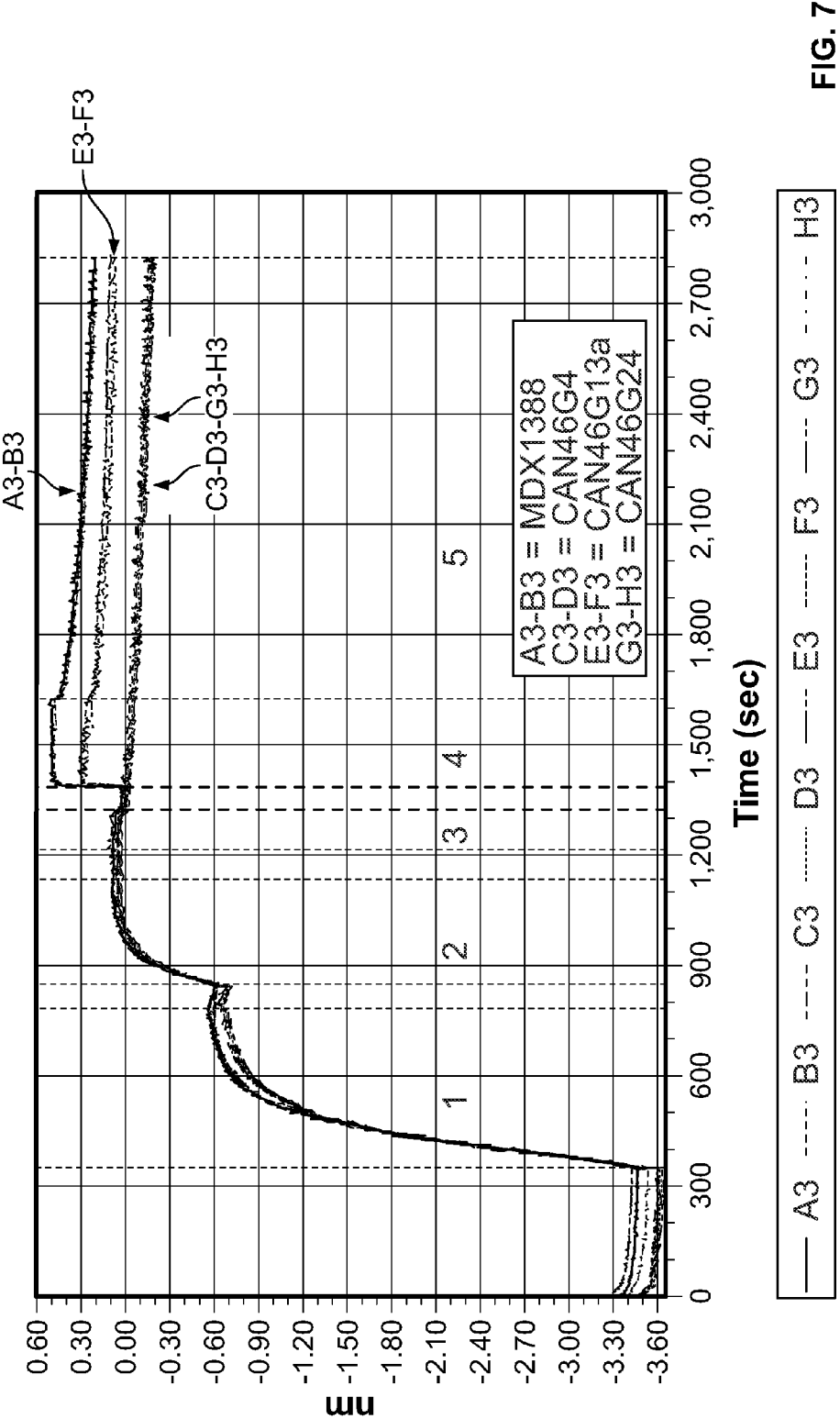
FIG. 7 is an epitope binning graph for murine CAN46G4, CAN46G13a and CAN46G24.

Results: In FIG. 7, the nm shift for both the MDX1388 and CAN46G13a samples indicate binding to an exposed and distinct epitope. There is no nm shift for CAN46G4 and CAN46G24 samples indicating shared or spatially related epitopes to CAN46G19.

Example 8

*Clostridium difficile* Toxin B Neutralization Assay with HT-29 Cells (Human Colon Carcinoma Epithelial Cells) Using the xCELLigence™ Platform Cell Line The HT-29 cells are an adherent human colon carcinoma epithelial cell line. These cells have been selected since they represent a relevant in vitro model to infection with TcdB.

xCELLigence™ Platform

The xCELLigence™ is a real-time label-free cell analysis (RTCA) system based on an electronic impedance cell sensing measurement that evaluates changes in cell characteristics in real-time. Cell growth and cytotoxicity can be detected by monitoring the increase or decrease of a dimensionless parameter called cell index (CI). When adherent cells are cultured within the custom 96-well plate, cell growth characteristics can be monitored in real-time by changes in electrical impedance as measured by the gold electrodes embedded within each well.

The CI measurement is based upon four parameters: 1) cell number, 2) cell size and morphology, 3) cell viability, and 4) cell adhesion. An increase in any one of these parameters leads to an increase in the CI. Conversely, a decrease in any one of these parameters leads to a decrease in CI.

Procedure

HT-29 cells were trypsinized from a T-75 flask and added to a Roche 96-well E-plate® at 8000 cells/well, and incubated about 4 hours at 37° C. During the 4-hr incubation, sample dilutions were prepared on a 96-well U-bottom plate. Samples were then overlayed with an appropriate dilution of TcdB (0.5-50 ng/mL range, dilution dependant on toxin lot). The plate is then incubated at 37° C. for about 60 minutes. After completion of initial cell incubation, the cells were overlayed with the toxin/sample preparation then incubated for a minimum of 72 hours at 37° C. Impedance measurements were taken every 30 minutes throughout the incubation period. This data is plotted in real-time using the xCELLigence™ RTCA software. A single time point representing the optimal time point (either toxin cytotoxicity or neutralization) was selected. The data from that single time point is used to create a 4-parameter logistic (4-PL) curve for analysis. If sample potency is being determined, the sample curves are constrained against the "reference" sample. Curve constraint is used to constrain the upper/lower asypmtotes, and slope of the curve. This allows for each curve to shift horizontally along the x-axis based upon the curves $IC_{50}$ value. For potency determination the $IC_{50}$ value of the standard is divided by the IC50 value of the sample.

Initial Evaluation for TcdB Cytopathogenicity Detection with xCELLigence

Figure 8:
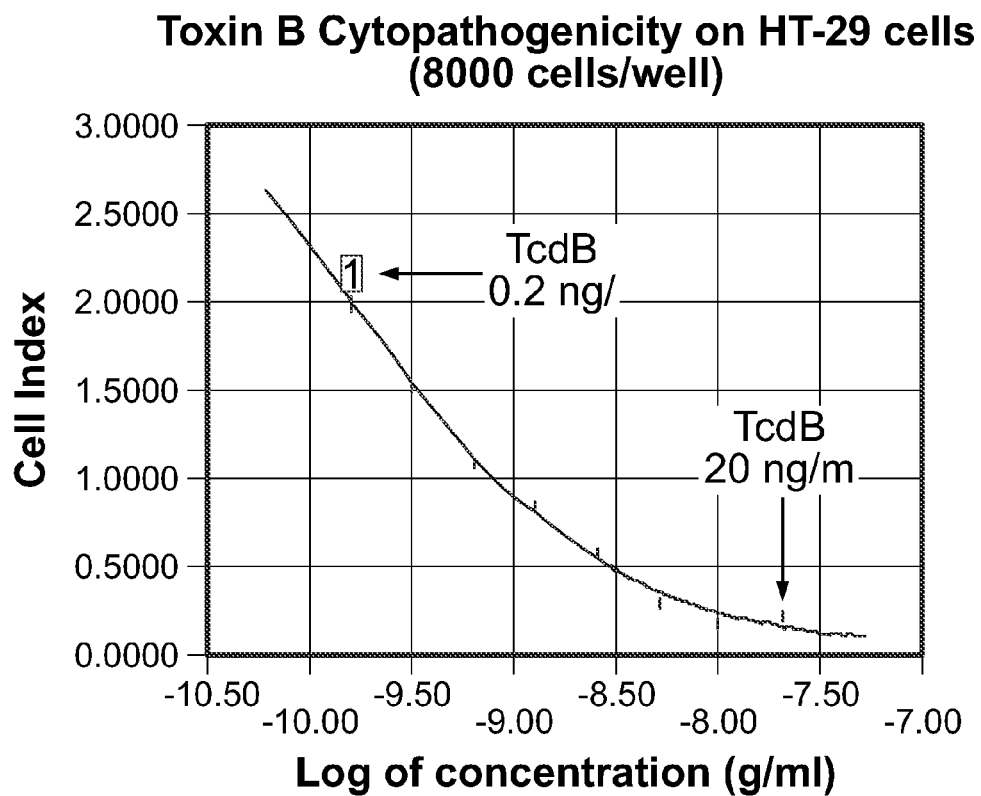
FIG. 8 shows a 4-PL toxin titration curve of TcdB on HT-29 cells using the xCelligence platform.

Toxin B cytopathogenicity on HT-29 cells was first evaluated to determine the suitability of the xCELLigence™ platform. FIG. 8 shows the dose response curve of TcdB at 2-fold dilutions, demonstrating that increasing concentrations of Tcd B on HT-29 cells leads to cytopathogenicity as indicated by a decrease in the cell index. The increasing cell index with decreasing concentrations of TcdB demonstrates a suitable detection of cytopathogenicity. A TcdB concentration of 5 ng/mL is showing approximately full cytopathic effect and indicates this as a suitable concentration to evaluate toxin neutralization.

Cell attachment Phase—xCelligence™ Method

This phase included the following steps. (1) Trypsinized cells in source flask. (2) Added 2 mL of trypsin to flask and washed cells to remove traces of media then aspirated. (3) Added 3 mL of trypsin and incubated at 37° C. for approximately 8 minutes. (4) Added 6 mL of assay media to flask. (4) Centrifuged suspended cells at 800 rpm for 7 minutes. (5) Aspirated supernatant and resuspended cells with 6 mL of assay media. (6) Counted cells and calculated required volume of cells for plating at 8000 cells/well. (7) To a 96 well E-plate added 100 µL of assay media to all wells. (8) Performed background reading on xCelligence. (10) Added 50 µL of $1.0 \times 10^6$ cells/mL suspension to these wells for a final 8000 cells/well seeding density. (11) (15) Incubated plate at room temperature for 20-30 minutes to allow cells to settle evenly. (16) Placed plate in 37° C. incubator with 5% $CO_2$ overlay 4-5 hours.

Toxin B Preparation: (1) Prepared Toxin B Overlay by Diluting Primary Stock (409.6 µg/mL) to 5 ng/mL (2) Prepared Toxin B for titration by diluting primary stock to 80 ng/mL. (3) Dilutions of primary stock were performed as shown in Table 5.

TABLE 5

| Sample | TcdB Test Concentration | Volume of TcdB (µL) | Volume of 10% Medium (µL) |
|---|---|---|---|
| Toxin Overlay (Stock = 409.6 µg/mL) | (i) 500 ng/mL | 12.2 | 9988.8 |
| | (ii) 5.0 ng/mL | 120 of (i) | 11,880 |
| Toxin titration | 80 ng/mL | 160 of (i) | 840 |

Sample Preparation: To test potency, all the monoclonal antibodies were prepared at appropriate concentrations as shown in Table 6.

TABLE 6

| Sample | Sample Test Concentration | Volume of TcdB (µL) | Volume of 10% Medium (µL) |
|---|---|---|---|
| MDX1388 (Standard; Medarex anti-TcdB) 2.1 mg/mL | 30 µg/mL | 10 | 690 |
| hPA-41.1 (5.3 mg/mL) (Progenics anti-TcdB) | (i)1000 µg/mL | 10 | 43 |
| | (ii) 10 µg/mL | 10 of (i) | 990 |
| S1 = CAN46G4-1-2 (8.6 mg/mL) | (i)100 µg/mL | 10 | 850 |

TABLE 6-continued

| Sample | Sample Test Concentration | Volume of TcdB (µL) | Volume of 10% Medium (µL) |
|---|---|---|---|
| S2 = CAN46G19-3-2 | (i)100 µg/mL | 10 | 530 |
| S3 = CAN46G13-1-5 (17.5 mg/mL) | (i)1000 µg/mL (ii) 300 µg/mL | 10 150 of (i) | 165 350 |
| S4 = CAN46G24-2-3 (2.7 mg/mL) | 300 µg/mL | 30 | 780 |
| S5 = CAN46G13-1-8 (20.4 mg/mL) | (i)1000 µg/mL (ii) 300 µg/mL | 10 150 of (i) | 194 350 |
| S6 = CAN46G13-1 (5.4 mg/mL) | (i) 1000 µg/mL (ii) 30 µg/mL | 10 15 of (i) | 42 450 |

Dilution Plate Preparation—xCelligence

The following was performed using a U-bottom 96-well plate: (1) Added 112.5 µL of assay media to wells B2-H11, and E12-H12. (2) Added 225 µL of media to wells A12-D12. (3) Added 100 µL of assay media to wells B1-H1. (4) Added 150 µL of sample to corresponding wells as shown below in Table 7. (5) Serially diluted each sample 4-fold by transferring 37.5 µL from Row A and adding to Row B, mixed and repeated down through to Row H. (6) Serially diluted the toxin titration wells 3-fold by transferring 50 µL from row A to row B, mixing, then continuing to serially dilute through to row H. (7) Samples and Toxin Control (TC) were overlayed with 112.5 µL of Toxin B (5 µg/mL). (8) The toxin titration wells were overlayed with 100 µL of assay media. (9) Plate(s) was shaken on a plate shaker until homogeneous. (10) Incubated at 37° C. with 5% $CO_2$ for 60-90 minutes. Table 7 shows the xCelligence dilution plate layout.

TABLE 7 xCelligence Dilution Plate Layout

| | 1 | 2 | 3 | 4 | 5 | 6 | 7 | 8 | 9 | 10 | 11 | 12 |
|---|---|---|---|---|---|---|---|---|---|---|---|---|
| A | Toxin B Titration | Standard (MDX1388) | Internal Control Standard (hPA-41.1) | Sample 1 | Sample 2 | Sample 3 | Standard (MDX1388) | Internal Control Standard (hPA-41.1) | Sample 1 | Sample 2 | Sample 3 | CC |
| B | | | | | | | | | | | | |
| C | | | | | | | | | | | | |
| D | | | | | | | | | | | | |
| E | | | | | | | | | | | | TC |
| F | | | | | | | | | | | | |
| G | | | | | | | | | | | | |
| H | | | | | | | | | | | | |

CC = Cell control (8000 cells/well);
TC = Toxin control (5 ng/mL)

Sample Addition to Cell Plates: (1) Following completion of incubations, the cell and dilution plates were removed from incubator. (2) (3) Transferred 50 µL of samples from dilution plate to appropriate wells of cell plate. (4) Incubated 72 hours at 37° C. with a 5% $CO_2$ overlay.
Data Analysis: (1) Plate data at the 72 hour time point was fit to a 4-parameter logistics (4-PL) curve for each individual sample using Softmax Pro (v.5.4) software. (2) Standard and sample curves were constrained (upper/lower asymptotes, and slope), and the $IC_{50}$ value of the standard was divided by the $IC_{50}$ of the sample to determine a potency estimate (when applicable).

The procedures of this Example were also performed on mAbs.
Results

The murine CAN46 mAbs show similar $EC_{50}$ values to MDX-1388, with CAN46G24 demonstrating an even greater level of neutralization in vitro.

Table 8 summarizes the $EC_{50}$ data for each mAb demonstrating that CAN46G24 and CAN46G13 are the most neutralizing of the clones when compared to MDX1388.

TABLE 8

| Sample | Mean $EC_{50}$ (µg/mL)[1] | n = |
|---|---|---|
| Progenics hPA-41 | 18.3 | 6 |
| CAN46G24 | 44.2 | 2 |
| Medarex MDX1388 | 125.4 | 6 |
| CAN46G13 | 136.0 | 2 |
| CAN46G19 | 141.5 | 2 |
| CAN46G4 | 142.5 | 2 |

[1]The EC50 value is the concentration of antibody which neutralizes 50% of the TcdB toxin dose.

Example 9

*Clostridium difficile* Toxin B In Vitro Neutralization Assays with HT-29 Cells

For the in vitro neutralization assays with HT-29 cells, the percent neutralization ranges in Table 9 were compiled from data from the murine antibodies. The concentration of toxin B used was 5 µg/ml.

TABLE 9

| Antibody Concentration (µg/mL) | Neutralization % of 5 ng/ml Toxin B |
|---|---|
| 100 | 57.8-99.5% |
| 25 | 34.1-102.6% |
| 6.25 | 24.2-76.7% |
| 1.56 | 14-71.9% |
| 0.39 | 7.8-64.6% |
| 0.1 | 0-53.3% |
| 0.02 | 0-28.4% |
| 0.01 | 0-20.4% |

Example 10

Mouse In-Vivo Toxin Challenge

The mouse in vivo toxin challenge test was based on previous publications with some modifications (Babcock et al., Human Monoclonal Antibodies Directed against Toxins A and B prevent *C. difficile*-Induced Mortality in Hamsters, Infection and Immunity (2006)). Balb/c mice weighing 20-30 g were given 250 µg of mAb or controls at day 0 and allowed to rest. After 24 hrs, the mice were given a lethal dose of TcdB (75 ng). This dose kills 90-100% of animals by 24 hours in an unprotected state. The mice were observed for 4 days for signs of abnormality and local and systemic disease. All observations were recorded and the % survival was determined for each treatment group.

Results

Figure 9:
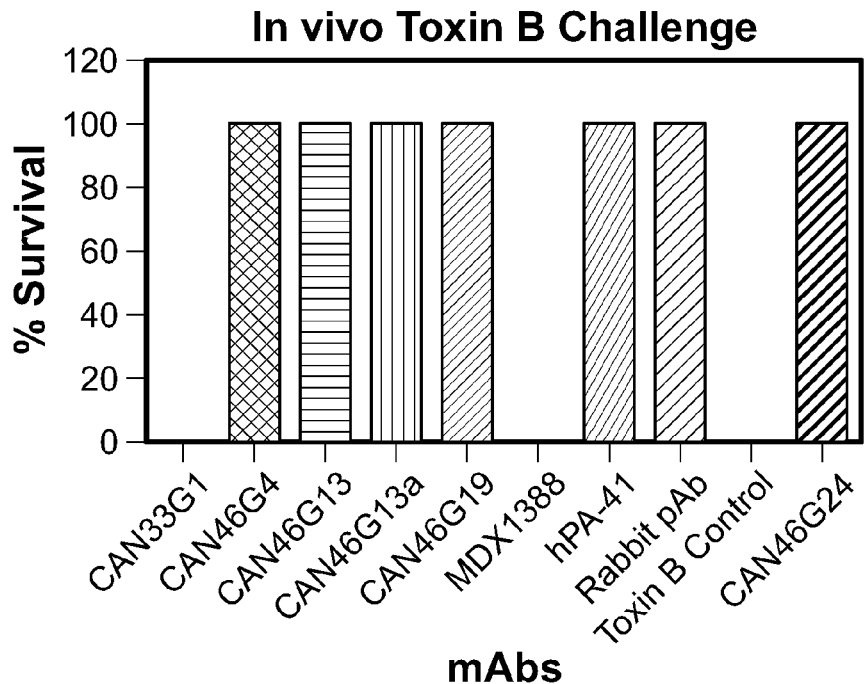
FIG. 9 is a bar graph showing the effects of *C. difficile* toxin B on mouse survival and the efficacy of the murine CAN33 and murine CAN46 mAbs against the toxin B challenge.

As shown in FIG. 9, the study results show that the CAN46 mAbs protect mice against toxin B. All the Can46 mAbs, CAN46G4, CAN46G13, CAN46G13a, CAN46G19 and CAN46G24, were efficacious at the dose of 0.25 mg/mouse in protecting against lethal toxin B challenge with 100% survival 4 days after the toxin B challenge. CAN33G1 was not able to protect mice at a dose of 0.25 mg/mouse with 0% survival 4 days after the toxin B challenge.

Example 11

V Gene Sequencing

RNA was isolated from each of the CAN46G parental hybridoma clonal cell line using the RNeasy Mini Kit. The amplification of V genes from the RNA was performed using the Qiagen OneStep RT-PCR Kit. Several combinations of primer sets were used as follows: for immunoglobulin variable region gene sequence confirmation from the hybridomas, a set of Variable region gene (V-gene) subgroup-specific oligonucleotide primers are used. These could include 5'mVK-Lead-1, 3'KappaConstRT, 5'mVH-Lead-2, 5'mVH-Lead-2A, and 3'mIG1-2C RT. In order to rule out potential contamination from the known and endogenous aberrant kappa light chain V-gene mRNA (found within P3X63 myelomas) (Yuan, X. et al., J. Immunol. Methods, 294: 199-207 (2004)), the RT-PCR was also performed using non-subgroup specific primer sets that could include, 5'mVK-Lead-1A, 5'mVK-Lead-1A, 5'mVK-Lead-3, 5'mVK-Lead-3A, 5'mVH-IGHV1-Lead, 5'mVH-Lead-1, 5'mVH-Lead-3, 5'mVH-Lead-4, and 5'mVH-Lead-5. Refer to FIG. 10 for a list of the primers and their sequences. The primers use degenerate base symbols are IUPAC (International union of pure and applied chemistry) codes for representing degenerate nucleotide sequence patterns.

The results of the PCR amplification reactions were determined by examining the PCR products on an analytical agarose gel, and the visualized bands at approximately 300-500 bp were gel isolated for cloning. The extracted DNA was directly TA cloned into the pCR2.1-TOPO vector using the low melt agarose method in the TOPO TA Cloning manual. Each CAN46G clone reactions were sequenced in both directions using the M13 Forward and M13 Reverse primers. Sequence data was analyzed using DNAStar Lasergene software. FIG. 11 shows the resulting rearranged V-gene sequences compared to IMGT/V-Quest reference directory sets and to the NCBI immunoglobulin blast search. The figure includes results for both the VH and VL sequences of the murine parental clones CAN46G4, CAN46G13a, CAN46G19, CAN46G24, CAN46G13 and CAN33G1. Analysis of CAN46G24 and CAN46G13 revealed identical sequences for VH and VL sequences of the murine parental clones.

Example 12

Humanization of CAN46G

Three humanized IgG/k versions of each CAN46G mAb have been created. For the humanized versions, maximum identity alignment with human germline alleles was used (NCBI website) to help to identify acceptor frameworks. All 6 CDRs corresponding to heavy and light chains were inserted. Other residues were changed or maintained due to surface exposure or involvement in folding or interchain contacts, respectively. This resembles the "superhumanization" approach where CDR matching rather than total framework is used in a variation of the use of germline sequences as acceptor frameworks. In the case of Tan et al., J. Immunol. 2002, 169:1119-1125, the authors used the CDR sequences and tried to match the so called canonical classes of CDRs based upon the Kabat classification system. However, because particular CDRs are germline encoded and particular canonical conformations tend to be found in certain frameworks, the "Superhumanization" method of choosing acceptor frameworks does not in all cases result in the selection of a different candidate acceptor framework. It is empirical and remains to be tested for multiple mAb specificities. This is in part because the straight-up alignment of frameworks for identity inherently encompasses the CDRs as well in the comparison.

cdrCAN46G CDR Grafted Only (FIG. 12)

The best matching human germline allele for both $V_H$ and Vk were used as an acceptor framework for grafting the CDRs. No other changes were made to the acceptor frameworks.

huCAN46 and rehuCAN46 "Human Engineered" (FIGS. 13 and 14)

This humanized versions were generated using a strategy most similar to the "human engineering" strategy used by Studnicka et al. to humanize a murine mAb to CD5 (Studnicka et al, Human-engineered monoclonal antibodies retain full specific binding activity by preserving non-CDR complementarity-modulating residues, *Protein Eng.* 1994 June; 7(6):805-14). Essentially, the closest human germline allele for CAN46G mAbs $V_H$ and Vk were identified, individually, and designed for use as acceptor frameworks. The rehuCAN46 mAbs were further resurfaced by substitution(s) made on surface exposed amino acids to correspond to the adopted human frameworks without disruption of the CDRs.

Example 13

ELISA Assay of Humanized Monoclonal Antibodies

An ELISA was used to test the binding of the mAbs against whole toxin B and toxin A to determine if they were cross-reactive to whole toxin A. The ELISA plate was coated with 400 ng of whole toxin B or toxin A so that coating was equimolar. The wells were blocked with 5% skim milk then probed with serially diluted CAN46 series mAbs (0.1 μg/ml to 1 μg/ml) and binding was detected with a commercial goat anti-human IgG-HRP antibody. Negative and positive controls were also run. The plate was read at 405 nm after 15 min incubation with substrate. The titration data for each antibody is shown in FIG. 37.

Results: As shown in FIG. 37, humanized CAN46 mAbs expressed in CHOK1 SV cells from the CHO construct, have retained the binding characteristics of their respective mouse mAbs and bind to whole toxin B. Humanized CAN46G13a mAbs bind to toxin B at a reduced level compared to the other Cangene mAbs and control mAbs. None of the CAN46 mAbs showed cross-reactivity to toxin A.

Example 14

Western Blot of Humanized Monoclonal Antibodies

A 4-12% gradient SDS-PAGE gel was run for 1.0 hour at 200 volts with a combination of *C. difficile* proteins: whole toxin B, recombinant toxin B fragment 1, recombinant toxin B fragment 4, and whole toxin A. The gel was then transferred to a nitrocellulose membrane for 1 hour at 45 volts. The membrane was blocked for one hour at room temperature or overnight at 4° C. with 5% skim milk in 1×TBST. The mAbs (1° Ab) were diluted in 5% skim milk in 1×TBST at concentrations ranging from 0.038 µg/ml to 5 µg/ml depending on the antibody and used to probe the membrane containing the transferred products for 5 hours at room temperature (RT) or overnight at 4° C. on a shaker. The membranes were then washed with 1×TBST to remove unbound 1° Ab and probed with anti-human IgG-HRP (2° Ab) at a dilution of 1:4000 to 1:5000 for 1.5 hours at RT on a shaker.

Figure 34:
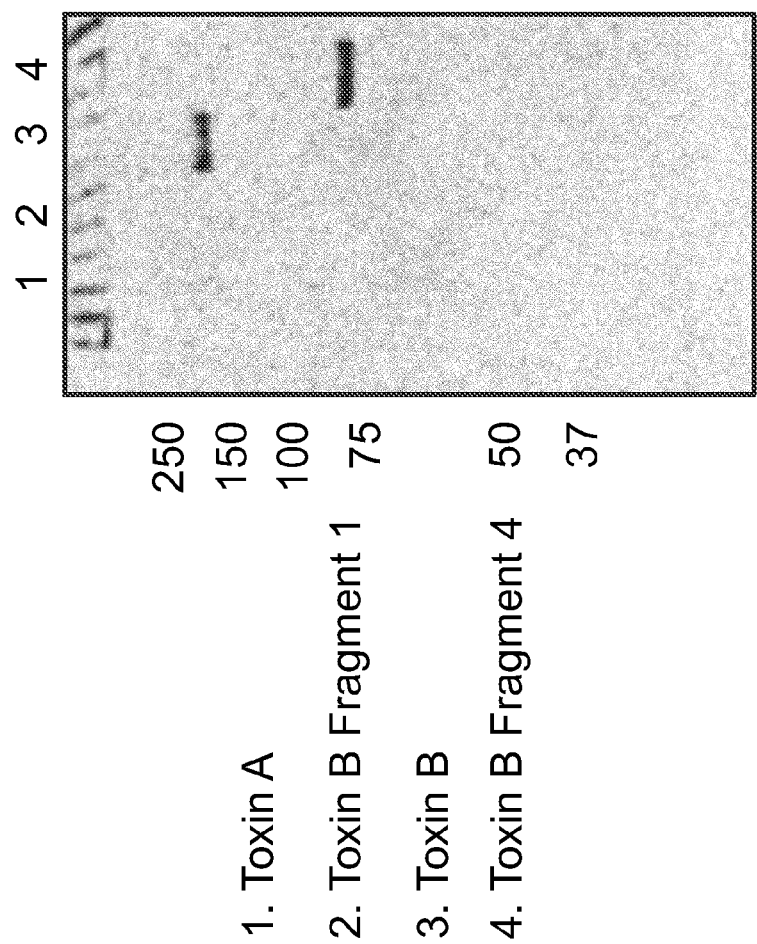
FIG. 34 shows Western immunoblots of humanized CAN46 mAbs purified from CHOKS1V cells expressing the CHO construct.
Figure 35:
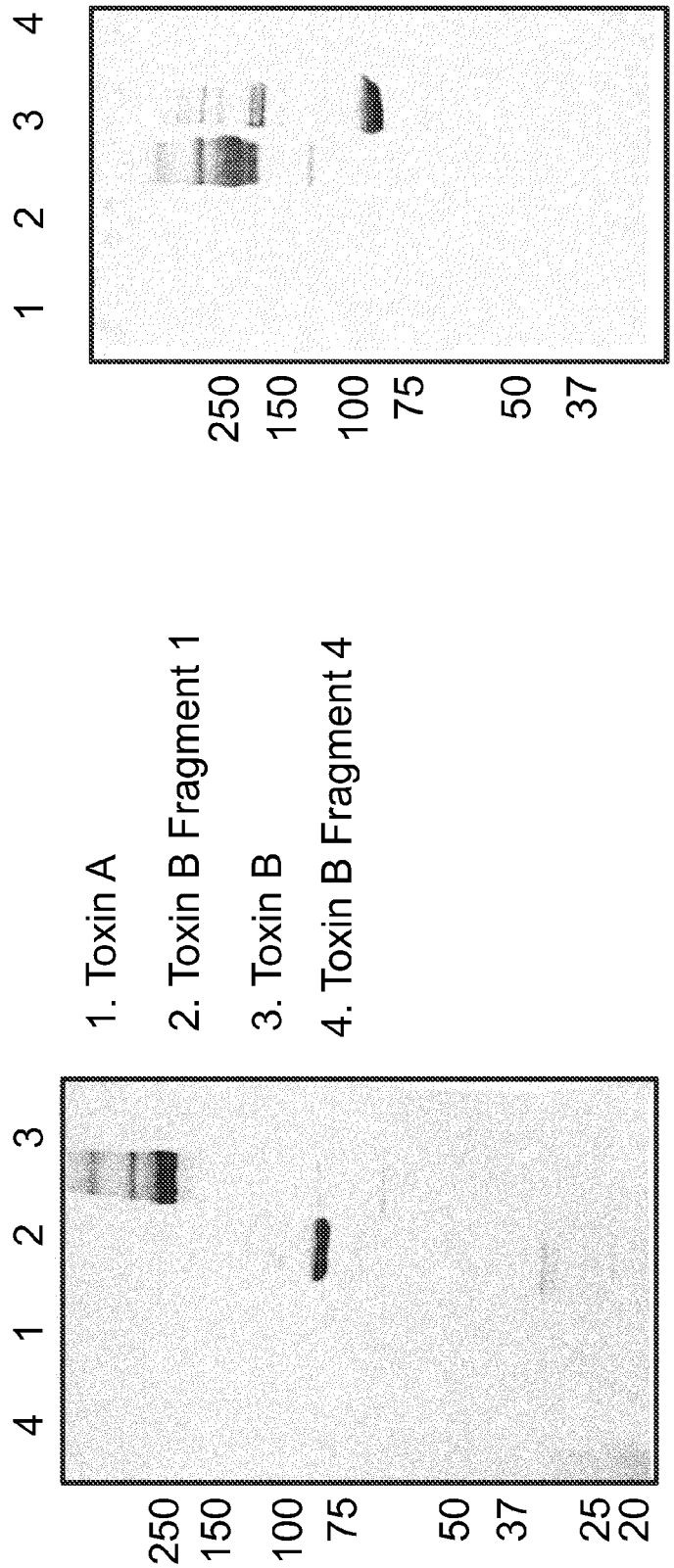
FIG. 35 shows Western immunoblots of humanized CAN46 mAbs purified from HEK293 cells expressing the Per.C6-based construct.

Results: As shown in FIGS. 34 and 35, humanized versions of CAN46G19 and CAN46G24 showed binding to recombinant toxin B fragment 4 (85 kDa) and whole toxin B (280 kDa). Humanized versions of CAN46G13a showed binding to recombinant toxin B fragment 1 (82 kDa) and whole toxin B (280 kDa). None of the humanized CAN46 mAbs tested were cross reactive to Toxin A (308 kDa).

Example 15

In Vitro Neutralization Assay of Humanized Antibodies

An in vitro neutralization assay for *C. difficile* toxins using CT.26 cells was performed to test the neutralization capability of the humanized mAb variants against *C. difficile* toxin B. The CT.26 cells were seeded in a 96 well plate at a concentration of $2.5-3\times10^4$ cells/100 µl/well and the plate was incubated in a 5% $CO_2$ incubator for 4-5 hours at 37° C. Two blank wells containing media (no cells) were also included in the plate.

Toxin and toxin/Ab stock solutions were prepared and diluted to the desired concentrations using Roswell Park Memorial Institute (RPMI) media. The diluted toxin controls and toxin/Ab test mixtures were incubated at room temperature for 1 hour. Thereafter, media was removed from the wells and incubated for 48 hours at 37° C. and 5% $CO_2$ in the presence of either media alone (Cell control), toxin alone (Toxin control), or toxin/Ab mixtures. Plates were returned to incubate for 48 hours at 37° C. and 5% $CO_2$. Next, WST-1 detection reagent was added to each well (10 µl of reagent/100 µl volume in the well) and incubated an additional hour at 37° C. and 5% $CO_2$ prior to shaking the plate for 1 minute and reading absorbance at 450 nm.

Cell viability was determined based on the cell controls as below:

% Cell viability=Mean *OD* of test/Mean *OD* of cell control×100.

Toxin neutralization is calculated by the formula as below:

% Neutralization=(Sample *OD*−Toxin control *OD*)/ Cell control *OD*−Toxin control *OD*)×100.

Results

Figure 15B:
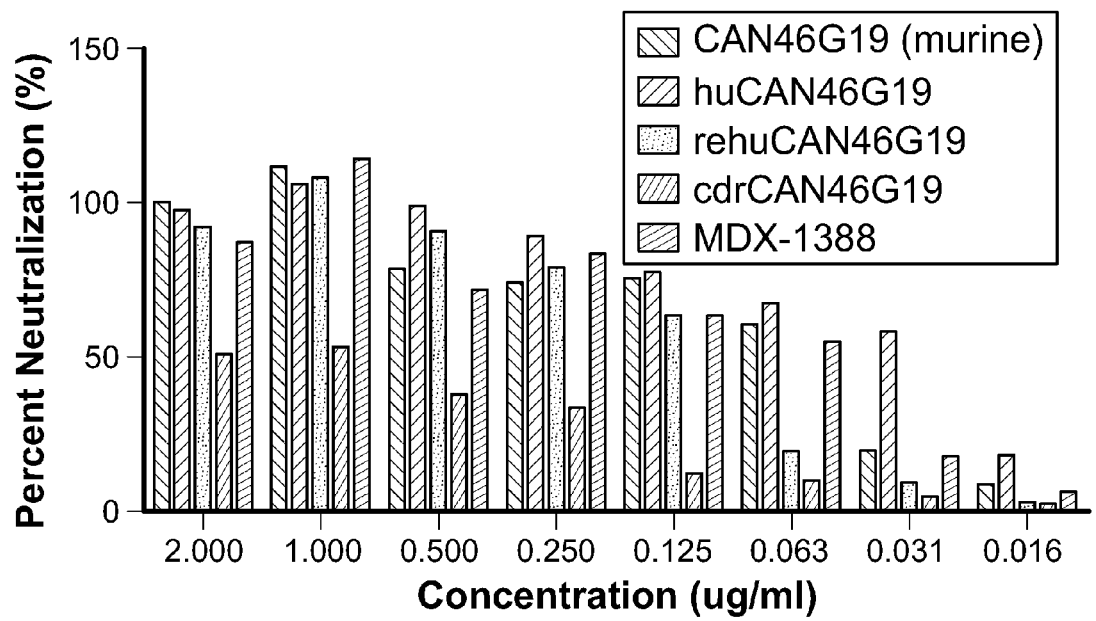
FIG. 15b shows a bar graph depicting in vitro neutralization data for purified humanized CAN46G19 variants in Per.C6 construct expressed in HEK293F cells at 250 pg/ml depicted as a bar graph.

As shown in FIGS. 15a and 15b, the huCAN46G4, rehuCAN46G4, huCAN46G19 and rehuCAN46G19 provided the highest level of protection (neutralization) at all mAb concentrations. These levels of neutralization were comparable to the original murine versions. MDX1388 mAb also shows comparable neutralizing ability while the cdrCAN46G4 and cdrCAN46G19 both show much reduced or no activity when compared to the original murine version or control mAb MDX1388.

For the in vitro neutralization assays with CT.26 wt cells, the percent neutralization ranges in Table 10 were compiled from data from two humanized mAbs huCAN46G4 and huCAN46G19. The concentration of toxin B used was 200-250 pg/ml.

TABLE 10

| mAb | % Neutralization | Antibody Concentration Range (µg/ml) |
| --- | --- | --- |
| huCan46G4 | >20% | 0.03125-2.0 |
| | >30% | 0.0625-2.0 |
| | >40% | 0.0625-2.0 |
| | >50% | 0.125-2.0 |
| | >60% | 0.25-2.0 |
| | >70% | 0.25-2.0 |
| | >80% | 0.5-2.0 |
| | >90% | 1.0-2.0 |
| huCan46G19 | >20% | 0.0156-2.0 |
| | >30% | 0.0156-2.0 |
| | >40% | 0.0156-2.0 |
| | >50% | 0.0156-2.0 |
| | >60% | 0.03125-2.0 |
| | >70% | 0.03125-2.0 |
| | >80% | 0.0625-2.0 |
| | >90% | 0.0625-2.0 |

Figure 19:
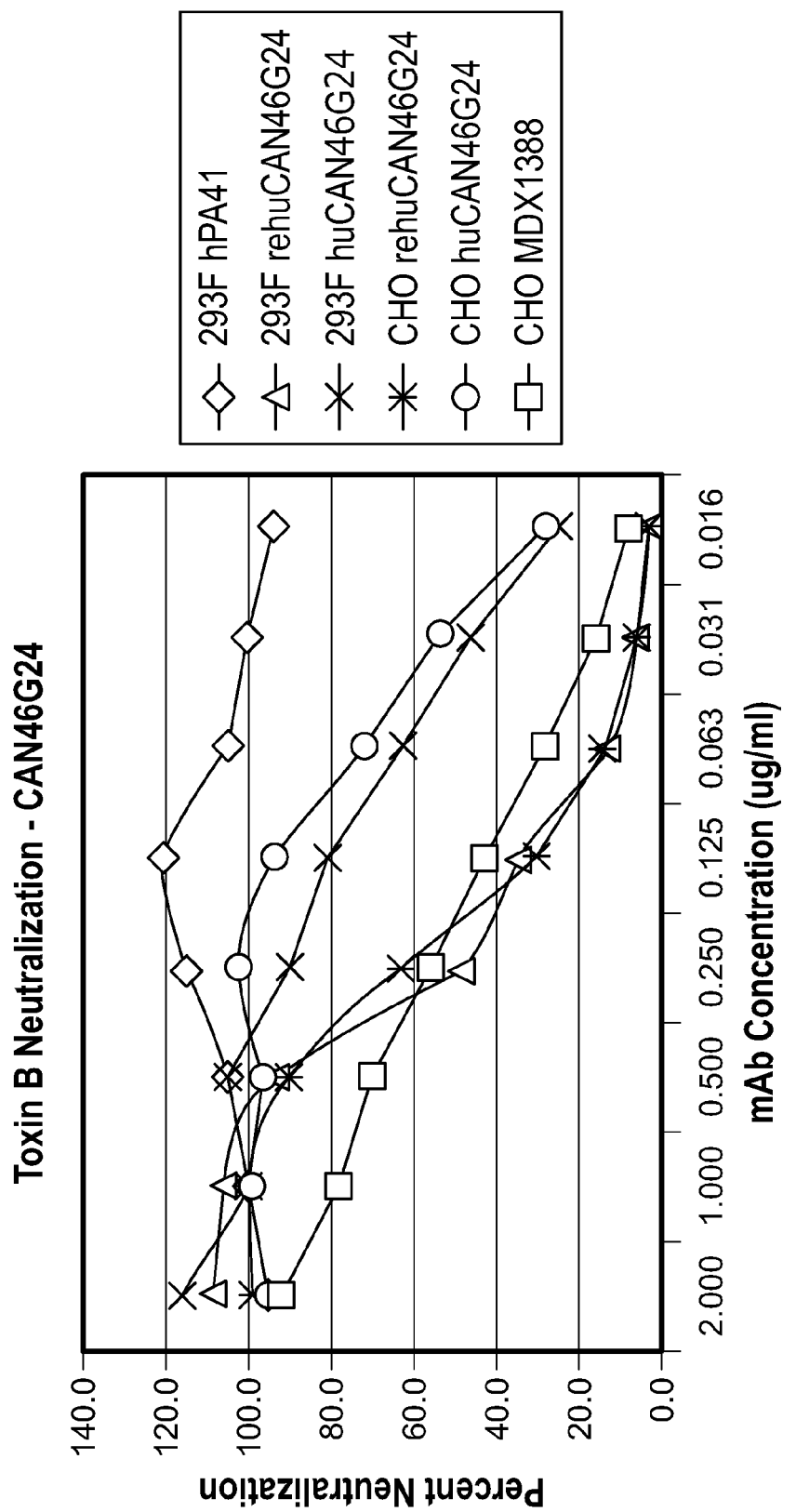
FIG. 19 is a line graph showing the in vitro Toxin B neutralization of the humanized CAN46G24 mAbs
Figure 20:
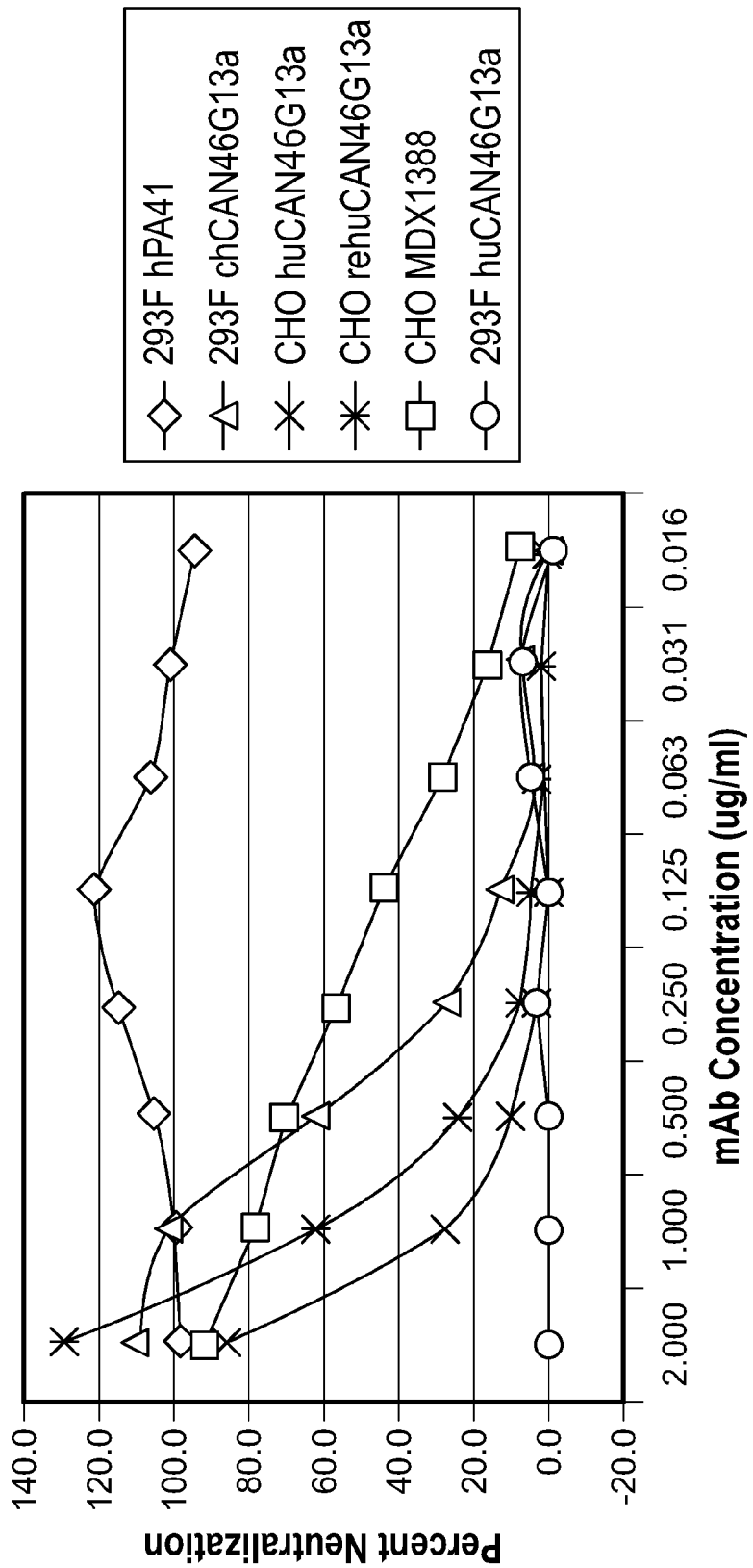
FIG. 20 is a line graph showing the in vitro Toxin B neutralization of the humanized CAN46G13a mAbs
Figure 21:
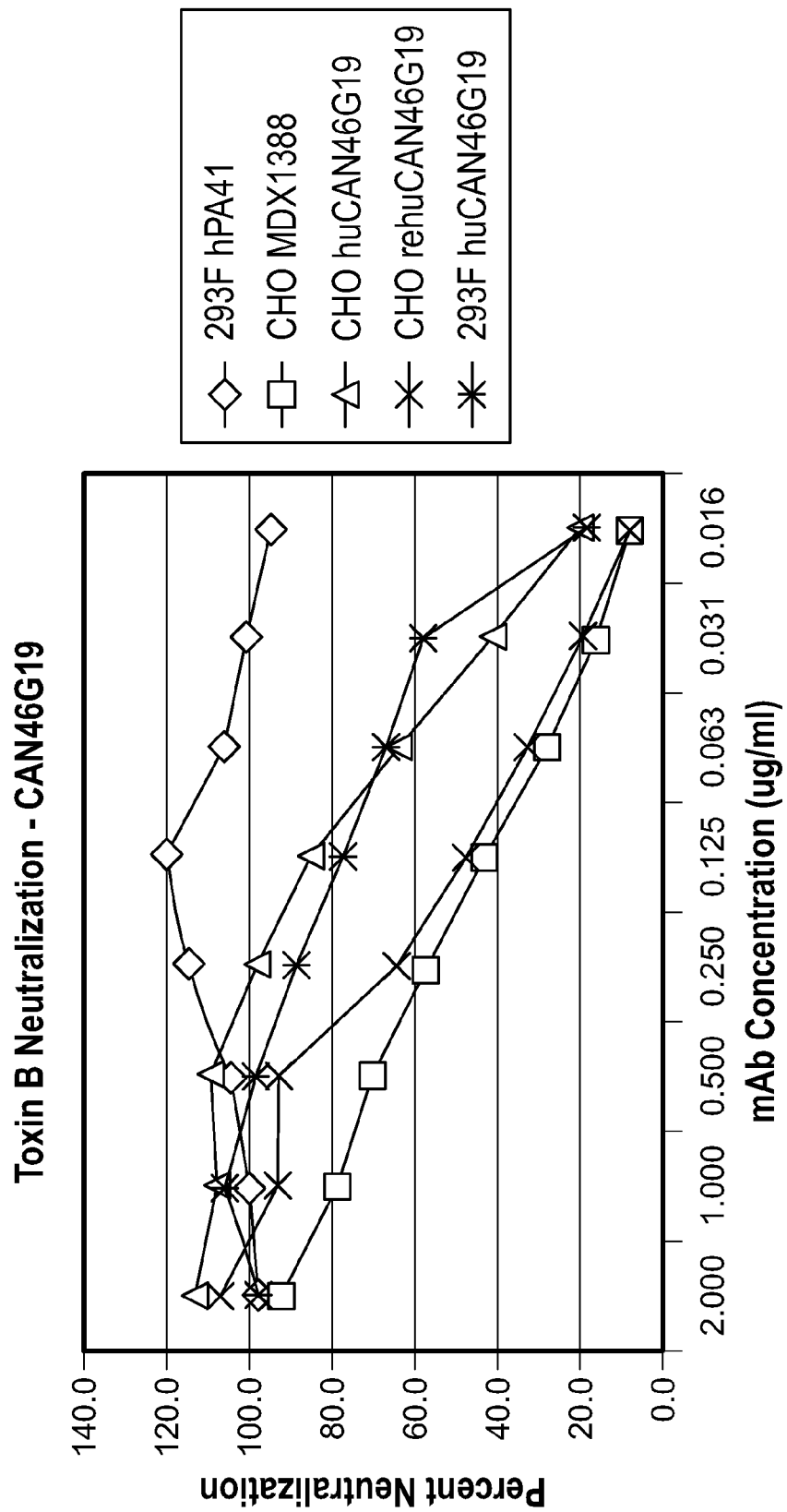
FIG. 21 is a line graph showing the in vitro Toxin B neutralization of the humanized CAN46G19 mAbs.
Figure 22:
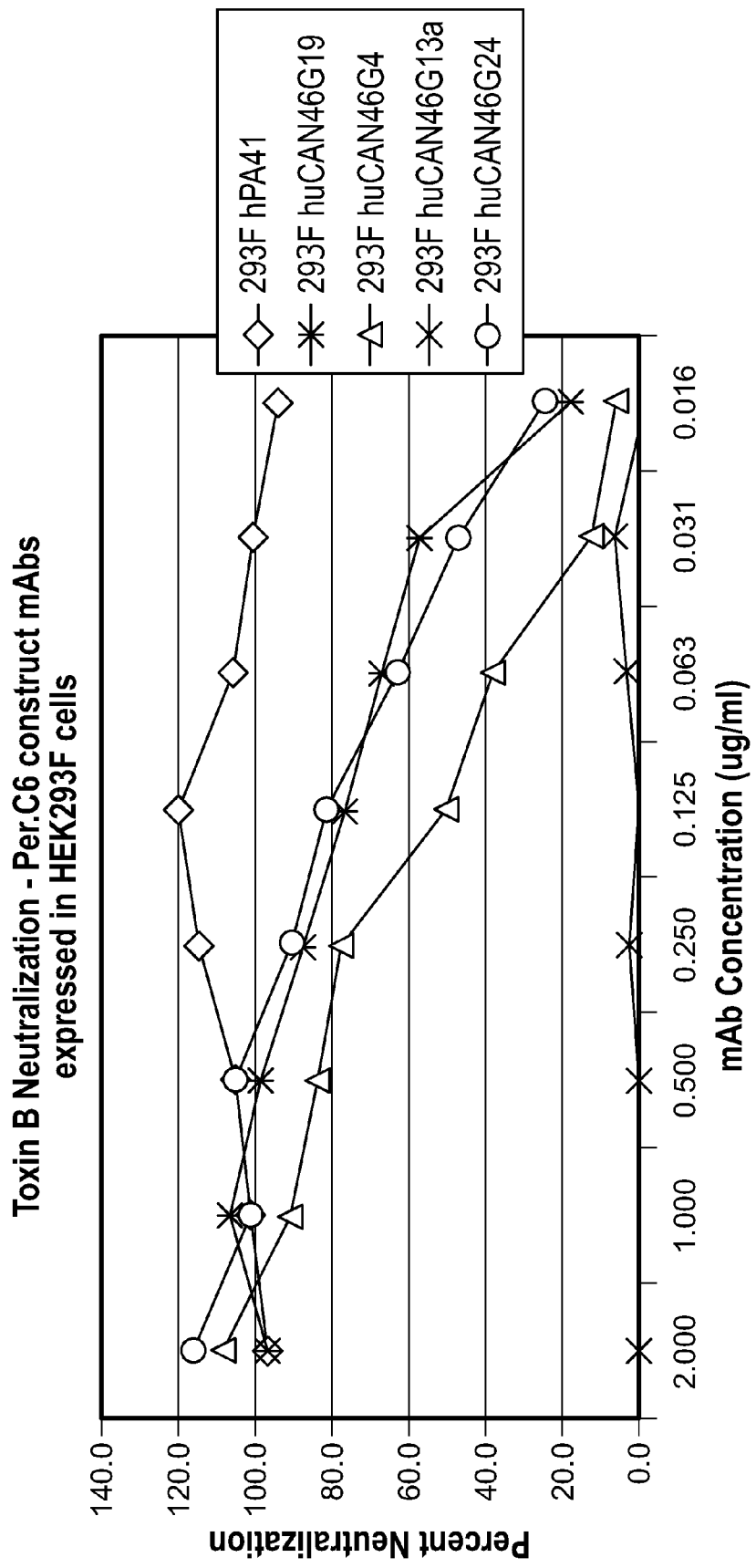
FIG. 22 is a line graph showing the in vitro Toxin B neutralization of the humanized huCAN46G mABs.
Figure 23:
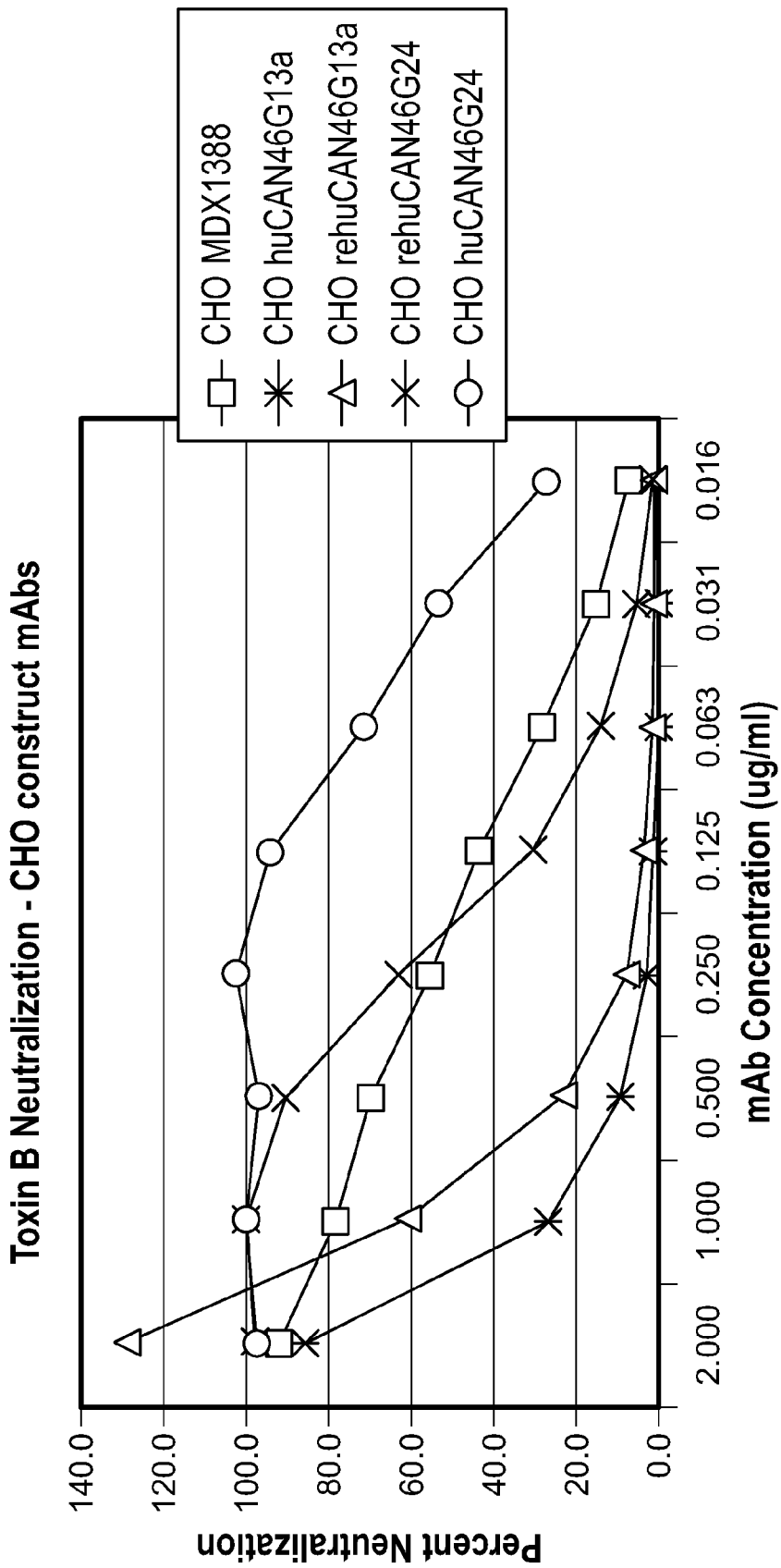
FIG. 23 is a line graph showing the in vitro Toxin B neutralization capabilities of the humanized CAN46G mAbs.

Furthermore, FIGS. 19-23 demonstrate the capacity of CAN46 mAbs purified from either HEK293F cells expressing the Per.C6-based construct (depicted as 293F in the figure legends) or CHOK1 SV cells expressing the CHO-based construct (depicted as CHO in the figure legends) in neutralizing Toxin B challenge against CT-26 cells. Specifically, huCAN46G24 mAbs in both CHO and Per.C6 constructs showed superior neutralization to the rehuCAN46G24 constructs (FIG. 19). In FIG. 20, the chimeric CAN46G13a mAb showed superior neutralization to the rehuCAN46G13a in CHO and the huCAN46G13a in both constructs. In FIG. 21, the huCAN46G19 mAbs in both constructs (CHO and HEK293F) showed superior neutralization to the rehuCAN46G19 constructs. In FIG. 22, the three mAbs, huCAN46G4, huCAN46G19 and huCAN46G24 showed comparable neutralization, with 100% neutralization between 1-2 ug/ml. In FIG. 23, the rehuCAN46G24 showed moderate neutralization of Toxin B and the huCAN46G13a and rehuCAN46G13a mAbs showed weak neutralization of Toxin B, in comparison to huCAN46G24. In FIG. 25, the huCAN46G24 mAb in CHO showed the highest neutralizing capability of the CHO humanized CAN46 mAbs tested, with 100% neutralization at about 0.18 ug/ml. The rehuCAN46G19 and rehuCAN46G24 in CHO showed moderate neutralization, with 100% neutralization at about 0.3 ug/ml. Taken together, these results demonstrate the CAN46 mAbs neutralize the cytotoxic effects of toxin B against CT26 cells in vitro using humanized monoclonal antibodies describe in the invention with specificity against either domain 1 or 4 of toxin B.

Example 16

Mouse In-Vivo Toxin Challenge

The mouse in vivo toxin challenge test was based on previous publications with some modifications (Babcock et al., Human Monoclonal Antibodies Directed against Toxins A and B prevent *C. difficile*-Induced Mortality in Hamsters, Infection and Immunity (2006)). Balb/c mice weighing 20-30 g were given 250 µg of mAb or controls at day 0 and allowed to rest. After 24 hrs, the mice were given a lethal dose of TcdB (75 ng). This dose kills 90-100% of animals by 24 hours in an unprotected state. The mice were observed for 4 days for signs of abnormality and local and systemic disease. All observations were recorded and the % survival was determined for each treatment group.

Results

Figure 16:
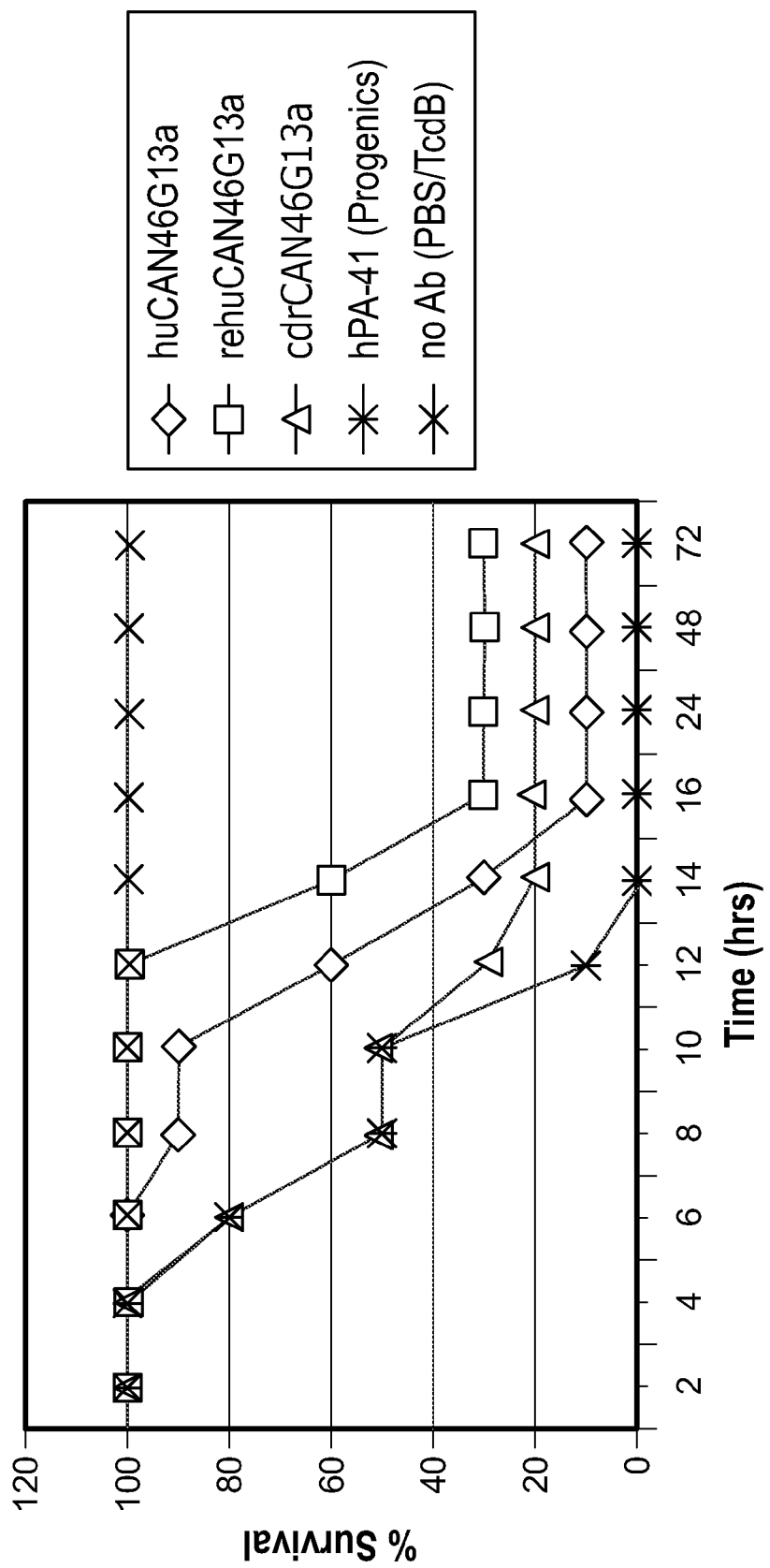
FIG. 16 is a Kaplan-Meier plot showing the effects of C. difficile toxin B on mouse survival and the efficacy of the humanized CAN46G13a mAbs (purified from HEK293F cells expressing the Per.C6-based construct) against the toxin B challenge.
Figure 17:
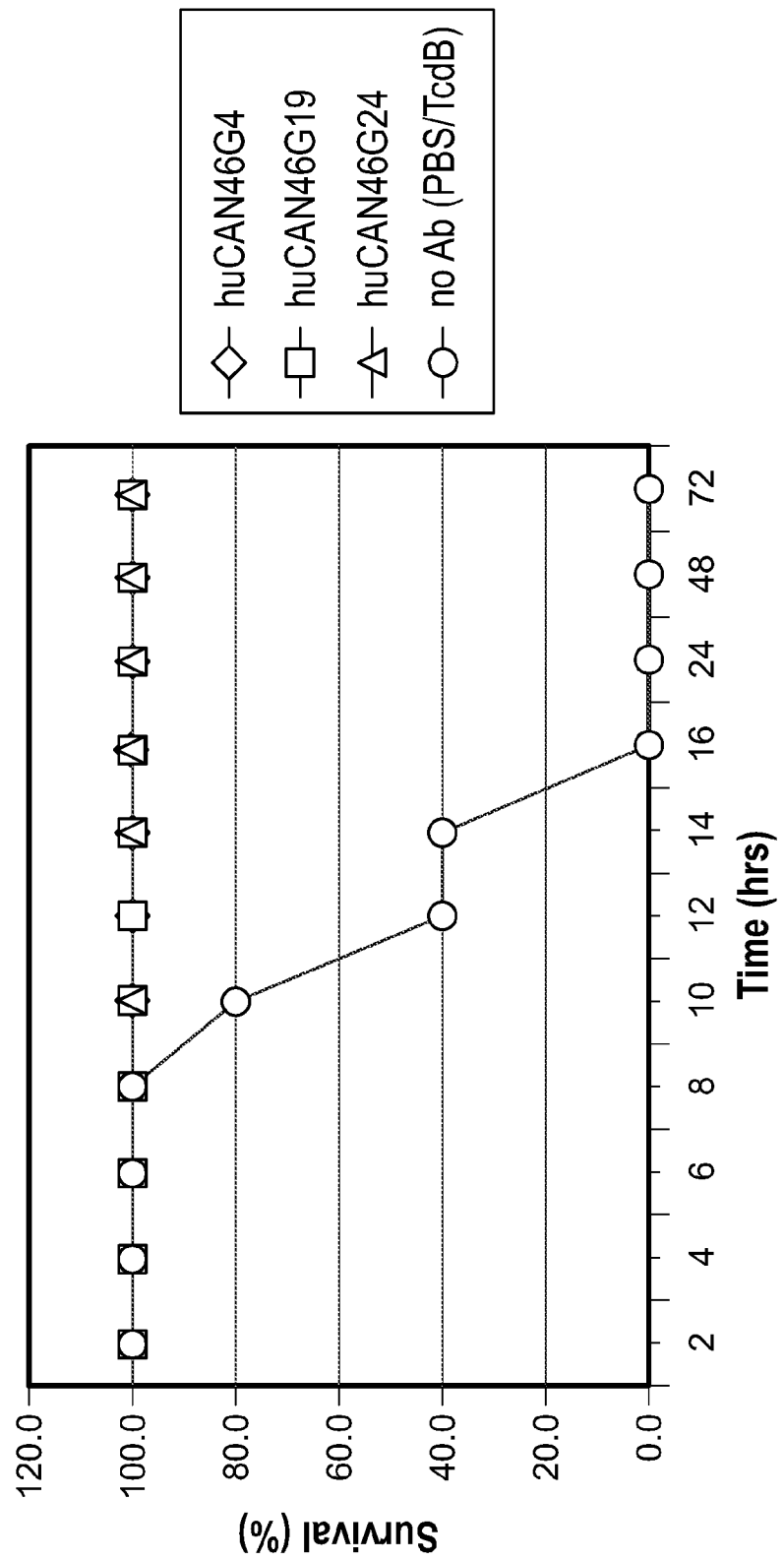
FIG. 17 is a Kaplan-Meier plot showing the effects of C. difficile toxin B on mouse survival and the efficacy of the humanized CAN46 mAbs (purified from HEK293F cells expressing the Per.C6-based construct) against the toxin B challenge.

As shown in FIG. 16-17, the study results show that the humanized versions of CAN46 mAbs (purified from HEK293F cells expressing the Per.C6 based construct) protect mice against toxin B challenge. FIG. 16 shows that all the CAN46G13a humanized mAbs, huCAN46G13a (10%), cdrCAN46G13a (20%), rehuCAN46G13a (30%) were not efficacious at the dose of 0.25 mg/mouse in protecting against lethal toxin B challenge 3 days after the toxin B challenge. FIG. 17 shows that huCAN46G4, huCAN46G19, huCAN46G24 were efficacious at the dose of 0.25 mg/mouse in protecting against lethal toxin B challenge with 100% survival 3 days after the toxin B challenge.

Example 17

Total Human IgG ELISA

The total human IgG ELISA was performed using the Human IgG ELISA Quantitation Set from Bethyl Laboratories (Cat No. E80-104) and following the kit instructions. The ELISA was performed on sera samples collected from mice undergoing Toxin B challenge. The sera was collected from the mice 12 hours after mAb injection, which was 12 hours prior to toxin challenge, and then again at the end of the study, day 4. The time between the first and second sample was 84 hours. The linear rate of decline of detectable circulating mAb was determined by the following calculation:

[(conc. of mAb in serum 12 hours pre-challenge)–
(conc. mAb in serum 96 hours post challenge)]/
84 hours Results:

As shown in FIG. 18, the concentrations of mAb were relatively stable over an 84 hour period in the mice injected with either the huCAN46G24 mAb (75 ug & 250 ug), or the rehuCAN46G19 mAb (250 ug). The mice injected with either huCAN46G19 (75 ug & 250 ug) or rehuCAN46G24 (250 ug) lost between 50-75% of detectable circulating mAb. Levels of circulating mAbs in the mice, for all mAbs tested, did not fall below 12 ug/ml after the 4 days post challenge. The mAbs tested were purified from HEK293F cells expressing the Per.C6-based construct.

Example 18

Toxin B Affinity

Affinity of the humanized CAN46 mAb variants and toxin B was measured using biolayer interferometry. Stock antibodies were diluted to 1 mg/ml with PBS and then biotinylated for 30 minutes at room temperature using a commercially-available kit (Fisher Cat No. P121329) using a ratio of 1 mmol biotin/1 mmol Ab. Desalting columns were used to remove excess or unbound biotin. The Octet QKe instrument was equipped with either streptavidin (SA), anti-human Fc (AHC), or anti-mouse Fc (AMC) sensors. The sensors were pre-washed in PBST until a stable baseline was obtained. The mAbs at a concentration of 40 ug/ml were coupled/loaded onto each of the 8 sensors. The sensors were washed again in PBST until a stable baseline was obtained and all unbound mab was removed. The sensors were associated with a dilution series (50 nM to 0 nM) of toxin B and then washed in PBST to assess dissociation of the toxin from each mAb. The Results were analyzed using ForteBio Data Analysis Software to determine the equilibrium dissociation constant (KD) or the strength of binding, the rate at which the mAb:toxin complex forms (kon), and the rate at which the mAb:toxin complex dissociates (kdis).

Figures 36, 37:
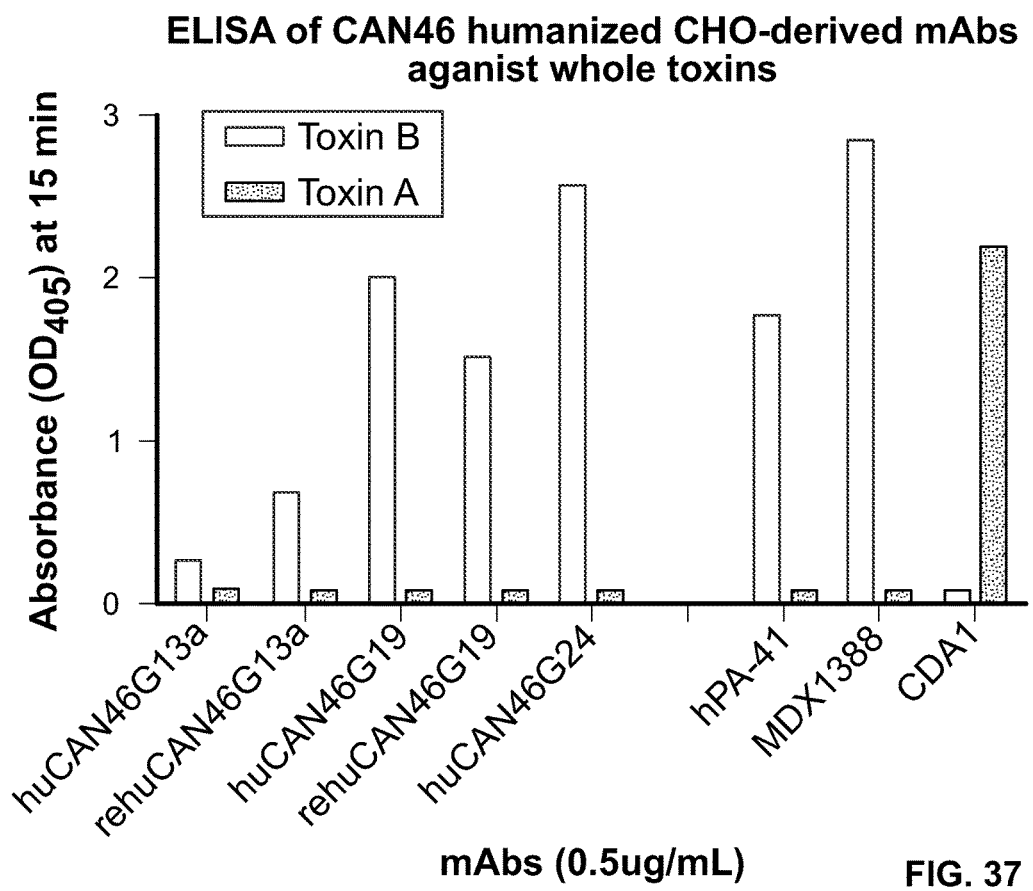
FIG. 36 is a table showing the affinity analysis of purified Tcd B humanized mAbs CAN46G24 and CAN46G13a from CHOK1SV cells expressing the CHO-based constructs.
FIG. 37 is a bar graph showing the binding specificities of humanized CAN46 mAbs against Toxin B and Toxin A.

Results:

Antibodies tested were purified from HEK293F cells expressing the Per.C6-based construct. As shown in FIG. 24, the huCAN46 mAbs had smaller KD values and therefore higher affinity for TcdB when compared to their murine counterparts. Although the rehuCAN46 mAbs did have smaller KD values from their murine counterparts, they did not have significantly different Kdis values. All humanized mAb versions showed similar KD values, 0.15-0.42M, indicating a similar level of high affinity for toxin B. Similar analysis of humanized variants purified from CHOK1 SV cells expressing the CHO-based construct are shown in FIG. 36. Similar affinity constants were obtained for the CAN46G13a variants, while CAN46G24 variants exhibited subnanomolar affinity constants following the humanization protocol.

Example 19

*Clostridium difficile* Clinical Isolate Toxin B Neutralization Assay with Vero Cells Using the xCELLigence™ Platform Cell Line—Vero cells are monkey kidney fibroblasts. These cells have been selected since they are highly sensitive to toxin B while relatively resistant to toxin A.

xCELLigence™ Platform

The xCELLigence™ is a real-time label-free cell analysis (RTCA) system based on an electronic impedance cell sensing measurement that evaluates changes in cell characteristics in real-time. Cell growth and cytotoxicity can be detected by monitoring the increase or decrease of a dimensionless parameter called cell index (CI). When adherent cells are cultured within the custom 96-well plate, cell growth characteristics can be monitored in real-time by changes in electrical impedance as measured by the gold electrodes embedded within each well.

The CI measurement is based upon four parameters: 1) cell number, 2) cell size and morphology, 3) cell viability, and 4) cell adhesion. An increase in any one of these parameters leads to an increase in the CI. Conversely, a decrease in any one of these parameters leads to a decrease in CI.

*C. Difficile* Clinical Isolate Culture Supernatants Preparation

Nine epidemic prevalent clinical isolates and one reference strain (ATCC43255) were selected for toxin B neutralization test. Spore stocks were streaked on brain heart infusion+0.1% taurocholate (BHI-T) plates and cultured at 35° C. in anaerobic chamber for 48 h. Single clones were transferred to 50 ml TY medium and cultured for 4 days. Bacteria cultures were centrifuged and supernates filtered through 0.2 µm filter. Supernatants were stored in 4° C. and cultured in BHI-T plates for 48 h to confirm sterilization. Culture supernatants were diluted with Vero medium to pre-determined concentrations (Table 11) that induces 80-90% cytotoxicity on vero cells.

TABLE 11

*C. difficile* strains for toxin B neutralization and dilutiong factors for cytotoxicity

| Description | Toxinotype | Dilution factors for supernatants |
|---|---|---|
| ATCC 43255 | 0 (A+B+CDI−) | 1:300,000 |
| C. difficile K-14 | 0 (A+B+CDI−) | 1:1,000 |
| C. difficile Y-2 | 0 (A+B+CDI−) | 1:8,200 |
| C. difficile B1 | 0 (A+B+CDI−) | 1:8,000 |
| C. difficile J9 | 0 (A+B+CDI−) | 1:500 |
| C. difficile BI-6 | III (A+B+CDI+) | 1:10,000 |
| C. difficile BI-1 | III (A+B+CDI+) | 1:16,500 |
| C. difficile BI-17 | III (A+B+CDI+) | 1:10,000 |
| C. difficile CF-2 | VIII (A-B+) | 1:2,000 |
| C. difficile R23 | 0 (A+B+CDI−) | 1:350 |

Vero cells were trypsinized from a T-75 flask and added to a Roche 96-well E-plate® at 7500 cells/well, and incubated about 4 hours at 37° C. During the 4-hr incubation, anti-TcdB mAb dilutions were prepared on a 96-well U-bottom plate. Samples were then mixed with an appropriate dilution of TcdB (0.5-50 ng/mL range, dilution dependant on toxin lot) by repetitive pipetting. The plate is then incubated at 37° C. for about 60 minutes. After completion of initial cell incubation, the cells were overlayed with the toxin/mAb preparation and incubated for a minimum of 72 hours at 37° C. Impedance measurements were taken every 30 minutes throughout the incubation period. This data is plotted in real-time using the xCELLigence™ RTCA software. A single time point representing the optimal time point (either for toxin cytotoxicity or neutralization) was selected. The data from that single time point is used to create a 4-parameter logistic curve for analysis. If sample potency was being determined, the sample curves are constrained against the "reference" sample. Curve constraint is used to constrain the upper/lower asypmtotes, and slope of the curve. This allows for each curve to shift horizontally along the x-axis based upon the curves $IC_{50}$ value. For potency determination the $IC_{50}$ value of the standard is divided by the IC50 value of the sample.

Cell Attachment Phase—xCelligence™ Method

This phase included the following steps. (1) Trypsinized cells in source flask. (2) Added 2 mL of trypsin to flask and washed cells to remove traces of media then aspirated. (3) Added 3 mL of trypsin and incubated at 37° C. for approximately 8 minutes. (4) Added 6 mL of assay media to flask. (4) Centrifuged suspended cells at 368×g for 8 minutes. (5) Aspirated supernatant and resuspended cells with 6 mL of assay media. (6) Counted cells and calculated required volume of cells for plating at 7500 cells/well. (7) To a 96 well E-plate added 100 μL of assay media to all wells. (8) Performed background reading on xCelligence. (10) Added 50 μL of 1.5×10$^5$ cells/mL suspension to these wells for a final 7500 cells/well seeding density. (11) Incubated plate at room temperature for 20-30 minutes to allow cells to settle evenly. (12) Placed plate in 37° C. incubator with 5% $CO_2$ overlay 4-5 hours.

Toxin B Preparation: (1) Prepared Toxin B overlay by diluting primary stock (409.6 μg/mL) to 200 pg/mL (2) Prepared Toxin B for titration by diluting primary stock to 80 ng/mL. (3) Dilutions of primary stock were performed as shown in Table 12.

TABLE 12

| Sample | TcdB Test Concentration | Volume of TcdB (μL) | Volume of 10% Medium (μL) |
|---|---|---|---|
| Toxin Overlay (Stock = 543 μg/mL) | (i) 5.43 μg/mL | 3 | 297 |
| | (ii) 54.3 ng/mL | 3 of (i) | 297 |
| | (iii) 200 pg/ml | 3 of (ii) | 811.5 |

Sample Preparation: To test potency, all the monoclonal antibodies were prepared at appropriate concentrations as shown in Table 13.

TABLE 13

| Sample | Sample Test start Concentration ($10^{-6}$ M) | Volume of TcdB (μL) | Volume of 10% Medium (μL) |
|---|---|---|---|
| MDX1388 (Standard; Medarex anti-TcdB) 1.5 mg/mL | 300 μg/mL | 30 | 120 |
| hPA-41.1 (1.5 mg/mL) (Progenics anti-TcdB) | 300 μg/mL | 30 | 120 |
| HuCAN46G24-2-3 (2.5 mg/mL) | 300 μg/mL | 18 | 132 |
| rehuCAN46G24 (1.25 mg/ml) | 300 μg/mL | 36 | 114 |
| Hu CAN46G13a (1.5 mg/mL) | 300 μg/mL | 30 | 120 |
| rehuCAN46G13a (1.5 mg/mL) | 300 μg/mL | 30 | 120 |
| HuCAN46G19-3-2 (2.5 mg/mL) | 300 μg/mL | 18 | 132 |

Dilution Plate Preparation—xCelligence

The following was performed using a U-bottom 96-well plate: (1) Added 45 μL of assay media to wells B3-H9, and C10-D11. (2) Added 100 μL of media to wells B10-11. (3) Added 50 μL of diluted mAbs ($10^{-6}$M or 300 μg/ml)) to corresponding wells B2-H2 as shown below in Table 14. (4) Serially diluted each sample 10-fold by transferring 5 μL from Row 2 and adding to Row 3, mixed and repeated through to Row 9, discarded 5 μl from Row 9. (5) Add 45 μl diluted toxin B (200 pg/ml) to C10, 11; Add 45 μl diluted isolate culture supernatant (Table 11) to D10, 11 (6) Add diluted isolate 1 culture supernatant (Table 11) to wells B2-H9, (7) Plate(s) was shaken on a plate shaker until homogeneous. (8) Incubated at 37° C. with 5% $CO_2$ for 60 minutes. Table 13 shows the xCelligence dilution plate layout.

TABLE 14 xCelligence Dilution Plate Layout: test of neutralization of *C. difficile* culture supernatant toxin B. Plate layout: Isolate 1, diluted culture supernatant from selected *C. difficile* isolates; CC: culture medium control; TC: pure toxin B control (100 pg/ml).

| | 1 | 2 | 3 | 4 | 5 | 6 | 7 | 8 | 9 | 10 | 11 | 12 |
|---|---|---|---|---|---|---|---|---|---|---|---|---|
| A | | $10^{-6}$ M | $10^{-7}$ M | $10^{-8}$ M | $10^{-9}$ M | $10^{-10}$ M | $10^{-11}$ M | $10^{-12}$ M | $10^{-13}$ M | | | |
| B | Isolate 1 | MDX-B | | | | | | | | CC | CC | |
| C | | hPA-41 | | | | | | | | TC | TC | |

TABLE 14-continued xCelligence Dilution Plate Layout: test of neutralization of *C. difficile* culture supernatant toxin B. Plate layout: Isolate 1, diluted culture supernatant from selected *C. difficile* isolates; CC: culture medium control; TC: pure toxin B control (100 pg/ml).

| | 1 | 2 | 3 | 4 | 5 | 6 | 7 | 8 | 9 | 10 | 11 | 12 |
|---|---|---|---|---|---|---|---|---|---|---|---|---|
| D | | HuCAN46G24-2-3 | | | | | | | | isolate | isolate | |
| E | | reHuCAN46G24 | | | | | | | | | | |
| F | | HuCAN46G13a | | | | | | | | | | |
| G | | reHuCAN46G13a | | | | | | | | | | |
| H | | HuCAN46G19-3-2 | | | | | | | | | | |

Sample Addition to Cell Plates: (1) Following completion of incubations, the cell and dilution plates were removed from incubator. (2) Transferred 50 μL of samples from dilution plate to appropriate wells of cell plate. (3) Incubated 72 hours at 37° C. with a 5% $CO_2$ overlay.

Data Analysis: (1) Plate data at the 72 hour time point was fit to a 4-parameter logistics (4-PL) curve for each individual sample using Softmax Pro (v.5.4) software. (2) Standard and sample curves were constrained (upper/lower asymptotes, and slope), and the $IC_{50}$ value of the standard was divided by the $IC_{50}$ of the sample to determine a potency estimate (when applicable).

Results

Figure 26:
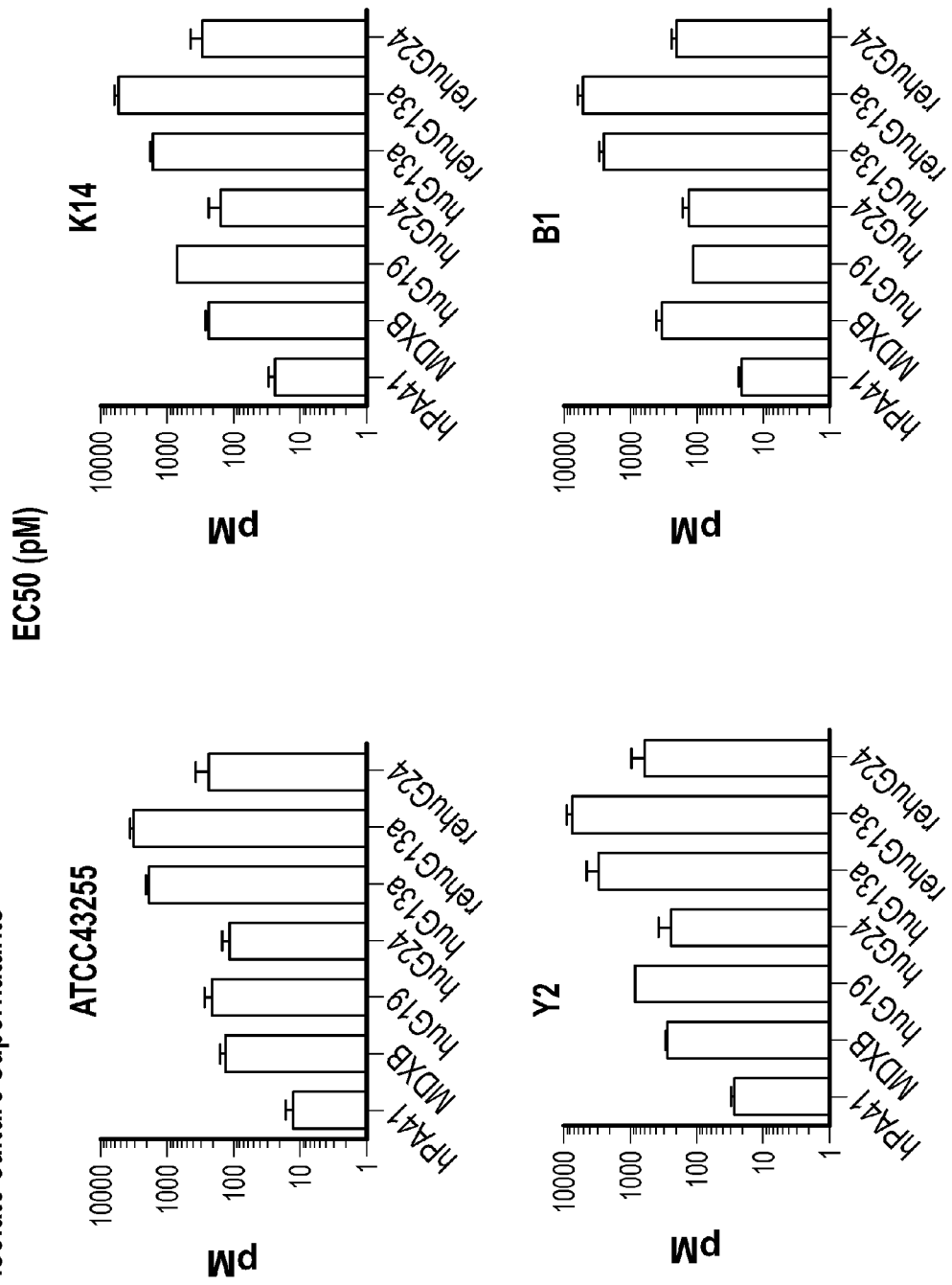
Figure 26:
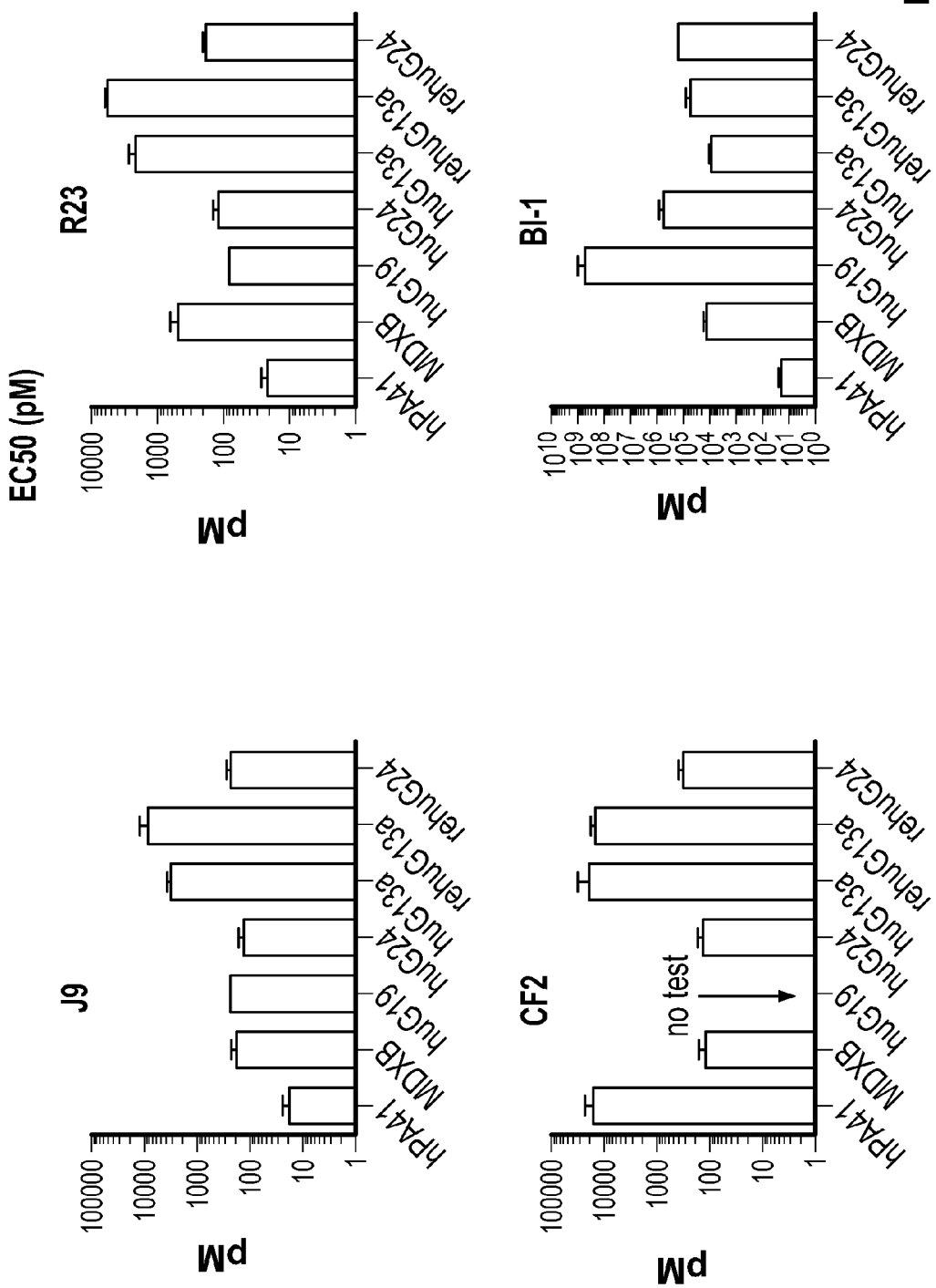

FIG. 26 summarizes the $EC_{50}$ data for each mAb demonstrating the ability of humanized CAN46G24, CAN46G13a, and CAN46G19 variants produced in CHOK1SV cells to neutralize the toxicity of *C. difficile* clinical isolates. The bar graphs show the EC50 of each mAb against a specific clinical isolate of *C. difficile*. The isolates include one reference strain (ATCC43255) and 9 representative clinical isolates including three hypervirulent 027 strains (BI-1, BI-6, and BI-17). The EC50 was different for each mAb against each clinical isolate. In general, humanized CAN46G24 and CAN46G19 mAbs neutralized non-NAP1 strains, whereas humanized CAN46G13a mAbs were more effective against NAP1 strains Example 20

Efficacy of Humanized Toxin B mAbs in a Hamster Gastrointestinal Primary Infection Model with *C. difficile* B1 Spores Groups of hamsters received 4 injections of anti-toxin A and anti-toxin B mAbs with either high (50 mg/kg body weight) or low dosages (20 mg/kg bodyweight) each day for four days before infection. On the third day of antibody injection, hamsters were also given 10 mg/kg (bodyweight) of clindamycin to clear gut bacteria flora to enhance *C. difficile* spore infection. Coincident with the last day of antibody injection, hamsters were intragastrically given 140 B1 spores and clinical signs and survival were recorded twice a day for 22 days, along with the body weights every two days. At day 22 after infection, all surviving hamsters were euthanized and sera collected for anti-toxin antibody levels assayed by Bio-Plex® MAGPIX™ multiplex assay. Refer to Table 15 for full experimental procedure and table 16 for the injections given to each group of hamsters.

The raw data of survival, clinical sign and body weights were analyzed by Graphpad Prism 5 software. Serum was collected prior to antibody injection (Day-3) for all animals and day 22 for all surviving hamsters. Serum specimens were analysed for the injected toxin-specific antibodies by Magplex.

TABLE 15

Experimental Procedure

| Day | Action |
|---|---|
| −8 | Receive and acclimatize hamsters. Two hamsters per cage with free access to sterile food and water and exhibit no clinical symptoms of CDI. |
| −3 | Administer antitoxins (50 mg/kg each, 200 μl, i.p.) to Group B and C, Administer antitoxins (20 mg/kg each, 200 μl, i.p.) to Group D and E. Administer saline (200 μl, i.p.) to Group A |
| −2 | Administer antitoxins (50 mg/kg each, 200 μl, i.p.) to Group B and C, Administer antitoxins (20 mg/kg each, 200 μl, i.p.) to Group D and E. Administer saline (200 μl, i.p.) to Group A |
| −1 | Administer antitoxins (50 mg/kg each, 200 μl, i.p.) to Group B and C, Administer antitoxins (20 mg/kg each, 200 μl, i.p.) to Group D and E. Administer saline (200 μl, i.p.) to Group A. Clindamycin (10 mg/kg) administration to all hamsters. |
| 0 | Administer antitoxins (50 mg/kg each, 200 μl, i.p.) to Group B and C, Administer antitoxins (20 mg/kg each, 200 μl, i.p.) to Group D and E. Administer saline (200 μl, i.p.) to Grp A. Gavage all hamsters with 140 spores *C. difficile* strain B1. |
| 1-22 | Monitor hamsters twice a day for clinical signs and record clinical scores up to day 21 after infection. Measure body weights every second day of surviving hamsters. Euthanize moribund animals, |
| 22 | Terminate experiment and euthanize any surviving animals. |

TABLE 16

Group Assignments

| groups | hamster | Spores/hamster | other |
|---|---|---|---|
| A | 5 | 140 | No anti-toxins (negative control) |
| B | 7 | 140 | CDA1/MDX-1388 50 mg/kg treatment |
| C | 7 | 140 | HeCan20G2/HuCAN46G24 50 mg/kg treatment |
| D | 8 | 140 | CDA1/MDX-1388 20 mg/kg treatment |
| E | 8 | 140 | HeCan20G2/HuCAN46G24 20 mg/kg treatment |

Figure 27:
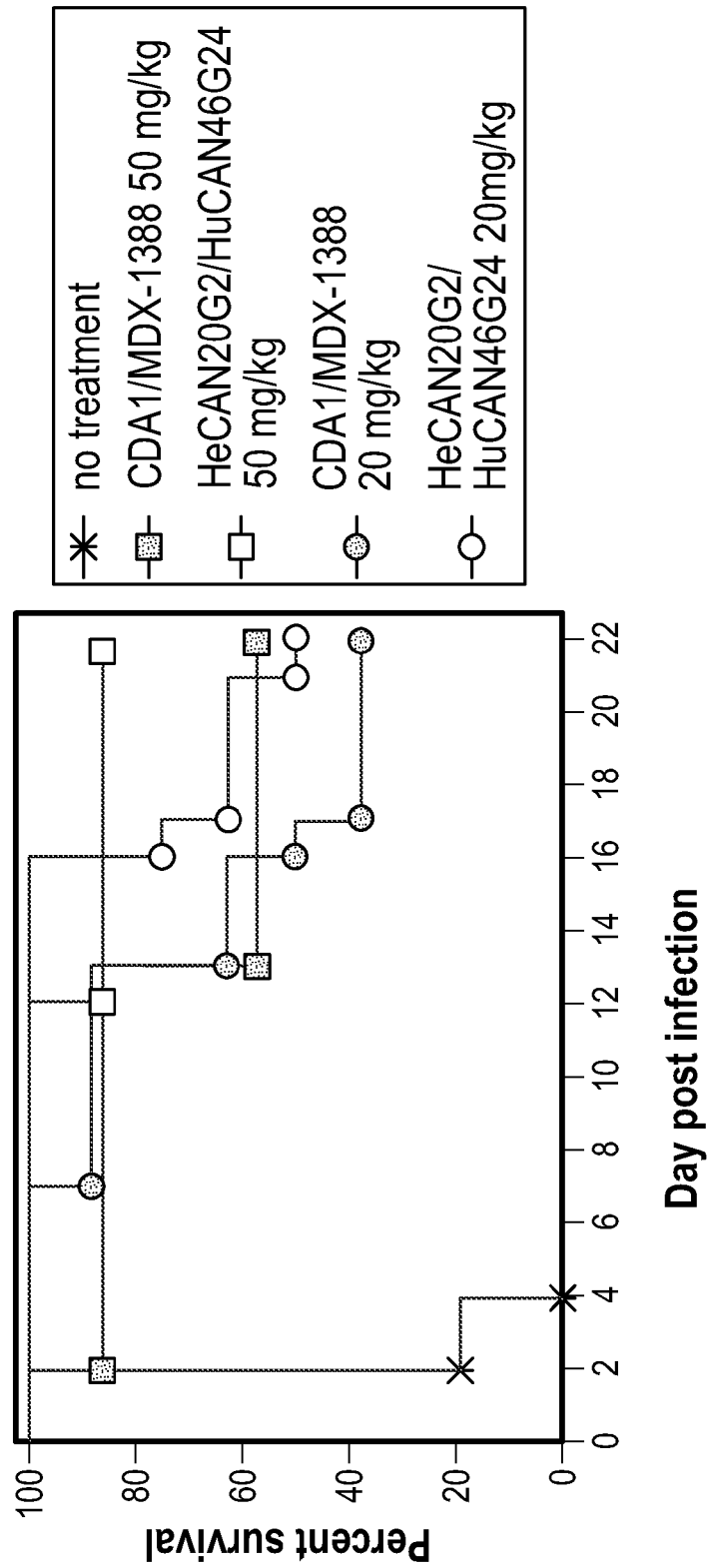
FIG. 27 is a Kaplan-Meier plot showing the protective effects on hamster survival of human CDA1/MDX1388 and humanized HeCAN20G2/HuCAN46G24mAbs doses against infection with B1 C. difficile spores.

Results:

Hamsters were infected with 117CFU/animal of *C. difficile* B1 spores and were observed twice per day for 22 days. Anti-TcdA and TcdB mAbs, purified from CHOK1 SV cells expressing the CHO-based construct, were administered once a day at 50 mg/kg or 20 mg/kg for −3, −2, and −1 days prior to infection, and 0 days with spores on the day of infection. Verification of B1 spores and viability was performed by serial dilutions of B1 spore inoculums plated on brain heart infusion+0.1% taurocholate (BHI-T) agar and incubated in anaerobic chamber for 48 hours, and confirmed 117 CFU/hamster was administered during infection. FIG. 27 shows the survival data from the hamster primary infection model. Four of five control hamsters (Group A; no treatment) died within 48 h after infection and the fifth one died 96 h after spore administration, indicating infection was established. For the animals treated with antibodies (groups B through E) the final survival rates were variable from 40% to over 80%, which is significantly different from the control group A (without antibody treatment), indicating the protective function of toxin-specific antibody treatment. The survival rates of mAb treated hamsters were found to be dose- and source-dependent. Three of seven hamsters from group B (CDA1/MDX-1388 50 mg/kg) died of infection (one died two days after infection (DAI), another two died 13 DAI) while only one of seven hamsters from group C (HeCan20G2/HuCAN46G24 50 mg/kg) died of infection on day 12 during the experiment period. For lower dosage (20 mg/kg) treatment groups, five of eight animals died in group D (CDA1/MDX-1388) and four of eight hamsters died in group E (HeCan20G2/HuCAN46G24) treated group. Cangene mAbs HECAN20G2 and huCAN46G24 were efficacious at a dose of 50 mg/kg with 100% survival after 12 days and 80% survival after 22 days. This combination was also efficacious at a dose of 20 mg/kg with 100% survival after 16 days and 60% survival after 20 days. Therefore, at equivalent doses, HeCan20G2/HuCAN46G24 treatment led to a higher survival in comparison to CDA1/MDX-1388 treatment, while for the same sourced mAbs, the higher dose was correlated with higher/longer survival rates.

Figure 28A:
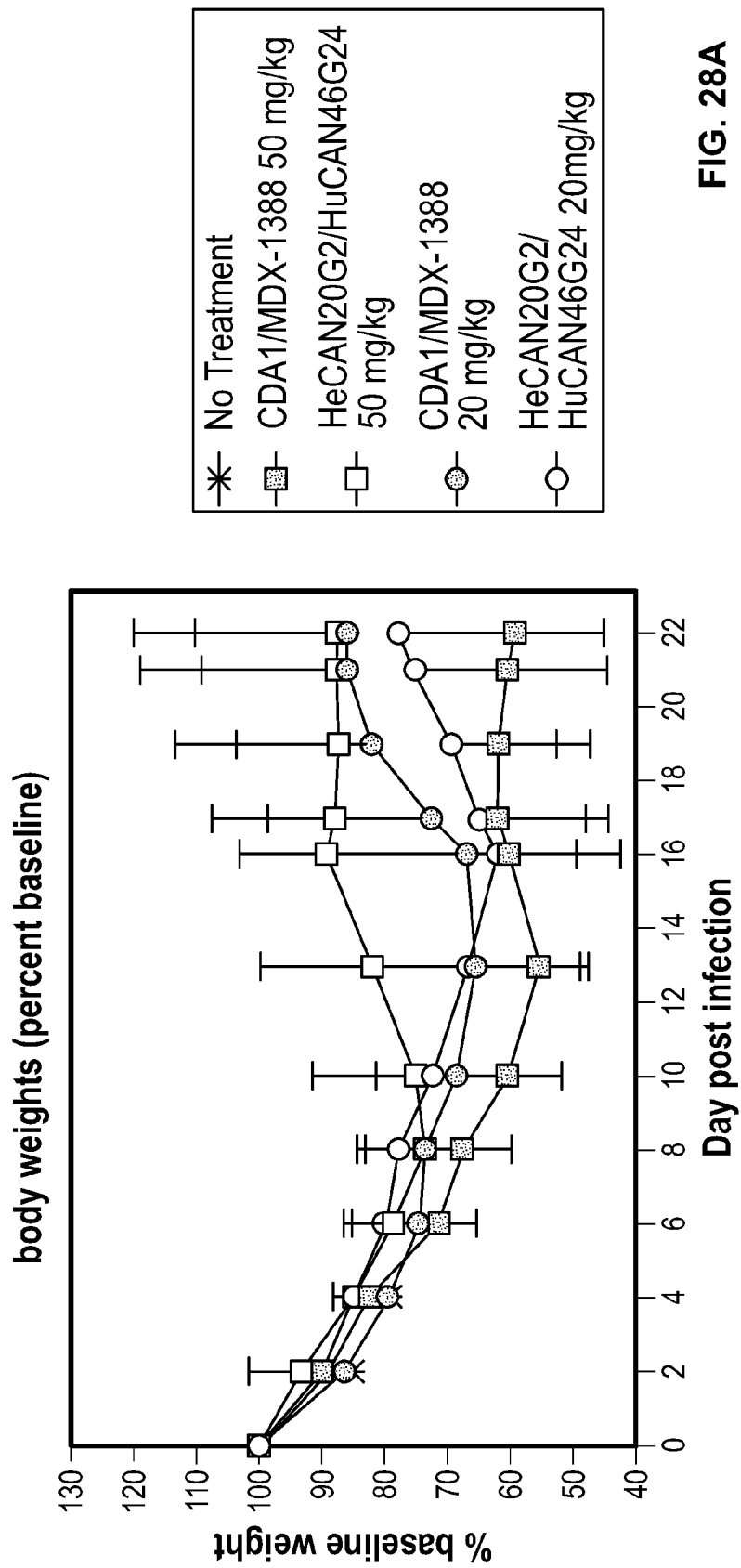
FIG. 28A shows the change from baseline in body weight of the hamsters after infection with C. difficile B1 spores.

FIG. 28A shows the average body weight (BW) of all groups decreased after infection and recovered during the course of treatment in the primary infection model. The BW of Group B (CDA1/MDX-1388 50 mg/kg) decreased to 55% of the original baseline BW by 13 DAI. In group C (HeCan20G2/HuCAN46G24 50 mg/kg) BW decreased after infection to 73%, started to recover by 8 DAI, reached 87% baseline BW by 16 DAI, and remained stable at about 90%. For 20 mg/kg treatment groups, BW of both group D (CDA1/MDX-1388) and group E (HeCan20G2/HuCAN46G24) decreased to 65% of baseline BW and started to recover thereafter. At the end of experiment, BW of group D animals reached 85% of original weight, while group E reached 80% of the original baseline BW.

Figure 28B:
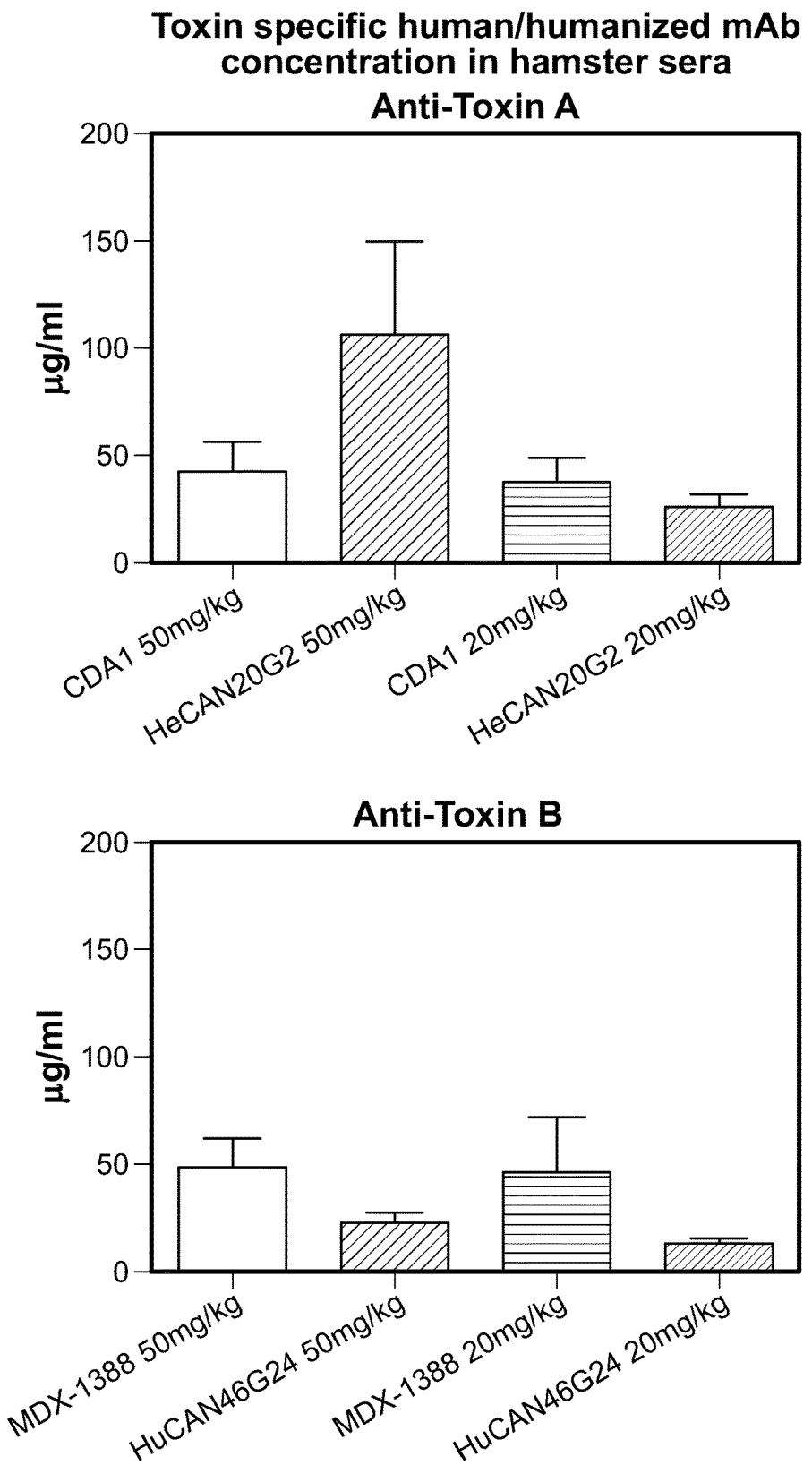
FIG. 28B shows the level of toxin specific human CDA1/ MDX1388 mAbs and humanized HeCAN20G2/ HuCAN46G24 mAbs in hamsters infected with C. difficile B1 spores.

FIG. 28B shows the concentration of toxin mAbs in the sera of surviving hamsters on day 22 in the treated groups (groups B, C, D, and E). Post-infection (day 22) hamster serum samples showed anti-Toxin A IgG antibody concentrations between 8.83 µg/mL-308.72 µg/mL. Anti-Toxin B IgG antibody concentrations ranged between 8.92 µg/mL-85.11 µg/mL.

The results from this study indicate that treatment of C. difficile B1-infected hamsters with the combination of humanized HeCan20G2/HuCAN46G24 at both dosage levels (50 mg/1 g and 20 mg/kg) effectively and robustly protected the hamsters from disease, both following infection and subsequent relapse, improving long term survival in comparison to hamsters treated with CDA1/MDX-1388.

Example 21

Characterization of Humanized mAbs Derived from Per.C6 Vector Against C. difficile Clinical Isolates Concentration of C. difficile Suspensions C. difficile were selected to represent various strains, including strains known to cause CDI in humans (NAP1 by PFGE). From these strains, C. difficile bacteria were grown from spores in TY broth (200 mL) for 4 days at 35° C. in an anaerobic chamber. Bacterial suspension was pelleted by centrifugation and the supernate was filtered (0.22 µm) to remove any remaining spores and vegetative cells. Supernates were concentrated (Centricon 70 plus) and precipitated with ammonium sulfate. The slurry was mixed by slow stirring 10-12 hours at 4° C. and centrifuged. The resulting pellet was washed 5 times with Tris/NaCl to remove residual ammonium sulfate. The resulting toxins were concentrated by Centricon as above and stored (in Tris/NaCl) at 4-8° C. until tested.

ELISA—Toxin B Determination, Sandwich ELISA

All the C. difficile strains in this study, with the exception of CF2 (A–B+), produce both Toxin A and B (A+B+). A sandwich ELISA was performed to determine concentration of Toxin B in the concentrated supernate derived from clinical isolate strains. Microtiter plates were coated with test articles (various mAb) at 1 µg/mL (16 hrs at 4° C.). After coating, the excess capture mAb was removed and the plates were blocked (5% milk for 1 hr at 37° C.). The blocking reagent was discarded and plates were washed (3× with PBST). Diluted standards and concentrates (in 2.5% milk) were added to the plates and incubated (1 hr at 37° C.). The standard/sample were removed, plates washed and detector Abs (rabbit pAbs to Toxin B) was added (1 hr at 37° C.). The detector was removed, plates washed and conjugate Abs (anti-Rabbit HRP) was added (1 hr at 37° C.). After removal and washing of the conjugate, substrate (TMB) was added and allowed to develop. Reaction was stopped with 1 N $H_2SO_4$. Plates were read at 450 nm. Analysis was done by SoftMax.

Direct ELISA—Cross-Reactivity ELISA

In addition, direct ELISA was performed to test the cross-reactivity of the humanized CAN46 mAbs with the clinical isolate strains. Microtiter plates were coated with C. difficile concentrates (16 hrs at 4° C.). After coating, the excess concentrate was removed and the plates were blocked (5% milk for 1 hr at 37° C.). The blocking reagent was discarded and plates were washed (3× with PBST). Diluted Abs (rabbit pAbs, mouse and humanized mAbs, in 2.5% milk) were added to the plates and incubated (1 hr at 37° C.). The Abs were removed and plates were washed. The appropriate conjugates were added (anti-rabbit, anti-mouse and anti-human, 1 hr at 37° C.). After removal and washing of the conjugate, substrate (TMB) was added and allowed to develop. Reaction was stopped with 1 N $H_2SO_4$. Plates were read at 450 nm.

Neutralization Assay—CT26 Cells

CT-26 cells were grown in RPMI-1600 media (with 10% FBS, 37° C., 5% $CO_2$), plated at $3 \times 10^4$ cells/well and allowed to attach to plates (~3 hrs). Toxin concentrations/dilutions used were pre-determined during cytotoxicity testing (% viability). Toxins and Ab preparations were mixed (1:1) and allowed to incubate (1 hr, room temperature) After cell attachment, the media from the CT-26 cells plates was removed and 100 µL of each toxin/Ab mixture was added the CT-26 plate. Plates were incubated for ~48 hrs (37° C., 5% $CO_2$). After incubation, plates were observed to determine cell rounding. For cell viability, 10 µL/well of WST-1 was added to each well and further incubated (1 hr, 37° C., 5% $CO_2$). Plates were read at 440 nm and analyzed for % viability by comparison to cells controls Results: Concentrated toxins from the C. difficile strains were coating on to plates and mAbs bound to the coated toxins. Binding to the coated toxins was defined as follows: High binding=OD>0.800, moderate binding=ODs<0.800 and >0.200, low binding=OD<0.2. FIG. 29 shows that all mAbs showed high binding to the reference strain, ATCC43255. The huCAN46G13a showed the most binding above low levels across the clinical strains tested. In general the antibodies binding to TcdB Fragment 1 showed better binding to the isolated toxins compared to the TcdB Fragment 4 binding mAbs. To standardize these responses, immunoreactivity relative to rabbit pAbs (rpAb) was done as follows: OD of the mAb tested ×100/OD of the rpAb. Both variants (Hu and rehu) for CAN46G24 and CAN46G13a were immunoreactive against the different C difficile toxin B. When similar analysis was performed using sandwich ELISA, toxin B from the different clinical isolates was immunoreactive to varying degrees (FIG. 31). FIG. 31 demonstrates that the huCAN46G13a mAb and the Progenics mAb showed similar binding characteristics to all NAP1 strains tested. The huCAN46G24 mAb and the Medarex mAb showed similar binding characteristics to all strains tested. To demonstrate the relationship between the two ELISA methods, results were analyzed by Pearson correlation. The correlation and significance values for several mAbs are found in Table 17.

TABLE 17

Pearson Correlation between sandwich and cross-reactivity ELISA and associated p values

Figure 30:
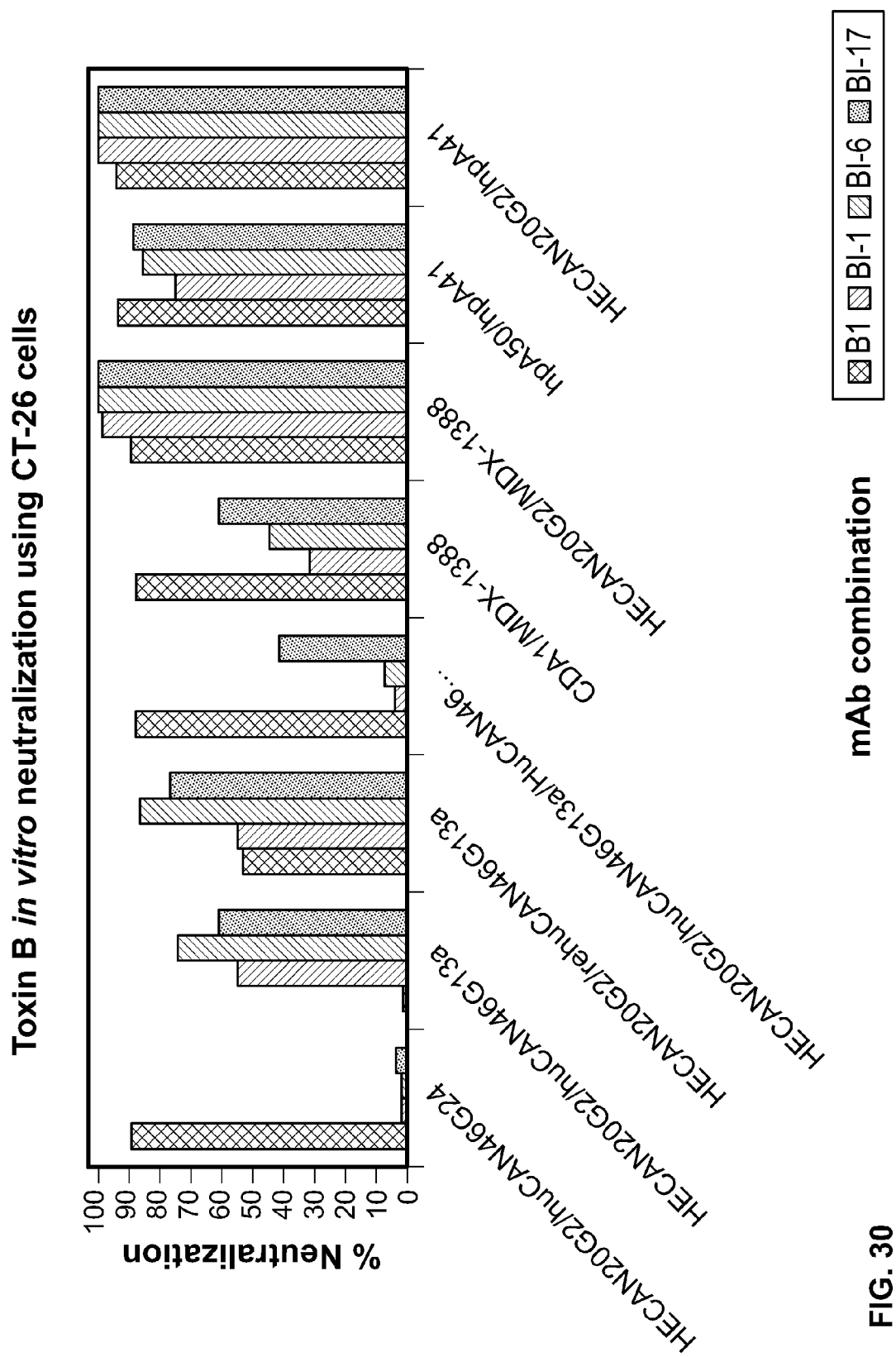
FIG. 30 shows the % Neutralization of different antibody combinations as determined from independent assays conducted across different experiments for the B1 and NAP1 strains (BI-1, BI-6, and BI-17)

| | | Pearson Correlation (r) | Correlation | p value | Statistical Significance |
|---|---|---|---|---|---|
| Cangene mAbs | huCAN46G24 | 0.93 | Strongly Positive | 0.00003 | Yes |
| | huCAN46G13a | 0.41 | Positive | 0.24 | No |
| Comparator mAbs | hpA41 | 0.63 | Positive | 0.04 | Yes |
| | <DX-1388 | 0.94 | Strongly Positive | 0.00002 | Yes | r values>0 indicates a positive relationship between results of the two ELISAs. p values≤0.05, indicate that there was statistical significance correlation between the results. For huCAN46G24, hpA41B and MDX-1388, the Pearson correlation is both positive and statistically significant. For huCAN46G13a, the correlation is positive but not statistically significant. Taken together, this suggests that either method provides a relative determination of TcdB:anti-TcdB interactions across the different clinical isolates Since the C. difficile concentrates contain both toxins A&B, when concentrates were used in neutralization experiments, Toxin A mAb (HECAN20G2) was combined with the Toxin B mAbs being investigated, to quench cytotoxic activity of TcdA. Monoclonal Ab concentration were tested from 10 μg/mL to 0.8 μg/mL and % neutralization was calculated at each Ab concentration. To standardize the responses, the average % neutralization between mAb concentrations 5 to 0.16 mg/mL were calculated and used to rank the effectiveness of the mAbs tested. These are illustratively shown in FIG. 30. HECAN20G2/huCAN46G24 neutralized B1, but had reduced protection against NAP1 strains (BI-1, BI-6, BI-17). In contrast, HECAN20G2/huCAN46G13a displayed the reverse trend; reduced protection against the non-NAP1 strain tested (B1) but neutralized BI-1, BI-6 and BI-17. When HECAN20G2 was combined with comparator anti-toxinB candidates (hpA41 or MDX1388), superior neutralization was observed in comparison to the comparator combinations alone (ProA/ProB, MDXA/MDXB).

Figure 32:
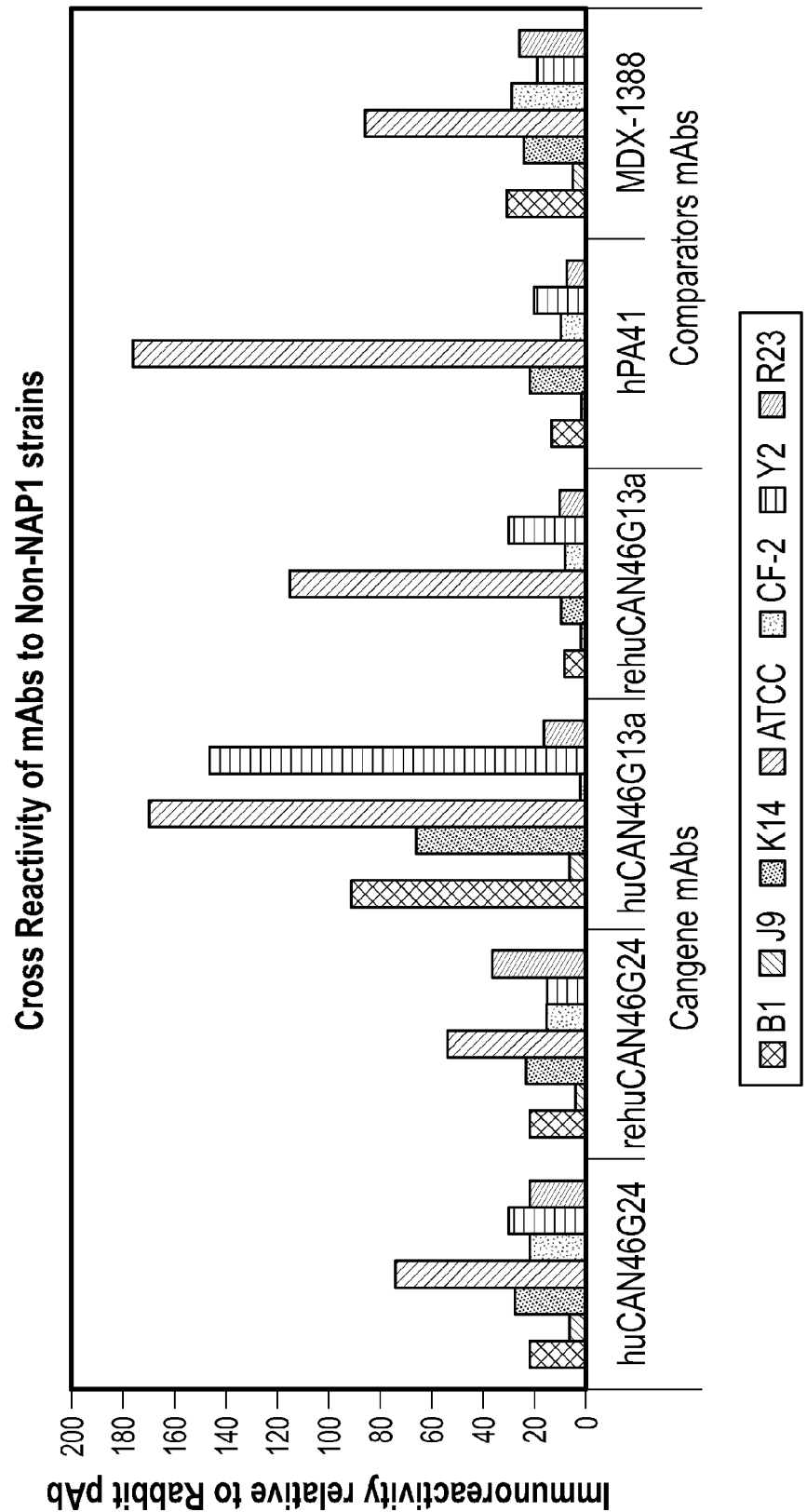
FIG. 32 is a graph showing the immunoreactivity of humanized CAN46 to captured toxins from different C. difficile non-NAP1 strains by ELISA.

In FIG. 32, the immunoreactivity to the non-NAP1 strains is presented as a percent relative to a rabbit polyclonal to Toxin B. The 6 mAbs tested showed high immunoreactivity to the ATCC reference strain and low immunoreactivity to strain J9, CF2, R23. Although most mAbs showed weak binding to B1, K14 and Y2, huCAN46G13a showed high immunoreactivity to B1 and Y2 and moderate immunoreactivity to K14

Figure 33:
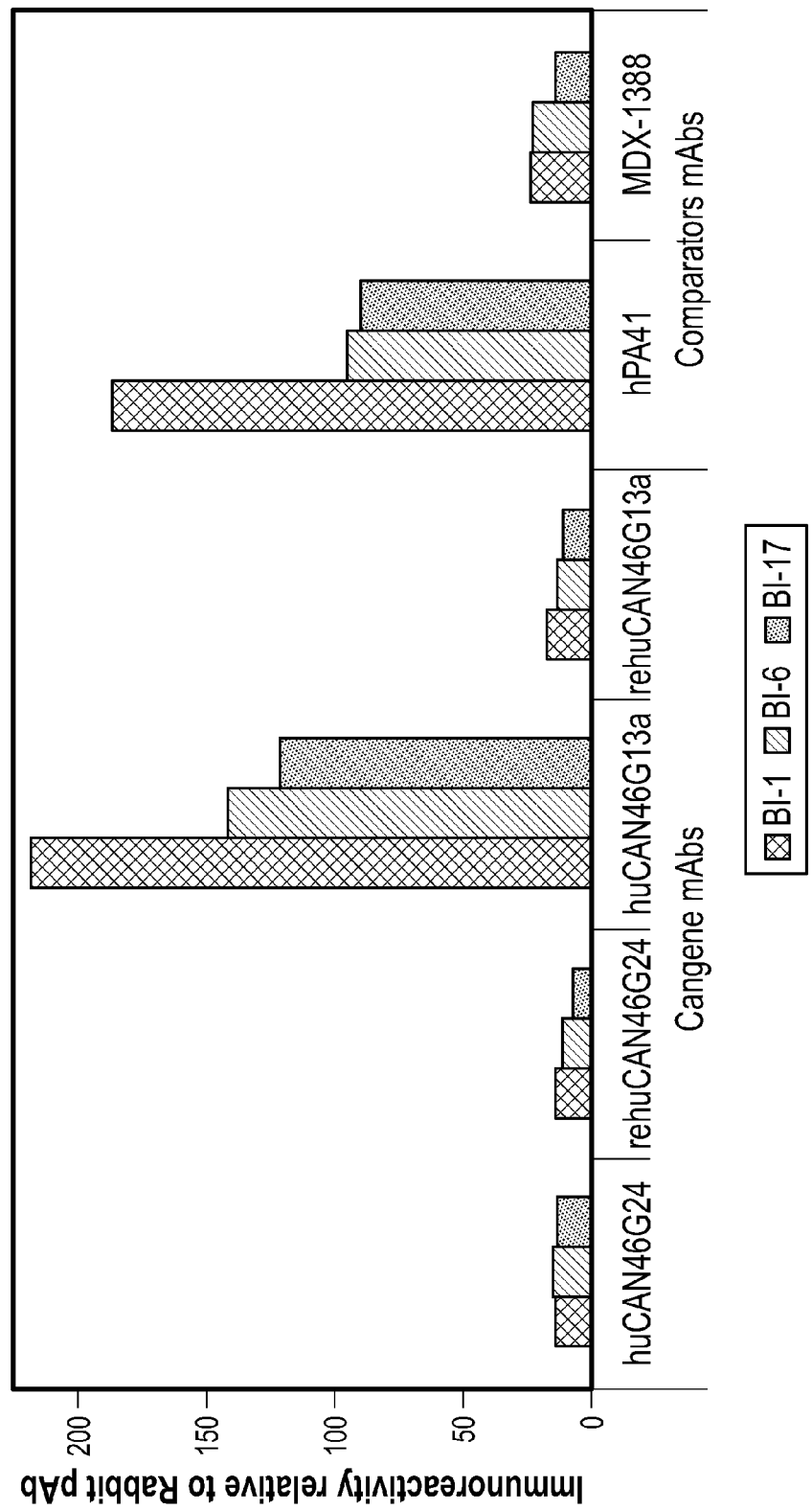
FIG. 33 is a graph showing the immunoreactivity of humanized CAN46G mAbs to captured toxin B from different NAP1 C. difficile strains by ELISA.

In FIG. 33, the immunoreactivity to the NAP1 strains is presented as a percent relative to a rabbit polyclonal to Toxin B. The huCAN46G13a mAb and the Progenics mAb showed high immunoreactivity to all strains tested. The other mAbs tested, huCAN46G24, rehuCAN46G24, rehuCAN46G13a, and the Medarex mAb showed weak immunoreactivity to all strains tested.

In summary, the 4 mAbs tested showed similar binding characteristics to all strains tested. The binding to toxin from C. difficile strain J9 was the most diverse across the mAbs with huCAN46G13a showing the weakest binding.

Example 22

Production of Humanized C difficile Toxin mAbs

For production of humanized C difficile toxin mAbs, individual IgG sequences encoding for heavy and light chains are co-expressed in vectors under the control of promoter, including a Kozak/HAVT20 leader sequence and terminator. Intron/exon sequences were added to the 3' end of each variable sequence followed by a double stop codon to signal the end of transcript translation. For the kappa light chain, this included one intron/exon (constant exon). For the heavy chain, this included four sets of introns/exons (CH1, CH2 and CH3 constant exons). Introns were included in the sequence to allow for eukaryotic processing of the mRNA transcript. Expression constructs could be used for transient expression in adapted mammalian cell lines (HEK293F, CHO-S, CHOK1SV, Per.C6) for transient transfection by lipofectamine. The expression vectors also included appropriate selectable markers for each expression system to enable stable expression in mammalian cell culture using electroporation. For experiments requiring comparative analysis, mAbs were synthesized from published sequences ecoding CDA1 (3D8 kappa chain GenBank accession number DJ444525; heavy chain GenBank accession number CS483823), MDX-1388 (124-152 kappa chain accession number CS483846, heavy chain CS483842), and hpA41 and hpA50 sequences from international publication WO2011130650(A2). Heavy and light chains were synthesized and cloned into full length IgG1 vectors for expression in CHO-K1SV, HEK293F, Per.C6 systems. The IgG1 mAbs were expressed and purified as outlined above and served as positive controls for anti-TcdA activity (CDA1, specificity against TcdA fragment 4) for HeCAN20G2, or anti-TcdB activity with specificity against fragment 1 (hpA41) for CAN46G13a or fragment 4 (MDX-1388) for CAN46G24, CAN46G19, and CAN46G4. Following transient transfection, supernatants were decanted, filtered (0.22 um) and concentrated using a stir-cell concentrator and a 30 kDa membrane. Concentrate was filtered (0.22 um) prior to purification. For stable transfections, clones were screened and isolated for assessment in batch and fed-batch growth. IgG, concentrated and filtered supernatants were purified on Protein G columns, buffer exchanged and concentrated. For final concentrates, protein content was determined by BCA assay or with an Octet QKe instrument equipped with Protein A biosensors against standard curves for human IgG equivalents.

Results: Table 18, shows representative expression titers for huCAN46G24 and huCAN46G13a in transient and stable transfections. From these means material was supplied to conduct characterization, in vitro and in vivo analysis

TABLE 18

Representative expression titers normalized to mg/L in transient and stable expression lines (BOG = batch overgrowth, FOG = fed batch overgrowth).

| C difficile anti-TcdB | Transient | Stable (CDCHO-v8 media) | |
|---|---|---|---|
| | | BOG | FOG |
| CAN46G24 | 7.4 | 647.8 | 4,129.5 |
| CAN46G13a | 6.3 | 8.8 | 117.6 |

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. An isolated antibody or antigen-binding portion thereof comprising a heavy chain variable region (VH) and a light chain variable region (VL),
   wherein the heavy chain variable region comprises three complementarity determining regions (CDRs), CDR1, CDR2, and CDR3, having the amino acid sequences set forth in SEQ ID NOs: 126, 127, and 128, respectively, or the amino acid sequences set forth in SEQ ID NOs: 110, 127, and 128, respectively, and
   wherein the light chain variable region comprises three CDRs, CDR1, CDR2, and CDR3, having the amino acid sequences set forth in SEQ ID NOs: 118, 119, and 120, respectively; and
   wherein the antibody or antigen-binding portion thereof specifically binds to Clostridium difficile(C. difficile) toxin B.

2. The antibody or antigen-binding portion thereof of claim 1, wherein the heavy chain variable region comprises the amino acid sequence SEQ ID NO: 109 and wherein the light chain variable region comprises the amino acid sequence SEQ ID NO: 101.

3. The antibody or antigen-binding portion thereof of claim 1, wherein the heavy chain variable region comprises the amino acid sequence SEQ ID NO: 125 and wherein the light chain variable region comprises the amino acid sequence SEQ ID NO: 117.

4. The antibody or antigen-binding portion thereof of claim 1, wherein the heavy chain variable region comprises the amino acid sequence SEQ ID NO: 141 and wherein the light chain variable region comprises the amino acid sequence SEQ ID NO: 133.

5. The antibody or antigen-binding portion thereof of claim 1, wherein the heavy chain variable region comprises the amino acid sequence set forth in SEQ ID NO: 43, and wherein the light chain variable region comprises the amino acid sequence set forth in SEQ ID NO: 35.

6. The antibody or antigen-binding portion thereof of claim 1, wherein the dissociation constant ($K_D$) of the antibody or antigen-binding portion thereof binding to C. difficile toxin B is less than about $8.6 \times 10^{-9}$ M.

7. The antibody or antigen-binding portion thereof of claim 1, which comprises an IgG constant region, IgE constant region, IgD constant region, IgM constant region, an IgA constant region, or any fragment thereof.

8. The antibody or antigen-binding portion thereof of claim 1, which is functionally linked to another molecule.

9. The antibody or antigen-binding portion thereof of claim 8, wherein the functionally linked molecule is an antibody, detectable agent, a cytotoxic agent, a pharmaceutical agent, a protein or peptide that mediates association with another molecule, an amino acid linker, a signal sequence, or an immunogenic carrier.

10. The antibody or antigen-binding portion thereof of claim 1, which is humanized or chimeric.

11. The antibody or antigen-binding portion thereof of claim 1, which is an scFv, a Fab fragment, an F(ab')2, or a disulfide-linked Fv.

12. A composition comprising the antibody or antigen-binding portion thereof of claim 1, and a pharmaceutically acceptable carrier.

13. A kit comprising the antibody or antigen-binding portion thereof of claim 1 and one or more of an antibody that binds to C. difficile toxin A, a therapeutic agent, a coupling agent, a material for preparing the antibody for administration, or a pharmaceutically acceptable carrier.

14. The kit of claim 13, further comprising: one or more of C. difficile whole toxin B, toxoid B, toxin B fragment 4, or toxin B fragment 1.

15. A method of treating a C. difficileassociated disease (CDAD), comprising administering to a subject an effective amount of the antibody or antigen-binding portion thereof of claim 1, wherein the subject is infected, or is believed to be infected, with C. difficile.

16. The method of claim 15, wherein the antibody or antigen-binding portion thereof is administered intravenously, subcutaneously, intramuscularly or transdermally.

17. The method of claim 15, further comprising administering a second agent.

18. The method of claim 17, wherein the second agent is a different antibody or antigen-binding portion thereof.

19. The method of claim 17, wherein the second agent is an antibiotic.

20. The method of claim 19, wherein the antibiotic is vancomycin, metronidazole, or fidaxomicin.

21. The antibody or antigen-binding portion thereof of claim 1, wherein the antibody or antibody-binding portion thereof binds to fragment 1 of C. difficile Toxin B.

22. An isolated antibody heavy chain variable region, wherein the heavy chain variable region comprises an amino acid sequence selected from the group consisting of SEQ ID NO: 43, 109, 125, and 141,
   wherein an antibody or antigen-binding binding portion thereof comprising the heavy chain variable region and a light chain variable region comprising the amino acid sequence SEQ ID NO: 35, 101, 117, or 133, respectively, can specifically bind to C. difficile toxin B.

23. An isolated antibody light chain variable region, wherein the light chain variable region comprises an amino acid sequence selected from the group consisting of SEQ ID NO: 35, 101, 117, or 133,
   wherein an antibody or antigen-binding binding portion thereof comprising the light chain variable region and a heavy chain variable region comprising the amino acid sequence SEQ ID NO: 43, 109, 125, or 141, respectively, can specifically bind to C. difficile toxin B.

* * * * *